US012455284B2

(12) United States Patent
Strick et al.

(10) Patent No.: US 12,455,284 B2
(45) Date of Patent: Oct. 28, 2025

(54) DOUBLE-STRANDED DNA MOLECULE FOR THE DETECTING AND CHARACTERIZING MOLECULAR INTERACTIONS

(71) Applicants: PARIS SCIENCES ET LETTRES—QUARTIER LATIN, Paris (FR); CENTRE NATIONAL DE LA RECHERCHE SCIENTIFIQUE (CNRS), Paris (FR); ECOLE NORMALE SUPERIEURE, Paris (FR); UNIVERSITÉ DE PARIS, Paris (FR); INSTITUT NATIONAL DE LA SANTE ET DE LA RECHERCHE MEDICALE (INSERM), Paris (FR)

(72) Inventors: Térence Strick, Paris (FR); Charlie Gosse, Paris (FR); Dorota Kostrz, Paris (FR); Jinglong Wang, Paris (FR); Marc Nadal, Paris (FR)

(73) Assignees: PARIS SCIENCES ET LETTRES—QUARTIER LATIN, Paris (FR); CENTRE NATIONAL DE LA RECHERCHE SCIENTIFIQUE (CNRS), Paris (FR); ECOLE NORMALE SUPERIEURE, Paris (FR); UNIVERSITÉ DE PARIS, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 1279 days.

(21) Appl. No.: 16/955,596

(22) PCT Filed: Dec. 21, 2018

(86) PCT No.: PCT/FR2018/053533

§ 371 (c)(1),
(2) Date: Jun. 18, 2020

(87) PCT Pub. No.: WO2019/122793

PCT Pub. Date: Jun. 27, 2019

(65) Prior Publication Data

US 2023/0054300 A1 Feb. 23, 2023

(30) Foreign Application Priority Data

Dec. 21, 2017 (FR) ...................................... 1762848

(51) Int. Cl.

| | |
|---|---|
| ***G01N 33/543*** | (2006.01) |
| ***C12Q 1/6825*** | (2018.01) |
| ***G01N 33/68*** | (2006.01) |
| *G01Q 60/24* | (2010.01) |

(52) U.S. Cl.

CPC ..... *G01N 33/54373* (2013.01); *C12Q 1/6825* (2013.01); *G01N 33/6803* (2013.01); *G01Q 60/24* (2013.01)

(58) Field of Classification Search

CPC ......... G01N 33/54373; G01N 33/6803; C12Q 1/6825; C12Q 1/6806; G01Q 60/24

See application file for complete search history.

(56) References Cited

U.S. PATENT DOCUMENTS

| | | | |
|---|---|---|---|
| 7,052,650 | B2 | 5/2006 | Strick et al. |
| 7,244,391 | B2 | 7/2007 | Strick et al. |

FOREIGN PATENT DOCUMENTS

| | | |
|---|---|---|
| EP | 0 152 886 | 8/1985 |
| WO | WO 92/16659 | 10/1992 |
| WO | WO 2011/147931 | 12/2011 |
| WO | WO 2013/067489 | 5/2013 |
| WO | WO 2016/089588 | 6/2016 |
| WO | WO 2017/055463 | 4/2017 |

OTHER PUBLICATIONS

Tashiro, Ryu, et al. "Linking two DNA duplexes with a rigid linker for DNA nanotechnology." Nucleic Acids Research 43.14 (2015): 6692-6700.*

Bedet et al., *Regulation of Gephyrin Assembly and Glycine Receptor Synaptic Stability*, 281(40) The Journal of Biological Chemistry 30046-30056 (Oct. 6, 2006).

Bouchiat et al., *Estimating the Persistence Length of a Worm-Like Chain Molecule from Force-Extension Measurements*, 76 Biophysical Journal 409-413 (Jan. 1999).

Conroy et al., *Force Spectroscopy with Optical and Magnetic Tweezers*, Handbook of Molecular Force Spectroscopy 23-96 (2008).

Duboc et al., *Preparation of DNA Substrates and Functionalized Glass Surfaces for Correlative Nanomanipulation and Colocalization (NanoCOSM) of Single Molecules*, 582 Preparation of DNA Substrates and Functionalized Glass Surfaces 275-296 (2016).

Gao et al., *Single Reconstituted Neuronal SNARE Complexes Zipper in Three Distinct Stages*, 337(6100) Science 1340-1343 (Sep. 14, 2012).

Gautier et al., *An Engineered Protein Tag for Multiprotein Labeling in Living Cells*, 15 Chemistry & Biology 128-136 (Feb. 2008).

Grunewald et al., *Sequences Flanking the Gephyrin-Binding Site of GlyRβ Tune Receptor Stabilization at Synapses*, 5(1) Neuronal Excitability 1-17 (Jan./Feb. 2018).

Halvorsen et al., *Nanoengineering a single-molecule mechanical switch using DNA self-assembly*, 22 Nanotechnology 1-8 (2011).

(Continued)

*Primary Examiner* — Kimberly Chong

(74) *Attorney, Agent, or Firm* — Panitch Schwarze Belisario & Nadel LLP; Erin M. Dunston

(57) ABSTRACT

The present application relates to a double-stranded DNA molecule comprising a first double-stranded DNA molecule (1) connected to a second double-stranded DNA molecule (2) by at least one covalent bond which is not a phosphodiester, phosphorothioate, phosphoramidate or phosphorodiamidate bond, preferably by a tether, said tether preferably being a double-stranded DNA molecule.

13 Claims, 22 Drawing Sheets

Specification includes a Sequence Listing.

(56) References Cited

OTHER PUBLICATIONS

Hein et al., *Click Chemistry, a Powerful Tool for Pharmaceutical Sciences*, 25(10) Pharm. Res. 2216-2230 (Oct. 2008).
Keppler et al., A general method for the covalent labeling of fusion proteins with small molecules in vivo, 21 Nature Biotechnology 86-89 (Jan. 2003).
Kilchherr et al., *Single-molecule dissection of stacking forces in DNA*, 353(6304) Science aaf5508-1-aaf5508-9 (Sep. 9, 2016).
Kim et al., *A mechanically stabilized receptor-ligand flex-bond important in the vasculature*, 466 Nature 992-997(Aug. 2010).
Lionnet et al., *Magnetic Trap Construction*, Cold Spring Harbor Protoc. 133-138 (2012).
Pingoud et al., *Structure and function of type II restriction endonucleases*, 29(18) Nucleic Acids Research 3705-3737 (2001).
Popa et al., *Direct Quantification of the Attempt Frequency Determining the Mechanical Unfolding of Ubiquitin Protein*, 286(36) The Journal of Biological Chemistry 31072-31079 (Sep. 9, 2011).
Rognoni et al., *Dynamic force sensing of filamin revealed in single-molecule experiments*, 109(48) PNAS 19679-19684 (Nov. 27, 2012).
Rothemund, *Folding DNA to create nanoscale shapes and patterns*, 440 Nature 297-302 (2006).
Sarkar et al., *A Guide to Magnetic Tweezers and Their Applications*, 4(Article 48) Frontiers in Physics 1-20 (Dec. 2016).
Tashiro et al., *Linking two DNA duplexes with a rigid linker for DNA nanotechnology*, 43(14) Nucleic Acids Research 6692-6700 (2015).
Wiita et al., *Force-dependent chemical kinetics of disulfide bond reduction observed with single-molecule techniques*, 103(19) PNAS 7222-7227 (May 9, 2006).
Woodside et al., *Nanomechanical measurements of the sequence-dependent folding landscapes of single nucleic aid hairpins*, 103(16) PNAS 6190-6195 (Apr. 18, 2006).
Yang et al., *Multiplexed single-molecule force spectroscopy using a centrifuge*, 7(11026) Nature Communications 1-7 (Mar. 17, 2016).

* cited by examiner

D

DOUBLE-STRANDED DNA MOLECULE FOR THE DETECTING AND CHARACTERIZING MOLECULAR INTERACTIONS

REFERENCE TO SEQUENCE LISTING SUBMITTED ELECTRONICALLY

This application contains a sequence listing, which is submitted electronically via EFS-Web as an ASCII formatted sequence listing with a file name Second_Substitute_Sequence_Listing, creation date of Feb. 2, 2022 and having a size of 104 KB. The sequence listing submitted via EFS-Web is part of the specification and is herein incorporated by reference in its entirety.

CROSS-REFERENCE TO RELATED APPLICATIONS

This application is a U.S. National Stage Application pursuant to 35 U.S.C. § 371 of International Patent Application PCT/FR2018/053533, filed on Dec. 21, 2018, and published as WO 2019/122793 on Jun. 27, 2019, which claims priority to French Patent Application 1762848, filed on Dec. 21, 2017, all of which are incorporated herein by reference in their entireties for all purposes.

FIELD OF THE INVENTION

The present invention relates to the field of molecular micromanipulation. More specifically, the present invention relates to molecules and methods for detecting and characterizing molecular interactions at the single molecule scale.

PRIOR ART

Micromanipulation techniques, such as optical tweezers and atomic force microscopy, make it possible to characterize molecular interactions between different test molecules and determine thermodynamic and kinetic information at the scale of a single molecule, in particular as a function of an applied force. These techniques are growing rapidly as they require few reagents as compared to more conventional methods (such as those involving biosensors based on surface plasmon resonance or optical interferometry), and allow higher quality mechanistic information to be obtained as a result of the individualization of molecular monitoring.

The detection of molecular interactions by micromanipulation techniques most often requires an attachment of test molecules between two supports. If it is conceivable that at least one of the test molecules can be directly attached to a support, this is not desirable as it is a source of artifacts given the support-support or molecule-support type nonspecific interactions. support that may occur. In order to reduce artifacts, various molecules have been described which make it possible to indirectly attach test molecules to supports, in particular via peptide and/or nucleotide molecules (see, e.g., Gao et al., 2012). These molecules can themselves be connected to one another directly or indirectly, e.g. by a third molecule, herein called a "tether" (see, e.g., Kim et al., 2010; Halvorsen et al., 2011; Rognoni et al., 2012; Kilchherr et al., 2016). Thus, a molecule used to study molecular interactions by micromanipulation generally corresponds to a molecule in which several "sub-molecules" are combined, including at least two test molecules.

The molecules currently used to study molecular interactions can be grouped into four distinct categories depending on the composition of the molecule (e.g. comprising polypeptide and/or polynucleotide elements), as described below.

The first category of molecules comprises molecules that are composed solely of amino acids, including polypeptides and/or proteins. More specifically, the test molecules are attached to two different supports by means of globular proteins (see, e.g., Wiita et al., 2006; Popa et al., 2011). Generally, the test molecules are bound to globular proteins and/or to a polypeptide tether within a fusion protein. However, the use of fusion proteins limits the type of test molecules that can be integrated into molecules that are solely of proteic nature. In addition, each time the test molecules are modified, these molecules require a major preparation effort as the tether and/or globular proteins are expressed and purified at the same time as the test molecules. In addition, depending on protein conformation, the positive interaction rate between test molecules may be artificially reduced due to conformational constraints (e.g. orientation, accessibility) related to the three-dimensional structure of the molecule. Finally, in order to reduce interactions between the tether and other elements of the molecule, and to prevent the formation of undesirable secondary structures, particularly during expression, the length of the polypeptide tether is limited to about 100 amino acids and its sequence must be carefully chosen. This limitation of length also increases the effective concentration of test molecules, which is determined by the average distance between these two molecules. As an example, the effective concentration of test molecules is in the range of 1 mM when a polypeptide tether of about fifty amino acids is used, such that only molecular associations having sufficiently slow rate constants can be studied. As an example, for a given temporal resolution, which makes it possible to detect the conformational changes in 10 ms, the limit value beyond which rate constants can no longer be measured is $10^5$ $M^{-1}s^{-1}$.

The second category of molecules comprises double-stranded DNA molecules, connected to one another by a polypeptide tether (see, e.g., Rognoni et al, 2012; Kim et al., 2010). The constraints associated with the use of a polypeptide tether therefore remain the same here as for the peptide-type molecules of the first category. Moreover, given the small number of tools available to this day allowing peptide bonds to be modified, the test molecules must, again, be solely of proteic nature and expressed at the same time as the tether (e.g. in fusion proteins).

Thus, these two types of molecules are not very flexible in their use, on one hand due to the nature of the test molecules that can be incorporated, and on the other hand due to the limit imposed to the lowest effective concentrations that may be studied.

A third category of molecules includes molecules composed of single-stranded DNA coated with oligonucleotides (see, e.g., WO 2013/067489; Halvorsen et al., 2011). In this case, the single-stranded DNA functions as a "support molecule" for the oligonucleotides, which hybridize and transform the single-stranded DNA into a discontinuous three-dimensional structure comprising only phosphodiester bonds, according to an "origami" type synthesis (see, e.g., Rothemund, 2006). However, the length of this type of molecule can hardly exceed the practical limit of about 25,000 nucleotides, which is the length of the largest single-stranded DNA genome existing in nature, and which could potentially function as "support molecule" (although, for the moment, the technique has only been illustrated with "support molecules" whose length was, at most, about 7250 nucleotides). In addition, when the oligonucleotides hybridize to the single-stranded DNA molecule, numerous nicks remain along the entire length of the resulting structure.

Finally, the "origami" technique remains difficult to implement. The oligonucleotides may in particular have secondary structures and/or interact with each other when they are mixed, and even more so when they are long (e.g. >20 bases). As an example, for a support composed of about 7250 nucleotides, 121 different oligonucleotides having a length of 60 bases were hybridized (Halvorsen et al., 2011). If the probability that an individual oligonucleotide is correctly hybridized is high, even with a probability of 99%, the probability that the support molecule comprises 121 hybridized oligonucleotides is only $0.99^{121}$, or about 30%. If the probability that an individual oligonucleotide is correctly hybridized reaches 99.9%, then the probability that the support molecule comprises 121 hybridized oligonucleotides is only 89%. These considerations indicate that the origami approach frequently produces DNA molecules with:

(1) Heterogeneous chemical properties (intact double-stranded hybridized regions, single-stranded unhybridized regions, and nicks between two hybridized oligonucleotides);
(2) Mechanical properties varying from one molecule to another, the precise mechanical response of a given molecule depending on the exact ratio between the total length of double-stranded hybridized regions and the total length of single-stranded unhybridized regions;
(3) Unfavorable topological properties (the molecule cannot be supercoiled for example);
(4) A significant risk of separation between the "support molecule" and the oligonucleotides, if high forces are applied to the structure.

This results in a large variability, from one molecule to another, of the intrinsic properties of the molecules used for these studies. The complexity of the assembly of this type of molecule makes it impossible to guarantee the homogeneity of a set of DNA molecules constructed in this manner. However, to measure interactions at the scale of a single molecule, it is necessary to be able to ensure a very high level of quality for each individual molecule incorporating said test molecules.

The fourth category of molecules comprises two bundles of double-stranded DNA molecules linked to each other by a single-stranded DNA tether (Kilchherr et al., 2016), thus comprising only phosphodiester-type bonds. As the assembly of a bundle of DNA molecules also depends on the "origami" technique, this molecule has the same disadvantages associated with this technique as those described above. In addition, given the large number of oligonucleotides that compose the bundles, these compositions are particularly rigid; the conformational freedom of the test molecules is therefore far removed from what it is in solution. In contrast to the rigidity of the bundles, the single-stranded DNA tether is flexible, consisting of a simple succession of phosphodiester bonds. As a result, it is impossible to perform studies involving the application of a torque on molecules comprising a single-stranded DNA tether. A single-stranded DNA tether is also likely to form secondary structures and/or interact with other elements of the molecule.

There exists, therefore, at present a need for new stable and homogeneous molecules, in which a large variety of test molecules could be integrated. There is also a need for new molecules in which non-specific interactions (e.g. between a test molecule and one or more other elements of the molecule, such as a tether) are reduced, advantageously wherein non-specific interactions are entirely absent. There is also a need for new molecules that are both flexible, in order to minimize conformational constraints experienced by the test molecules and thus to avoid an artificial reduction in the rate of interactions between the test molecules, but also rigid, in order to have easy access to the field of low forces starting under about 2 pN. Indeed, currently used molecules, e.g. that are composed of bundles of DNA molecules or polypeptides, cannot be used to characterize molecular interactions that occur at low forces (e.g. below 2 pN).

There is also a need for new molecules that would be easily modulated. More specifically, there is a particular need for new molecules that would make it possible to measure interactions between test molecules having a large diversity of structures and/or compositions, in particular above and beyond nucleic acids and amino acids (e.g. polymers, small chemical molecules, nanoparticles, etc.). There is also a need for new molecules comprising elements that are easily adjustable in length (e.g. not limited to 25,000 nucleotides), such as the tether and/or the molecules connecting the test molecules to the supports, in order to be able to modulate the effective concentrations test molecules and thus be able to measure association rate constants greater than about $10^5\ M^{-1}s^{-1}$.

There is also a need for a new device for the measurement of molecular interactions, said device comprising a molecule having at least one of the advantages described above, as well as a new method for characterizing the molecular interactions using such a molecule or device. Finally, there is a need for a method of manufacturing said molecules and devices that is fast, simple, inexpensive, and/or that involves a minimum number of steps.

SUMMARY OF THE INVENTION

The present invention pertains to a new molecule that makes it possible to meet all of the above-mentioned needs. More particularly, present invention pertains to a double-stranded DNA molecule comprising a first double-stranded DNA molecule (1) connected to a second double-stranded DNA molecule (2) by at least one covalent bond which is not a phosphodiester, phosphorothioate, phosphoramidate or phosphorodiamidate bond, advantageously by a tether, said tether being advantageously a double-stranded DNA molecule.

Indeed, the inventors have advantageously demonstrated that the double-stranded DNA molecule according to the invention is more homogeneous than the molecules known to date, which makes it possible to improve the quality of results obtained when such a molecule is used to perform molecular interaction studies. The chemical homogeneity of the molecule makes it possible to eliminate a large number of potential artifacts related to the differential interactions between proteins and different types of nucleic acids (e.g. single-stranded). The chemical homogeneity of the molecule also enhances the stability of the molecule by reducing the number of ways the molecule can degrade. Advantageously, the double-stranded DNA molecule according to the invention does not comprise either secondary structure or tertiary structure. The inventors have also surprisingly demonstrated that the double-stranded DNA molecule according to the invention can be used to study a large number of different interactions, with different types of test molecules (e.g. proteins, polynucleotides, small chemical molecules) without needing to adapt the different elements of the molecule (e.g. the double-stranded DNA molecules (1) and (2) and/or the tether). This is particularly advantageous as compared to molecules comprising polypeptide elements as described above (according to the first or second category of molecules).

Surprisingly, the inventors have also demonstrated that the double-stranded DNA molecule according to the invention is flexible, which advantageously makes it possible to minimize the conformational constraints experienced by the test molecules, thereby avoiding an artificial reduction in the rate of interactions between the test molecules. In addition, the inventors have surprisingly demonstrated that the double-stranded DNA molecule is also sufficiently rigid to be able to characterize molecular interactions occurring at low forces starting below about 2 pN.

Advantageously, the invention pertains to a double-stranded DNA molecule wherein said tether is attached by at least one covalent bond which is not a phosphodiester bond to the first double-stranded DNA molecule (1) and by at least one covalent bond which is not a phosphodiester bond to the second double-stranded DNA molecule (2).

Advantageously, the invention pertains to a double-stranded DNA molecule comprising a first double-stranded DNA molecule (1) connected to a second double-stranded DNA molecule (2) by a tether comprising double-stranded DNA, wherein said tether is attached by (i) at least one covalent bond to a nucleotide of the first double-stranded DNA molecule (1) and by (ii) at least one covalent bond to a nucleotide of the second double-stranded DNA molecule (2), wherein said covalent bond of (i) and said covalent bond of (ii) are not phosphodiester, phosphorothioate, phosphoramidate or phosphorodiamidate bonds, and said nucleotide of (i) and said nucleotide of (ii) are not ultimate nucleotides of said double-stranded DNA molecules (1) and (2).

Advantageously, the invention pertains to a double-stranded DNA molecule wherein said tether is attached to the first double-stranded DNA molecule (1) by a first covalent bond between the first extremity of said tether and an intermediate region of the first double-stranded DNA molecule (1) and the second double-stranded DNA molecule (2) by a second covalent bond between the second extremity of said tether and an intermediate region of the second molecule of double-stranded DNA (2).

Advantageously, the invention pertains to a double-stranded DNA molecule in which a first test molecule is linked to a first extremity of said first double-stranded DNA molecule (1) and a second test molecule is linked to a first extremity of said second double-stranded DNA molecule (2).

Advantageously, the invention pertains to a double-stranded DNA molecule in which the second extremity of said first double-stranded DNA molecule (1) is linked to a first support and the second extremity of said second molecule of double-stranded DNA (2) is linked to a second support, advantageously wherein at least one of the two supports is a moveable support.

Advantageously, there is extensive liberty in the choice of supports to which the double-stranded DNA molecule can be attached.

Advantageously, the length of said first double-stranded DNA molecule (1) and/or said second double-stranded DNA molecule (2) and/or said tether can be easily adjusted. This notably makes it possible to optimize the resolution of extension measurements during the characterization of interactions between the test molecules. This also makes it easier to distinguish between signals resulting from a specific interaction between two test molecules and signals resulting from a nonspecific interaction (e.g. between test molecules and nearby surfaces or supports). Particularly advantageous, the length of said tether can be easily adjusted in order to be able to modulate the effective concentrations of the test molecules ($C_{eff}$) and notably allow association rate constants greater than approximately $10^5$ $M^{-1}s^{-1}$ to be determined. This is furthermore facilitated as the double-stranded DNA has a large persistence length (about 50 nm, or about 160 base pairs).

According to a preferred embodiment, the invention pertains to a double-stranded DNA molecule in which:

- said first double-stranded DNA molecule (1) and/or said second double-stranded DNA molecule (2) has a length of 300 to 5000 base pairs, preferably 650 to 1500 base pairs;
- the first extremity of the first double-stranded DNA molecule (1) and/or the first extremity of the second double-stranded DNA molecule (2) has a length of 10 to 150 base pairs, advantageously 30 to 50 base pairs; and/or
- said tether has a length of from about 300 to about 50,000 base pairs, preferably from about 500 to 10,000 base pairs, more preferably from about 600 to 3,000 base pairs.

Advantageously, the invention pertains to a double-stranded DNA molecule in which said first and/or second test molecule is selected from the group consisting of the following molecules: polymers, amino acids, peptides, polypeptides, proteins, nucleosides, nucleotides, polynucleotides, oligonucleotides, sugars, polysaccharides, small molecules, drugs, aptamers, antigens, antibodies, lipids, lectins, hormones, vitamins, viruses, virus fragments, nanoparticles, cell surface molecules, and transcription factors.

Advantageously, the invention pertains to a DNA molecule for use in the characterization of interactions between at least two test molecules.

Advantageously, the invention pertains to a device comprising the double-stranded DNA molecule described herein with its supports.

Advantageously, the invention pertains to a double-stranded DNA molecule comprising a first double-stranded DNA molecule (A) and a second double-stranded DNA molecule (B), said molecule (A) comprising a cleavage site which is present only in said double-stranded DNA molecule (A), said double-stranded DNA molecule (A) being connected to the double-stranded DNA molecule (B) by two covalent bonds which are not phosphodiester, phosphorothioate, phosphoramidate or phosphorodiamidate bonds, on either side of said cleavage site.

The double-stranded DNA molecule comprising a first double-stranded DNA molecule (1) connected to a second double-stranded DNA molecule (2) by at least one covalent bond which is not a phosphodiester bond, a phosphorothioate bond, a phosphoramidate bond or a phosphorodiamidate bond according to the present invention is advantageously manufactured from the double-stranded DNA molecule comprising a first double-stranded DNA molecule (A) and a second double DNA molecule strand (B) as described above, referred to as the "intermediate" DNA molecule.

Also, the invention pertains to a method of manufacturing the double-stranded DNA molecule as described herein, characterized in that it comprises the following step:

a) cleavage of the double-stranded DNA molecule strand (A) (present in the "intermediate" DNA molecule as described above) at said cleavage site, thereby generating a DNA molecule comprising a first double-stranded DNA molecule (1) and a second molecule double-stranded DNA (2).

Such a manufacturing process is highly advantageous as it is very easy to implement. In addition, advantageously, the intermediate molecule is obtained at a satisfactory yield (e.g. at least 8%). Advantageously, the "intermediate" molecule clears the way for a succession of synthesis steps which lead, with yields of more than 90%, to the double-stranded DNA molecule according to the invention (data not shown).

In a particular aspect, the invention pertains to the double-stranded DNA molecule obtained by this method.

The present invention also relates to a method for characterizing an interaction between at least two test molecules linked to a double-stranded DNA molecule or as comprised in the device, comprising:

a) applying a low physical force, $F_{LF}$, to the double-stranded DNA molecule, which allows the test molecules to associate;
b) applying a high physical force, $F_{HF}$, to the double-stranded DNA molecule, which makes it possible to determine whether the test molecules are associated or dissociated; and
c) detecting a change in the conformational properties of the DNA molecule comprising:
   determining the $z_{LF}$ extension between the second extremity of the first double-stranded DNA molecule (1) and the second extremity of the second double-stranded DNA molecule (2) in step a);
   determining the $z_{HF\text{-}A}$ and $z_{HF\text{-}D}$ extensions between the second extremity of the first double-stranded DNA molecule (1) and the second extremity of the second double-stranded DNA molecule (2), at step b); and
   the comparison of the extensions $z_{LF}$, $z_{HF\text{-}A}$, and $z_{HF\text{-}D}$, as a function of time t.

Advantageously, the invention pertains to a method wherein the physical force in step a) is from 0.01 picoNewton (pN) at 0.4 pN and/or wherein the physical force in step b) is from 0.5 to 70 pN, advantageously from 0.5 to 40 pN.

Advantageously, the invention pertains to a method wherein the characterization of the interaction comprises the determination of at least one of the characteristics chosen from among: the characteristic association time, the characteristic dissociation time, the dissociation rate constant, the dissociation activation energy, the distance separating the transition state from the complex during dissociation, and the equilibrium dissociation constant.

Indeed, the inventors have demonstrated that the double-stranded DNA molecule according to the invention is particularly suitable for use in devices and methods for characterizing molecular interactions between at least two test molecules.

DETAILED DESCRIPTION OF THE INVENTION

Figure 1:
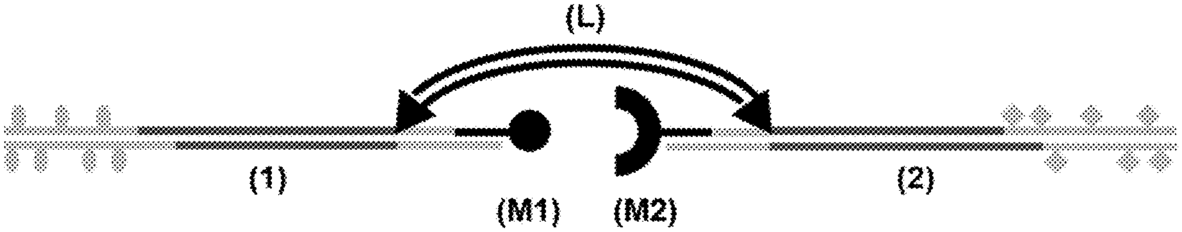
FIG. 1. Conceptual representation of a double-stranded DNA molecule according to the invention comprising a first double-stranded DNA molecule (1) connected to a second double-stranded DNA molecule (2) by a tether (L), wherein a first test molecule (M1) is linked to a first extremity of the first double-stranded DNA molecule (1) and a second test molecule (M2) is linked to a first extremity of the second double-stranded DNA molecule (2). Functional groups are present on the second extremity of the first double-stranded DNA molecule (1) and on the second extremity of the second double-stranded DNA molecule (2) (ovals and diamonds, respectively), allowing their attachment to the supports. Both extremities of the double-stranded DNA molecules (1) and (2) are shown in light gray, and the intermediate region of each molecule is shown in dark gray. The tether is represented in black. The non-phosphodiester covalent bonds between the tether (L) and the double-stranded DNA molecules (1) or (2) are illustrated by triangles.

As indicated previously, in the context of the present invention, the inventors have demonstrated new double-stranded DNA molecules comprising a first double-stranded DNA molecule (1) linked to a second DNA molecule double-strand (2) by at least one covalent bond which is not a phosphodiester bond, a phosphorothioate bond, a phosphoramidate bond or a phosphorodiamidate bond, advantageously by a tether. These new double-stranded molecules are highly advantageous as they have improved stability, flexibility and homogeneity, in particular as a result of the use of double-stranded DNA molecules and their configuration.

DNA Molecule

A first aspect of the invention therefore relates to a double-stranded DNA molecule comprising a first double-stranded DNA molecule (1) linked, by at least one covalent bond which is not a phosphodiester bond, a phosphorothioate bond, a phosphoramidate bond or a phosphorodiamidate bond, to a second double-stranded DNA molecule (2).

By "comprising" or "containing" is meant herein that the listed elements are required or mandatory, but that other optional elements may or may not be present. Thus, as a non-limiting example, a double-stranded DNA molecule according to the invention may notably comprise other molecules, including other double-stranded DNA molecules, in addition to molecules (1) and (2).

The terms "a" and "the" as used herein include plural forms unless the content of the present application clearly indicates otherwise. For example, a "restriction site" may therefore include two or more restriction sites.

By "nucleic acid", "deoxyribonucleic acid molecule" or "DNA molecule" is meant, within the context of the present invention, a polymer composed of deoxyribonucleotide monomers or analogs thereof. More particularly, the deoxyribonucleotide monomers described herein refer to monomers comprising a triphosphate group, the nitrogenous adenine ("A"), cytosine ("C"), guanine ("G"), or thymine ("T") base, and a deoxyribose sugar. In general, a nucleotide analog will have the same specificity of base pairing (e.g. an analogue of "A" pairs with "T"). Modified nucleotides are also included herein, and may include, for example, modifications in the base, sugar, and/or phosphate moieties (i.e., phosphorothioate backbones). Said DNA molecule may also comprise one or more modified nucleotides, such as a locked nucleic acid (LNA), which is a nucleotide in which the ribose moiety is modified by an additional bridge linking the 2' oxygen and the 4' carbon, a peptide nucleic acid (PNA), the backbone of which is composed of repeating N-(2-aminoethyl)-glycine units linked by peptide bonds, modified nucleotides such as hypoxanthine, xanthine, 7-methylguanine, or 5-methylcytosine, or analogs of the morpholino type.

The double-stranded DNA molecule according to the invention is a polymer composed mainly of deoxyribonucleotides (i.e. more than 50%). Advantageously, the double-stranded DNA molecule according to the invention is a polymer composed of at least 50% deoxyribonucleotides, more advantageously at least 60%, at least 70%, at least 75%, at least 80%, at least 85%, even more preferably at least 90%, at least 95%, at least 96%, at least 97%, at least 98%, or at least 99% deoxyribonucleotides. Advantageously, the double-stranded DNA molecule according to the invention is a polymer composed entirely (i.e. 100%) of deoxyribonucleotides. Thus, according to a preferred embodiment, the first double-stranded DNA molecule (1) and/or the second double-stranded DNA molecule (2), comprised in the double-stranded DNA molecule according to the invention, are advantageously polymers composed of at least 50%, at least 60%, at least 70%, at least 75%, at least 80%, at least 85%, at least 90%, at least 95%, at least 96%, at least 97%, at least 98%, or at least 99%, more advantageously composed entirely of deoxyribonucleotides. The first double-stranded DNA molecule (1) and the second double-stranded DNA molecule (2) may be polymers composed of different proportions of deoxyribonucleotides, for example according to the percentages described above. When other double-stranded DNA molecules are present in the composition (e.g. a DNA molecule (3)), they are also advantageously polymers composed of at least 50% deoxyribonucleotides or more, according to the percentages described above, and have the same characteristics as the double-stranded (1) and/or (2) DNA molecules described herein. Most often, the double-stranded nucleic acid will be a DNA molecule, but it is understood that the invention also applies to duplexes of two single-stranded DNA molecules, perfectly paired or not perfectly paired. In addition, the duplex may consist of the at least partial pairing of two unique strands obtained from samples of different origins. Finally, the invention also applies to the secondary structures of a sole single-stranded DNA, which forms double-stranded structures.

The double-stranded DNA molecule according to the invention may be of natural (e.g. of eukaryotic or prokaryotic origin) or artificial origin, or comprise a mixture of DNA of natural and artificial origin in any ratio. The first double-stranded DNA molecule (1) and the second double-stranded DNA molecule (2) can therefore be composed of DNA of the same origin or of different origins. Most often, the origin of the DNA will depend on experimental requirements (e.g. need for a DNA molecule with a particular length, having specific restriction site(s), etc.). Similarly, the sequences of the first and second double-stranded DNA molecules (1) and (2) may be the same or different. Advantageously, the first double-stranded DNA molecule (1) and the second double-stranded DNA molecule (2) have different sequences.

The lengths of the first and second double-stranded DNA molecules (1) and (2) can be selected according to the experimental requirements, as detailed below, and/or in view of the other elements of the DNA molecule (e.g. such that the two double-stranded DNA molecules (1) and (2) each have a specific length or according to the length of a tether). The lengths of the first double-stranded DNA molecule (1) and the second double-stranded DNA molecule (2) may be the same or different. The length of the first double-stranded DNA molecule (1) may, for example, be shorter than that of the second double-stranded DNA molecule (2), or longer. A difference in the length of the first double-stranded DNA molecule (1) relative to the second double-stranded DNA molecule (2) is particularly advantageous when the DNA molecule is used to detect and/or measure molecular interactions. Indeed, the inventors have surprisingly demonstrated that, when the DNA molecule is used to detect and/or measure molecular interactions, a difference in the length of the first double-stranded DNA molecule (1) relative to the second double-stranded DNA molecule (2) makes it possible to better differentiate the signals resulting from a specific interaction between two test molecules from the signals resulting from a non-specific interaction (i.e. between a support and a test molecule (see e.g. FIG. 16 and Example 11).

While the "length" of a DNA molecule is generally expressed in number of nucleotides or base pairs (bp), it can also be expressed according to its physical length, for example in nanometers or micrometers (1 base pair corresponds to about 0.32 nm). Preferably, the length of a DNA molecule is expressed herein in base pairs. For example, the first double-stranded DNA molecule (1) and/or the second double-stranded DNA molecule (2) can have a length of 300 to 5,000 base pairs, 500 to 5,000 base pairs, or 650 to 1,500 base pairs. Thus, the total length of the double-stranded DNA molecules (1) and (2) can be between 600 and 10,000 base pairs, between 1,000 and 10,000, or between about 1,300 and 3,000 base pairs (±50 base pairs).

According to a preferred embodiment of the invention, the first double-stranded DNA molecule (1) and/or the second DNA molecule (2) has a length of 300 to 5,000 base pairs, preferably 650 to 1500 base pairs. According to a particular embodiment, the first double-stranded DNA molecule (1) and the second double-stranded DNA molecule (2) each have a length of 1500 base pairs. According to another particular embodiment, the first double-stranded DNA molecule (1) has a length of 650 base pairs while the second DNA molecule (2) has a length of 1,350 base pairs.

Advantageously, the total length of the double-stranded DNA molecules (1) and (2) is comprised between 600 and 10,000 base pairs, between 1,000 and 10,000, or between 1300 and 3000 base pairs. According to a particular embodiment of the invention, the total length of the double-stranded DNA molecules (1) and (2) is between 2050 base pairs and 3000 base pairs, preferably about 2050 or about 3000 base pairs (±50 base pairs).

In some cases, the DNA is selected to not include elements that could interact with one or more of the test molecules. As an example, when a test molecule is a protein capable of interacting with a double-stranded DNA molecule having a particular sequence and/or structure (e.g. MutS, Zα), the double-stranded DNA molecule according to the invention does not include these sequences and/or structures (e.g. absence of mismatch, no Z-DNA type structure) except on the site designed to accommodate the second test molecule (e.g. sequence with a mismatch, Z-DNA).

The double-stranded DNA molecule may notably comprise a part (e.g. 0.6, 1, 5, 20, 30, 40, 50, 60, 70, 80 or 90%) or all (100%) of a double-stranded DNA genome of a group I virus, such as a genome of a virus of the Caudovirales, Herpesvirales, or Ligamenvirales order, more particularly of the Siphoviridae family. As a non-limiting example, the double-stranded DNA molecule comprises part or all of a double-stranded DNA genome of a bacteriophage, such as phage lambda, *Mycoplasma* phage P1, *Lactococcus* phage c2, *Pasteurella* phage F108, or any other double-stranded DNA phage genome. As a non-limiting example, the length of the genome incorporated in the double-stranded DNA molecule according to the invention may comprise from about 1500 to about 50,000 base pairs (±50 base pairs). When the double-stranded DNA molecule according to the invention comprises an entire genome, said genome is advantageously in linear form. When a double-stranded DNA molecule is in circular form (e.g. a circular genome, a plasmid), it is advantageously linearized before being incorporated in the double-stranded DNA molecule according to the invention. The double-stranded DNA molecule according to the invention can be continuous or discontinuous. A DNA molecule is discontinuous when at least one phosphodiester, phosphorothioate, phosphoramidate or phosphorodiamidate bond, linking two nucleotides located next to one another on a single strand is absent, or when the DNA molecule comprises a single-stranded DNA region. In some cases, a DNA molecule may have one or more discontinuous sites on the two strands, provided that the discontinuous sites are not present between two nucleotides paired on the two strands. However, in the context of the present invention, the double-stranded DNA of the first double-stranded DNA molecule (1) and/or the second double-stranded DNA molecule (2) is advantageously continuous. According to a preferred embodiment, the double-stranded DNA molecule according to the invention comprising a first double-stranded DNA molecule (1) connected to a second double-stranded DNA molecule (2) by a covalent bond which is not a phosphodiester, phosphorothioate, phosphoramidate or phosphorodiamidate bond is continuous. Indeed, the continuity of the molecule advantageously makes it possible to guarantee the mechanical properties of the double-stranded DNA molecule, including its persistence length and its ability to be supercoiled.

Advantageously, any discontinuous site in the double-stranded DNA molecule according to the invention is closed, for example by a ligase during the manufacture of said double-stranded DNA molecule, before its use. Advantageously, the double-stranded DNA molecule according to the invention is perfectly paired. The double-stranded DNA molecule according to the invention more particularly comprises at least two distinct double-stranded DNA molecules, referred to herein as the double-stranded DNA molecules (1) and (2), which are connected to one another by at least one covalent bond.

By "covalent bond" is meant herein a chemical bond in which at least one pair of electrons is shared between two atoms. Advantageously, according to the present invention, at least one covalent bond is formed between an atom of a first functional group and an atom of a second functional group. As a non-limiting example, a covalent bond may be one or more amide or ester bond(s) or a disulfide bond. The term "covalent bond" thus includes several types of covalent bond. As a non-limiting example, said covalent bond may also comprise other elements, such as one or more polymers, cyclic compounds, or particles, capable of connecting the two subunits by forming a covalent bond with each subunit. According to a preferred embodiment, said at least one covalent bond is not a phosphodiester bond. A phosphodiester bond is a bond between the 3' carbon of a first deoxyribose and the 5' carbon of a second deoxyribose by the formation of a phosphoester bond of each of the carbons with a phosphate group. Within the context of the present invention, a phosphodiester bond is more particularly a bond between two deoxyribonucleotides, as is known to the skilled person. According to another preferred embodiment, said at least one covalent bond is not a phosphorothioate bond. Such a bond is a phosphodiester bond where a sulfur replaces a non-bonding oxygen in the phosphate group. According to another preferred embodiment, said at least one covalent bond is not a phosphoramidate bond or a phosphorodiamidate bond. A phosphoramidate bond is a phosphodiester bond in which the phosphate group comprises a phosphorus bonded to three oxygen atoms and one nitrogen atom. A phosphorodiamidate bond is a phosphodiester bond in which the phosphate group comprises a phosphorus bonded to two oxygen atoms and two nitrogen atoms. The phosphorothioate, phosphoramidate and phosphorodiamidate bonds are mainly found in synthetic nucleic acids (such as those described above), to which they confer advantageous properties. As an example, these bonds generally confer an increased stability on the nucleic acids in which they are found. As a non-limiting example, a covalent bond other than a phosphodiester bond, a phosphorothioate bond, a phosphoramidate bond or a phosphorodiamidate bond may be a bond formed on the basis of click chemistry, such as a bond formed by the cycloaddition of an azide to an alkyne (see, e.g., Hein et al., 2008). Advantageously, said covalent bond connecting the two double-stranded DNA molecules (1) and (2) is formed by a reaction between an azide functional group and an alkyne functional group, between an azide functional group and a dibenzocyclooctyne functional group (DBCO), between a tetrazine functional group and a transcyclooctene functional group, between a thiol functional group and an alkyne functional group, between a thiol functional group and an alkene functional group, between a thiol functional group and a thiol functional group (thus generating a disulfide bridge), between a thiol functional group and a maleimide functional group, between an amine functional group and an activated acid (e.g. by reagents such as N-hydroxysuccinimide, N,N'-dicyclohexylcarbodiimide or 1-ethyl-3-(3-dimethylaminopropyl) carbodiimide), between a hydroxyl functional group and a maleimide functional group, and/or between an azide functional group and a phosphine functional group (Staudinger reaction).

In some cases, said first double-stranded DNA molecule (1) is linked to said second double-stranded DNA molecule (2) by a tether. By "tether" is meant in the context of the present invention a third distinct molecule, which is linked to both the first (1) and the second (2) double-stranded DNA molecule. Advantageously, when the double-stranded DNA molecule according to the invention is used to characterize molecular interactions between at least two test molecules, the tether makes it possible to keep the two test molecules in proximity to one another after their dissociation.

When the two double-stranded DNA molecules (1) and (2) are linked by a tether, said tether may be linked to each DNA molecule by at least one covalent bond which is not a phosphodiester, phosphorothioate, phosphoramidate or phosphorodiamidate bond. Thus, the double-stranded DNA molecule according to the invention advantageously comprises at least two covalent bonds which are not phosphodiester, phosphorothioate, phosphoramidate or phosphorodiamidate bonds (see, e.g., FIG. 1). Alternatively, said tether may be composed of several distinct molecules, which are themselves advantageously connected to each other by covalent bonds which are not phosphodiester, phosphorothioate, phosphoramidate or phosphorodiamidate bonds. According to a preferred embodiment, said first double-stranded DNA molecule (1) is thus connected to said second double-stranded DNA molecule (2) by a tether.

The tether may be composed of any type of material and/or include any type of molecule, such as polypeptides, polynucleotides, such as double-stranded DNA, and/or polymers. As a non-limiting example, the tether is a polymer composed of at least 50%, 60%, 70% deoxyribonucleotides, preferably at least 75%, 80%, 85%, more preferably at least 90%, 95%, 96%, 97%, 98%, even more preferably at least 99% deoxyribonucleotides. As a non-limiting example, the tether is a polymer composed of deoxyribonucleotides and one or more other polymers such as polyethylene glycol (PEG), propylene glycol, a polyamide, and/or one or more single-stranded nucleic acid regions (e.g. of single-stranded DNA). Preferably, the tether is a polymer composed entirely (i.e. 100%) of deoxyribonucleotides. When the tether comprises double-stranded DNA, said double-stranded DNA may comprise any characteristic as detailed above. For example, the double-stranded DNA tether is continuous. Preferably, when the tether comprises double-stranded DNA, the length of said tether is at least 150 base pairs, more preferably at least 200, 300, 400, 500 or 600 base pairs. Advantageously, such a length of double-stranded DNA allows the test molecules to meet with significant efficiency and limits the mechanical stresses applied to the complex once it has been formed. According to a preferred embodiment, the tether comprises double-stranded DNA having a length of at least 150 base pairs, preferably at least 600 base pairs, said double-stranded DNA being continuous (i.e. without nicks). When the tether is a double-stranded nucleic acid molecule (e.g. a double-stranded DNA or RNA molecule), it itself comprises phosphodiester, phosphorothioate, phosphoramidate or phosphorodiamidate bonds. However, as indicated above, the at least one covalent bond between the tether and said first or second double-stranded DNA molecule (1) or (2) is not a phosphodiester, phosphorothioate, phosphoramidate or phosphorodiamidate bond. In some cases, said tether may itself comprise covalent bonds (e.g. crosslinking between the two strands of a double-stranded DNA molecule, when the tether is a double-stranded DNA polymer). This is particularly advantageous when forces greater than 70 pN will be applied to the double-stranded DNA molecule.

According to a preferred embodiment, the tether is a double-stranded DNA molecule. Advantageously, the double helix structure of a double-stranded DNA tether is only present when it is in linear form. The tether cannot fold into any tertiary structure. In addition, when the tether is a double-stranded DNA molecule, it is stable and is therefore disinclined to interact with one or more of the test molecules. The length of the tether is also advantageously easily adjustable.

The use of a double-stranded DNA tether is also advantageous as double-stranded DNA molecules have a persistence length of about 50 nm under typical laboratory conditions. By "persistence length" is meant a mechanical property allowing for the characterization of the stiffness of a linear polymer (Doi, 1996, and Bouchiat et al., 1999). It is more specifically the typical length over which a linear polymer can remain aligned despite the deformations due to thermal agitation. With such a persistence length, a change in tether length results in a significant variation in the average distance between the junctions with the double-stranded DNA molecules (1) and (2), which makes it possible to adjust the effective concentration of test molecules, $C_{eff}$. As an example, with a double-stranded DNA molecule according to the invention comprising a double-stranded DNA tether of approximately 50,000 base pairs, the $C_{eff}$ is in the range of nM. This means that it is possible to measure the characteristic association time, $\tau_A$, for reactions having kinetic association constants between test molecules as large as $3\times10^9$ $M^{-1}s^{-1}$, for example, via video acquisition operating at a few tens of Hz (e.g. 10 to 30 Hz). The persistence length of the double-stranded DNA tether also makes it possible, when the double-stranded DNA molecule is used to measure interactions between at least two test molecules, to investigate the dependence of the lifetime of a molecular complex (e.g. between two test molecules) as a function of physical force. Indeed, the double-stranded DNA molecule stretches easily, making it possible to measure the difference in extension between associated and dissociated conformations of test molecules when weak forces, below about 2 pN, are applied. Advantageously, it is possible to measure the difference in extension between associated and dissociated conformations of test molecules when forces as low as 0.1 pN are applied (e.g. with a tether of about 700 bp). However, to achieve the same result with molecules having a smaller persistence length (e.g. single-stranded DNA, polypeptide molecules), larger forces must be applied to significantly extend the tether in the dissociated state and thus have a chance of distinguishing it from the associated state. This therefore prevents any studies using forces below the range of a few pN with these molecules.

The length of the tether is an important parameter in the measurement of interactions between molecules and it can vary according to experimental requirements (i.e. according to the purpose of the experiment, according to the lengths of the double-stranded DNA molecules (1) and (2) and/or the test molecules). A tether that is too short (e.g. less than 300 bp) may in particular cause an interaction that has just ended between two test molecules to reform so quickly that it is not possible to distinguish it from the previous one. Conversely, an increase in the length of the tether reduces the frequency with which the interactions between test molecules are observed. This can be useful for the study of reactions where association occurs very quickly, but can be prohibitive for the study of reactions where association is slow. The appropriate length of the tether may be determined by the skilled person according to experimental requirements, notably taking into account the aspects detailed above. For example, in the context of the present invention, the tether may have a length of about 300 to about 50,000 base pairs (±50 base pairs).

Preferably, the double-stranded DNA tether has a length from about 300 to about 50,000 base pairs, preferably from about 500 to 10,000 base pairs, preferably from 1,000 to 10,000 base pairs, from 600 to 3000 base pairs (±50 base pairs), more preferably from 600 to 1000 base pairs, even more preferably of about 700 base pairs (±50 base pairs) or of about 6000 base pairs; base pairs (±50 base pairs). Advantageously, when the tether is long enough, for example when it has a length of 6,000 kbp, the distance $z_{LF-A}$ can easily be distinguished from distance $z_{LF-D}$.

The tether may be attached to the first molecule (1) and/or the second molecule (2) of double-stranded DNA by one or more covalent bonds that are not phosphodiester, phosphorothioate, phosphoramidate or phosphorodiamidate bonds. Advantageously, at least one non-phosphodiester, non-phosphorothioate, non-phosphoramidate or non-phosphorodiamidate covalent bond is formed between a nucleotide of the tether comprising a functional group and a nucleotide of the first molecule (1) and/or the second molecule (2), comprising another functional group. As a non-limiting example, the first double-stranded DNA molecule (1) may comprise an azide functional group which reacts with a DBCO functional group present on the tether via the click chemistry technique, thus forming a non-phosphodiester, non-phosphorothioate, non-phosphoramidate or non-phosphorodiamidate covalent bond between the two molecules.

The tether can be attached to double-stranded DNA molecules (1) and (2) by its two extremities, respectively, or by nucleotides located in the intermediate region of the tether. By "intermediate region" is meant in the sense of the present invention a segment of a molecule which is located between the two extremities of said molecule. Such intermediate regions are notably schematized for DNA molecules (1) and (2), as an example, in FIG. 1 (segments in dark gray).

By "extremity" is meant, in the sense of the present invention, the 30 to 150 base pairs located at the extremity of a molecule (e.g. of the tether, the first double-stranded DNA molecule (1), the second double-stranded DNA molecule (2)), preferably the 30 to 50 base pairs located at the extremity of a molecule, such extremities being notably schematized for DNA molecules (1) and (2), as an example, in FIG. 1 (segments in light gray). Thus, as an example, a tether, (or the first or second double-stranded DNA molecule (1) or (2)), comprising 1000 base pairs, comprises two extremities, a first extremity corresponding to base pairs 1 to 150 and a second extremity corresponding to base pairs 850 to 1000. In the present context, the terms first extremity and second extremity should not be interpreted as corresponding to specific extremities of the tether, but simply allow one extremity of the tether to be differentiated from the other. Thus, there is no notion of direction or orientation associated with said first and second extremities. The skilled person will readily identify the extremities of a double-stranded DNA molecule as defined herein.

A bond between one extremity of a tether and a double-stranded DNA molecule (1) or (2) can thus occur at one or more nucleotide bases of one extremity of a tether. Preferably, at least one ultimate nucleotide, preferably an ultimate base, sugar or phosphate, of one extremity of the tether is attached by a non-phosphodiester, non-phosphorothioate, non-phosphoramidate or non-phosphorodiamidate covalent bond to the first or second molecule of double-stranded DNA (1) or (2).

Thus, according to a preferred embodiment, the tether is attached by its first extremity to the first double-stranded DNA molecule (1) and by its second extremity to the second double-stranded DNA molecule (2), advantageously by an ultimate nucleotide, preferably an ultimate base, sugar or phosphate, at each extremity of the tether. Preferably, the tether is attached by at least two nucleotides, preferably at least two nucleotide bases, in each extremity to the first and second double-stranded DNA molecules (1) and (2), respectively, said at least two nucleotide bases preferably comprising an ultimate nucleotide, preferably an ultimate base, sugar or phosphate, at each extremity of the tether.

According to an alternative embodiment, the tether may be attached to the first double-stranded DNA molecule (1) and/or the first double-stranded DNA molecule (2) by at least one base located in the intermediate region of the tether, said bases being preferably separated by at least 300 base pairs, more preferably by at least 500 base pairs, even more preferably by at least 600 base pairs. As a non-limiting example, the tether may be attached to the first double-stranded DNA molecule (1) by at least a first base, said base being located between the central point of the tether and its first extremity and/or attached to the second double-stranded DNA molecule (2) by at least one second base, said base being located between the central point of the tether and its second extremity. By "central point" is meant a location that is substantially equidistant between the first and second extremities of the molecule. This is particularly advantageous when at least one extremity of the tether comprises a further element of the double-stranded DNA molecule according to the invention (e.g. is linked to another test molecule).

In some cases, the site of the covalent bond between the tether and the first double-stranded DNA molecule (1) and/or the second double-stranded DNA molecule (2) is located in the intermediate region of said double-stranded DNA molecule (1) or (2), that is to say between the two extremities of said DNA molecule (1) or (2). As a non-limiting example, a non-phosphodiester, non-phosphorothioate, non-phosphoramidate or non-phosphorodiamidate covalent bond is formed between one extremity of the tether (or any other point of the tether that would be appropriate as described above), and a center point of said double-stranded DNA molecule (1). The non-phosphodiester, non-phosphorothioate, non-phosphoramidate or non-phosphorodiamidate covalent bond between the tether and said first double-stranded DNA molecule (1) thus forms a junction with three branches (see, e.g., FIG. 1).

In other cases, a covalent bond between the tether and the first double-stranded DNA molecule (1) and/or the second double-stranded DNA molecule (2) may be located in one extremity of said double-stranded DNA molecule (1) or (2), or a nucleotide base, which makes it possible to distinguish the extremity of the double-stranded DNA molecule (1) or (2) from its intermediate region (see, e.g., example, FIG. 1). In the context of the present invention, no covalent bond is advantageously formed between an ultimate nucleotide, preferably an ultimate base, sugar or phosphate, of the DNA molecule (1) or (2) and any base of the tether.

Thus, according to a preferred embodiment of the invention, the tether is attached to the first double-stranded DNA molecule (1) by a first covalent bond between the first extremity of said tether and an intermediate region of the first molecule of double-stranded DNA (1) and to the second double-stranded DNA molecule (2) by a second covalent bond between the second extremity of said tether and an intermediate region of the second double-stranded DNA molecule (2).

As the extremities of the double-stranded DNA molecules (1) and (2) are not attached to the tether, they remain advantageously available for other purposes (e.g. for other interactions). As an example, the two extremities of the first double-stranded DNA molecule (1) or the second double-stranded DNA molecule (2) may notably be linked respectively to a test molecule and to a support.

Advantageously, a first extremity of said first double-stranded DNA molecule (1) is linked to a first test molecule and a first extremity of said second double-stranded DNA molecule (2) is linked to a second test molecule. The test molecule can be linked directly or indirectly to the extremity. The binding of a first or a second test molecule at a first extremity of the first or second double-stranded DNA molecule (1) or (2) is advantageous because it allows the test molecules to be distanced from the tether and the rest of the double-stranded DNA molecule (1) and/or (2). The test molecules are notably less likely to be subject to steric hindrance and to have the characteristics of their interaction be modified in this configuration. In addition, the use of a double-stranded DNA molecule according to the invention allows the tether and double-stranded DNA molecules (1) and (2) to remain relatively free to be reoriented in space independently of one another, such that the test molecules are not deprived of any degree of freedom of movement. Finally, the binding of the test molecules to the extremities of the double-stranded DNA molecules (1) and (2) also makes it possible to distance the test molecules from the supports, which reduces nonspecific interactions. In some cases, a test molecule may be directly or indirectly linked to an ultimate nucleotide, preferably an ultimate base, sugar or phosphate, at one extremity of the double-stranded DNA molecule (1) or (2). When the test molecule is indirectly linked, it is preferably linked by a "spacer". The spacer may be, e.g., a double-stranded or single-stranded nucleotide base sequence, a polymer, a peptide, or a small molecule, and may be readily selected by the skilled person. The addition of spacers to double-stranded DNA molecules (1) and (2) can be performed with any of the methods commonly used in molecular biology.

According to a preferred embodiment of the invention, at least one test molecule is linked directly or indirectly to an ultimate nucleotide, preferably an ultimate base, sugar or phosphate, of an extremity of a given double-stranded DNA molecule. According to another preferred embodiment, a test molecule is indirectly linked to an ultimate nucleotide, preferably an ultimate base, sugar or phosphate, of an extremity of a DNA molecule (1) or (2), preferably by a spacer.

In a typical configuration of the invention, the two test molecules are specifically bound to the first and second double-stranded DNA molecules (1) and (2), respectively. As an example, one extremity of the first double-stranded DNA molecule (1) and one extremity of the second double-stranded DNA molecule (2) are digested with one or more nucleases, e.g. the Nb.BbvCl enzyme, to generate two different cohesive extremities (see also FIG. 5A). Synthetic oligonucleotides to which test molecules have been bound can then be specifically hybridized and ligated to the extremities via complementary cohesive ends (see also FIG. 5B). Alternatively, each test molecule can be specifically linked to an extremity of the double-stranded DNA molecule (1) or (2) by a covalent bond, for example a non-phosphodiester, non-phosphorothioate, non-phosphoramidate or non-phosphorodiamidate covalent bond, according to the methods described herein, for example by the click chemistry technique.

As a non-limiting example, at least one of the test molecules, such as said first and/or said second test molecule, is selected from the group consisting of the following molecules: polymers, amino acids, peptides, polypeptides, proteins, nucleosides, nucleotides, polynucleotides, oligonucleotides, sugars, polysaccharides, small molecules, drugs, aptamers, antigens, antibodies, lipids, lectins, hormones, vitamins, viruses, virus fragments, nanoparticles, cell surface molecules, and transcription factors, or analogs or peptidomimetics of one of these. In some cases, the first and the second test molecule are of the same type (e.g. two proteins, two polymers, two double-stranded DNA molecules, etc.), or are even identical (e.g. two subunits of a protein, two proteins forming a homodimer such as cadherin fragments). In other cases, the first test molecule and second test molecules are of different types (e.g. antigen/antibody, virus/receptor, transcription factor/DNA, protein/small molecule, etc.). When at least one of the test molecules is a double-stranded DNA molecule, said molecule is preferably directly linked to the extremity of one of the DNA molecules (1) or (2).

In some cases, one or more other test molecules may be linked to the double-stranded DNA molecule according to the invention. Advantageously, the one or more other test molecules may also be chosen from the group of molecules above. As an example, a third test molecule may be linked to an extremity of a double-stranded DNA molecule (3) or to one extremity of the tether when this is free. In some cases, at least one other test molecule can be brought into contact with the double-stranded DNA molecule according to the invention comprising at least two test molecules, e.g. in an aqueous suspension. As a non-limiting example, said third molecule may be a cofactor of the first and/or second test molecule.

According to a preferred embodiment of the invention, said first and/or second test molecule is selected from the group consisting of the following molecules: polymers, amino acids, peptides, polypeptides, proteins, nucleosides, nucleotides, polynucleotides, oligonucleotides, sugars, polysaccharides, small molecules, drugs, aptamers, antigens, antibodies, lipids, lectins, hormones, vitamins, viruses, virus fragments, nanoparticles, cell surface molecules, and transcription factors. Preferably, said first test molecule and said second test molecule are of different types. Preferably, said first test molecule and said second test molecule are of the same type, or even identical.

In a typical configuration of the invention, the first and second double-stranded DNA molecules (1) and (2) can be specifically attached to supports. By "support" is meant any type of surface or solid substrate, said support being advantageously functionalized to react with a functionalized extremity of the double-stranded DNA molecule according to the invention. As a non-limiting example, the support may be a bead (e.g. silica beads, controlled pore glass, magnetic beads, biomagnetic separation beads such as Dynabeads®, Wang resin, Merrifield resin, chloromethylated copolystyrene resin-divinylbenzene (DVB), Sephadex®/Sepharose® beads, cellulose beads, etc.), a flat support such as a fiberglass filter, a dielectric surface (e.g. glass, silica, silicon nitride, alumina), a metal surface (e.g. steel, gold, silver, aluminum, and copper), a semiconductor surface (e.g. silicon, III-V semiconductor, II-VI semiconductor), plastic materials, including multiwell plates or membranes (e.g. polyethylene, polypropylene, polyamide, polyvinylidene fluoride), a needle, a micropipette, or a cantilever used in atomic force microscopy. A bead according to the invention can have any three-dimensional structure and any size. Preferably, the size of the bead is between 0.5 and 100 μm in diameter.

The supports are advantageously solid substrates (for example a glass surface such as a microscope slide, a micropipette, a microparticle), which may be of the same type (i.e. two microparticles) or of different types (e.g. a glass surface and a microparticle). Advantageously, in the context of the present invention, when test molecules are linked to the first extremities of the first and second DNA molecules (1) and (2), the second extremity of said first double-stranded DNA molecule strand (1) is linked to a first support and the second extremity of said second double-stranded DNA molecule (2) is linked to a second support.

Advantageously, at least one of the two supports is a bead such as a microbead, a microparticle, a glass surface, a micropipette, or a cantilever used in atomic force microscopy.

In order to attach double-stranded DNA molecules to supports, any technique known in the art can be used. As an example, the DNA may be directly linked to a support, e.g. a microbead, which implies a functionalization of this support, for example by coating it with streptavidin, with a polymer carrying COOH groups, etc., capable of reacting with a functionalized extremity of the double-stranded DNA.

Such methods generally require the functionalization of a double-stranded DNA molecule, especially at one of its extremities, that is to say, grafting at least one appropriate functional group thereon. To this end, different procedures may be adopted. In the context of the present invention, the simplest is to functionalize, using synthetic oligonucleotides, one extremity of the first double-stranded DNA molecule (1) with a functional group and one extremity of the second double-stranded DNA molecule (2) with a functional group. Advantageously, in the context of the present invention, the extremity of the first DNA molecule (1) is functionalized with a first functional group and the second DNA molecule (2) is functionalized with a second functional group, which makes it possible to attach one extremity to each of the two supports which have been pretreated differently (e.g. a first extremity functionalized with biotin attaches to a streptavidin-coated support whereas a second extremity, functionalized with an amine group, attaches to a support coated with a polymer carrying COOH groups, respectively).

The advantage of this method lies in its ability to functionalize any type of double-stranded DNA molecule of any length while using the same reagents. In this case, the two extremities of the double-stranded DNA molecules (1) and (2) intended to be attached to supports are cleaved using, e.g., two (or more) restriction enzymes, which makes it possible to obtain a first DNA molecule having a first restriction site at one of extremity thereof and a second DNA molecule having a second restriction site at one extremity thereof. This makes it possible to treat the two extremities differently.

In some cases, it may be advantageous to add a "spacer" followed by a functional group at one extremity of the first double-stranded DNA molecule (1) and/or at one extremity of the second molecule double-stranded DNA (2); the two spacer sequences thus providing each functional group with additional space to bind their respective supports. The spacer may be a double-stranded or single-stranded nucleotide base sequence, a polymer, a peptide, or a small molecule as described above. The spacer preferably comprises at least one functional group. The addition of spacers to the double-stranded DNA molecules (1) and (2) can be performed with any of the methods commonly used in molecular biology. As these methods are well-known to the skilled person, there is therefore no need to detail them here.

As for the attachment techniques themselves, they are numerous and derived from attachment techniques of macromolecules (proteins, DNA, etc.) to pretreated supports which are commercially available or easily obtainable in the laboratory. Most of these techniques have been developed for immunology tests, and connect proteins (immunoglobulins) to supports carrying groups (—COOH, —NH2, —OH, etc.) capable of reacting with the carboxyl (—COOH) or amine extremities (—NH2) of the proteins.

The attachment of the double-stranded DNA molecule according to the invention to a support can be performed directly, via the free phosphate of the 5' extremity of the molecule, which reacts with a secondary amine (Covalink-NH surface commercialized by Polylabo in Strasbourg) to form a covalent bond. It is also possible to functionalize the DNA with an amine group and then to proceed as with a protein. As an alternative example, a thiol-functionalized (S—H) DNA molecule covalently bonds to a gold support by formation of an S—Au thiolate bond.

Streptavidin-coated supports (e.g., Dynal beads and the like) also exist, which allow for near-covalent attachment of streptavidin to a biotinylated DNA molecule. Finally, by grafting an antibody directed against digoxigenin to a support (by the methods mentioned above), a DNA molecule functionalized with digoxigenin can be attached thereto. This is simply an example of one of the many possible attachment techniques. Among the anchoring and attachment techniques, those described in patent EP 152 886 using an enzymatic coupling to anchor DNA to a solid support such as cellulose can, for example, be mentioned. EP 146,815 also describes various methods of attaching DNA to a support. Similarly, patent application WO 92/16659 proposes a method using a polymer for attaching the DNA. Naturally, a DNA molecule can be directly attached to a support but, where appropriate, and in particular in order to limit the influence of the supports, the DNA molecule can be fixed at the extremity of a peptide- (or other-) type inert arm (in other words, a spacer), as is described e.g. in EP 329 198. The two double-stranded DNA molecules (1) and (2) being linked to different supports, they can be linked to their respective supports by different means.

According to a preferred embodiment of the invention, said second extremities of said first and second double-stranded DNA molecules (1) and (2) are directly or indirectly attached to said first and second supports. Preferably, at least one of the two supports is a moveable support, advantageously a bead, more preferably a magnetic bead. Preferably, said second extremities of said first and second double-stranded DNA molecules (1) and (2) are attached to said first and second supports at a single point or at multiple points. Preferably, said second extremities of said first and second double-stranded DNA molecules (1) and (2) are attached to the first and second supports respectively by a nucleotide base, said base preferably being functionalized. Preferably, said second extremities of said first and second double-stranded DNA molecules (1) and (2) are attached by at least two nucleotide bases, said bases more preferably being functionalized.

According to a particular aspect of the invention, the double-stranded DNA molecule according to the invention comprises two test molecules. However, depending on the configuration of the molecule (i.e. depending on the number of extremities in the various DNA molecules and/or the tether comprised in the double-stranded DNA molecule according to the invention, said molecule may comprise at least three, four, five, or six test molecules. Said test molecules could notably be linked to the extremities of the tether or to other double-stranded DNA molecules (e.g. a third double-stranded DNA molecule (3), a fourth double-stranded DNA molecule (4), etc.). Preferably, when the double-stranded DNA molecule according to the invention comprises at least three double-stranded DNA molecules, said molecules are also attached to the tether, advantageously to different bases.

The invention also relates to the double-stranded DNA molecule as described herein, for use in the detection and/or characterization of interactions between at least two test molecules, preferably the determination of the thermodynamic and/or kinetic properties of these interactions. As a non-limiting example, the characterization of the interaction comprises the determination of at least one of the characteristics chosen from: the characteristic association time, the characteristic dissociation time, the dissociation rate constant, the dissociation activation energy, the distance separating the transition state from the complex during dissociation, and the equilibrium dissociation constant. Thus, according to a preferred embodiment, the double-stranded DNA molecule is used for the characterization of at least one molecular interaction, preferably chosen from the characteristics described above, between at least two test molecules.

Device

Figure 2:
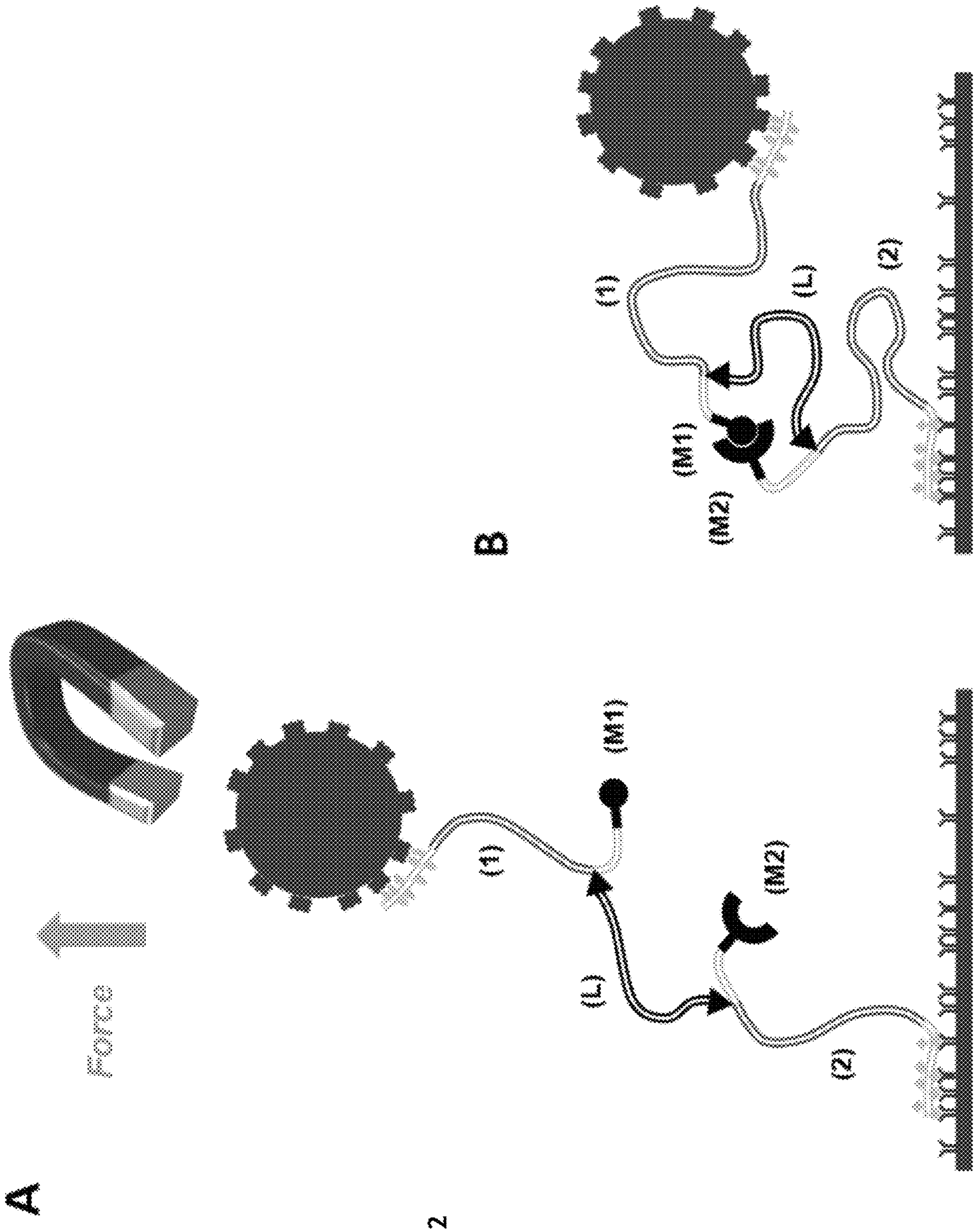
FIG. 2. Conceptual representation of a device comprising a double-stranded DNA molecule according to FIG. 1 and its supports, in which A) the two test molecules, (M1) and (M2), are dissociated and B) the two test molecules, (M1) and (M2), are associated.

The invention also pertains to a device comprising the double-stranded DNA molecule as described herein with its supports. An example of such a device is illustrated in FIG. 2. Advantageously, the device according to the invention is used for detecting and/or measuring interactions, preferably for measuring thermodynamic and/or kinetic properties, between at least two test molecules, such as those described above.

While the characterization of an interaction occurs at the level of a single molecule, it is possible to measure individual interactions simultaneously, within at least two different double-stranded DNA molecules. A detection method having a sufficiently high level of resolution to distinguish between the interactions occurring within the different double-stranded DNA molecules can notably be used. In order to measure several (e.g. at least two) individual interactions simultaneously, several double-stranded DNA molecules can be bound to the same support. The distribution of the double-stranded DNA molecules can be done in a regular manner, for example, on a network- or chip-type support, or randomly, preferably at a density making it possible to measure the interactions within each double-stranded DNA molecule separately. In some cases, it may be advantageous to separate the double-stranded DNA molecules within the device (e.g., by distribution in individual wells). The double-stranded DNA molecules can be bound to the same fixed support and to the same moveable support (e.g. a multichannel system, comprising e.g. a glass surface as a fixed support and a network of microfabricated cantilevers on a same substrate as a moveable support). Alternatively, the double-stranded DNA molecules can be bound to a same fixed support and to different moveable supports (e.g. magnetic tweezers, e.g. comprising a glass surface as a fixed support and beads as moveable supports, each molecule of double-stranded DNA being bound to a different bead). Alternatively, the double-stranded DNA molecules can be bound to different fixed supports and to different moveable supports (e.g. multiplexed optical tweezers, including e.g. beads as fixed supports and as moveable supports, each double-stranded DNA molecule being bound to a different pair of beads).

In a typical configuration, the double-stranded DNA molecule according to the invention is specifically attached between two solid supports, one of the extremities of the first double-stranded DNA molecule (1) being directly or indirectly attached to a support, while one of the extremities of the second double-stranded DNA molecule (2) is directly or indirectly attached to a moveable support. One of the extremities of the first double-stranded DNA molecule (1) can more particularly be directly or indirectly attached to a fixed or moveable support.

Said device according to the invention preferably comprises at least two double-stranded DNA molecules according to the invention, said molecules being linked to the supports, the different double-stranded DNA molecules being able to be linked to the same and/or different supports. Advantageously, when linking the double-stranded DNA molecules to the supports, said molecules are bound at a density allowing each individual molecule to be individually resolved, preferably wherein each individual molecule is or can become spatially addressable.

As the extension of the at least two double-stranded DNA molecules can be measured simultaneously yet independently, the test molecules and thus the molecular interactions to be characterized in the at least two double-stranded DNA molecules can be different. The characterization of different interactions is particularly advantageous when a large number of test molecules must be evaluated, for example when screening identify a molecule interacting with a particular receptor or modulating the interaction between two proteins. As an example, different test molecules can be linked to one of the DNA molecules (1) or (2) or introduced in aqueous solution to characterize the interactions between said molecule and the test molecule(s) linked to the double-stranded DNA molecule. In some cases, it is possible that no molecular interaction is detected between the test molecules.

In some cases, the DNA molecule according to the invention, as well as the device comprising said molecule and its supports, can be used in the context of high-throughput studies, for example, in a pharmaceutical screening to search for new molecules having particular characteristics of interaction with a particular molecule (e.g. a receptor, a protein complex). Indeed, it is known that different drugs can interact with the same receptor with different kinetics, leading to different effects. It is also known that different drugs can interact with protein assemblies and modulate their stability. Thus, the use of the present device is highly advantageous for the determination of different kinetic and/or thermodynamic characteristics. Alternatively, the same molecular interaction can be characterized in parallel for each DNA molecule, when these comprise the same test molecules. This notably makes it possible to average the measurements, and thus advantageously improve accuracy. This also ensures measurement reproducibility. When the at least two double-stranded DNA molecules comprise the same test molecules, they are preferably linked to the two supports in the same orientation (e.g. the first test molecule is linked to the first double-stranded DNA molecule (1), itself linked to a first support for each double-stranded DNA molecule).

"Intermediate" DNA Molecule

Another aspect of the invention relates to an "intermediate" molecule from which the double-stranded DNA molecule according to the invention can be obtained. The invention therefore also relates to a double-stranded DNA molecule comprising a first double-stranded DNA molecule (A) and a second double-stranded DNA molecule (B), said double-stranded DNA molecule strand (A) comprising a cleavage site which is present only in said double-stranded DNA molecule (A), said double-stranded DNA molecule (A) being connected to the double-stranded DNA molecule (B) by two covalent bonds which are not phosphodiester, phosphorothioate, phosphoramidate or phosphorodiamidate bonds, on either side of said cleavage site. Examples of such an "intermediate" molecule are in particular illustrated in FIG. 3.

Advantageously, said first extremities of the double-stranded DNA molecules (1) and (2) are different from the second extremities of the double-stranded DNA molecules (1) and (2). First and second extremities refer to the two different extremities within the double-stranded DNA molecule (1) or (2). However, the terms "first and second extremities" should not be interpreted as corresponding to specific extremities, but simply allow the differentiation of one extremity of a molecule from the other extremity. Thus, there is no notion of direction or orientation associated with said first and second extremities.

Advantageously, the four extremities of the double-stranded DNA molecule (e.g., the two extremities of the double-stranded DNA molecule (1) and the two extremities of the double-stranded DNA molecule (2)) are different. The double-stranded DNA molecule (A) preferably has a length of between about 600 and 10,000 base pairs, preferably between about 1,000 and 4,000 base pairs, preferably between about 1,500 and 3,000 base pairs (±50 base pairs). The double-stranded DNA molecule (B) preferably has a length of between about 300 to about 50,000 base pairs, preferably chosen according to the purpose of the experiment and the test molecules of about 500 to 10,000 base pairs, preferably 600 to 3000 base pairs, more preferably 600 to 1000 base pairs, even more preferably about 700 base pairs (±50 base pairs).

In the context of the present invention, the term "cleavage site" refers to a polynucleotide structure or sequence which is capable of being cleaved in a specific manner by a cleavage agent, such as a restriction enzyme, a nuclease, a nickase, a ribozyme, a DNAzyme, and fragments thereof. As a non-limiting example, the cleavage site may therefore be a restriction enzyme site, a ribozyme site, a nickase site, a DNAzyme site or a nuclease cleavage site. Such agents and sites are well-known to the skilled person. By "restriction enzyme" is more particularly meant an enzyme which cuts double-stranded DNA at or near a specific nucleotide sequence. The specificities of many restriction enzymes are well-known in the art and a large number of restriction enzymes are commercially available and their reaction conditions, the need for the presence of cofactors and other requirements established by enzyme suppliers are well-known. As a non-limiting example, the restriction enzyme may be a type II, type III or artificial restriction enzyme (such as a zinc finger nuclease, a transcription activator-like effector nuclease (TALEN), a meganuclease, or a CRISPR endonuclease), even more preferably a type II restriction enzyme. Type II restriction enzymes include IIP, IIS, IIC, IIT, IIG, IIE, IIF, IIG, IIM and IIB categories, as described e.g. in Pingoud and Jeltsch, 2001. The restriction enzyme can generate blunt ends (i.e. the two strands having the same length) or cohesive ends (one strand being longer than the other strand, usually by a few nucleotides).

According to a preferred embodiment of the invention, the cleavage site in the double-stranded DNA molecule (A) of the "intermediate" double-stranded DNA molecule is a restriction enzyme site, preferably a type II restriction enzyme site, more preferably two restriction sites, even more preferably two restriction sites generating two different ends (e.g. a blunt end and a cohesive end, or two non-complementary cohesive ends). As a non-limiting example, the cleavage site may consist of a SacI restriction enzyme site and a XbaI restriction enzyme site. When the cleavage site comprises at least two different sites, said sites may be separated from one another, for example by at least 1, at least 2, at least 3, at least 4, at least 5, at least 6, at least 12, at least 25, at least 50, at least 100, at least 200, at least 500, or at least 1000 base pairs. Preferably, said sites are separated by at least 6 base pairs ("Restriction Endonucleases Technical Guide", New England Biolabs).

Method of Manufacturing the DNA Molecule

Another aspect of the invention relates to a method of manufacturing a double-stranded DNA molecule from an "intermediate" double-stranded DNA molecule. The invention thus further relates to a manufacturing method characterized in that it comprises the following step: a) cleaving the double-stranded DNA molecule (A) at said cleavage site, thus generating a molecule of double-stranded DNA comprising a first double-stranded DNA molecule (1) and a second double-stranded DNA molecule (2).

The cleavage step may be performed by techniques well-known to the skilled person, such as simultaneous or sequential dual digestion with two restriction enzymes. Preferably, cleavage is performed with at least one cleavage agent as defined above, more preferably with at least one restriction enzyme as defined above. Preferably, cleavage is performed by two different restriction enzymes making it possible to obtain two different cohesive ends, preferably said cohesive ends being non-complementary. Preferably, the two cleavage sites are separated from each other according to one of the embodiments described above.

Preferably, after step a), at least one additional step can be performed. Such a step could comprise, e.g., a step of functionalizing an extremity of the first and/or second double-stranded DNA molecule (1) and (2), and/or the binding of a test molecule at one extremity of the first and/or second double-stranded DNA molecule (1) and (2).

Advantageously, the method of manufacturing the double-stranded DNA molecule according to the invention further comprises, after step a), the following step: b) attaching at least one functionalized base to one extremity of said first double-stranded DNA molecule (1) and attachment of another functional base to one extremity of said second double-stranded DNA molecule strand (2).

Figure 4:
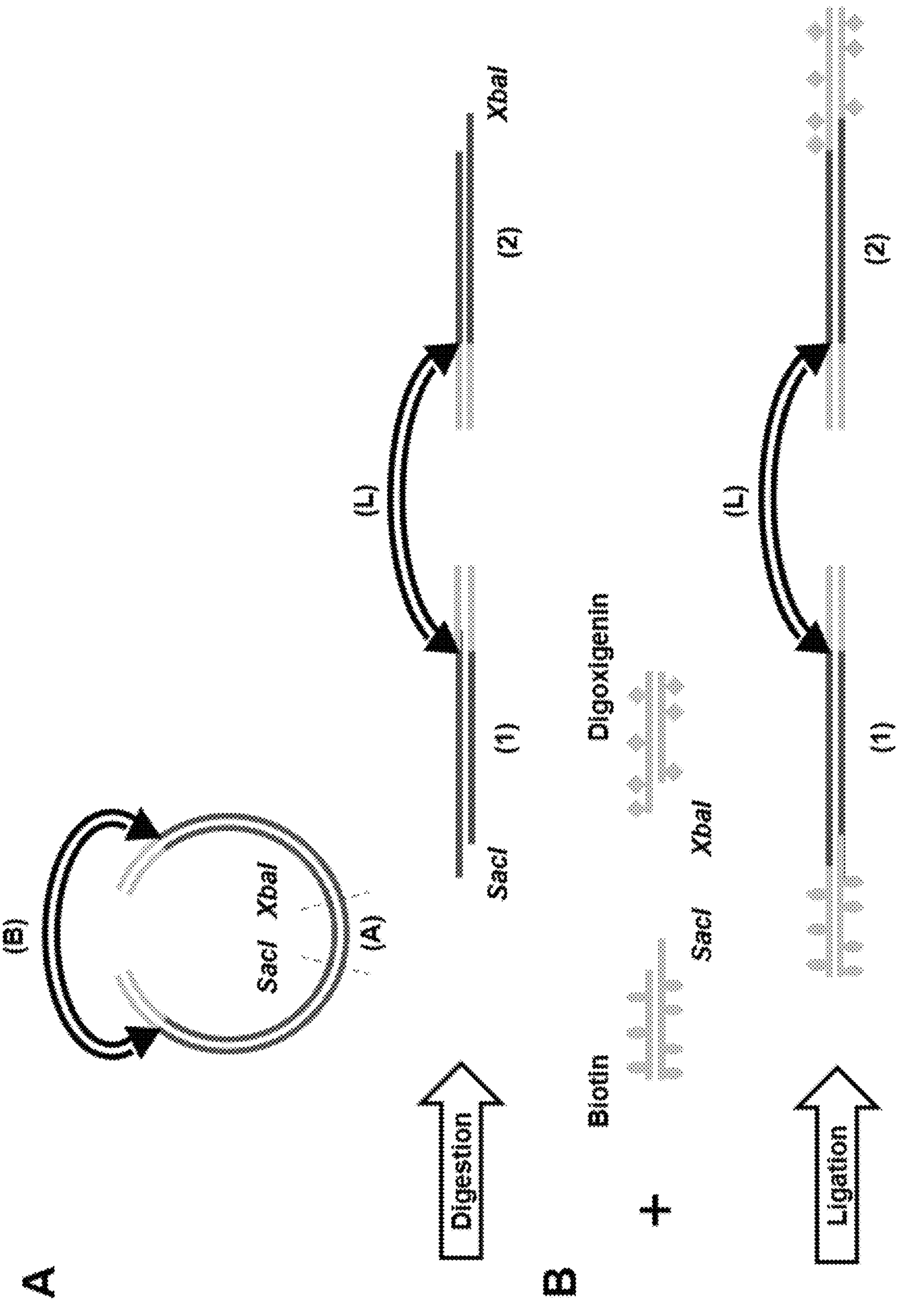
FIG. 4. Schema of a method of manufacturing a double-stranded DNA molecule from an "intermediate" double-stranded DNA molecule, comprising steps A) Synthesis of double-stranded DNA molecules (1) and (2); B) Synthesis and assembly of the functionalized extremities intended for the supports.

According to a first embodiment, the functionalized extremities are those generated during step a). According to a second embodiment, the functionalized extremities are those already present in the double-stranded DNA molecule (A) of the "intermediate" double-stranded DNA molecule" before step a). Preferably, the extremity of the first double-stranded DNA molecule (1) and the extremity of the second double-stranded DNA molecule (2) are functionalized by two different functional groups, such that they can be linked to different supports. As a non-limiting example, one extremity of the first double-stranded DNA molecule (1) is functionalized by the addition of at least one biotin group while one extremity of the second double-stranded DNA molecule (2) is functionalized by the addition of at least one digoxigenin group. Thus, the biotinylated extremity can nearly-covalently bind to a streptavidin-coated surface or support while the digoxigenin-functionalized extremity can bind to a surface or support coated with antibody directed against digoxigenin. Preferably, the extremity of the first double-stranded DNA molecule (1) and/or the extremity of the second double-stranded DNA molecule (2) are functionalized by the addition of several groups in order to improve the attachment of the extremity to the support. According to a particular embodiment, the functional group(s) are present in a single-stranded or double-stranded DNA molecule which is incorporated at the extremity of the first molecule of double-stranded DNA (1) and another single-stranded or double-stranded DNA molecule which is incorporated at the extremity of the second double-stranded DNA molecule (2) using techniques well-known to the skilled person (e.g. hybridization and ligation). As a non-limiting example, FIG. 4 illustrates steps a) and b) as described herein.

According to a preferred embodiment of the invention, said at least one functionalized base is included in a third (3) and/or fourth double-stranded DNA molecule (4), said third double-stranded DNA molecule (3) being preferably linked to the second extremity of said first double-stranded DNA molecule (1), and said fourth double-stranded DNA molecule (4) being advantageously linked to the second extremity of the second double-stranded DNA molecule (2). Preferably, said at least one functionalized base of said double-stranded DNA molecule (3) is functionalized with a different functional group than said at least one functionalized base of said double-stranded DNA molecule (4).

Preferably, the double-stranded DNA molecule (1), (2), (3) and/or (4) has a length of between 600 and 10,000 base pairs, more preferably between 650 and 1,500 base pairs.

When a single-stranded DNA fragment is present at the extremity of one of the double-stranded DNA molecules (1) or (2) after incorporation of a functionalized DNA molecule, said fragment can preferably be:

1) removed, e.g. by an enzyme having exonuclease activity, or
2) completed by the addition of a second complementary fragment, e.g. by the activity of a DNA polymerase (e.g. Klenow fragment, T4 polymerase, etc.) in the presence of dNTPs.

Preferably, the method of manufacturing the double-stranded DNA molecule according to the invention further comprises, after step a), the following step: c) the binding of a first test molecule to an extremity of said first double-stranded DNA molecule (1) and binding of a second test molecule at an extremity of said second DNA molecule (2).

Figure 5:
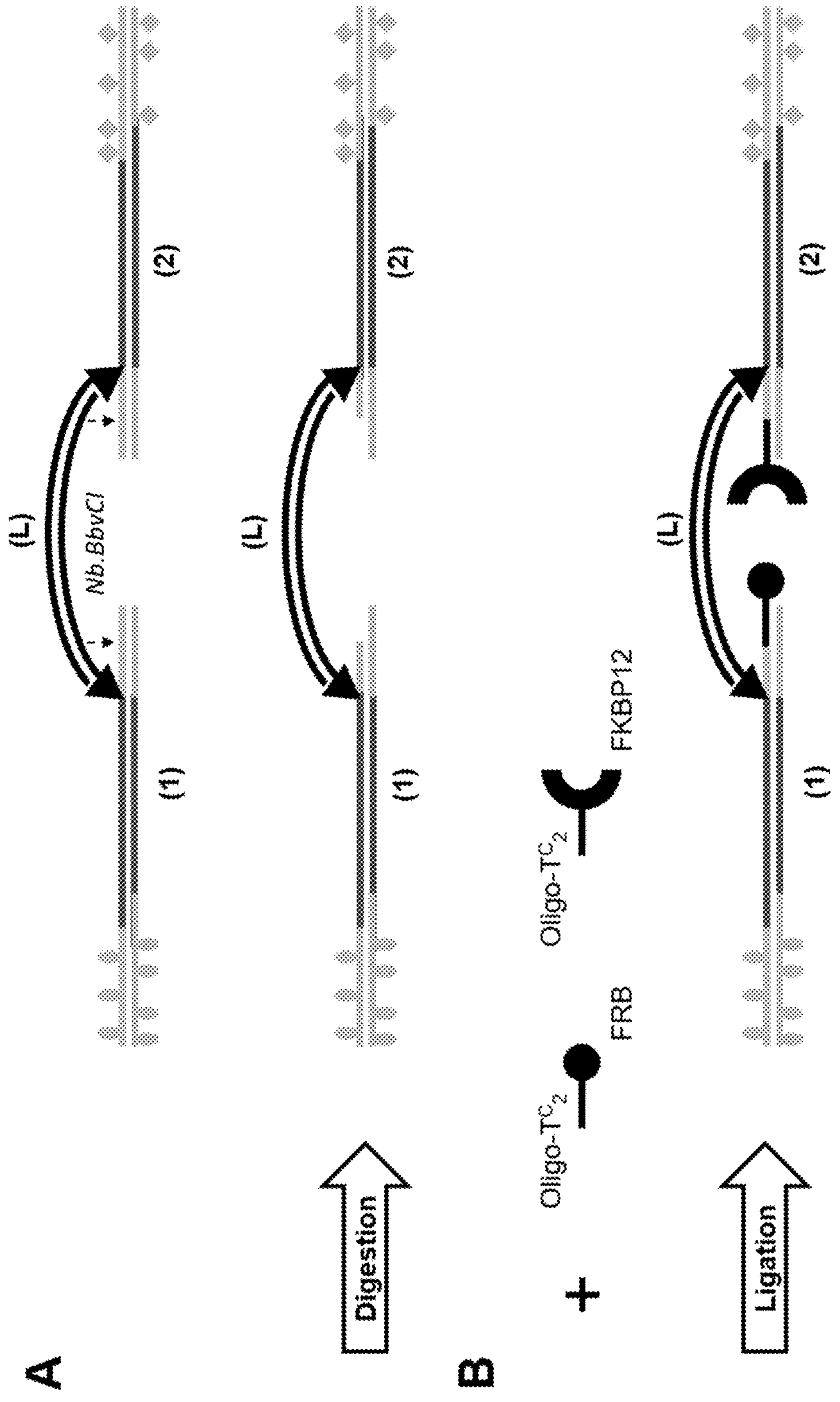
FIG. 5. Schema of the arrangement of the extremities intended for the test molecules, comprising the steps A) Digestion of the extremities (for example by the Nb.BbvCl enzyme); B) Binding of the test molecules to the extremities.

As a non-limiting example, FIG. 5 illustrates this step.

Preferably, the binding according to step c) comprises the binding of a fifth (5) DNA molecule comprising said first test molecule to said first extremity of the first double-stranded DNA molecule (1), and/or the binding of a sixth (6) DNA molecule comprising said second test molecule to said first extremity of the second double-stranded DNA molecule (2).

Said fifth (5) DNA molecule and/or sixth (6) DNA molecule comprising a test molecule may preferably be a double-stranded DNA molecule comprising an overhang or an oligonucleotide. In this case, the binding according to step c) advantageously comprises hybridization and ligation steps in order to link the DNA molecules together. However, the test molecules may be linked to said ends of the double-stranded DNA molecules (1) and (2) according to any technique known to the skilled person.

Step c) can be performed before or after step b). According to another embodiment, one of steps b) and c) is performed with step a) (i.e. by adding the test molecules or the functional groups to the extremities already present in the double-stranded DNA precursor molecule (A), and the other of steps b) and c) is performed after step a), when the two double-stranded DNA molecules (1) and (2) as well as their second extremities are generated. This may be advantageous when the first extremity of the double-stranded DNA molecule (1) and/or the first extremity of the double-stranded DNA molecule (2), included in the double-stranded DNA precursor molecule (A) have an identical ends (i.e. the same cohesive or blunt ends) at at least one of the extremities which is formed by cleavage of the double-stranded DNA molecule (A). This advantageously makes it possible to attach each functional group and each test molecule to a particular extremity, while using a reduced number of restriction enzymes. Preferably, before step c), the extremities to which the test molecules will be attached are cleaved, more preferably by a restriction enzyme, as described above. However, this step is not necessary when the extremities concerned have already undergone a cleavage step (e.g. before step a) or before step b)).

Alternatively, the test molecules can be directly linked to double-stranded DNA molecules (1) and (2) at blunt ends (e.g. according to the blunt-end ligation method). This technique is well-known to the skilled person. As a non-limiting example, the blunt-ended ligation comprises steps of dephosphorylation of the extremities of double-stranded DNA molecules (1) and (2) and phosphorylation of the free end of the DNA molecules comprising the test molecules before bringing the molecules into contact with one another in an appropriate buffer and in the presence of a ligase.

Advantageously, the attachment of at least one of the functionalized DNA molecules in step b) and/or the attachment of at least one of the test molecules in step c) comprises hybridization and ligation steps, preferably by hybridization of two complementary cohesive ends (i.e. one being present on the double-stranded DNA molecule (1) or (2) and the other being present on a DNA molecule comprising at least one functionalized base or a test molecule). As an alternative, the attachment of at least one of the functionalized DNA molecules in step b) and/or the attachment of at least one of the test molecules in step c) comprises a conjugation step, preferably between at least two functional groups, more preferably according to click chemistry methods.

In the case of interaction studies between protein test molecules, it is conceivable to use labeling reactions where protein tags are fused with the test molecules and specifically react with ligands at the extremities of the DNA molecules (1) and/or (2) (as shown in FIG. 7B). Today, many systems are commercially available, which allows for as many orthogonal reactions. The adducts formed may, e.g., be covalent, as in the case of binding by the SNAP-tag protein of the benzylguanine ligand, by the CLIP-tag of benzylcytosine, by HaloTag of a chloroalkane group, or by a combination of at least two of these. Alternatively, the formation of non-covalent complexes such as those resulting from the interaction between streptavidin and biotin, between an epitope and an antigen, or between a protein target and its aptamer, may be used. In these latter three cases, it would be advantageous for complexing to be sufficiently strong to lead to the functionalization of a large number of extremities by the test molecules and such that there is no tensile breaking.

Advantageously, the use of protein tags renders superfluous the step of digestion of the extremities, shown in FIG. 5A. Advantageously, there is no longer any need to synthesize "oligonucleotide-test molecule" conjugates, which is rather long and can sometimes be complex due to problems related to the purification and stability of the species obtained. Thus, advantageously, one can simply rely on the expression and purification of fusion proteins.

Preferably, said first extremities of the double-stranded DNA molecules (1) and (2) are different from the second extremities of the double-stranded DNA molecules (1) and (2).

Preferably, the manufacturing method of the present invention uses biochemical synthesis techniques, and not an "origami" type assembly. The structure of the double-stranded DNA molecule according to the invention can be guaranteed to the base, and is therefore of very high quality. Indeed, the inventors have notably shown in supercoiling studies, that no phosphodiester, phosphorothioate, phosphoramidate or phosphorodiamidate bond is missing in the approximately 3600 bases which are comprised in the double-stranded DNA molecule exemplified in Example 9 and FIG. 12.

Manufacturing Method—Additional Steps

Figure 6:
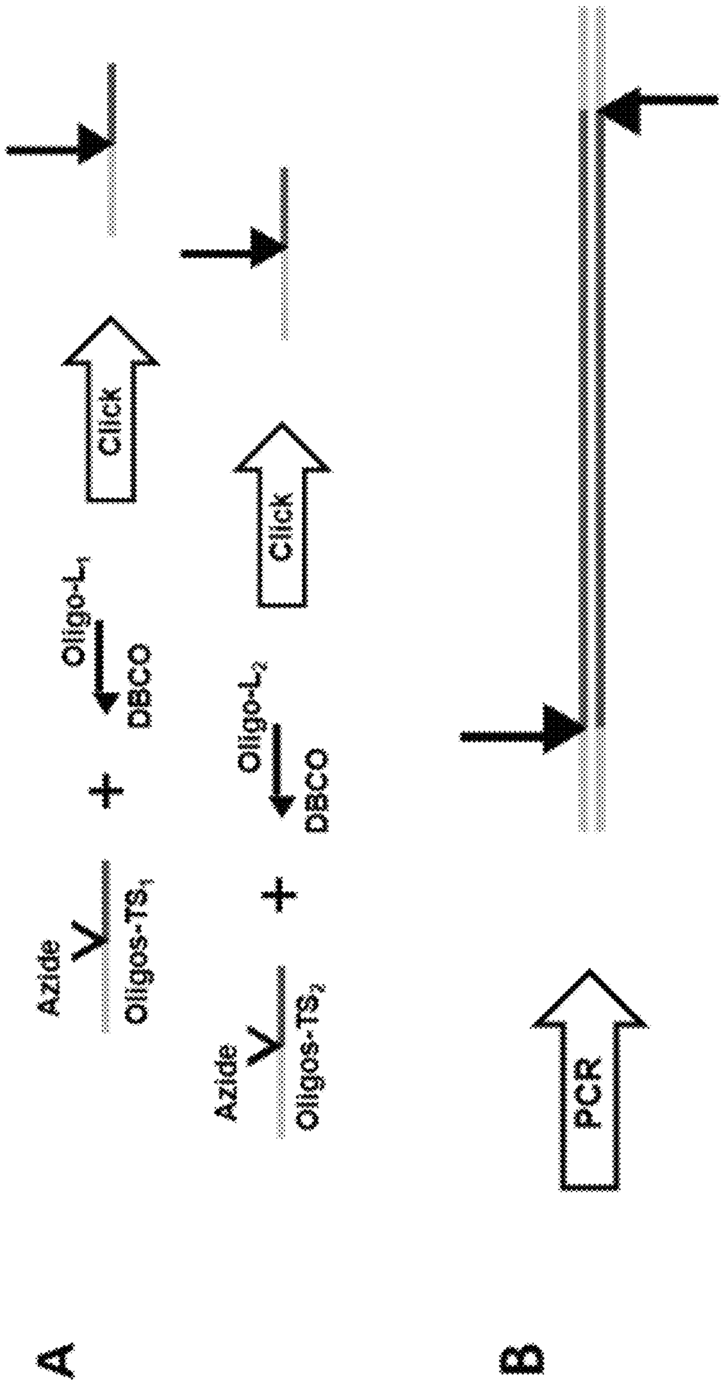
FIG. 6. Schema of a method of manufacturing an "intermediate" double-stranded DNA molecule, comprising steps A) Synthesis of the junctions; B) Synthesis of molecule (A), corresponding to a precursor of the first and second double-stranded DNA molecules (1) and (2); C) Synthesis and assembly of molecule (B), corresponding to the tether.
Figure 6:
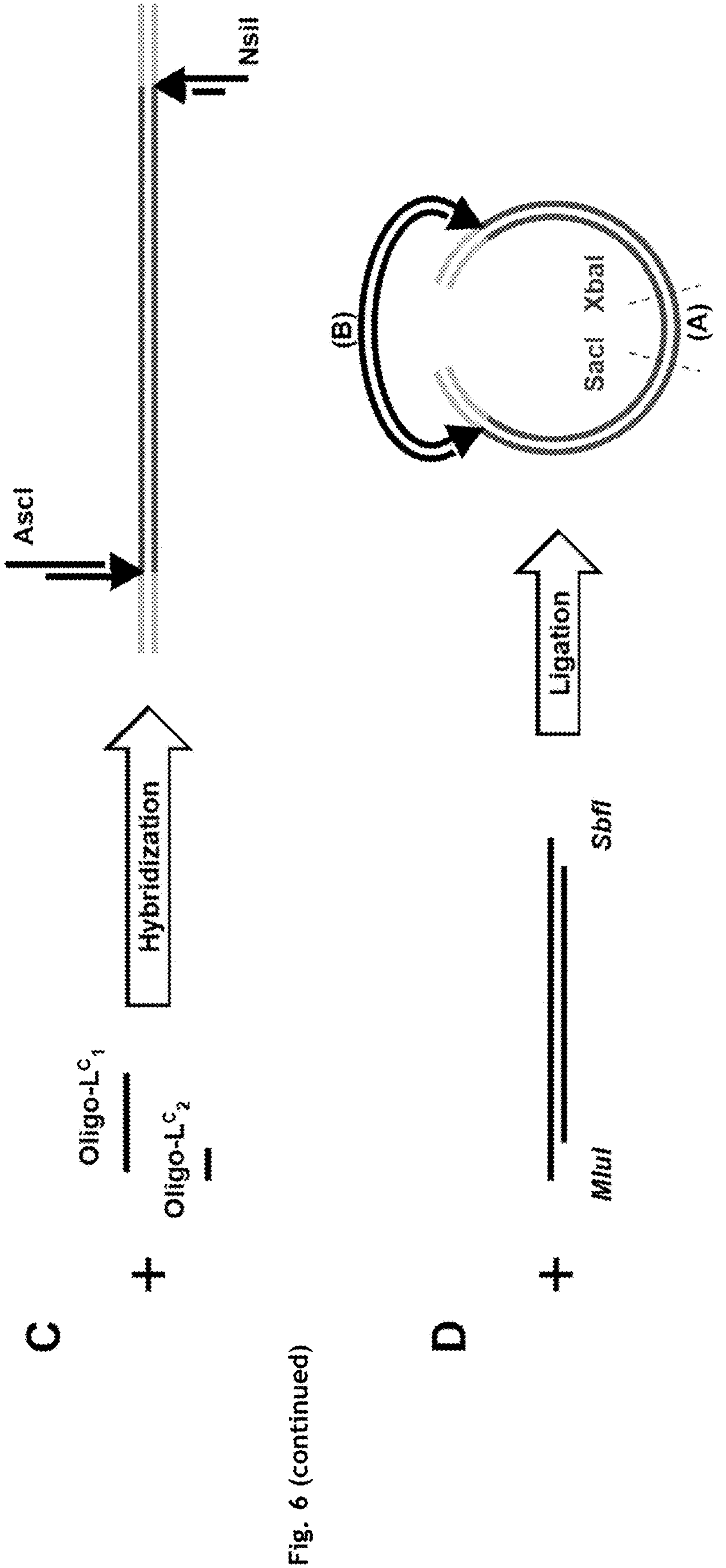

The manufacturing method according to the invention may further comprise one or more additional steps, such as one or more synthesis steps prior to step a), advantageously making it possible to generate the "intermediate" double-stranded DNA molecule from which the double-stranded DNA molecule according to the invention can be obtained. As a non-limiting example, the manufacturing method further comprises, prior to step a), the following steps:

- the synthesis of an oligonucleotide (1) comprising a junction obtained by reaction of a first functional group present on the extremity of a first oligonucleotide with a second functional group present on one of the intermediate nucleotides of a second oligonucleotide;
- the synthesis of an oligonucleotide (2) comprising a junction obtained by reaction of a first functional group present on the extremity of a third oligonucleotide with a second functional group present at an intermediate point of a fourth oligonucleotide (see also the examples illustrated in FIGS. 6A and 7A);
- the synthesis of said double-stranded DNA molecule (A), said DNA molecule (A) comprising the oligonucleotide (1) at its first extremity and the oligonucleotide (2) at its second extremity (see also the example illustrated in FIG. 6B); and
- the attachment of a tether, at the first and second extremities of said tether, to the junction of oligonucleotide (1) and oligonucleotide (2), respectively (see also the example illustrated in FIGS. 6C and 6D).

According to a first embodiment, the step of synthesizing the double-stranded DNA molecule (A) is performed by PCR using oligonucleotides (1) and (2) as primers. Preferably, the molecule (A) is produced by PCR, preferably followed by enzymatic digestion of each of its extremities by a restriction enzyme, advantageously by two different restriction enzymes.

According to a second embodiment, the step of synthesizing double-stranded DNA molecule (A) comprises hybridization and ligation steps of oligonucleotide (1) to the first extremity of a molecule of double-stranded DNA, such as a phage genome, and oligonucleotide (2) to the second extremity. Preferably, the double-stranded DNA molecule (A) comprises an overhang at each of its extremities, preferably comprises two different overhangs. Preferably, oligonucleotide (1) and oligonucleotide (2) comprise complementary DNA regions to said overhangs.

Preferably, the attachment of molecule (B) comprises the hybridization and ligation of a fifth oligonucleotide to the junction of oligonucleotide (1) and a sixth oligonucleotide to the junction of oligonucleotide (2), respectively, to generate overhangs on each junction (see, e.g., FIG. 6C).

Preferably, double-stranded DNA molecule (B) is synthesized by PCR, more preferably followed by enzymatic digestion of each of its extremities by a restriction enzyme, still more preferably by two different restriction enzymes (see, e.g., FIG. 6C).

The double-stranded DNA molecule (A) and/or the double-stranded DNA molecule (B) preferably has at least one of the characteristics (e.g., length) as described above. Preferably, another aspect of the invention is the double-stranded DNA molecule comprising a first double-stranded DNA molecule (A) and a second double-stranded DNA molecule (B), said molecule (A) comprising a cleavage site which is present only in said molecule (A), said molecule (A) being connected to molecule (B) by two covalent bonds which are not phosphodiester, phosphorothioate, phosphoramidate or phosphorodiamidate bonds on either side of said cleavage site obtained by the method described above.

Preferably, the length of the first double-stranded DNA molecule (1), the second DNA molecule (2), and the tether can be easily adjusted during the manufacture of the double-stranded DNA molecule according to the manufacturing method as described herein.

Advantageously, adjusting the length of the tether makes it possible to modulate the effective concentration of test molecules (also called "$C_{eff}$"). This is even easier as the double-stranded DNA has a large persistence length. The length of the tether may in particular be determined according to the length of double-stranded DNA molecules (1) and (2), or vice versa, and according to the effective concentration of the test molecules and/or the desired spatiotemporal resolution. Indeed, in some cases, a reduction in the total length of the double-stranded DNA molecule according to the invention by a numerical factor N, increases the spatiotemporal resolution of the experiment by approximately the same factor N, said factor N being advantageously comprised between 1 and 6. However, it may be preferable to maintain a length of at least 300 bp of the tether. It may also be advantageous to maintain a length of at least 100 bp of the double-stranded DNA molecules (1) and (2) in order to avoid interactions between the supports and the test molecules. For constructions already comprising a very short tether (e.g. less than about 300 base pairs), the only way to reduce the length of the construct is to shorten the length of first and second DNA molecules (1) and (2).

Method of Characterizing Molecular Interactions

The invention also pertains to a method for detecting and/or characterizing at least one molecular interaction between at least two test molecules, said test molecules being advantageously linked to a double-stranded DNA molecule according to the invention. invention. The characteristic determined may be, e.g., of a thermodynamic or kinetic nature. As an example, a characteristic association time, a characteristic dissociation time, a dissociation rate constant, a dissociation activation energy, a distance separating the transition state from the complex during dissociation, and/or an equilibrium dissociation constant may be determined.

More particularly, the invention pertains to a method of characterizing an interaction between at least two test molecules, said test molecules being linked to a double-stranded DNA molecule, or to a double-stranded DNA molecule as comprised in the device of the invention, comprising:

a) applying a low physical force, $F_{LF}$, to the double-stranded DNA molecule, which allows the test molecules to associate;
b) applying a high physical force, $F_{HF}$, to the double-stranded DNA molecule, which makes it possible to determine whether the test molecules are associated or dissociated; and
c) detecting a change in the conformational properties of the DNA molecule comprising:
    - determining the $z_{LF}$ extension between the second extremity of the first double-stranded DNA molecule (1) and the second extremity of the second double-stranded DNA molecule (2) in step a);
    - determining the $z_{HF-A}$ and $z_{HF-D}$ extensions between the second extremity of the first double-stranded DNA molecule (1) and the second extremity of the second double-stranded DNA molecule (2), at step b), in which $z_{HF-A}$ is the extension when the molecules are associated and $z_{HF-D}$ is the extension when the molecules are dissociated; and
    - comparing the extensions $z_{LF}$, $z_{HF-A}$, and $z_{HF-D}$, as a function of time t.

It may be advantageous to measure the association between the two test molecules, to initiate the cycle with a stage at high force whose value may be higher than $F_{HF}$. According to this preferred embodiment, the method will comprise an initial step of applying a physical force greater than the force $F_{HF}$ of step c).

In another preferred embodiment, the method of the invention advantageously makes it possible to distinguish the extensions $z_{LF-A}$ and $z_{LF-D}$. This is notably the case when the tether has a length of at least 700 bp. In this respect, it should be noted that it is particularly advantageous to use a tether of at least 6000 bp, which makes it easy to distinguish the extensions $z_{LF-A}$ and $z_{LF-D}$.

According to this preferred embodiment, said method further comprises the additional step:

d) detecting a change in the conformational properties of the DNA molecule comprising:
    - determining the $z_{LF-A}$ and $z_{LF-D}$ extensions between the second extremity of the first double-stranded DNA molecule (1) and the second extremity of the second double-stranded DNA molecule (2) at step a), wherein $z_{LF-A}$ is the extension when the molecules are associated and $z_{LF-D}$ is the extension when the molecules are dissociated;
    - determining the $z_{HF-A}$ and $z_{HF-D}$ extensions between the second extremity of the first double-stranded DNA molecule (1) and the second extremity of the second double-stranded DNA molecule (2) at step b), wherein $z_{HF-A}$ is the extension when the molecules are associated and $z_{HF-D}$ is the extension when the molecules are dissociated; and
    - comparing the extensions $z_{LF-A}$, $z_{LF-D}$, $z_{HF-A}$, and $z_{HF-D}$, as a function of time t.

In a more preferred embodiment, the tether has a length of at least 700 bp. Even more preferably, the tether has a length of at least 6000 bp.

In some cases, steps a) to c) or a) to d) as described above may be repeated several times, in order to follow multiple dissociation/association cycles. The repetition of the steps is highly advantageous as it makes it possible to increase the number of measurements and thus improve statistics and reliability of the characterization, notably by filtering the results according to reproducibility criteria. Thus, according to a preferred embodiment, steps a) to c) of the method are repeated several times.

More particularly, the invention pertains to a method of characterizing an interaction between at least two test molecules, said test molecules being linked to a double-stranded DNA molecule, or to a double-stranded DNA molecule as comprised in the device of the invention, comprising:

a) applying a constant force $F_{CF}$ to the double-stranded DNA molecule, which allows the test molecules to associate and dissociate; and
b) detecting a change in the conformational properties of the DNA molecule comprising:
   determining the spontaneous dissociation of the test molecules after time $t_{CF-A}$, and/or
   determining the spontaneous association after time $t_{CF-D}$.

Advantageously, the method of characterizing an interaction comprises adding at least one additional molecule in solution. Said molecule present in solution may be the same molecule as one of the test molecules which are attached to the extremities of the double-stranded DNA molecule according to the invention or a different molecule. Preferably, the force applied during the characterization of a spontaneous fluctuation interaction is at least 30 fN, preferably a force comprised between 30 and 60 fN.

A "physical force" or "force" according to the invention corresponds to any influence that causes an object to undergo a certain change, as regards its movement, its direction or its geometric construction (e.g. its conformation). It will be apparent to the skilled person that a force according to the invention is different from other physical parameters such as, e.g., temperature (which is a direct property of the material rather than an influence exerted on it). The physical forces according to the invention include forces such as friction, tension (also called "traction force"), rotation, normal force, resistance force of a fluid, applied force and elastic force. Preferably, the physical force according to the invention comprises a tension force, advantageously the physical force according to the invention consists of a tension force. The physical force according to the invention may also comprise a rotational force, advantageously a torque. Physical force can consist of a torque force. In some cases, the physical force includes tension and rotation, preferably tension and torque. Force is expressed herein in picoNewtons (pN) unless explicitly stated otherwise. The "application" of such physical forces is well-known to the skilled person, particularly in the context of the various apparatuses in which the DNA molecule, or the device comprising the DNA molecule, according to the invention can be incorporated (see e.g. Woodside et al., 2006; U.S. Pat. Nos. 7,052,650 and 7,244,391; WO 2011/147931; and Yang et al., 2016).

By "extension" is meant in the context of the present invention the distance between two extremities of a polymer. In the present invention, the extension more particularly corresponds to the distance "z" measured between the supports to which the double-stranded DNA molecule according to the invention is attached. The extension is therefore less than or equal to the length of the double-stranded DNA molecule. The extension of the double-stranded DNA molecule is expressed in nm or μm. The distance $z_{LF}$, corresponds to the distance between two extremities of the DNA molecule according to the invention, preferably the distance between the supports to which the double-stranded DNA molecule according to the invention is attached, when a low force $F_{LF}$ is applied. As an example, below an threshold of applied force, which varies according to the test molecules (generally between 0.01 and 0.4 pN), the supports are close to one another. The distance $z_{HF}$, corresponds to the distance between two extremities of the DNA molecule according to the invention, preferably the distance between the supports to which the double-stranded DNA molecule according to the invention is attached, when a high force $F_{HF}$ is applied. As an example, above an threshold of applied force, which varies according to the test molecules (generally between 0.5 and 70 pN), the supports are separated from one other. When the test molecules associate, two distances can be determined, corresponding to two extension states, $z_{HF-A}$ and $z_{HF-D}$. More precisely, the distances $z_{HF-A}$ and $z_{HF-D}$ correspond to the distance between two extremities of the DNA molecule according to the invention when a high force $F_{HF}$ is applied, and when the test molecules are associated ($z_{HF-A}$) or dissociated ($z_{HF-D}$). The distance $z_{HF-D}$ is greater than the distance $z_{HF-A}$, since the double-stranded DNA molecules (1) and (2) are linked to each other only by the tether (not by the test molecules), see also diagram in FIGS. 8, 10A. The conformation of the double-stranded DNA molecule can therefore be determined by direct measurements of the extension thereof, for example, under a force, as described herein.

The different "z" distances are determined over time and as a function of the applied force. In some cases, it may be advantageous to precisely measure distances (e.g. in nm). In general, the extension of the double-stranded DNA molecule when the test molecules are associated (A, e.g. $z_{HF-A}$) corresponds approximately to the extension of a linear double-stranded DNA molecule having the length that is the sum of the lengths of double-stranded DNA molecules (1) and (2), to which a force $F_{HF}$ is applied. In general, the extension of the double-stranded DNA molecule when the test molecules are dissociated (D, e.g. $z_{HF-D}$) corresponds approximately the extension of a linear double-stranded DNA molecule having the length that is the sum of the length of the tether plus the sum of the lengths of the double-stranded DNA molecules (1) and (2) excluding the parts located between the test molecules and the junctions, to which a force $F_{HF}$ is applied. At high force, extension and length are nearly proportional, which favors the establishment of correspondence between the different "z's".

The extension can notably be deduced from the measurement of the distance between the two supports (e.g. the fixed support and the moveable support), the latter being able, e.g., to be located by video tracking, as in the case of magnetic beads, or by laser beam deflection, as in the case of some optical traps or AFM. A physical force is advantageously applied to both extremities attached to the two supports when the supports are separated. When the conformational changes of the double-stranded DNA molecule are observed under physical force, e.g. under tension, the transition between association and dissociation of the test molecules is indicated by an increase in the extension of the double-stranded DNA molecule, the distance $z_{HF-A}$, corresponding to a state of association between the two molecules, being lower than the distance $z_{HF-D}$, corresponding to a state of dissociation between the two molecules.

However, the determination of the different "z" distances is not mandatory. Indeed, in some cases, it may be advantageous to simply determine whether each extension state is present, to determine whether test molecules are capable of interacting. As an example, such a determination can be made by identifying, on a temporal trace of $z_{HF}$, a change of the extension which is attributed to the passage between the measurement of the distance $z_{HF-A}$ and the measurement of the distance $z_{HF-D}$. Such a change may, e.g., be abrupt (e.g. in less than 3 acquisition points, corresponding to 90 milliseconds for a 30 Hz video acquisition rate), as illustrated in FIG. 10B.

Figure 10:
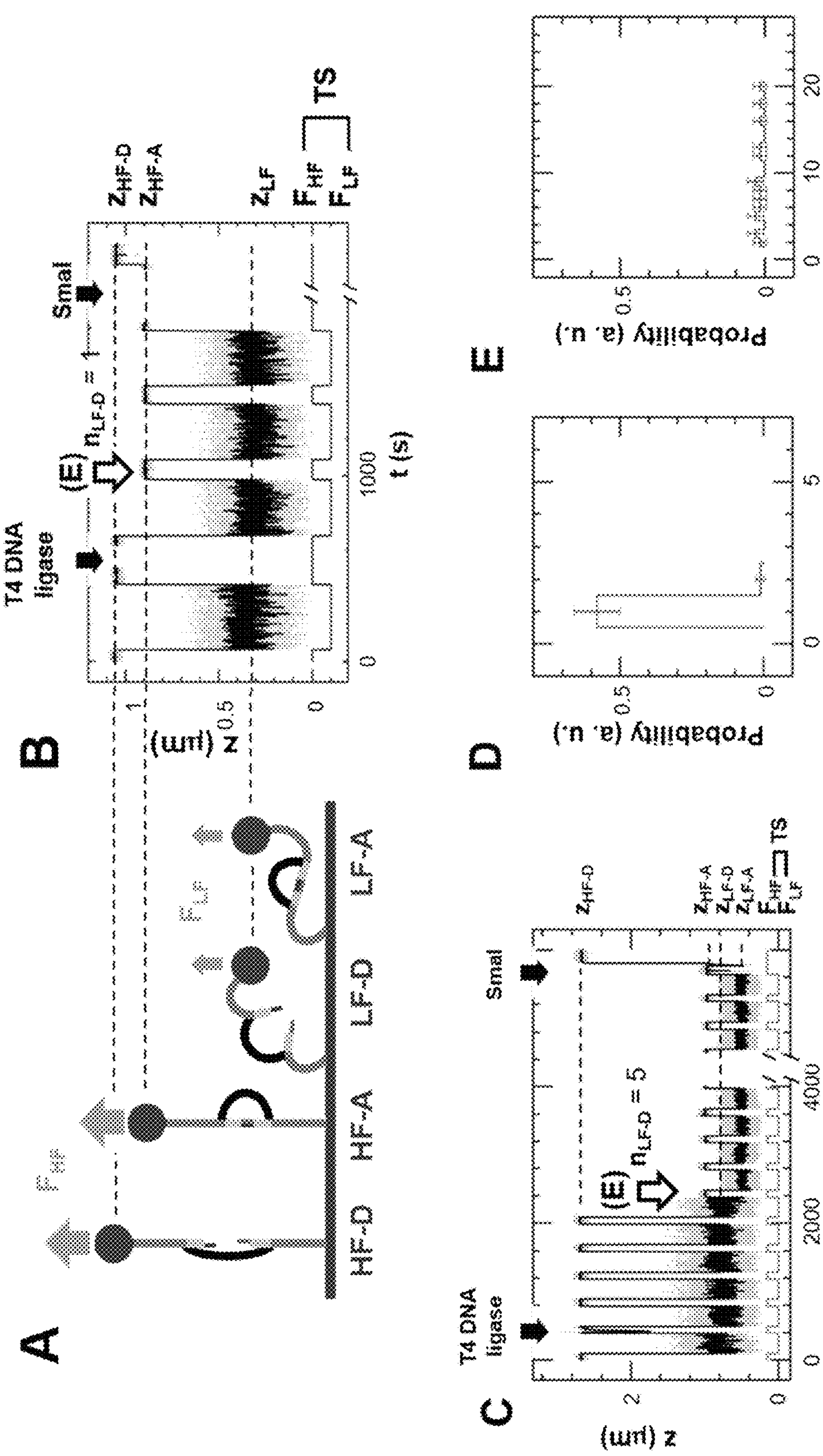
FIG. 10. Study of the covalent interaction between two cohesive ends of double-stranded DNA extremities in the presence of phage T4 DNA ligase followed by the restriction enzyme SmaI. These two cohesive ends, where terminal phosphate groups are present in 5' and terminal hydroxyl groups are present in 3', constitute themselves the two test molecules here. The DNA molecule used corresponds to that shown in FIG. 1 in a device as illustrated in FIG. 2, and obtained by the manufacturing method described in Examples 3, 1 and then 8. Experiments were performed at 34° C. in RB buffer. A) Schema of the four configurations in which the DNA molecule may be found. The device can be subjected to either a high force (HF for "High Force") or a low force (LF for "Low Force"). The test molecules may be either associated (A for "Associated") or dissociated (D for "Dissociated"). B) Temporal monitoring of the extension (z) of the DNA molecule having a tether of ~0.7 kbp when the force is cycled between a high force $F_{HF}$=1.4 pN for a time $T_{HF}$=100 s and a low force $F_{LF}$=0.04 pN for a time $T_{LF}$=300 s (TS: schematic diagram of the cycles $F_{HF}/F_{LF}$). C) Temporal monitoring of the extension (z) of the DNA molecule having a tether of ~6 kbp when the force is cycled between a high force $F_{HF}$=1.1 pN for a time $T_{HF}$=100 s and a low force $F_{LF}$=0.04 pN for a time $T_{LF}$=300 s (TS: schematic diagram of the $F_{HF}/F_{LF}$ cycles). D) Histogram of the number of passages at low force, $n_{LF-D}$, necessary to obtain ligation when the tether measures ~0.7 kbp. E) Histogram of the number of passages at low force, $n_{LF-D}$, necessary to obtain ligation when the tether measures ~6 kbp.
Figure 11:
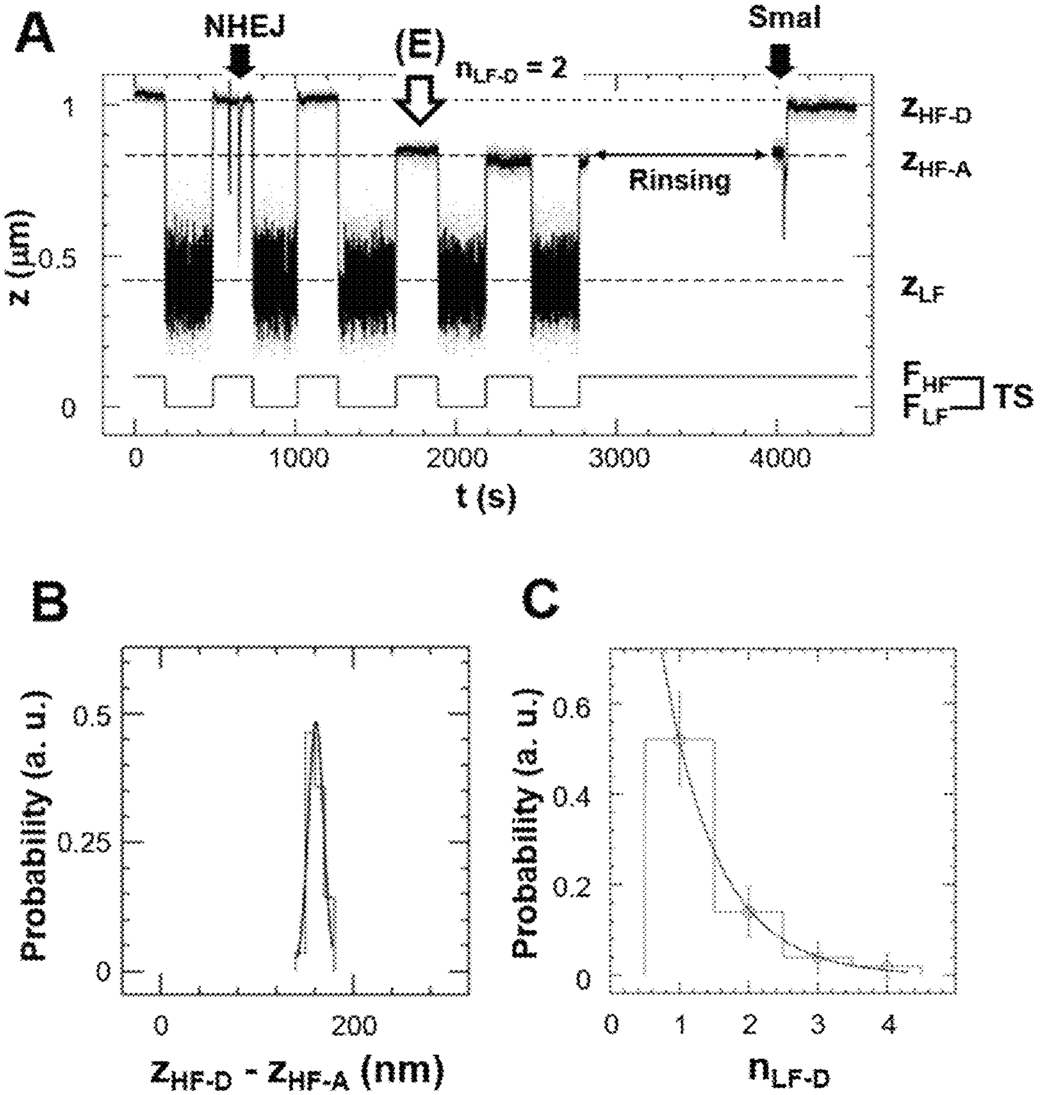
FIG. 11. Measurement, by force cycling, of the characteristic association time/ligation of two blunt ends of the extremities of the double-stranded DNA molecule in the presence of proteins participating in the human NHEJ repair system. These two blunt ends, where terminal phosphate groups are present in 5' and terminal hydroxyl groups are present in 3', constitute themselves the two test molecules here. The DNA molecule used corresponds to that shown in FIG. 1 in a device as illustrated in FIG. 2, and obtained by the manufacturing method described in Examples 3, 1 and then 9. Experiments were performed at 34° C. in RB buffer. A) Temporal monitoring of the extension of the double-stranded DNA molecule when the force is cycled between a high force $F_{HF}$=1.4 pN for time $T_{HF}$=300 s and a low force $F_{LF}$=0.05 pN for time $T_{LF}$=300 s (TS: schematic diagram of the $F_{HF}/F_{LF}$ cycles). HF corresponds to the application of a high force ("High Force"); LF corresponds to the application of a low force ("Low Force"). Test molecules can be either associated (A for "Associated") or dissociated (D for "Dissociated"). Test molecules are initially alone, then the proteins composing the NHEJ system are introduced into the capillary (indicated by the arrow). This leads to the formation of covalent bonds between the blunt ends after a certain number of passages at low force, a reaction which results in a shortening of the extension measured at high force. Here two passages at low force were necessary to obtain ligation. Finally, addition of the SmaI restriction enzyme allows the bonds between the blunt ends to be cleaved and maximum extension at high force to be recovered. Identification of the change of extension event (E) on the temporal trace is indicated by the white arrow. B) Histogram of the differences in extension, "$z_{HF-D}$-$z_{HF-A}$", between the HF-A (state of high force-test molecules associated) and HF-D states (state of high force-test molecules dissociated), and extraction of the average value, "$z_{HF-D}$-$z_{HF-A}$"=161 nm, by Gaussian fitting. C) Histogram of the number of passages at low force, $n_{LF-D}$, necessary to obtain the association/ligation and extraction of the characteristic association/ligation time, $\tau_A$, by exponential adjustment. The result expressed in number of passages, $n_{LF-D}$ is equal to 0.8±0.2; it can be converted into time by multiplication by $T_{LF}$, which leads to $\tau_A$=240±60 s.

By "temporal trace" we mean the monitoring of a molecular interaction (e.g. association/dissociation) as a function of an applied force and over time (as an example, see FIG. 10B or FIG. 11A).

In some cases, the measured extension (e.g. $z_{LF}$, $z_{HF-A}$, and/or $z_{HF-D}$) can be compared with an extension predicted by a theoretical model, such as the WLC (worm-like chain) elasticity model applied to the two conformations, A and D, for the two forces studied, $F_{LF}$ and $F_{HF}$. This model is particularly advantageous for describing the elastic behavior of the double-stranded DNA molecules (Bouchiat et al., 1999 and Sarkar and Rybenkov, 2016). However, other models, such as the freely jointed chain, may also be suitable (Doi, 1996, and Sarkar and Rybenkov, 2016).

Figure 8:
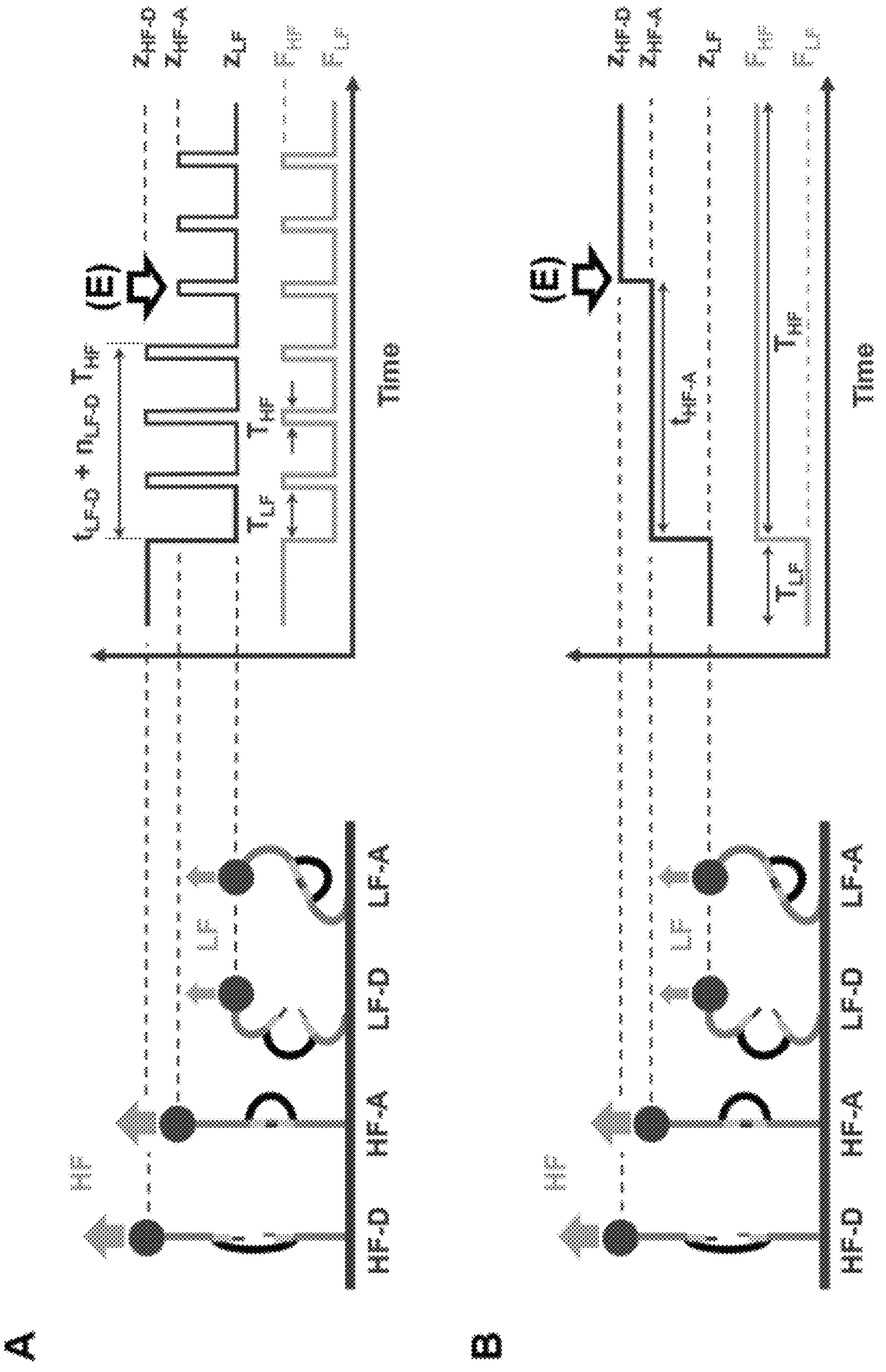
FIG. 8. Principle of measurement, by force cycling, of the lifetime, t, A) for the test molecules in their dissociated form and B) for the test molecules in their associated form. A single measurement cycle is represented here for each of the techniques; a sole lifetime is thus obtained for the test molecules attached to the single molecule of DNA considered. The conformation of the DNA molecule can be determined from the recording of the extension, z, over time when the force F is cycled between a high value ($F_{HF}$) and a low value ($F_{LF}$), for durations T ($T_{HF}/T_{LF}$, respectively). HF corresponds to the application of a high force ("High Force"); LF corresponds to the application of a low force ("Low Force"). The test molecules can be either associated (A for "Associated"); or dissociated (D for "Dissociated"). Plotting changes of extension event (E) on the time traces makes it possible to determine t. "n" corresponds to the number of cycles performed before detecting an event in association experiments. More precisely, the measurement of the lifetime for the test molecules in dissociated form, $t_{LF\text{-}D}$, involves the determination of $n_{LF\text{-}D}$, the number of cycles performed before detection of an event and the multiplication of that by $T_{LF}$. The measurement of the lifetime for the molecules in associated form, $t_{HF\text{-}A}$, is done directly on the temporal monitoring.

In a preferred embodiment, a physical force, e.g., a tension, is applied to the double-stranded DNA molecule when the supports are separated. When the high physical force is greater than or equal to 0.5 pN, 1 pN, 5 pN, 10 pN, 15 pN, 20 pN, 30 pN, 40 pN, 50 pN, or 60 pN it becomes easy to distinguish conformational changes by measuring the z-extension, and thus to determine if the test molecules are associated or dissociated (FIG. 8). When the force is low (e.g. less than 0.4 pN) the extension decreases and the test molecules associate more easily as they are closer. However, at low force it is impossible to determine conformation (FIG. 8, FIG. 10A).

Preferably, the low force corresponds to a constant force (i.e. only one applied low force). Preferably, the high force corresponds to a constant force (i.e. a single applied high force). Preferably, the applied force is cycled between a constant high force (e.g. greater than or equal to 0.5 pN) and a constant low force (e.g. equal to or less than 0.4 pN), as illustrated in FIG. 8.

Figure 17:
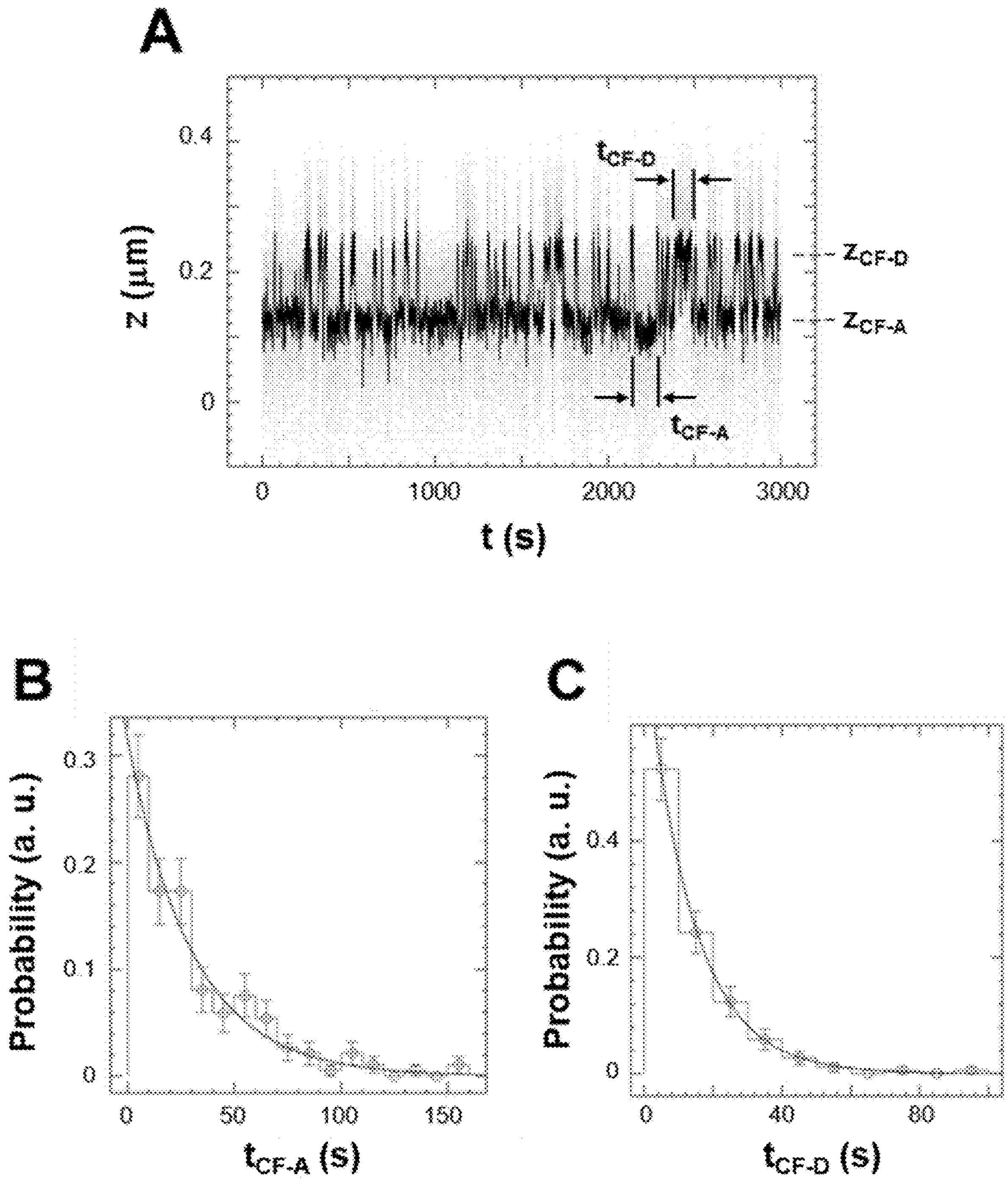
FIG. 17. Measurement, by study of spontaneous fluctuations, of the characteristic dissociation time and the characteristic association time of the non-covalent bond linking the FKBP12 and FRB proteins in the presence of rapamycin at 500 nM. FKBP12 and FRB proteins constitute the two test molecules here. The DNA molecule used corresponds to that shown schematically in FIG. 1 in a device as illustrated in FIG. 2, and obtained by the manufacturing method illustrated in FIG. 6 followed by the methods illustrated in FIGS. 4 and then 5 (described in Examples 3, 1 and then 2). Experiments are performed at 25° C. in the DB buffer. A) Temporal monitoring of the extension of the double-stranded DNA molecule when the force is maintained at a constant value ($F_{CF}$=0.04 pN). CF corresponds to the application of a constant force ("Constant Force"). Test molecules can be either associated (A for "Associated") or dissociated (D for "Dissociated"). The dissociation of the test molecules occurs at the end of a time indicated as $t_{CF-A}$ and the association at the end of a time noted $t_{CF-D}$. B) Histogram of $t_{CF-A}$ at a constant force of 0.04 pN and extraction of the characteristic dissociation time, $\tau_D$=30.4±2.7 s, by exponential adjustment. C) Histogram of $t_{CF-D}$ at a constant force of 0.04 pN and extraction of the characteristic association time, $\tau_A$=13.7±1.1 s, by exponential adjustment. D) Temporal monitoring of the extension of the double-stranded DNA molecule when the force is maintained at a constant value (TS: $F_{CF}$ schematic trace) and molecules identical to one of the test molecules are present in solution. CF corresponds to the application of a constant force ("Constant Force"). The test molecules can be either associated (A for "Associated") or dissociated (D for "Dissociated"), in the latter case one of the test molecules can be either free or complexed by one of the molecules in solution. $F_{CF}$=0.04 pN permanently and [FRB]=100 nM. The test molecules associate and dissociate spontaneously, one of the two can also react spontaneously with the molecules present in solution. The dissociation of the test molecules occurs after a time indicated as $t_{CF\text{-}A}$ and the association at the end of a time indicated as $t_{CF\text{-}D}$. E) Variation of the characteristic dissociation time averaged over several molecules, $<\tau_D>$, as a function of the concentration of [FRB], obtained at a constant force of 0.04 pN. The horizontal continuous line corresponds to the average value obtained at all concentrations; 30.6 s is obtained. F) Variation in the fraction of time spent by the test molecules in associated form, $(\Sigma t_{CF\text{-}A})/t_{total}$, as a function of the concentration of [FRB], obtained at a constant force of 0.04 pN. The data is then adjusted using $(\Sigma t_{CF\text{-}A})/t_{total}=((1+K_0)+[FRB]/C_{eff})^{-1}$, which leads to $C_{eff}=12.3$ nM and $K_0=0.59$.
Figure 17:
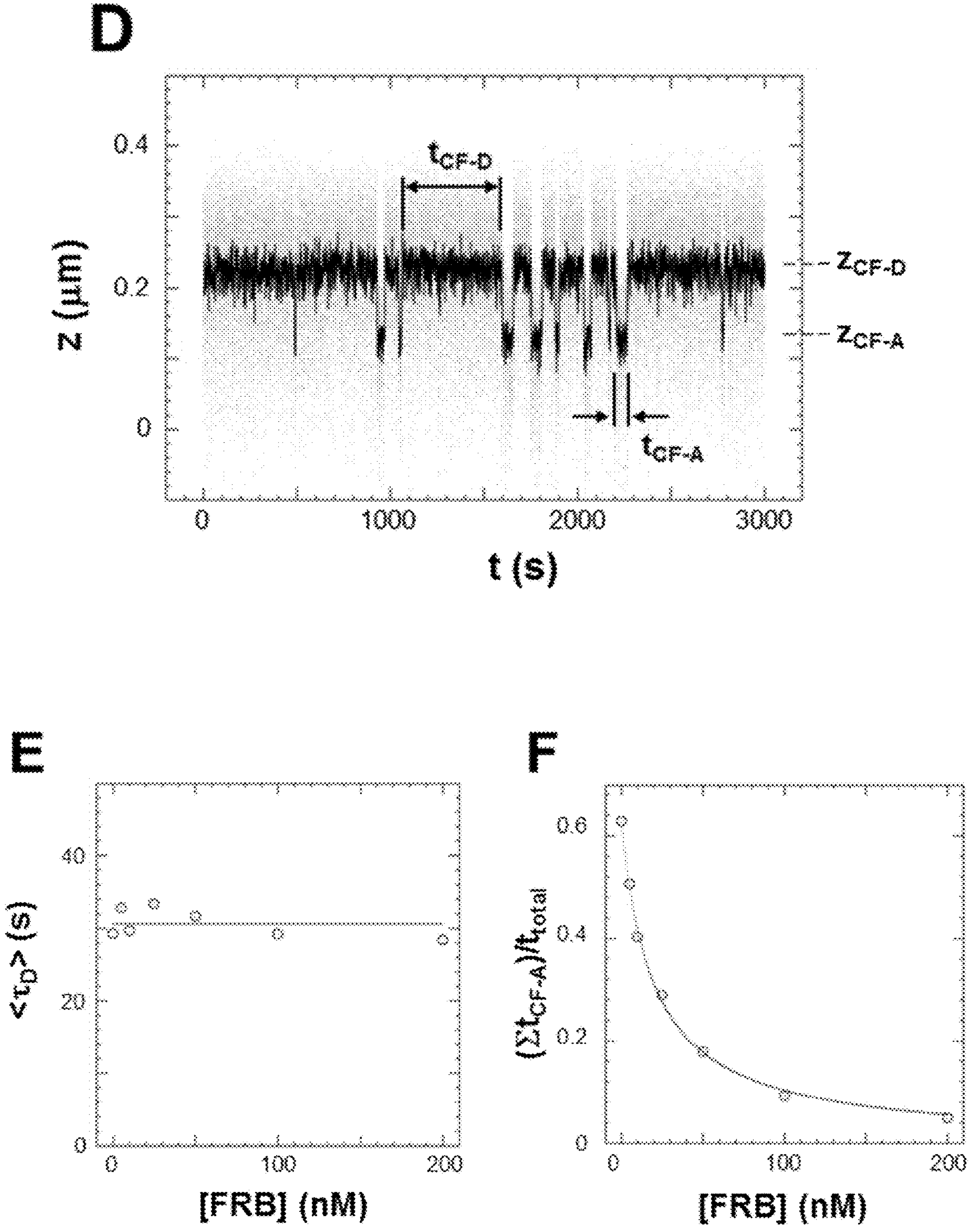

Alternatively, the spontaneous fluctuations in the distance between the supports, respectively of the force, are observed at constant applied force (see, e.g., Kim et al., 2010), respectively at a constant distance (see, e.g., Kilchherr et al. al., 2016), as shown in FIG. 17. In a third embodiment, the applied force can be increased between a low force and a high force linearly over time (e.g. an increase in force of 0.01 pN/s) and the entire curve giving the extension as a function of the measured force (see, e.g., Kim et al., 2010, Halvorsen et al., 2011 and Kilchherr et al., 2016).

Preferably, the physical force applied in step a) is of the order of 0.01 pN to 0.4 pN, preferably comprised between 0.01 pN and 0.1 pN. Indeed, below a physical force of 0.01 pN, it becomes difficult to determine $z_{LF}$ specifically enough due to background noise. Advantageously, the physical force applied in step a) is constant.

Preferably, the physical force applied in step b) is greater than or equal to 0.5 pN, preferably between 0.5 and 70 pN. Indeed, at a physical force beyond 70 pN, the tether risks opening as the attachment points to double-stranded DNA molecules (1) and (2) are located on opposite strands. However, in some cases the physical force applied may be greater than 70 pN, in particular when stronger interactions must be investigated and/or both strands of the tether have been cross-linked by chemical agents (e.g. psoralen or cisplatin). Preferably, the physical force applied will remain below the threshold of plastic deformation of the DNA (e.g., 70 pN, in the absence of crosslinking of the tether). Preferably, the physical force applied in step b) is constant.

According to a first preferred embodiment, when interaction studies involve small molecules as test molecules, the physical force in step b) is preferably comprised between 0.5 and 70 pN.

According to a first preferred embodiment, when interaction studies involve proteins as test molecules, the physical force in step b) is preferably comprised between 0.5 and 40 pN. Indeed, above this threshold, certain proteins begin to denature.

The physical force applied can vary with the temperature, the type of test molecule and the buffer, but the skilled person will easily adapt said physical force with respect to these parameters in order to measure molecular interactions.

Figure 12:
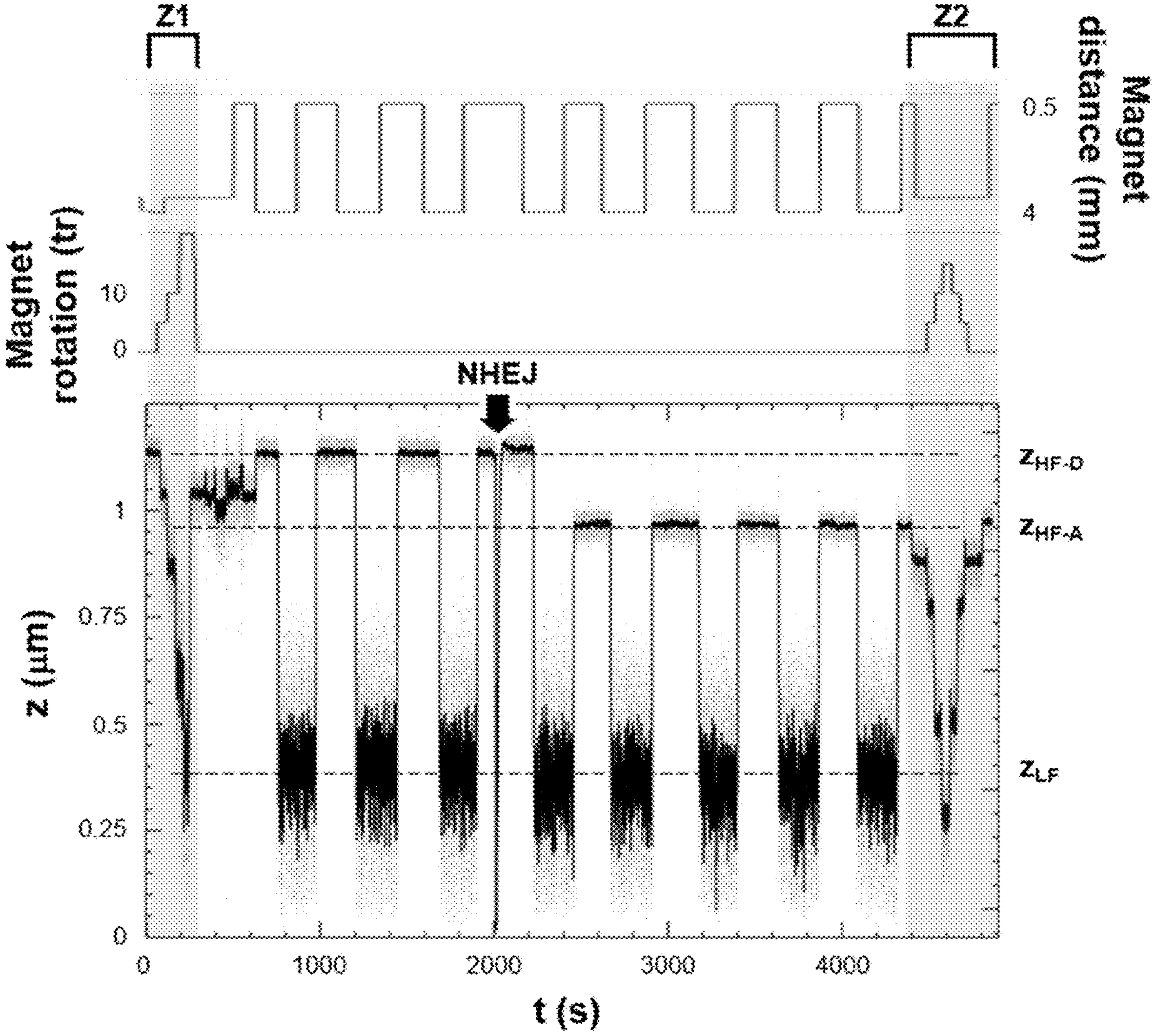
FIG. 12. Demonstration of the ability of the device to apply a torque to the test molecules when they are associated, this during the study of the interactions between two blunt ends of the extremities of the double-stranded DNA molecule and the proteins involved in the human NHEJ repair system. These two blunt ends, where terminal phosphate groups are present in 5' and terminal hydroxyl groups are present in 3', constitute themselves the two test molecules here. The DNA molecule used corresponds to that shown in FIG. 1 in a device as illustrated in FIG. 2, and obtained by the manufacturing method described in Examples 3, 1 and then 9. Experiments were performed at 34° C. in RB buffer. The extension of the double-stranded DNA molecule (lower panel) is followed as a function of the variation of magnet position, which corresponds to a variation of the force (upper panel), and magnet orientation (middle panel). A first test of low-force supercoiling (about 0.4 pN, first zone, Z1) is performed prior to the introduction of the repair proteins and no variation in the height of the bead is observed as the junctions allow a free rotation of the various functional elements of the DNA molecule (e.g. the tether and double-stranded DNA molecules (1) and (2)). A second supercoiling test (second zone, Z2) is performed after the introduction of the NHEJ system proteins and repair at the blunt ends, the height of the bead now varies according to magnet angle, indicating that both extremities have been ligated and no nicks exist along the sequence of the double-stranded DNA molecule (1) or the double-stranded DNA molecule (2).

In some cases, a torque may also be applied to the double-stranded DNA molecule. The double-stranded DNA molecule according to the invention is highly advantageous as it can be used to perform mechanical studies of torsional response of the complex formed by the test molecules (FIG. 12).

The comparison of distances $z_{LF}$, $z_{HF-A}$, and $z_{HF-D}$ as a function of time (t) advantageously makes it possible to determine at least one of the characteristics chosen from: the dissociation rate constant, the activation energy of dissociation, the equilibrium dissociation constant. It is also advantageously possible to determine the characteristic dissociation time, which is the inverse of the dissociation rate constant, and the equilibrium association constant, which is the inverse of the equilibrium dissociation constant. Specifically, comparing these distances over time gives the "lifetime" of the associated and/or dissociated conformation of the test molecules, noted $t_{LF-D}$ for association experiments and $t_{HF-A}$ for dissociation experiments.

The "characteristic dissociation time" corresponds more particularly to the length of time during which the z extension of the molecule, corresponding to an associated state, is detected. Likewise, the "characteristic association time" corresponds more particularly to the length of time during which the z extension of the molecule, corresponding to a dissociated state, is detected.

When the applied force is cycled between a constant high force and a constant low force, one or more "t" values may be collected. The "t" values are preferably grouped in the form of a histogram, to be analyzed by exponential adjustment and to determine the characteristic dissociation time $\tau_D$ the characteristic dissociation time $\tau_A$. For example, the $t_{LF-D}$ histogram gives the characteristic association time $\tau_A$ using the formula Probability$\propto$exp$[-t_{LF-D}/\tau_A]$ and the histogram of $t_{HF-A}$ gives the characteristic association time $\tau_D$ using the formula Probability$\propto$exp$[-t_{HF-A}/\tau_D]$. From the characteristic dissociation time, $\tau_D$, it is notably possible to calculate the dissociation rate constant, $k_D$, by inversion: $k_D=1/\tau_D$.

The "distance separating the transition state from the complex during dissociation" corresponds to the distance at which the configuration of the test molecules (e.g. associated state) will always go towards another configuration (e.g. dissociated state). The transition state is a feature well-known to the skilled person (see, e.g., Pilling and Seakins, 1995). As an example, by performing experiments for different $F_{HF}$ and/or temperature values, the skilled person can determine the distance separating the transition state from the complex during dissociation, this using the Arrhenius/Bell equation (Popa et al., 2011). Similarly, the skilled person can determine the activation energy of the dissociation reaction (Popa et al., 2011).

In some cases, the method further comprises a step of comparing said characteristic with a reference value.

The method as described above may further comprise the following step:

d) adding at least a third molecule.

When the third molecule is not incorporated in the double-stranded DNA molecule according to the invention, it is preferably added in the environment of the device, more preferably in aqueous solution. Thus, according to a preferred embodiment, the method of characterizing an interaction takes place in an aqueous environment. According to a particular embodiment, the concentration of said third molecule may vary over time. The method according to the invention may notably be used to characterize interactions in the presence or absence of at least a third molecule which has an agonistic or antagonistic activity on interactions, such as a cofactor, an orthosteric or allosteric inhibitor, etc.

In some embodiments, association and dissociation kinetics may be determined by measuring the lengths of the DNA molecule over a period of time, possibly in one or more experimental conditions (e.g., by changing the physical force applied in step b), pH, salinity, buffer, temperature, etc.).

Thus, the process according to the invention is highly advantageous as it makes it possible to perform complex experiments on the same pair of test molecules, by introducing other molecules interacting with the two test molecules, and/or by changes in the experimental conditions (e.g. physical force, pH, salinity).

Advantageously, the method of the invention makes it possible to measure parameter $\tau_D$, which makes it possible to evaluate the lifetime of the interactions between test molecules, e.g. by plotting the histogram of the lifetime of the associated form (Example 7).

However, it is also advantageous to measure $\tau_A$, the characteristic time of formation of the interactions, e.g. by plotting the histogram of the lifetime of the dissociated form (Example 7). When the tether has a fixed length, different experimental conditions can be compared: presence/absence of certain reagents (e.g. to understand recruitment mechanisms), pH, salinity, temperature.

The methods for characterizing molecular interactions according to the invention involve the detection of changes in length of the double-stranded DNA molecules according to the invention. The interactions may be detected or determined using a number of techniques known in the art, including those which also allow micromanipulation and application of force: atomic force microscopy, optical tweezers, magnetic tweezers, centrifugal force microscopy, biomembrane force probe, acoustic force spectroscopy, micromanipulation using mechanical cantilevers or microneedles, etc. The detection of changes in length of the double-stranded DNA molecules according to the invention can also be performed using techniques that do not allow micromanipulation: tethered particle motion, fluorescence microscopy (possibly in an evanescent field), fluorescence spectroscopy (possibly resolved in space and/or time) according to quenching modes, resonance energy transfer, etc. Any of these techniques may be used in conjunction with the double-stranded DNA molecule, the device, and the methods described herein. These techniques are known in the art and some are briefly described below (see also, e.g., Conroy, 2008).

As an example, the force between two test molecules incorporated in the double-stranded DNA molecule according to the invention can be measured by atomic force microscopy (AFM). In some embodiments, AFM can be used to measure the stretching and breaking forces of a single molecule linker. In some embodiments, the measured force may be in the range of a few pN. In some embodiments, the AFM is performed in static or dynamic mode.

The force between two test molecules incorporated in the double-stranded DNA molecule according to the invention can be measured using an optical tweezer (also called a single beam gradient force trap). Optical tweezers use a highly focused laser beam to provide an attractive or repulsive force (typically in the range of pN), as a function of refractive-index mismatch, to physically maintain and move microscopic dielectric objects, such as DNA. In some embodiments, optical tweezers are used to manipulate the double-stranded DNA molecule by exerting extremely low forces via a highly focused laser beam. In some embodiments, optical traps can be used to detect the displacement of DNA as a measure of molecular force.

The force between two test molecules incorporated in the double-stranded DNA molecule according to the invention can be measured using a magnetic tweezer. Magnetic tweezers exert a force and a torque on a molecule such as the double-stranded DNA molecule of the invention. The extension of the molecule corresponds to its response to the applied stress. Advantageously, a magnetic tweezer apparatus is equipped with magnets that are used to manipulate magnetic particles, the position of which is measured with video-microscopy. The force between two test molecules incorporated into the double-stranded DNA molecule according to the invention can be measured using centrifugal force microscopy. CFM exerts a force on a molecule such as a nucleic acid complex of the invention using a centrifugal force. The extension of the molecule corresponds to its response to the applied stress. In some embodiments, a complex is attached at extremity end to a fixed support and at the other to a particle that can be visualized using, e.g., optical microscopy. The position of the particle and its motion relative to the fixed support can be observed and measured as a function of the centrifugal force applied to the double-stranded DNA molecule.

Other mechanical force measurement technologies can be used with the embodiments described herein, e.g. mechanical cantilevers, biomembrane force probes, and the like.

The molecule, the device, and the method according to the invention can be used in a large number of applications, notably in conjunction with one of the techniques described above. In addition to studies of the mechanical properties and interactions between two test molecules, they can also be used to detect analytes in solution, to perform competitive binding studies, to screen molecules, etc.

For example, competitive binding assays can be performed, notably by introducing molecules before or after the establishment of a bond between the at least two test molecules. In some embodiments, once the two test molecules are bound to one another, soluble forms or fragments of the first and/or second test molecule may be added in excess; these bind to the first and/or second test molecule and compete with their bound counterpart, before detecting a change in binding (e.g. by determining the z-extension).

In one aspect, the molecule, device, and method of the invention can be used to detect the presence of an analyte of interest in a sample, e.g. for diagnostic purposes. According to this aspect, the DNA molecule comprises at least two test molecules that have a specificity for a same analyte. In some cases, the at least two test molecules may be identical, provided that they can simultaneously bind to the analyte. For example, they may be identical antibodies, provided that the antigen to which they bind has multiple epitopes that can be bound by the different antibodies simultaneously and without interference. Alternatively, the at least two test molecules may be different from each other but have a binding affinity for the same analyte. For example, they may be antibodies that bind to different epitopes on the same antigen provided they can bind to the antigen simultaneously and without interference. The length of the DNA molecule when test molecules bind the analyte or not can be used to determine the presence or absence of an analyte in a sample. If the analyte is present, the test molecules will bind to the analyte. In the absence of the analyte, no binding will occur and the extension will correspond to $z_{HF-D}$.

In another aspect, the molecule, device, and method of the invention can be used in methods for screening molecules. In this case, only one or both test molecules may be known to interact. In some embodiments, one of the two test molecules is a member of a library of molecules identified as being able to putatively interact with the other test molecule, and the method is designed to screen the different molecules of the library in order to identify molecules having an affinity for a particular target (i.e. the other test molecule). In some embodiments, the test molecules are known to have affinity for each other, whereas in other embodiments, it is not a priori known whether they have mutual affinity or if the extent of affinity of a given pair is known.

Kit

The invention also pertains to kits for the manufacture of the double-stranded DNA molecule according to the invention. Such a kit may include at least:

- an intermediate DNA molecule having pre-established lengths of molecules (A) and (B) according to experimental requirements,
- optionally, oligonucleotides and/or DNA molecules comprising functional groups,
- optionally, one or more test molecules, advantageously linked to oligonucleotides.

According to a preferred embodiment, the kit comprises at least the double-stranded DNA molecule according to the invention, with or without the integration of the test molecules into said DNA molecule.

According to another preferred embodiment, the kit comprises the device according to the invention, with or without the integration of the test molecules in the double-stranded DNA molecule according to the invention which is included in said device.

The kit may further contain at least one of any of the other molecules or reagents described herein (e.g., a polymerase, a ligase, dNTPs, one or more reaction buffers, one or more supports such as magnetic beads or glass slides). The different components of the kit may be present in separate containers. When certain components are compatible, they may be pre-combined into a single container, as desired.

In addition to the components mentioned above, the kits according to the invention may further comprise instructions for using said components of the kit, more particularly for implementing the methods of the invention (e.g. instructions for synthesizing the DNA molecule double-strand according to the invention, instructions for generating the device according to the invention, etc.).

The practice of the invention uses, unless otherwise indicated, conventional techniques of protein chemistry, molecular biology, microbiology, recombinant DNA technology and pharmacology, which are within the skill of the art. Such techniques are fully explained in the literature. (See Ausubel et al., Current Protocols in Molecular Biology, Eds., John Wiley & Sons, Inc. New York, 1995; Remington's Pharmaceutical Sciences, 17th ed., Mack Publishing Co., Easton, Pa., 1985; Sambrook et al., Molecular cloning: A Laboratory Manual, 2nd Edition, Cold Spring Harbor Laboratory Press—Cold Spring Harbor, NY, USA, 1989; Lahann, Click Chemistry for Biotechnology and Materials Science, John Wiley & Sons, Chichester, England, 2009).

EXAMPLES

The invention is illustrated by the following non-limiting examples. These teachings include alternatives, modifications and equivalents, which may be recognized by a skilled person.

Example 1: Method of Manufacturing the Double-Stranded DNA Molecule

The protocol provided below corresponds to the synthesis of the DNA molecules used in Examples 8 and 9. With regard to those used for Examples 10 and 12, several variants were provided, which are summarized in Table 1, below.

TABLE 1

Summary of information concerning molecular sizes and sequences, according to the Examples

| | Examples 8 and 9 | Example 10 | Example 8 (tether of 6 kbp) | Example 12 |
|---|---|---|---|---|
| SEQ ID NO of molecule (A) | 9 | 30 | 9 | 45 |
| Size of molecule (A) prior to digestion of step A) | 3,000 bp | 2,100 bp | 3,000 bp | 2,100 bp |
| SEQ ID NO of molecule (B) | 10 | 10 | 43 | 10 |
| Size of molecule (B) | Approx. 700 bp (689 bp) | Approx. 700 bp (689 bp) | Approx. 6,000 bp (6,058 bp) | Approx. 700 bp (689 bp) |
| Total size of the DNA molecule prior to Step A) | 3,700 bp | 2,800 bp | 9,000 bp | 2,800 bp |
| Size of fragments connected to the tether after the digestion of Step A) | 1,500 bp and 1,500 bp | 700 and 1,400 bp | 1,500 bp and 1,500 bp | 700 and 1,400 bp |
| Enzyme used to digest the molecule of SEQ ID NO: 1, labelled with biotin | SacI | XbaI | SacI | XbaI |

TABLE 1-continued

Summary of information concerning molecular sizes and sequences, according to the Examples

| | Examples 8 and 9 | Example 10 | Example 8 (tether of 6 kbp) | Example 12 |
|---|---|---|---|---|
| Enzyme used to digest the molecule of SEQ ID NO: 1, labelled with digoxigenin | XbaI | SacI | XbaI | SacI |
| Total size of the DNA molecule after Step B) | Between 5,700 and 6,300 bp | Between 4,800 and 5,300 bp | Between 11,000 and 11,600 bp | Between 4,800 and 5,300 bp |
| SEQ ID NO of molecule (1) | 26 or 27 | 28 or 29 | 26 or 27 | 47 or 48 |
| SEQ ID NO of molecule (2) | 31 or 32 | 33 or 34 | 31 or 32 | 49 or 50 |

Step a) Synthesis of Double-Stranded DNA Molecules (1) and (2)

Figure 3:
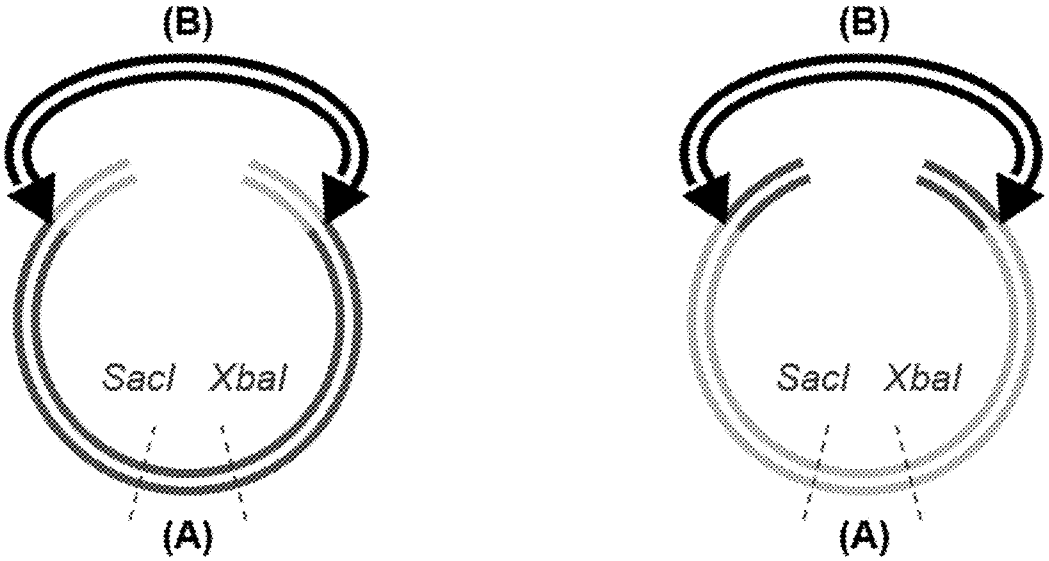
FIG. 3. Conceptual representations of an "intermediate" double-stranded DNA molecule comprising a first double-stranded DNA molecule (A) and a second double-stranded DNA molecule (B). The molecule (B) corresponds to the tether. The molecule (A) corresponds to the precursor of the double-stranded DNA molecules (1) and (2). As an example, the regions of the double-stranded DNA molecule (A) that can correspond to the extremities of the two double-stranded DNA molecules (1) and (2) to which test molecules can be linked are illustrated in light gray, according to two different configurations.

Digestion of the "intermediate" DNA molecule (shown in FIG. 3, having the sequences of SEQ ID NO: 9 (corresponding to the sequence of the DNA molecule (A)) and SEQ ID NO: 10 (corresponding to the sequence of the DNA molecule (B)) with two restriction enzymes allows for linearization. At the same time, two non-complementary cohesive ends are obtained (FIG. 4A). In this embodiment, the enzymes XbaI and SacI are used.

More specifically, after digestion with XbaI and SacI enzymes, a DNA product of about 3.7 kbp (kilobase pairs) composed of molecule (B) of about 700 bp (corresponding to the tether) and of two linear double-stranded DNA molecules (corresponding in part to double-stranded DNA molecules (1) and (2)) of 1.5 kbp is obtained. In each DNA molecule (1) and (2), each extremity of the tether is attached to a nucleotide base which is located about 40 to 50 bp from the ends being opposite those generated by digestion with XbaI and SacI.

XbaI and SacI digestion of the intermediate DNA molecule is performed simultaneously for 7 to 8 hours at 37° C. in a total volume of 80 μl of aqueous solution, the ionic conditions of which are fixed by the use of the CutSmart reaction buffer according to the manufacturer's recommendations (New England Biolabs). The reaction comprises 6 μg of the "intermediate" DNA molecule, 100 units of XbaI, and 50 units of SacI. The reaction is stopped by inactivating the restriction enzymes by passage through a purification column of the Nucleospin Gel and PCR Cleanup kit (Macherey-Nagel).

Step B): Synthesis and Assembly of Functionalized Extremities for Supports

A first double-stranded DNA fragment having a length of about 2,300 base pairs is synthesized by PCR by incorporating nucleotides modified by biotin, the molecule complementary to streptavidin that coats the magnetic bead which will serve as the support. The oligonucleotides used to amplify this first fragment (having the sequence of SEQ ID NO: 1, amplified from the phage A genome) have the corresponding 5'-GCGTATTAGCGACCCATCGTCTTTCTG-3' et 5'-GATGCACGCAATGGTGTAGCAATAATTGC-3' sequences, respectively, corresponding to sequences of SEQ ID NO: 2 and 3). More specifically, the PCR reaction is performed in a final volume of 100 μl of aqueous solution, distributed in two tubes of 50 μl each. These 100 μl include 50 ng of template (the bacteriophage λ genome), 30 pmol of priming oligonucleotides, 10 nmol of each deoxyribonucleotide triphosphate, 3.5 units of the "Expand High Fidelity" thermostable polymerase mixture (Roche), 5 nmol of biotin-16-dUTP (Roche), and the reaction buffer provided by the manufacturer (Roche) at a final concentration of 1× according to the manufacturer's instructions (Roche). The PCR program employed consists of a first step of 2 min at 95° C., followed by a second step of 15 s at 95° C., followed by a third step of 30 s at 56° C., followed by a fourth step of 80 s at 72° C., followed by 25 repetitions of the second, third, and fourth steps in succession. At the end of the program a final step of 3 min at 72° C. is performed, then the sample is brought to 16° C. The reaction product is then purified with a PCR Cleanup Kit (Macherey-Nagel).

This first fragment is then digested with SacI to generate two fragments of about 1300 bp and about 950 bp, each having a cohesive end complementary to that of molecule (1). More specifically, the PCR product is first quantified by UV spectrophotometry. The digestion is then performed for 2 hours at 37° C. in a reaction volume of 50 μl of aqueous solution comprising 5 μg of labeled DNA, 100 units of SacI (New England Biolabs), and the "CutSmart" reaction buffer provided by the manufacturer (New England Biolabs) at a final concentration of 1× according to the manufacturer's instructions. The fragments obtained can then be purified by agarose gel electrophoresis and extracted from the gel with a Nucleospin Gel and PCR Cleanup kit (Macherey-Nagel). Alternatively, the fragments can also be simply purified with a Nucleospin Gel and PCR Cleanup kit (Macherey-Nagel). The digested and purified fragments are then quantified by UV spectrophotometry.

A second double-stranded DNA fragment of approximately 2300 base pairs in length is synthesized by PCR by incorporating nucleotides modified with digoxigenin, a molecule complementary to the antibody that will coat the glass coverslip and which will serve as the second support. The protocol followed for this PCR is the same as above, using the same oligonucleotides (according to the sequences of SEQ ID NO: 2 and 3) amplifying the same fragment of the phage λ genome, with the biotin-16-dUTP being replaced with the stable form under alkaline conditions of digoxigenin-11-dUTP (Roche).

This second double-stranded DNA fragment is then digested with XbaI to prepare two fragments of about 1050 bp and about 1200 bp each carrying a cohesive end complementary to that of molecule (2). More specifically, the PCR product is first quantified by spectrophotometry. The digestion is then performed for 2 h at 37° C. in a reaction volume of 50 μl of aqueous solution comprising 5 μg of labeled DNA, 250 units of XbaI (New England Biolabs), and the "CutSmart" reaction buffer provided by the manufacturer (New England Biolabs) at a final concentration of 1× according to the manufacturer's instructions. The fragments obtained can then be purified by gel electrophoresis and extracted from the gel with a Nucleospin Gel and PCR Cleanup kit (Macherey Nagel). Alternatively, the fragments can also be simply purified with a Nucleospin Gel and PCR Cleanup kit (Macherey-Nagel). The digested and purified fragments are quantified by UV spectrophotometry.

The substrate used for the PCR reactions here is the genome of phage λ, though this is not obligatory. The length of the functionalized extremities may vary up to 10,000 bp though the value of about 1000 bp is a good compromise between production yield and the attachment efficiency of the DNA molecules according to the invention under a microscope. It is also possible to imagine shorter DNA fragments and/or carrying a single small reactive molecule at their extremity. Finally, in other possible variants, functional groups other than biotin and digoxigenin may be employed, for example thiols which will attach to a gold-covered surface.

The synthesis of the double-stranded DNA molecule is finalized by ligation of the biotin and digoxigenin-labeled fragments to DNA molecules (1) and (2), respectively, using the DNA ligase of phage T4 (FIG. 4B).

Specifically, a ligation reaction in a total volume of 10 μl was performed under the conditions recommended by the manufacturer (1×T4 DNA Ligase buffer of New England Biolabs), the DNA molecule was at a concentration of 3 nM, the biotin and digoxigenin labeled fragments were each at 9 nM; 200 units (0.5 μl) of T4 DNA ligase were used to ligate the DNA for 3 hours at room temperature before thermally inactivating the ligase.

Double-stranded DNA molecules (1) and (2) having the sequences according to the SEQ ID NOs indicated in Table 1 above are obtained.

Example 2: Arrangement of the Extremities for the Test Molecules

The sequences of the extremities were chosen so as to be able to generate, by enzymatic digestion, non-complementary cohesive ends allowing the binding of two oligonucleotide-test molecule conjugates by specific hybridization and then ligation (see FIG. 5).

Step A): Digestion of the Extremities

The Nb.BbvCl enzyme was used for digestion of the extremities (FIG. 5A). This "nicking" enzyme cleaves only one of the two strands of the double helix, which allows relatively long cohesive ends to be generated. In addition, the cohesive ends formed may have any sequence desired by the developer, within the exception of a few immutable bases at the recognition site. This is in contrast with conventional restriction enzymes which often yield only four nucleotides of fixed sequence. In the present case, 5'-overhang ends having 9 nucleotides are generated. This value of 9 nucleotides is advantageous at it is, on the one hand, large enough to allow stable and specific targeting of each of the extremities by molecular recognition (the sequences produced are, of course, neither identical nor complementary) and, on the other hand, short enough to avoid any problems of extraneous folding/hybridization. This digestion step may be performed at the same time as step A of Example 1.

More specifically, the Nb.BbvCl digestion of the intermediate DNA molecule is performed simultaneously with XbaI and SacI digestion of the intermediate DNA molecule, for 7 to 8 hours at 37° C. in a total volume of 80 μl of aqueous solution, the ionic conditions of which are fixed by use of the "CutSmart" reaction buffer according to the manufacturer's recommendations (New England Biolabs). The reaction comprises 6 μg of the "intermediate" DNA molecule, and, in addition to 100 units of XbaI and 50 units of SacI, 30 units of Nb.BbvCl (New England Biolabs). The reaction is stopped by inactivating the restriction enzymes by passage through a purification column of the Nucleospin Gel and PCR Cleanup kit (Macherey-Nagel). The removal of the complementary fragments after digestion is relatively easy, it is performed by purification on a 1% electrophoresis gel at 37° C. overnight.

Step B): Binding of Test Molecules to the Extremities

The test molecules, here the FRB and FKBP12 proteins, are conjugated to two oligonucleotides called oligo-$T^c$. Each of these has, at its 3' extremity, a sequence that is complementary to one of those present at the non-complementary cohesive ends of the extremities of DNA molecules (1) and (2). The conjugation of the proteins to the oligonucleotides was performed by click chemistry between a DBCO functional group carried at the 5' extremity of the oligo-$T^c$ and an azide functional group introduced into the protein sequence by mutagenesis and incorporation of an artificial amino acid, azido-phenylalanine, during expression. The FRB protein having the sequence of SEQ ID NO: 6, and comprising an azide group at position 2,020 by substitution of the alanine amino acid with 4-azido-L-phenylalanine, is conjugated to Oligo-$T^C_1$, having the 5'-TATATGAGGC-3' sequence of SEQ ID NO: 4. The FKBP12 protein having the sequence of SEQ ID NO: 7, comprising an azide group at position 1 by substitution of the methionine amino acid by 4-azido-L-phenylalanine, is conjugated to Oligo-$T^c_2$, having the sequence 5'-TTGTAAGAGC-3' of SEQ ID NO: 5. The first 5' "T" base in oligos-$T^c$ corresponds to DBCO-dT. Other conjugation systems between oligonucleotides and proteins are of course possible: the first may thus carry, for example, a maleimide, carboxylic or benzylguanine functional group which will react respectively with a cysteine, amine, or SNAP-tag functional group located on the second. These functional groups may also be located at the 3' extremity of the oligo-$T^c$ provided that the design of the extremities is modified such that oligonucleotide hybridization remains possible. Example 4 below describes a method of binding test molecules to extremities using such a conjugation system without the use of a "nicking" enzyme.

In the present embodiment, the oligonucleotide is directly linked to the test molecule. It is, however, conceivable to link the two species via a biopolymer-type spacer (e.g. double-stranded DNA, single-stranded DNA, RNA, polypeptide, protein), an organic polymer (e.g. PEG) or even a colloid (e.g. gold nanoparticle, quantum dot). The extremities may thus be lengthened and the nature of the interaction may be modulated (e.g. elimination of non-specific behavior, modification of the electrostatic environment).

The final step in the synthesis of the device is to hybridize the "oligonucleotide-protein" conjugates to the cohesive ends of the extremities and perform ligation using phage T4 DNA ligase (see also FIG. 5B). This ligation is performed in a total volume of 50 μl of aqueous solution for 5 h at 16° C. and comprises: 2.5 μmol of the DNA construct according to the invention, the extremities of which are already labeled with biotin and digoxigenin, 2.5 fmoles of the nucleoprotein complex corresponding to the FKBP12 protein coupled to Oligo-TC1, and 2.5 fmoles of the nucleoprotein complex corresponding to the FRB protein coupled to Oligo-TC2. The aqueous solution further contains DTT (2 mM), ATP (1 mM) and 200 units of T4 DNA ligase (New England Biolabs). The aqueous solution also contains a buffering agent (20 mM Tris, pH 7.5) and salt (300 mM NaCl). No thermal inactivation or purification step is applied thereafter.

Example 3: Method of Manufacturing the "Intermediate" Double-Stranded DNA Molecule Step A): Junction Synthesis This step consists of preparing, by covalent coupling of oligonucleotides, two Y-shaped structures (also called "junctions") which will make the link between DNA molecules (1) or (2) and the tether. More specifically, for each junction, a functional group carried by one of the extremities of a first oligonucleotide called oligo-L is reacted with a functional group present in the middle of a second oligonucleotide called oligo-TS (FIG. 6A). More particularly, in the present case, a DBCO functional group located at the 5' extremity of oligo-L and an azide functional group located in the middle of oligo-TS were used.

Alternative functional groups can however be used. For example, the reactive 5' extremity of oligo-L may be a maleimide-type group, in which case oligo-TS must carry a thiol-like modification in its middle. A 5' NHS group on oligo-L and an $NH_2$ group in the middle of oligo-TS can also be used. Other chemistries may also be found or developed in future, which will be compatible with this assembly procedure. In addition, for each chemistry, a certain number of variations are possible: exchange the 5' functional group of the oligo-L with the functional group located in the middle of the oligo-TS, position the functional group carried on oligo-L in 3', position the functional group integrated in the middle of the oligo-TS elsewhere than on a base (e.g. on the phosphate skeleton, on a sugar, on a spacer, etc.). In our embodiments, the two junctions are of the same functional nature. However, the two junctions may be of different functional natures, for example, according to one of the variants that are been listed above.

Figure 7:
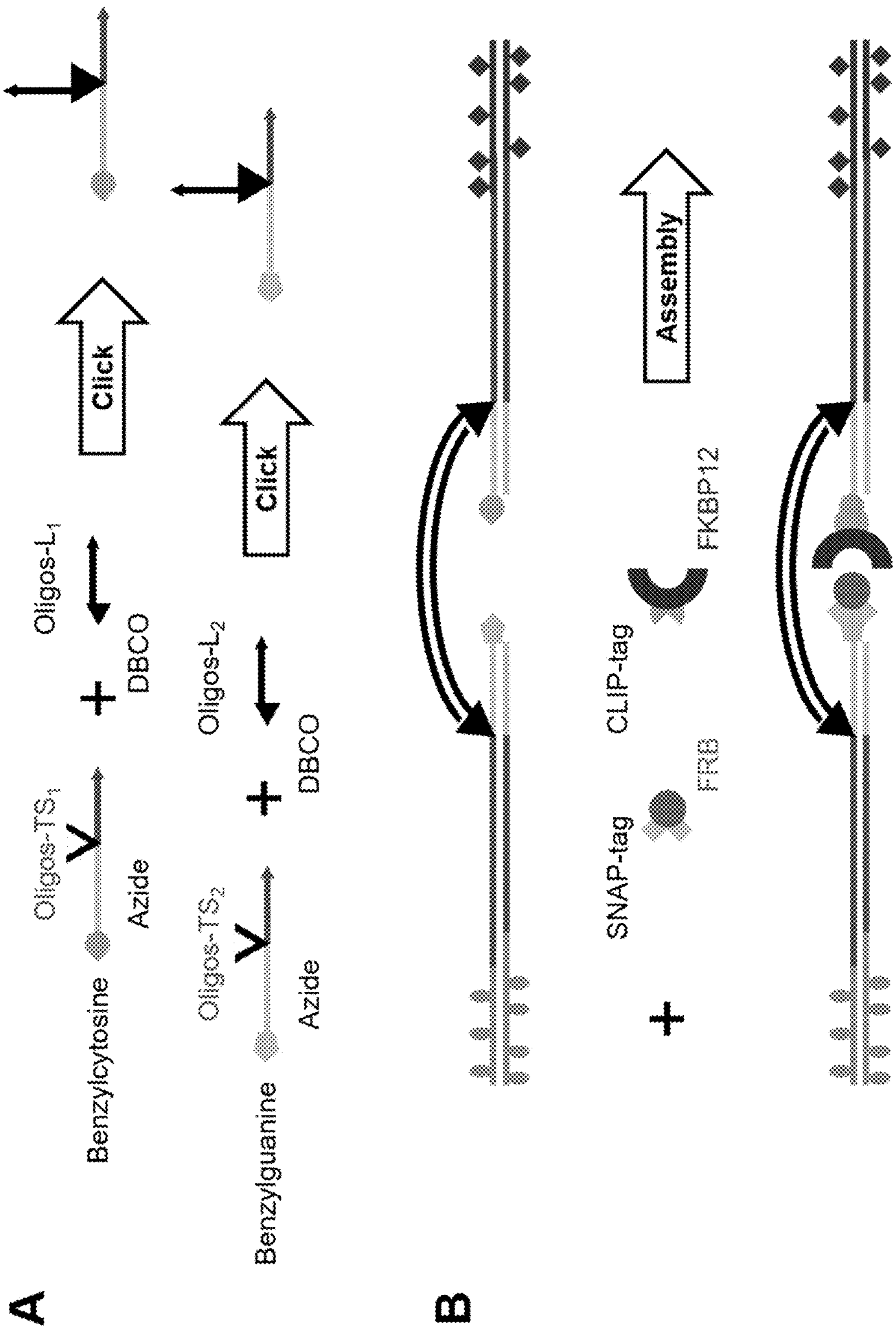
FIG. 7. Schema of the arrangement of the extremities intended for the test molecules, comprising the steps A) Synthesis of the junctions, B) Binding of the test molecules to the extremities.

The sequences of the four oligonucleotides, i.e. those of the two oligo-Ls and the two oligo-TSs are neither identical nor complementary, in order to be able to specifically hybridize. The number of bases of each oligo-L must simply allow the protocol to be continued, it is typically equal to 20 to 30 bases. The is also the case for the number of bases separating the functional group from the 3' extremity of each oligo-TS, its value is typically equal to 15 to 20 bases. In contrast, in the present example, the number of bases separating the functional group from the 5' extremity of each oligo-TS conditions the length of the extremities. Here, the length of the extremity is equal to 30 to 60 bases, but oligonucleotide synthesis capabilities can reach values of around 150 bases. Finally, the present step may correspond to the start of the introduction of functional groups or sequences (e.g. restriction sites) intended for the specific binding of the test molecules at the extremities. More specifically, two main binding modes are envisaged: either by hybridization of an oligonucleotide as detailed in Example 2 (FIG. 5), or by chemical reaction between specific functional groups as detailed in Example 4 (FIG. 7). In the first case we will choose the sequences judiciously in order to be able to generate ad hoc cohesive ends, i.e. capable of reacting orthogonally, in due course. In the second case, we will choose the functional groups judiciously in order to be able to orthogonally attach the test molecules in due course.

More specifically, in the present case, the oligonucleotides oligo-$L_1$ and oligo-$L_2$, where the first 5' thymine is a DBCO-dT base, and oligonucleotides oligo-$TS_1$ and oligo-$TS_2$, comprising an Azido-dT base in the middle of the oligonucleotide, as defined below in Table 2, were resuspended at 10 μg/μl in formamide at 37° C. 50 μg of each oligonucleotide Oligo-$L_1$ and Oligo-$TS_1$ were combined. Similarly, 50 μg each of Oligo-$L_2$ and Oligo-$TS_2$ were combined. As indicated in Table 2, the sequences of the oligonucleotides that are combined differ when the intermediate molecule is used downstream for performing Examples 8 and 9 or for performing Examples 10 or 9. Combined oligonucleotides were incubated 8 h at 37° C. and products corresponding to the covalently coupled oligonucleotides were separated on an 8% acrylamide:bisacrylamide (29:1) gel containing 8 M of urea operating at about 10V/cm in Tris borate-EDTA buffer. Gel slices corresponding to the product were excised from the gel, using a sacrificial imaging pathway to perform UV shading to identify the relevant bands. The DNA was purified by first eluting the DNA from the crushed gel fragment overnight in 10 mM phosphate buffer pH 8.0 with shaking at 4° C. A SepPak C18 (Waters) cartridge was conditioned with acetonitrile and then with water; the eluate was loaded onto the cartridge, washed with water, and the oligonucleotide was released from the cartridge by eluting with acetonitrile. The acetonitrile was evaporated by vacuum centrifugation and the oligonucleotide was resuspended at about 10 mM.

TABLE 2

Oligonucleotides used to synthesize junctions

| Oligonucleotide | Sequence* | SEQ ID NO | Example(s) |
|---|---|---|---|
| Oligo-$TS_1$ | 5'-GAGAGACCCGGGCACGACTTATCGCCACTGG CAGCAGCCACTGG<u>**T**</u>AACAGGATTAGCAGAGC-3 | 11 | 8 (tether of 0.7 and 6 kbp) and 9 |
| Oligo-$L_1$ | 5'-***T***GAGCCAAGACGCCTCCATCCATGCA-3' | 12 | 8 (tether of 0.7 and 6 kbp) and 9 |
| Oligo-$TS_2$ | 5'-GAGAGACCCGGGCACCGTCTCCTTCGAACTTA TTCGCAATGGAG<u>**T**</u>GTCATTCATCAAGGACG-3' | 13 | 8 (tether of 0.7 and 6 kbp) and 9 |
| Oligo- $L_2$ | 5'-***T***CCATGGGCATACTGATCGGTAGGG-3' | 14 | 8 (tether of 0.7 and 6 kbp) and 9 |

TABLE 2-continued

| Oligonucleotides used to synthesize junctions | | | |
|---|---|---|---|
| Oligo-nucleotide | Sequence* | SEQ ID NO | Example(s) |
| Oligo-$TS_1$ | 5'-ATATGAGGCTGAGGAAGCGGTTAGCTCCTTC GGTCCTCCGATCGTTG**<u>T</u>**CAGAAGTAAGTTGGCC GCAG-3' | 15 | 10 |
| Oligo-$L_1$ | 5'-***T***CCATGGGCATACTGATCGGTAGGG-3' | 16 | 10, 12 |
| Oligo-$TS_2$ | 5'-TGTAAGAGCTGAGGCGGTGACCAATATCTACA ACATCAGCC**<u>T</u>**TGGTATCCAGCGTGATG-3' | 17 | 10 |
| Oligo-$L_2$ | 5'-***T***GAGCCAAGACGCCTCCATCCATGCA- 3' | 18 | 10, 12 |
| Oligo-$TS_2$ | 5-***Z***GTAAGAGCTGAGGCGGTGACCAATATCTACA ACATCAGCC**<u>T</u>**TGGTATCCAGCGTGATG-3' | 39 | 12 |
| Oligo-$TS_2$ | 5'-***Q***TCTCAAGCTGAGGAAGCGGTTAGCTCCTTC GGTCCTCCGATCGTTG**<u>T</u>**CAGAAGTAAGTTGGCC GCAG-3' | 40 | 12 |

*the first "T" base indicated in bold and italic in 5' of the oligos-L corresponds to DBCO-dT (Glen Research, USA and Trilink, USA);
the "T" base indicated in bold and underlined in oligos-TS corresponds to Azido-dT (Trilink, USA),
*Z* corresponds to $O^2$-benzylcytosine-dT (New England Biolabs/Trilink), and
*Q* corresponds to $O^6$-benzylguanine-dA (New England Biolabs/Trilink).

Step B): Synthesis of Molecule (A)—the Precursor of DNA Molecules (1) and (2)

The two Y structures obtained above are used as primers in a PCR reaction to generate a double-stranded DNA molecule which will later be transformed into DNA molecules (1) and (2) (FIG. 6B). More specifically, the sequences at the 3' extremity of the two oligo-TSs hybridize to the substrate and serve to initiate polymerization. The two oligo-Ls do not intervene and are not modified by the PCR reaction. The double-stranded DNA produced therefore has, at each extremity, a junction having an oligo-L on one side and and an extremity whose functionalization with a specific sequence or functional group has been initiated on the other side. The sequence of this double-stranded DNA can be chosen by substrate selection: the Charomid 9-5 ΔSbfI cloning vector (a 9-5 Charomid plasmid derivative in which the naturally occurring SbfI site was removed by SbfI digestion, filling-in and re-ligation, having the sequence of SEQ ID NO: 8) was chosen here. In addition, the length of the product is determined by the position of the primers on the substrate: it is about 3050 base pairs in the case of Examples 8 and 9, of about 2100 base pairs in the case of Examples 10 and 12. This number can actually be up to about 10,000 base pairs, beyond which the yield of PCR reactions declines.

The PCR reaction is assembled by combining 1.25 μg of template DNA (Charomid 9-5 ΔSbfI, SEQ ID NO: 8), 90 pmol of "Y" structure oligonucleotide obtained by coupling Oligo-$TS_1$ (SEQ ID NO: 11) and Oligo-$L_1$ (SEQ ID NO: 12), 90 pmoles of "Y" structure oligonucleotide obtained by coupling Oligo-$TS_2$ (SEQ ID NO: 13) and Oligo-$L_2$ (SEQ ID NO: 14), 125 nmol of each of the four deoxyribonucleotide triphosphates, 5 μl of DMSO, 17.5 units of "Expand High Fidelity PCR System" thermostable polymerase mixture (Roche), 25 μl of reaction buffer provided by the manufacturer (Roche), and ultrapure water to reach a total volume of 250 μl. This volume is divided into ten tubes, each containing 25 μl. These ten tubes are subjected to thermal cycles according to the following protocol. The tubes are heated for 2 minutes at 94° C. Then, the tubes are subjected to 8 thermal cycles, each cycle comprising a step of 15 seconds at 94° C., followed by a step of 30 seconds at 72° C., followed by a step of 4 minutes at 68° C. At each iteration of these 8 cycles, the temperature used for the 30-second step is decreased by 2° C. compared to the previous iteration. Then, the tubes are subjected to 22 thermal cycles, each cycle comprising a step of 15 seconds at 94° C., followed by a step of 30 seconds at 56° C., followed by a step of 4 minutes at 68° C. Then the tubes are held for 7 minutes at 72° C. before their temperature is reduced to 16° C. to complete the reaction. The DNA molecule thus produced was then purified by column extraction using the Nucleospin Gel and PCR Cleanup kit (Macherey-Nagel).

Step C): Synthesis and Assembly of Molecule (B), Corresponding to the Tether

The tether is produced by PCR followed by digestion of the resulting double strand with two restriction enzymes in order to generate two different cohesive extremities (FIG. 6D). While not imperative, it is the Charomid 9-5 ΔSbfI cloning vector, having the sequence of SEQ ID NO: 8, which was once again used as a substrate for amplification here. More specifically, in the present case the tether (having the sequence of SEQ ID NO: 10) was obtained by PCR amplification of the Charomid C9-5 ΔSbfI template with the oligonucleotides 5'-GAGAGAACGCGTTACCTGTCCGCCTTTCTCCCTTCGGG (SEQ ID NO: 19) and 5'-GAGAGACCTGCAGGCCTCACTGATTAAGCATTGGTAACTGTCAGACC (SEQ ID NO: 20) (in order to generate a fragment having the sequence of SEQ ID NO: 25), digestion with MluI and SbfI and purification by agarose gel electrophoresis followed by column extraction using the Nucleospin Gel and PCR Cleanup kit (Macherey-Nagel). These steps are performed according to standard molecular biology protocols, following the manufacturer's instructions.

The tether generated here has a length of about 700 base pairs, but the PCR method can allow up to 10,000 base pairs if this is desirable. To reach even greater lengths one can resort to "natural" DNA as described herein. For example, the phage λ genome is 48,502 base pairs.

As a particular example, a tether having a length of about 6 kbp can be generated by PCR amplification of the phage λ matrix with oligonucleotides having the sequence of SEQ ID NO. 41 and 42 5'-GAGAGAACGCGTTCCGGATGCG-GAGTCTTATCCGTGGAAATC et 5'-GAGAGACCTG-CAGGACCAGAGCGGAGATAATCGCGGTG- ACTCTG, respectively). The amplified product, here with blunt ends, is then cloned into the pUC18 vector using the SmaI restriction site. The plasmid is introduced into *E. coli* cells and cultured in a volume of 250 mL according to techniques well-known in the art. The plasmid is purified using the NucleoBond Xtra maxiprep kit (Macherey-Nagel) according to the manufacturer's instructions then digested with MluI and SbfI restriction enzymes. The digestion products are separated by agarose gel electrophoresis and the band of interest (corresponding to fragment of approximately 6 kbp having the sequence of SEQ ID NO: 46 which will be used as a tether) is recovered. More specifically, the band of interest is cut from the agarose gel and purified on a column using the Nucleospin Gel and PCR Cleanup kit (Macherey-Nagel) following the manufacturer's instructions. The use of a cloning step advantageously makes it possible to amplify the matrix in the bacteria. In addition, when the DNA is purified and the digested fragments subsequently separated by agarose gel electrophoresis, bands corresponding to the DNA fragments are very well separated on gel, advantageously allowing the tether to be efficiently isolated. Also, according to a preferred embodiment, the tether is obtained by the following steps: a) insertion of a DNA fragment into a vector b) introduction of said vector into a host cell, for example a bacterium c) host cell culture advantageously amplifying the number of copies of the vector d) purification of said vector from the host cell, and e) isolation of said DNA fragment of said vector. Advantageously, the vector is a plasmid vector, preferably with a high copy number.

The following steps are the same, regardless of the size of the tether.

Step D): Assembly of the "Intermediate" Molecule

Two oligonucleotides called oligo-$L^c$ are hybridized on the oligo-Ls of the molecule to generate cohesive ends complementary to those flanking the tether (FIG. 6C). A ligation reaction then makes it possible to assemble molecule (B) corresponding to the tether with molecule (A) to obtain an "intermediate" DNA molecule (FIG. 6D).

In order to obtain a significant yield for the formation of the "intermediate" DNA molecule (8.5%), it is advantageous to work with four restriction sites and perform the ligation, for example by phage T4 DNA ligase, in the presence of the four corresponding enzymes. The use of two different restriction sites, present both at the junctions and at the extremities of the tether limits the formation of by-products resulting from undesired ligation reactions as described below. Indeed, it is difficult to adjust the concentrations in order to reduce the quantity of by-products resulting from reactions between (B) molecules or between (A) molecules when only two different restriction sites, present at both the junctions and at the extremities of the tether, are used.

More precisely, one of the extremities of the tether is digested with Sbf1, which creates a cohesive 3'-overhang with a 5'-TGCA-3' sequence preceded by the bases GG. The sequences of oligo-$L_2$ and oligo-$L^c_2$ are chosen so as to obtain a cohesive 3'-overhang with a 5'-TGCA-3' sequence preceded by base A, which corresponds to the Nsil restriction site. During ligation, it is therefore possible to form molecule (B)-molecule (B), molecule (A)-molecule (A) and molecule (B)-molecule (A) dimers as the two types of cohesive extremities can bind to one other. However, if Sbf1 and Nsil enzymes are added to the reaction mixture, the homodimers are continuously digested and the monomers recycled. Only heterodimers are stable and accumulate as the ligation site then has a sequence that cannot be recognized by either of the two enzymes, i.e. 5'-ATGCAGG-3'. A similar strategy is applied at the other extremity of the tether and at the junction bearing the duplex resulting from the hybridization between oligo-$L_1$ and oligo-$L^C_1$; in this case, it is the enzymes Mlul and Ascl that are used.

More specifically, oligonucleotides oligo-$L_1$ and oligo-$L_2$ (sequences indicated above, in Table 2, depending on the embodiment), integrated into molecule (A) according to steps A and B, were hybridized respectively, to single-stranded DNA oligonucleotides oligo-$L^C_1$ and oligo-$L^C_2$ in an equimolar ratio at a final concentration of about 300 nM each for one hour at room temperature in 1× SureCut buffer (New England Biolabs). As shown in Table 3, below, the oligonucleotide sequences differ when the intermediate molecule is used downstream for performing Examples 8 and 9 or for performing Example 10.

TABLE 3

Oligonucleotides used to assemble the "intermediate" molecule

| Oligo-nucleotide | Sequence | SEQ ID NO | Example(s) |
|---|---|---|---|
| Oligo-$L_1^C$ | 5'-TGGATGGAGGCGTCTTGG CTCA-3' | 21 | 8 (tether of 0.7 and 6 kbp) and 9 |
| Oligo-$L_2^C$ ATGC | 5'-CGCGCCCTACCGATCAGT CCATGGA-3' | 22 | 8 (tether of 0.7 and 6 kbp) and 9 |
| Oligo-$L_1^C$ | 5'-CGCGCCCTACCGATCAGT ATGCCCATGGA-3' | 23 | 10, 12 |
| Oligo-$L_2^C$ | 5'-TGGATGGAGGCGTCTTGG CTCA-3' | 24 | 10, 12 |

Next, DNA molecules (A) and (B) prepared as above were combined to a final concentration of about 130 nM each in 30 μl of 1× SureCut buffer (New England Biolabs), with 0.5 μl each of Sbfl-HF (10 units), MluI-HF (10 units), Nsil-HF (10 units) and AscI (5 units), HC-T4 DNA ligase (1000 units) (New England Biolabs) and 1 mM ATP and 2 mM DTT, and left overnight at room temperature. The reaction was stopped by inactivation for 20 minutes at 65° C.

Example 4: Alternative Method of Binding Test Molecules to Extremities

This alternative method is illustrated in FIG. 7, and uses a system of conjugation between nucleic acids and proteins. In this system, nucleic acids can be conjugated, for example, to a benzylcytosine (BC) or benzylguanine (BG) molecule which will react respectively with a CLIP or SNAP tag protein fused with the proteins. Said BC or BG molecule is linked to one extremity of the nucleic acid. Two examples are provided below for steps B and C using the test molecules FRB and FKP12, or the glycine receptor β loop (also called the "PHLoop") and gephyrin, respectively.

Step A): Preparation of the DNA Molecule

The synthesis of the DNA molecule for this strategy is the same as previously used for Example 10 with the exception of several modifications. First, the $TS_1$ and $TS_2$ primers now have the sequences according to SEQ ID NOs: 39 and 40, respectively (see Table 2 above). Secondly, the "nicking" step using the Nb.BbvCl enzyme is omitted. Thirdly, the assembly of the test molecules on the DNA molecule no longer requires ligation but a simple placement in contact.

Step B): Preparation of the Test Molecules

The test molecules are bound and fused with the CLIP and SNAP tag proteins, respectively, as described below.

FRB and FKBP12 of the mTOR Protein Complex

FRB and FKBP12 were cloned into a pGEX6P-1 vector, the GST tag of which was replaced by the SNAP and CLIP tags, respectively, using engineering based on the Ncol and BamHI restriction sites. The proteins therefore have an N-terminal 10×His tag followed by a SNAP or CLIP tag then a "PreScission" cleavage site and have the sequences according to SEQ ID NOs: 35 and 36, respectively. Genetic constructs were then introduced into *E. coli* BL21 cells (Invitrogen). These cells were cultured in LB medium (10 g/l NaCl) supplemented with 200 μg/ml ampicillin until an optical density at 600 nm comprised between 0.9 and 1.0 was reached. IPTG was then added to a final concentration of 0.1 mM. The culture was then continued with vigorous agitation in order to obtain protein expression, overnight at 20° C. for 10×His-SNAP-FRB and 4 h at 30° C. for 10×His-CLIP-FKBP12.

The 10×His-SNAP-FRB and 10×His-CLIP-FKBP12 proteins (having the sequence according to SEQ ID NO 35 and 36, respectively) were then purified as follows. BL21 cells were resuspended in lysis buffer (25 mM Tris-HCl, pH 8.0, 250 mM NaCl, 25 mM imidazole and protease inhibitor (Roche)) and lysed with Emulsiflex C5 (Avestin). Lysate was clarified by centrifuging and loaded onto a HisTrap column (5 mL, GE Healthcare) pre-equilibrated with binding buffer (25 mM Tris-HCl, pH 8.0, 250 mM NaCl, 25 mM imidazole) and maintained at 4° C. The resin was then washed with binding buffer containing 50 mM imidazole and the protein eluted with the binding buffer containing 350 mM imidazole. The protein was dialyzed overnight in a buffer containing 50 mM Tris-HCl, pH 7.5 and 300 mM NaCl, concentrated, and then purified again on a Superdex 75 16/600 column (preparative grade, GE Healthcare) equilibrated with this same buffer. Samples were finally analyzed on 4-20% SDS-PAGE gel, concentrated, and stored at −80° C. Protein concentrations were determined using a Pierce Coomassie Plus (Bradford) test (Thermofisher Scientific).

Glycine Receptor β Loop and Gephyrin

The glycine receptor β loop (also referred to herein as the "PHloop"; Bedet et al., 2006) having the sequence of SEQ ID NO: 44 was cloned into a pGEX6P-1 vector whose GST tag was replaced with a CLIP tag, using engineering based on the Ncol and BamHI restriction sites. The protein (SEQ ID NO: 37) therefore has an N-terminal 10×His tag followed by a CLIP tag and a PreScission cleavage site. The genetic construct was then introduced into *E. coli* BL21 cells (Invitrogen). These cells were cultured in LB medium supplemented with 200 μg/ml ampicillin until an optical density at 600 nm of 0.7 was reached. IPTG was then added to a final concentration of 0.1 mM. The culture was then continued to obtain protein expression for 5 h at 25° C.

The CLIP-PHloop protein was then purified as follows. BL21 cells were resuspended in lysis buffer (25 mM sodium phosphate buffer, pH 8.0, 250 mM NaCl, 25 mM imidazole, 12.5 mM 2-mercaptoethanol, 10% glycerol and protease inhibitor (Roche)) and lysed with an Emulsiflex C5 (Avestin). Lysate was clarified by centrifuging and loaded on a HisTrap column (5 mL, GE Healthcare) pre-equilibrated with binding buffer (25 mM Tris-HCl, pH 8.0, 250 mM NaCl, 25 mM imidazole, 12.5 mM 2-mercaptoethanol and 10% glycerol) and maintained at 4° C. The resin was then washed with binding buffer and the protein eluted with a gradient of 15-75% of binding buffer containing 500 mM imidazole. The fractions of interest were then pooled, concentrated, and further purified on a Superdex 75 16/600 column (preparative grade, GE Healthcare) equilibrated with buffer (20 mM Tris-HCl, pH 8.0, 200 mM NaCl, 1.5 mM 2-mercaptoethanol and 10% glycerol). The samples were finally analyzed on 4-20% SDS-PAGE gel, concentrated, and stored at −80° C. Protein concentrations were determined using a Pierce Coomassie Plus (Bradford) test (Thermofisher Scientific).

The SNAP sequence was cloned into the Gephyrin construct rC4_pQE80L (Grunewald et al., 2018) using SacI and KpnI restriction sites. The protein (SEQ ID NO: 38) comprises an N-terminal 6×His tag followed by a PreScission cleavage site and a SNAP tag. The genetic construct was then introduced into *E. coli* BL21 RIPL cells (Invitrogen). These cells were cultured in LB medium supplemented with 200 μg/ml ampicillin and 50 μg/ml chloramphenicol until an optical density at 600 nm of 0.7 was reached. IPTG was then added to a final concentration of 0.1 mM. The culture was then continued in order to obtain the expression of the proteins for 4 h at 20° C. The proteins were purified by affinity chromatography and size exclusion as previously described (Grunewald et al., 2018). Samples were finally analyzed on 4-20% SDS-PAGE gel, concentrated, and stored at −80° C. Protein concentrations were determined using a Pierce Coomassie Plus (Bradford) test (Thermofisher Scientific).

Step C): Arrangement of Test Molecules at the Extremities of the DNA Molecule

CLIP and SNAP tags react respectively with the BC and BG small molecules located at the extremities of the DNA molecule (see also FIG. 7B). These reactions lead to the formation of a covalent thioether bond (Keppler et al, 2003, Gautier et al., 2008). Typically, a 15 μL reaction volume contains 2 μM of each protein and 1 μM of DNA molecule in DB buffer (composition provided in Example 6 and corresponding to the experiments on FRB and FKBP12 described in Example 12). Incubation takes place overnight at 25° C. The reaction mixture is then diluted 20-fold in DB buffer, glycerol is added to a final concentration of 10% and the sample is aliquoted, frozen in liquid nitrogen and then stored at −80° C. The molecule of DNA functionalized with the test molecules as a result of the protein tags can then be used in the same way as that functionalized with the targeting oligonucleotide of Example 2. Such a use is notably described in Example 5. More specifically, just prior to measurements under a microscope, the DNA molecule functionalized with the test molecules is mixed with magnetic beads coated with streptavidin. This mixture is then injected into the flow cell whose walls are covered with anti-digoxygenin, and the force spectroscopy experiments can In the case of the "PHloop" and gephyrin molecules, and by way of example, a second functionalization protocol of the extremities is proposed. The DNA molecule not yet functionalized by the test molecules is mixed with the streptavidin-coated magnetic beads and this mixture is injected into the flow cell whose walls are covered with anti-digoxygenine. After incubation and power-up, the CLIP-PHloop and SNAP-gephyrin rC4 molecules are then injected sequentially such that they react with the BC and BG extremities of the DNA molecule, respectively: first CLIP-PHloop then after rinsing SNAP-gephyrin rC4. The concentration of each molecule is 500 nM in GB buffer (composition provided in Example 6) is used. Each protein is incubated for at least 2 hours at 19.2° C. and then extensive rinsing is performed with the GB buffer.

Example 5: Assembling the DNA Molecule on a Microscope

For the assembly on the microscope of the DNA molecule obtained in Example 1, after the possible enzymatic digestion steps described in Examples 8 or 9, or that obtained in Examples 2 or 4, the final reaction mixture is diluted to a nominal DNA concentration of 50 μM in Tris buffer (10 mM TrisCl, pH 8). In parallel magnetic beads (of type Dynal MyOne C1 from Thermofisher) were prepared by taking 10 μl of stock solution supplied by the manufacturer, washing them with 100 μl of buffer used for the micromanipulation experiments, i.e. RB for Examples 8 and 9 and DB for Examples 10 and 12 (see Example 6 for the compositions), concentrating them with a magnet, removing the supernatant and resuspending the beads in 10 μl of the same buffer. Next, 0.5 μl of the solution of double-stranded DNA molecule according to the invention is mixed with 10 μl of washed bead suspension. After 5 to 10 seconds the volume of the mixture is finally adjusted by adding buffer to reach a total volume of 25 μl and then injected into the measuring cell.

The measuring cell consists of two glass slides of thickness no. 1 (~180 μm) separated by two thicknesses of parafilm (~2×80 μm) in which a channel (1 mm×50 mm) was cut. Both slides are functionalized with anti-digoxigenin and passivated as described in Duboc et al., 2017. One of the slides has holes 2 mm in diameter located above each extremity of the channel and which are used to fill and drain the channel filled with reagents. The surface, also called a support, is mounted on a custom-designed stage and placed over an oil immersion microscope objective (PlanA, 100×, NA 1.25, Olympus). This objective is part of a magnetic trap device (Lionnet et al., 2012 and Sarkar and Rybenkov, 2016) in which a pair of high-quality permanent magnets located above the sample can be translated vertically to the sample: the force applied to the magnetic beads is increased, alternately reduced, by bringing closer or alternatively moving away, the magnets to the sample. The pair of permanent magnets can also rotate around the optical axis of the microscope objective, which imposes a rotational movement to the bead and allows DNA supercoiling. As a whole, the magnetic trap device makes it possible to modify the mechanical stresses applied to the DNA. Real-time particle tracking software, PicoJai (PicoTwist SARL), allows video-microscopy tracking of magnetic beads with nanoscale resolution and in real time (in this embodiment at about 30 Hz, but potentially also at 10 kHz).

A typical sample consists of a field of view of the microscope containing about 30 to 50 individual double-stranded DNA molecules that can be monitored simultaneously. The operation of the devices according to the invention (the force of the attachment to the supports, the absence of non-specific interactions with the supports, etc.) are systematically verified before any characterization of the test molecules. For example, the appropriate change in the extension of the double-stranded DNA molecules according to the invention is verified when the applied force is varied between 0.05 pN and about 1 to 3 pN (e.g., 1.4 pN). When necessary, it can further be verified that only one DNA molecule is attached between each bead and the glass surface. For this it is ensured that the position of the bead along the optical axis does not change when the magnets are rotated, which is to be expected with free rotation around the junctions. However, this would not be the case if two or more DNA molecules were wrapped around each other.

Example 6: General Experimental Conditions

Examples 8 and 9 were performed at 34° C. in RB reaction buffer (20 mM K-Hepes pH 7.8, 100 mM KCl, 5 mM $MgCl_2$, 1 mM DTT, 0.05% Tween-20, 0.5 mg/ml BSA). For ligation/repair experiments, phage T4 DNA ligase (New England Biolabs) is used at a concentration of 200 U/ml and the NHEJ components (laboratory preparation) are used at a concentration of 10 nM Ku70/80 (dimer), 100 μM DNA-PKcs, 20 nM PAXX, 20 nM XRCC4, 20 nM XLF and 20 nM ligase IV. In order to digest DNA molecules that have undergone ligation/reparation, we perfused the capillary with 100 μl of RB containing either 20 units of XmaI or 10 units of SmaI (New England Biolabs).

Example 10 was performed either at 25° C. or at 30° C. in DB reaction buffer (20 mM K-Hepes pH 7.8, 100 mM KCl, 5 mM $MgCl_2$, 2 mM DTT, 0.1% Tween-20, 0.1 mg/ml BSA). Measurements were also performed at 19.2° C., 21.7° C., 25.4° C. and 29.1° C. (see FIG. 15E). Rapamycin (Sigma) is used diluted to 500 nM in the buffer. These conditions are also those used for Example 12 for measurements involving FRB and FKBP12 (FIG. 18A-C).

Figure 18:
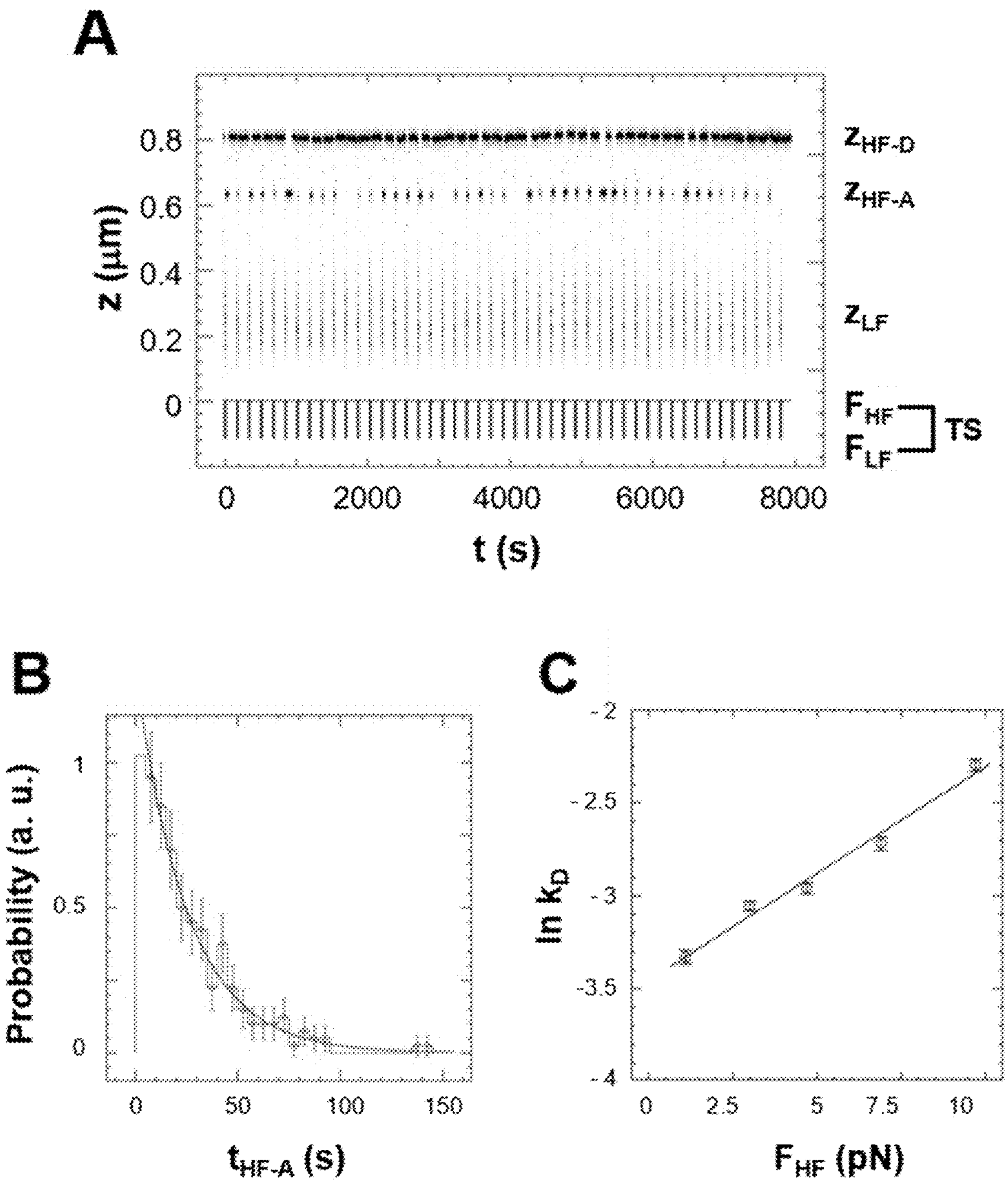
FIG. 18. Measurement, by force cycling, of the characteristic dissociation time of the non-covalent bond of two test molecules attached to the DNA molecule using the SNAP and CLIP labeling system. The DNA molecule used corresponds to that shown schematically in FIG. 7B in a device as illustrated in FIG. 2, and obtained by the manufacturing method illustrated in FIG. 7A followed by the methods illustrated in FIGS. 6B-D, 4, then 7B (described in Examples 3 and 1 with the variations described in Example 4). A-C). Test molecules are the FKBP12 and FRB proteins which interact in the presence of rapamycin. Experiments are performed at 21.7° C. in DB buffer. A) Temporal monitoring of the extension of the double-stranded DNA molecule when the force is cycled between a high value and a low value (TS: schematic diagram of the $F_{HF}/F_{LF}$ cycles). HF corresponds to the application of a high force ("High Force"); LF corresponds to the application of a low force ("Low Force"). The test molecules can be either associated (A for "Associated") or dissociated (D for "Dissociated"). At each passage at $F_{LF}=0.01$ pN for a time of 13 s, the test molecules associate, then, after passage at $F_{HF}=1.1$ pN, they separate at the end of a time indicated as $t_{HF\text{-}A}$ (see B)). The high force is applied for a time of 155 s. B) Histogram of $t_{HF\text{-}A}$ under a high force of 1.1 pN and extraction of the characteristic dissociation time $\tau_D=25.3\pm2.4$ s, by exponential adjustment. C) Variation of the logarithm of the dissociation rate constants, calculated as $\ln[k_D]=\ln[1/<\tau_D>]$, as a function of $F_{HF}$, the applied high force ($<\tau_D>$ indicates that the time characteristics were averaged over several DNA molecules). The linear fit is in agreement with the Arrhenius-Bell model, $\ln[k_D]=\ln[k_D^0]+X_D F_{HF}/k_B T$, making it possible to determine $\ln[k_D^0]=-3.45\pm0.03$ and $X_D=4.7\pm0.2$ Å. D) The test molecules are gephyrin and the glycine receptor β loop. Experiments are performed at 19.2° C. in GB buffer. Temporal monitoring of the extension of the double-stranded DNA molecule when the force is cycled between low value $F_{LF}=0.01$ pN for 13 s and high value $F_{HF}=1.1$ pN for 52 s.
Figure 18:
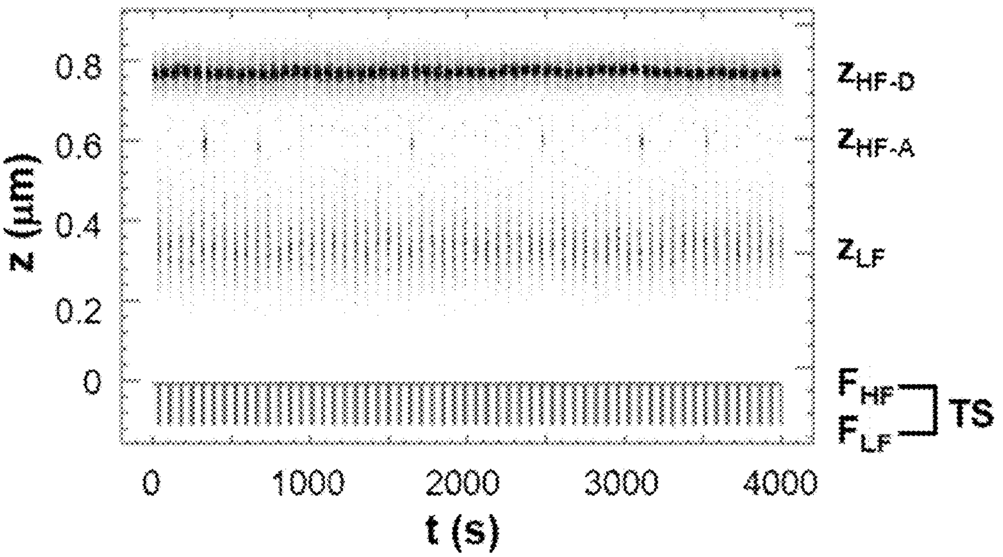

Example 12 was performed at 19.2° C. in GB reaction buffer (20 mM Tris pH 8.0, 250 mM NaCl, 5 mM $MgCl_2$, 0.1% Tween-20, 0.5 mg/mL BSA, 5 mM 2-mercaptoethanol) with regard to those involving "PHloop" and gephyrin (FIG. 18D).

Example 7: Data Collection and Analysis

Magnetic tweezer data at the single molecule scale, giving the position of each magnetic bead as a function of time and under cycles modulating the applied force, was obtained using the PicoJai software suite (Picotwist SARL). This real-time particle tracking program can analyze up to 100 single molecules in parallel, with nanometric resolution in the 3 dimensions of space (Lionnet et al., 2012, Sarkar and Rybenkov, 2016). It also makes it possible to determine the tension applied to DNA molecules by analyzing the Brownian fluctuations of the beads acting as a support. In the context of Examples 8, 9, 10 and 12, the forces $F_{HF}$ and $F_{LF}$ are inferred from the position of the magnets along the optical axis, using a prior calibration on longer DNA molecules (Charomid 9-11, 11 kbp). The homogeneity of the magnetic charge of the beads used as well as the slow variation of force as a function of the position of the magnets makes this process robust.

With regard to the measurements associated with the characterization of molecular interactions between the test molecules, the z extension of the DNA molecules according to the invention was determined by analysis of the time traces, this during varied cycles where the force applied F varies as a function of time according to an established temporal program (FIG. 8). More specifically, the measurement of the lifetime, t, for the test molecules in their dissociated form "D" or in their associated form "A", requires a variation of F between a low value, $F_{LF}$, and a value high, $F_{HF}$, the time cycles followed being different according to the type of measurement, e.g. association or association (FIG. 8). The chosen value of $F_{LF}$ must allow for an efficient association of the test molecules while the chosen value $F_{HF}$ must make it possible to distinguish between conformations "A" and "D" by measurement of the extension z. Events giving rise to a change in the high-force extension between forms A and D are identified and the lifetime associated with these events enter into subsequent analysis only if the value "$z_{HF-D}$-$z_{HF-A}$" observed is less than 3 standard deviations from the expected amplitude (i.e. about 160 nm in the case of a tether of about 700 bp). The standard deviation is that obtained by plotting the histogram of the measured "$z_{HF-D}$-$z_{HF-A}$" and fitting with a Gaussian (FIGS. 13B and 11B).

The duration of the low and high force passages, of respective durations $T_{LF}$ and $T_{HF}$, are chosen according to assumptions on the characteristic times of association and dissociation, $\tau_A$ and $\tau_D$. The objective here is to be able to detect, with the greatest possible precision, the greatest number of conformational transitions over the duration of an experiment. Each cycle shown in FIG. 8 leads to the eventual measuring of a lifetime t, denoted $t_{LF-D}$ for association experiments (FIG. 8A, 11A) and $t_{HF-A}$ for dissociation experiments (FIG. 8B, 13A). These cycles are reproduced in series on the same molecule and the data are acquired in parallel on approximately twenty molecules. The collected t values are then gathered as a histogram such that they can be analyzed by exponential adjustment. The histogram of $t_{LF-D}$ gives the characteristic association time $\tau_A$ using the formula Probability∝exp[$-t_{LF-D}/\tau_A$] (FIG. 11C) and the histogram of $t_{HF-A}$ shows the characteristic dissociation time $\tau_D$ using the formula Probability∝exp [$-t_{HF-A}/\tau_D$] (FIG. 13C).

Figure 9:
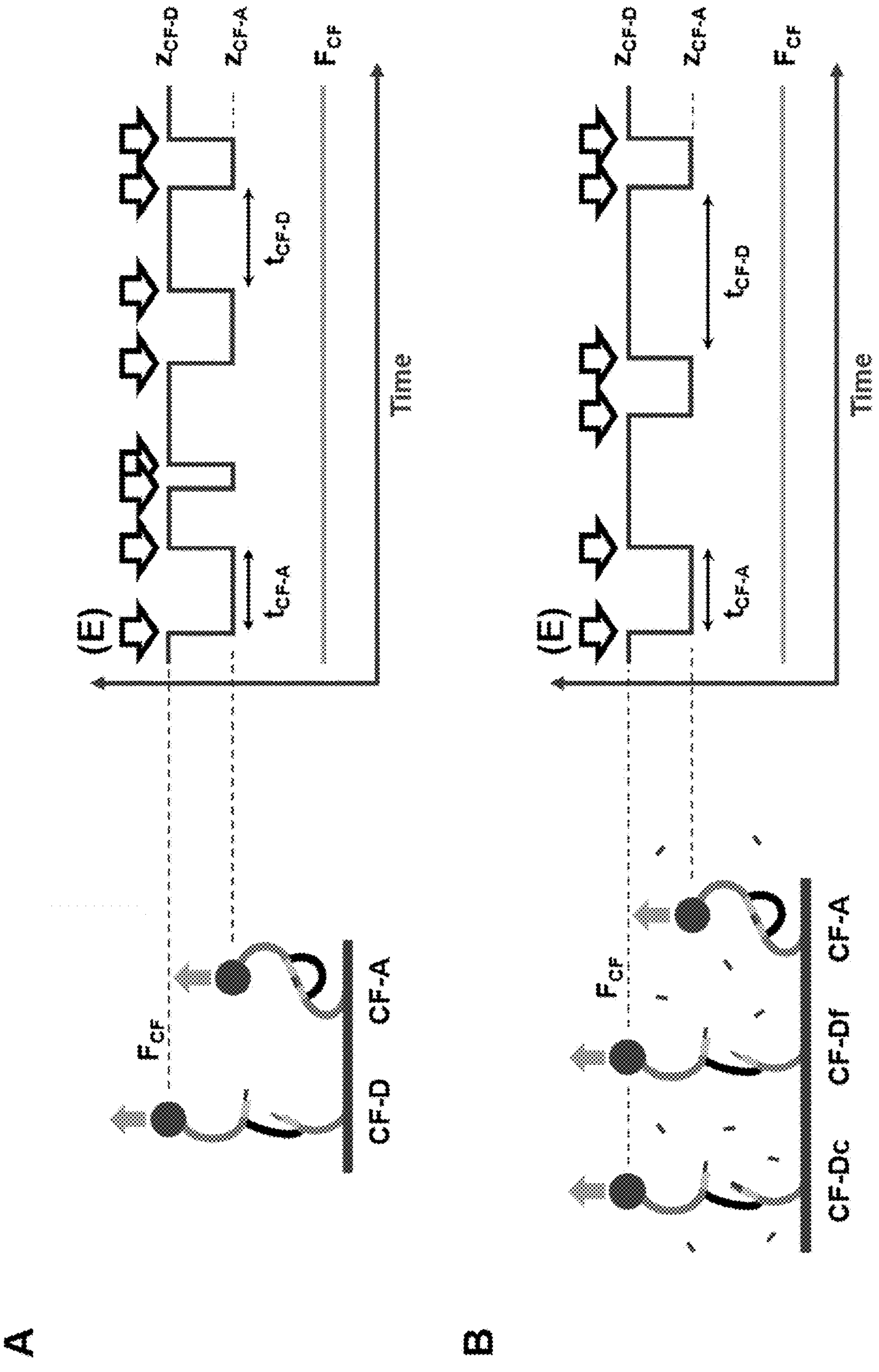
FIG. 9. Principle of measurement, by recording the spontaneous fluctuations observed at a constant force, $F_{CF}$, of the lifetime for the test molecules in their dissociated form, $t_{CF-D}$, and for the test molecules in their associated form, $t_{CF-A}$. A portion of the temporal monitoring is represented here for each of the two modes of acquisition considered A) in the absence and B) in the presence, in solution, of molecules similar to one of the test molecules. The conformation of the DNA molecule can be determined from the recording of the extension, z, over time. CF corresponds to the application of a constant force ("Constant Force"). The test molecules can be either associated (A for "Associated"); or dissociated (D for "Dissociated"). When the test molecules are dissociated, they may both be uncomplexed (Df, D for "Dissociated" and f for "free") or one of them may form a complex with the one of the molecules present in solution (Dc, D for "Dissociated" and c for "complexed"). Identification of change of extension event (E) on the temporal traces makes it possible to determine t.

The characteristic dissociation time can then be converted into dissociation reaction rate by inversion: $k_D=1/<\tau_D>$, where the characteristic dissociation times on a set of molecules have been averaged. By then performing experiments for different $F_{HF}$ and/or temperature values, the skilled person can ultimately extract the activation energy of the dissociation reaction and the distance separating the transition of the complex during dissociation from the collected data, using the Arrhenius/Bell equation (see Example 10) (Popa et al., 2011). Alternatively, to the force cycling measurement mode presented above, the characterization of molecular interactions between test molecules can be performed by studying spontaneous extension fluctuations at constant force (FIG. 9A). The value chosen for this force $F_{CF}$ must be high enough that the extension difference "$z_{CF-D}$-$z_{CF-A}$" can be measured; however, it must be small enough that the proportion of test molecules present in associated form is sufficient to perform the measurements in a reasonable amount of time. The extension z of the DNA molecules according to the invention is determined by analysis of the temporal traces. Events leading to a change in the extension between forms A and D are identified and it is possible to determine a lifetime t, denoted $t_{CF-D}$ for the dissociated form and $t_{CF-A}$ for the associated form (FIGS. 9A, 17A). The histogram of $t_{LF-D}$ provides the characteristic association time $\tau_A$ using the formula Probability∝exp [$-t_{LF-D}/\tau_A$] (FIG. 17C) and the histogram of $t_{HF-A}$ provides the characteristic dissociation time $\tau_D$ using the formula Probability∝exp[$-t_{HF-A}/\tau_D$] (FIG. 17B). The characteristic dissociation time can then be converted into the dissociation reaction rate by inversion: $k_D=1<\tau_D>$, where the characteristic dissociation times on a set of molecules have been averaged.

If it is desired to determine the association reaction rate, spontaneous fluctuations can be measured in the presence of one of the test molecules free in solution (FIG. 9B). The analysis of the temporal traces (FIGS. 9B, 17D) makes it possible to determine, for the test molecules attached to the DNA molecule, the fraction of time spent in the associated state, $(\Sigma t_{CF-A})/t_{total}$. Plotting the variations of this parameter as a function of $C_I$, the concentration of the test molecule free in solution, then leads to the determination of $C_{eff}$ and $K_0$, where $C_{eff}$ is the effective concentration of test molecules when they are attached to the DNA molecule and where $K_0=K_D/C_{eff}$ with $K_D$ the equilibrium dissociation constant of the complex. To obtain these two parameters, the data are adjusted to formula $(\Sigma t_{CF-A})/t_{total}=((1+K_0)+C_I/C_{eff})^{-1}$ (FIG. 17F). Finally, the association constant is derived via $k_A=k_D/K_D$.

Example 8: Covalent Interaction Between Two Cohesive Ends of Double-Stranded DNA, in the Presence of DNA Ligase from T4 Phage and the SMAI Restriction Enzyme Materials and Methods The double-stranded DNA molecule is made by following steps (A) to (C) of Example 3 (FIG. 6) followed by steps (A) and (B) of Example 1 (FIG. 4) using a DNA molecule having the sequences of SEQ ID NO: 9 and SEQ ID NO: 10, for DNA molecules (A) and (B) respectively. Enzymatic digestion is then performed by XmaI to generate a cohesive 5'-overhang of sequence 5'-CCGG-3' at each end.

This digestion is performed by combining 1 µl of solution at 3 nM of the DNA molecule according to the invention obtained in step B of Example 1 and 10 units of XmaI (New England Biolabs) in a final volume of 30 µL buffered by the CutSmart solution (New England Biolabs) according to the manufacturer's instructions. Digestion is performed at 37° C. overnight. The restriction enzyme was heat inactivated according to the manufacturer's recommendations, and the construct was diluted 30-fold to a nominal DNA concentration of 100 µM and stored at −20° C.

The two complementary cohesive ends can subsequently be paired by Watson-Crick interaction. The test molecules are thus the cohesive ends of the extremities themselves here. The double-stranded DNA molecules according to the invention are then coupled to streptavidin-coated magnetic microbeads having a diameter 1 µm (as described, for example in Example 5). Finally, this is introduced into a capillary coated with anti-digoxigenin which makes it possible to finalize the assembly of the device by fixing the double-stranded DNA molecules to the supports (FIG. 2).

Results

At this point, the cohesive ends of the extremities do not stably pair. For the tether of ~0.7 kbp, under the effect of a force alternating between 0.04 and 1.4 pN we see the bead-support distance goes from $z_{LF}$=400 nm to $z_{HF-D}$=1, 080 nm and vice versa, indicating that the double-stranded DNA molecules pass between the LF-D, "Low Force-Dissociated", and HF-D, "High Force-Dissociated" states (FIG. 10A-B). However, after addition of phage T4 DNA ligase, at the experimental time of about 500 s, we observe that the maximum extension of the double-stranded DNA molecule, under the effect of a force of $F_{HF}$=1.4 pN, is only $z_{HF-A}$=880 nm (FIG. 10B). This reduction results from the ligation of complementary cohesive ends during the first passage at low force. This reaction has the effect of excluding the tether from the measurement of the extension in the HF-A, "High Force-Associated," state and of replacing it with the two associated ends in series (FIG. 10A). More precisely, the difference in position of the bead between the two "High Force" states, determined by "$z_{HF-D}$-$z_{HF-A}$", corresponds to 170 nm, a value in agreement with the estimate that can be drawn from the WLC elasticity model, (worm-like chain; c.f. Bouchiat et al., 1999) when a linear double-stranded DNA molecule goes from 3,610 to 2,990 base pairs and the traction is 1.4 pN. Furthermore, this same model tells us that the variation in extension between the two "Low Force" states, i.e. under a traction $F_{LF}$=0.04 pN, should be drowned out by the background noise of the measurement, which is also shown here (FIG. 10B). Finally, the addition of restriction enzyme SmaI, at the experimental time of about 1600 s, allows the covalent bond between the cohesive ends of the extremities to be cleaved and maximum extension of the construction to be recovered, as measured at the beginning of the experiment (FIG. 10B).

Similar observations are made when the tether measures ~6 kbp. However, the variation in extension is much greater: it is now 1,800 nm (FIG. 10C) as one passes from $z_{HF-A}$=900 nm to $z_{HF-D}$=2700 nm. This is in agreement with the WLC elasticity model when a linear double-stranded DNA molecule goes from 3000 to 9000 base pairs and the traction is 1.1 pN. It is also noted that the low-force associated and dissociated states can now be resolved. Another behavioral change is that more cycles passed at low force are required for ligation to take place: this is in agreement with the dilution in test molecules inherent to the use of a longer tether (FIG. 10D-E).

Discussion

This example demonstrates that double-stranded DNA molecules according to the invention, as well as devices comprising said molecules and their supports, can be manufactured and are fully functional. It validates the principle of the detection of interactions between test molecules located at the ends of the extremities by measuring the distance between the extremities of the DNA molecules (1) and (2) attached to the supports (e.g. the second extremity of the first double-stranded DNA molecule (1) and the second extremity of the second double-stranded DNA molecule (2)). In addition, tethers of different lengths can be used, which is highly advantageous as it makes it possible to modulate the speed with which the test molecules associate with each other, as well as the difference in extension that is to be measured in order to detect the interaction.

Example 9: Covalent and Non-Covalent Interactions Between Two Blunt Ends of Double-Stranded DNA, in the Presence of Proteins Participating in the NHEJ Repair System Materials and Methods The double-stranded DNA molecule is made by following steps (A) to (C) of Example 3 (FIG. 6) followed by steps (A) and (B) of Example 1 (FIG. 4), using a DNA molecule having the sequences of SEQ ID NO: 9 and SEQ ID NO: 10, for DNA molecules (A) and (B) respectively. Enzymatic digestion is then performed with SmaI in order to generate a blunt end at each extremity. This digestion is performed by combining 1 μl of a 3 nM solution of the construct obtained in step B of Example 1 and 20 units of SmaI (New England Biolabs) in a final volume of 30 μl buffered with the CutSmart solution (New England Biolabs) according to the manufacturer's instructions. Digestion is performed at 25° C. overnight. The restriction enzyme was heat inactivated according to the manufacturer's instructions, and the construct was diluted 2-fold to a nominal DNA concentration of 50 pM and stored at −20° C.

The preparation protocol is stopped at this stage if the repair phenomenon up until the formation of the covalent bonds connecting each of the strands of the double helix is to be studied. On the other hand, a step of dephosphorylation of the blunt ends of the extremities is performed using antarctic phosphatase if one wishes to study the transient interactions between the two DNA extremities. Specifically, the ends of the extremities of the DNA molecule were dephosphorylated by combining, in a volume of 10 ml of 1× buffer ad hoc provided by the supplier, 2 units of antarctic phosphatase (New England Biolabs) and 0.6 fmol of the digestion product obtained above. The reaction lasted at least 1 hour at 37° C. before being thermally inactivated according to the manufacturer's recommendations.

Again, the test molecules here the ends of the extremities themselves.

Results

In the same way that we have studied the repair of breaks having cohesive ends by T4 phage ligase (FIG. 10B), we are interested in the functioning of the human NHEJ ("non-homologous end-joining") system which repairs breaks having blunt ends. The latter is more precisely composed of Ku70/Ku80, DNA-PKcs, PAXX, XRCC4, XLF and Ligase IV proteins. FIG. 11A shows an experiment very similar to that performed in Example 8. In the absence of a covalent bond between the blunt ends, the extension varies between $z_{LF\text{-}D}$=400 nm and $z_{HF-D}$=1080 nm when the force varies between $F_{LF}$=0.05 pN and $F_{HF}$=1.4 pN. However, after adding the NHEJ system, at the experimental time of about 600 s, the maximum extension of the DNA under the effect of a force $F_{HF}$=1.4 pN is only $z_{HF-A}$=880 nm. This reduction is attributed to the ligation of the blunt ends during the second passage at low force. As before, the addition of SmaI restriction enzyme after a number of cycles between "High Force" and "Low Force", at the experimental time of about 4,000 s, allows the covalent bond that had been formed to be cleaved and to recover the maximum extension as it was initially measured. When this protocol is reproduced on a large number of beads, the measurement of the difference in extension between the HF-A and HF-D forms can be improved (FIG. 11B): the average value "$z_{HF-D}$-$z_{HF-A}$"=161 nm determined at $F_{HF}$=1.4 pN is in agreement with the estimate found in Example 8 and with the predictions derived from the WLC worm-like chain model. Finally, one can also plot the histogram of the number of low-force passages, $n_{LF-D}$ necessary to obtain ligation (FIG. 11C). With exponential adjustment this curve provides an estimate of the characteristic time necessary for the formation of covalent bonds between the test molecules, $\tau_A$=0.8±0.2 cycles, i.e. 240±60 s if the result given in cycles is multiplied by the duration of a passage at low force, namely $T_{LF}$=300 s.

These covalent ligation experiments also made it possible to test the supercoiling of the double-stranded DNA molecules (1) and (2) associated in series (FIG. 11); there is no nick in the above-mentioned functional elements.

In a second type of experiment, we aimed to measure the characteristic dissociation time of the nucleoprotein complex in which the blunt ends were dephosphorylated, which prevents the NHEJ system from creating covalent bonds. Each passage at $F_{LF}$=0.05 pN allows the blunt ends to associate and it is therefore the HF-A form that is observed when the force is increased to $F_{HF}$=1.4 pN. Then, at the end of a time noted $t_{HF-A}$ the extension of the construction increases to its maximum value, indicating that the blunt ends have dissociated and that it is now the tether which is placed under tension (FIG. 13A). Plotting the histogram of the differences in extension between the HF-A and HF-D forms gives a mean value of "$z_{HFD}$-$z_{HF-A}$"=166 nm (FIG. 13B). Furthermore, a characteristic dissociation time $\tau_D$=2.2±0.3 s can be extracted from the histogram of $t_{HF-A}$ by exponential adjustment (FIG. 13C).

Discussion

This example demonstrates the utility of the DNA molecule according to the invention, as well as devices comprising said molecules and their supports, for conducting studies on DNA repair processes. In addition, being able to inject various mixtures of proteins and to being able to characterizing the complexes formed each time (data not shown) is highly advantageous for screening studies.

From a technical point of view, this example illustrates:

(i) a protocol for measuring the characteristic association time when a constant force is applied to test molecules interacting with one another;

(ii) a protocol for measuring characteristic dissociation time when a constant force is applied to test molecules interacting with one another; and (iii) the possibility of applying, through magnet rotation, a torque to the complex formed by the test molecules.

Example 10: Non-Covalent Interaction Between FKBP12 and FRB Proteins, in the Presence of the Rapamycin Drug This example relates to a relevant pharmaceutical system in the field of drug discovery/design that would be highly advantageous to characterize.

Materials and Methods

The double-stranded DNA molecule is that obtained according to the description given in Example 3, followed by Examples 1 and 2 (see also FIG. 6, FIG. 4 and FIG. 5, respectively for an illustration of these steps), using a DNA molecule having the sequences of SEQ ID NO: 30 and SEQ ID NO: 10, for DNA molecules (A) and (B) respectively. This allows us to specifically graft the two test molecules, at one extremity the FRB subunit of the mTOR protein complex and at the other the FKBP12 protein.

Results

The rapamycin drug disrupts the activity of the mTOR signaling pathway by binding to both FRB and FKBP12.

Figure 13:
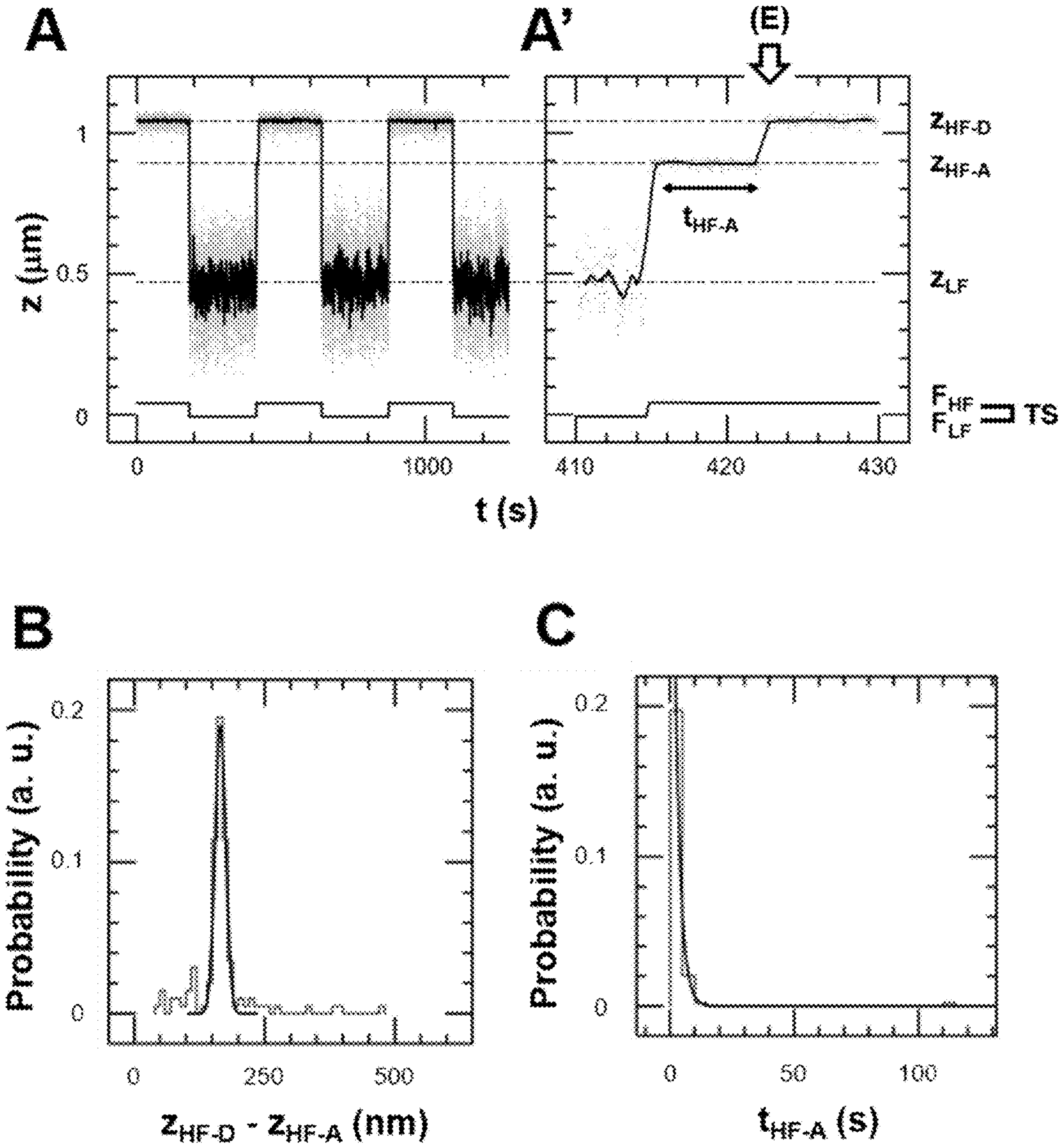
FIG. 13. Measurement, by force cycling, of the characteristic dissociation time of the non-covalent bond formed by two blunt ends of the extremities of the double-stranded DNA in the presence of proteins participating in the human NHEJ repair system. These blunt ends, which have only terminal hydroxyl groups, constitute themselves the two test molecules here. The DNA molecule used corresponds to that shown in FIG. 1 in a device as illustrated in FIG. 2, and obtained by the manufacturing method described in Examples 3, 1 and then 9. Experiments were performed at 34° C. in RB buffer. A) Temporal monitoring of the extension, z, of the DNA molecule when the force F is cycled between a high value $F_{HF}$ and a low value $F_{LF}$ (TS: schematic diagram of the $F_{HF}/F_{LF}$ cycles). HF corresponds to the application of a high force ("High Force"); LF corresponds to the application of a low force ("Low Force"). The test molecules can be either associated (A for "Associated") or dissociated (D for "Dissociated"). At each passage at $F_{LF}$=0.05 pN for time $T_{LF}$=250 s the test molecules associate and then after passage at $F_{HF}$=1.4 pN they separate after a time indicated as $t_{HF-A}$. The high force is applied during $T_{HF}$=250 s. A') Magnification of a measurement of $t_{HF-A}$. Identification of the change of extension event (E) on the temporal trace is indicated by the white arrow. B) Histogram of the differences in extension, "$z_{HF-D}$-$z_{HF-A}$", between the HF-D (state of high force-test molecules dissociated) and HF-D states (state of high force-test molecules associated), and extraction of the average value, "$z_{HF-D}$-$z_{HF-A}$"=166 nm, by Gaussian fitting. C) Histogram of synapse lifetime, $t_{HF-A}$, at a high force $F_{HF}$=1.4 pN, and extraction of the characteristic dissociation time, $\tau_D$=2.2±0.3 s, by exponential adjustment.
Figure 14:
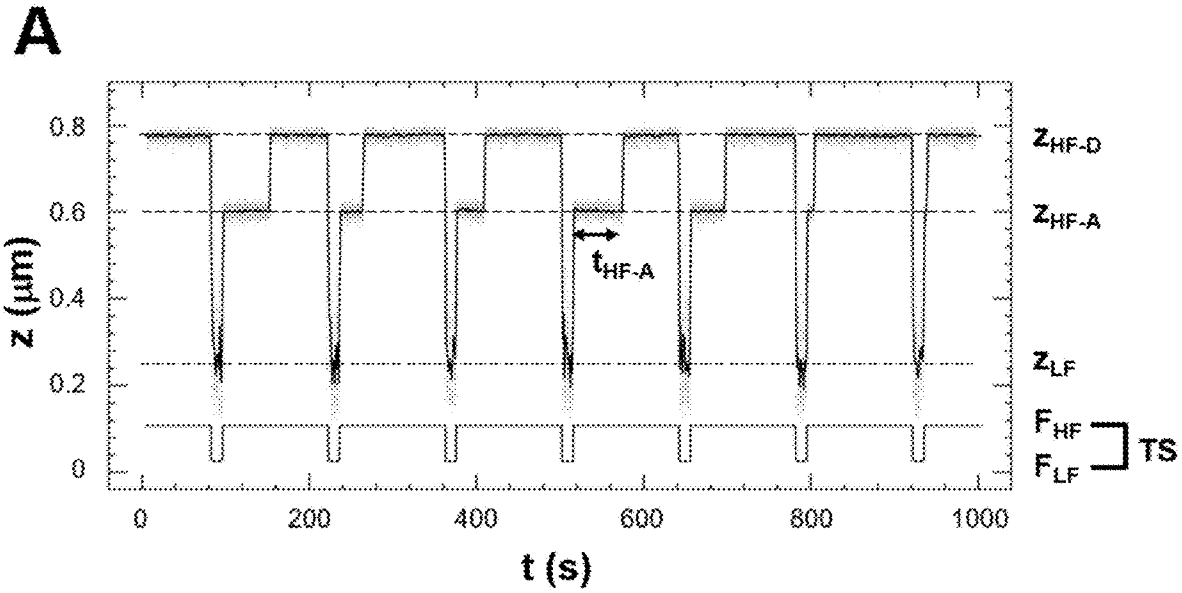
FIG. 14. Measurement, by force cycling, of the characteristic dissociation time of the non-covalent bond linking the FKBP12 and FRB proteins in the presence of rapamycin at 500 nM. FKBP12 and FRB proteins constitute the two test molecules here. The DNA molecule used corresponds to that shown in FIG. 1 in a device as illustrated in FIG. 2, and obtained by the manufacturing method illustrated in FIG. 6 followed by the processes illustrated in FIGS. 4 and then 5 (described in Examples 3, 1 and then 2). Experiments are performed at 25° C. in DB buffer. A) Temporal monitoring of the extension of the double-stranded DNA molecule when the force is cycled between a high value and a low value (TS: schematic drawing of the $F_{HF}/F_{LF}$ cycles). HF corresponds to the application of a high force ("High Force"); LF corresponds to the application of a low force ("Low Force"). Test molecules can be either associated (A for "Associated") or dissociated (D for "Dissociated"). At each passage at $F_{LF}$=0.05 pN for time $T_{LF}$=13 s, the test molecules associate, then, after passage at $F_{HF}$=1.4 n, they separate after a time, indicated as $t_{HF}$. The high force is applied for $T_{HF}$=125 s. B) Histogram of $t_{HF-A}$ at a high force of 1.4 pN and extraction of the characteristic dissociation time, $\tau_D$=31.1±2.3 s, by exponential adjustment.
Figure 14:
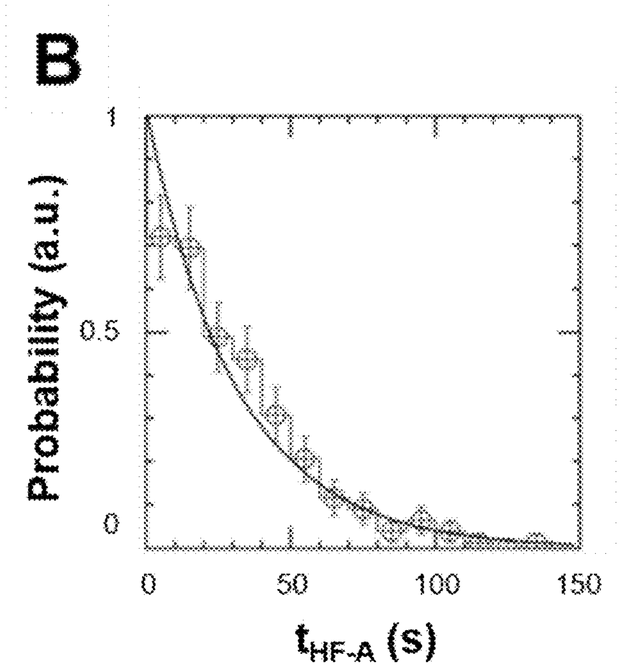

First, in order to estimate $\tau_D$, the characteristic dissociation time of this ternary complex, we used an experimental protocol very similar to that used for non-covalent associations involving the NHEJ system (FIG. 13). The temporal traces recorded at 25° C. during a modulation of the force between values $F_{LF}$=0.05 pN and $F_{HF}$=1.4 pN (FIG. 14A) have been converted into a histogram of $t_{HF-A}$ from which $\tau_D$=31.1±2.3 s could be extracted by monoexponential adjustment (FIG. 14B). In addition, we estimated the difference in extension between the HF-A and HF-D forms "$z_{HF-D}$-$z_{HF-A}$" at about 170 nm, it is essentially unchanged with regard to the measurements made in Examples 8 and 9. Indeed, the length of the tether minus that of the ends remained the same in the DNA molecule used in the present Example 10, i.e. about 700 bp, and the WLC model is very close to linearity for the high forces, which explains a contribution identical to these 700 bp at full extension, despite the use of DNA molecules (1) and (2) of different sizes in Examples 8 and 9 and in present Example 10.

Figure 15:
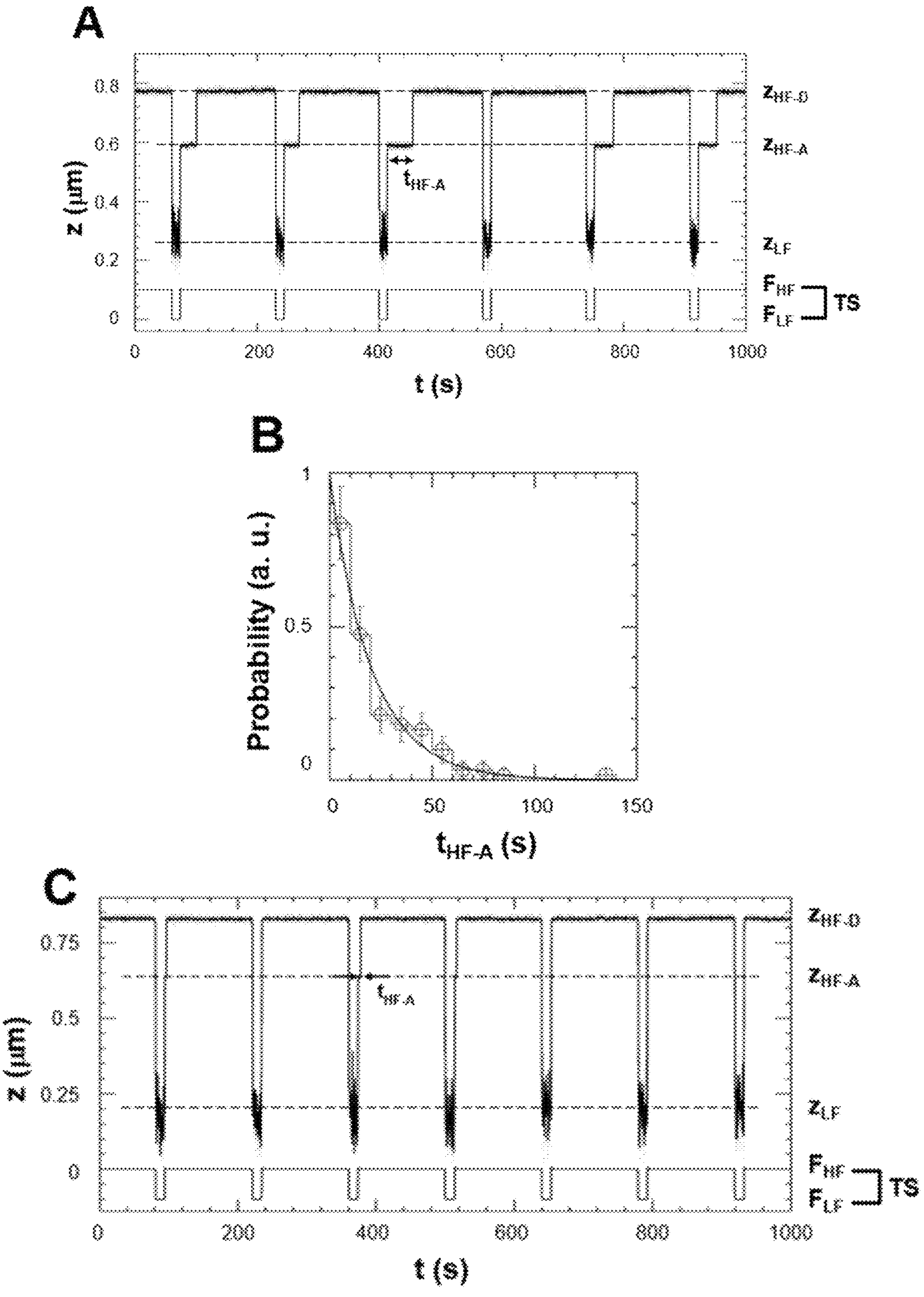
FIG. 15. Measurement, by force cycling, of the characteristic dissociation time of the non-covalent bond linking the FKBP12 and FRB proteins in the presence of rapamycin at 500 nM, this for other high force, $F_{HF}$, values and/or temperature than those used in FIG. 12. FKBP12 and FRB proteins constitute the two test molecules here. The DNA molecule used corresponds to that shown in FIG. 1 in a device as illustrated in FIG. 2, and obtained by the manufacturing method illustrated in FIG. 6 followed by the processes illustrated in FIGS. 4 then 5 (described in Examples 3, 1 and then 2). Experiments are performed at 30° C. in the DB buffer. A) Temporal monitoring of the extension of the double-stranded DNA molecule when the force is cycled between a high value and a low value (TS: schematic drawing of $F_{HF}/F_{LF}$ cycles). HF corresponds to the application of a high force ("High Force"); LF corresponds to the application of a low force ("Low Force"). Test molecules can be either associated (A for "Associated") or dissociated (D for "Dissociated"). At each passage at $F_{LF}$=0.05 pN for time $T_{LF}$=13 s, the test molecules associate, then, after passage at $F_{HF}$=1.4 pN, they separate after a time indicated as $t_{HF-A}$. The high force is applied for time $T_{HF}$=155 s. B) Histogram of $t_{HF-A}$ at a high force of 1.4 pN and extraction of the characteristic dissociation time $\tau_D$=20.6±2.6 s, by exponential adjustment. C) Temporal monitoring of the extension of the double-stranded DNA molecule when the force is cycled between high value and low value (TS: schematic diagram of the $F_{HF}/F_{LF}$ cycles). At each passage at $F_{LF}$=0.05 pN for time $T_{LF}$=14 s the test molecules associate and then, after passage at $F_{HF}$=6 pN, they separate after a time indicated as $t_{HF-A}$. The high force is applied for time $T_{HF}$=125 s. D) Histogram of $t_{HF-A}$ at a high force of 6 pN and extraction of the characteristic dissociation time, $\tau_D$=15.4±1.9 s, by exponential adjustment. E) Variation of the logarithm of the dissociation rate constant, calculated as $\ln[k_D]=\ln[1/\langle\tau_D\rangle]$, as a function of $F_{HF}$, the applied high force ($\langle\tau_D\rangle$ indicates that the times characteristics were averaged over several DNA molecules). The curves are provided for several temperatures: OT=29.1° C.; □T=25.4° C.; ◇ T=21.7° C.; x T=19.2° C. Linear fits in agreement with the Arrhenius-Bell model, $\ln[k_D]=\ln[k_D^0]+X_DF_{HF}/k_BT$, make it possible to determine $\ln[k_D^0]$ and $X_D$. F) Variation of $X_D$, the distance separating the transition state from the complex during dissociation, as a function of temperature. The average value is equal to 4.31±0.03 Å. G) Variation of $\ln[k_D^0]$, the logarithm of the dissociation rate extrapolated to zero force, as a function of temperature. A linear fit in agreement with the Arrhenius-Bell model, $\ln[k_D^0]=A-E_D/k_BT$, makes it possible to determine $E_D$, the activation energy of the dissociation reaction. $E_D$=58.8±1.7 kJ $mol^{-1}$ is obtained.
Figure 15:
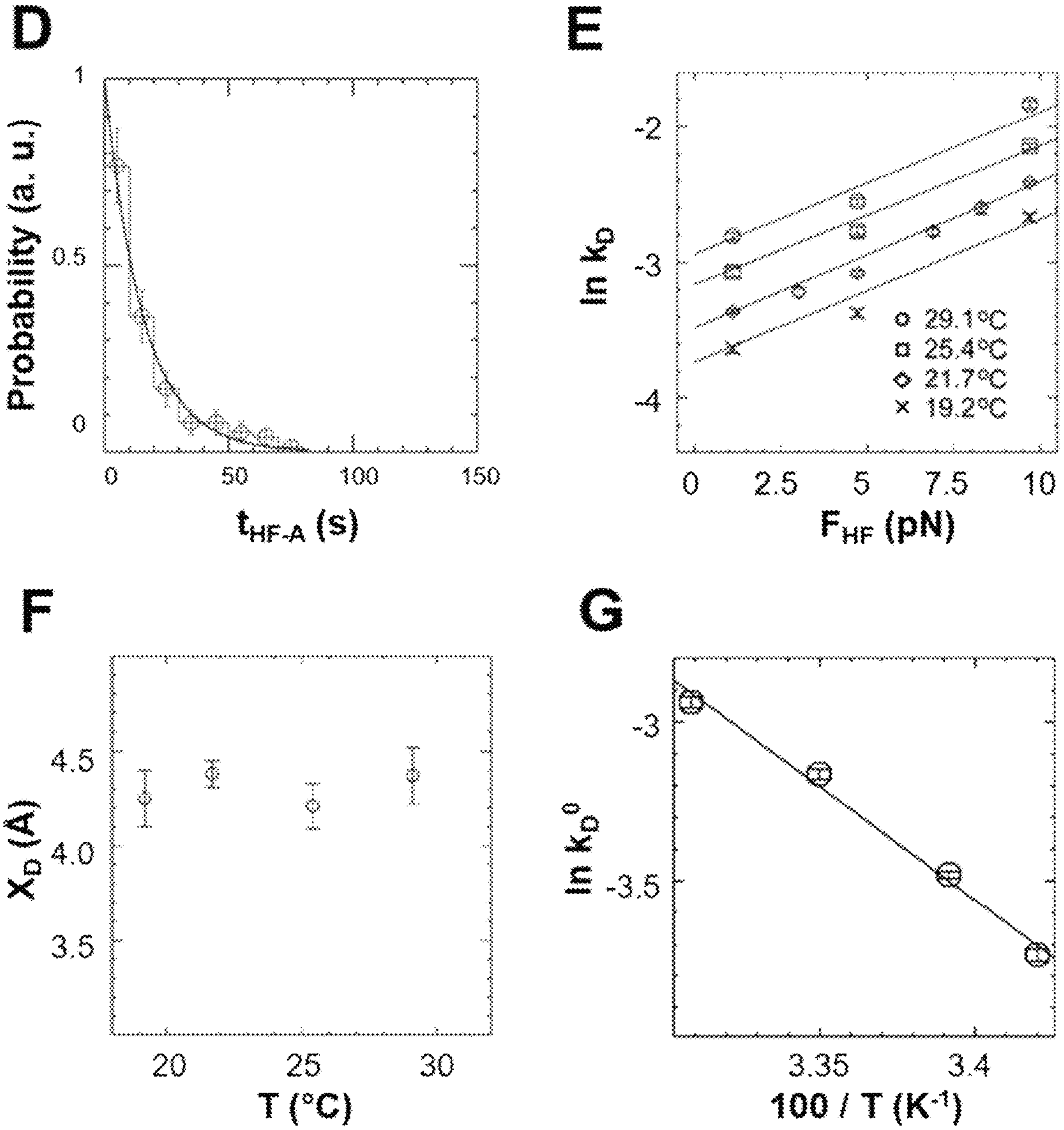

From the characteristic dissociation time, $T_D$, it is possible to calculate the dissociation rate constant, $k_D$, by averaging over several molecules and inversion: $k_D=1/\langle\tau_D\rangle$. It therefore comes in the case of FIG. 14, which corresponds to an applied force $F_{HF}$=1.4 pN and at a temperature T=298 K, $k_D=32.2\times10^{-3}$ $s^{-1}$. The same measurements can be made at a different force and/or temperature, as shown in FIGS. 15A-D. For example, at T=303 K we obtain $k_D=48.4\times10^{-3}$ $s^{-1}$ for $F_{HF}$=1.4 pN and $k_D=64.9\times10^{-3}$ $s^{-1}$ for $F_{HF}$=6 pN. It is then possible to use the Arrhenius/Bell equation, $k_D(F_{HF}, T)=A\times\exp[-E_D/RT]\times\exp[X_DF_{HF}/k_BT]$, to calculate $E_D$, the activation energy of the dissociation reaction, and $X_D$, the distance separating the transition state from the complex during dissociation (Popa et al., 2011). A is a prefactor here, R the universal ideal gas constant and $k_B$ the Boltzmann constant; R=8.31 J $K^{-1}$ $mol^{-1}$ and $k_B=1.38\times10^{-23}$ J $K^{-1}$. More specifically, first linear regressions on the curves giving $\ln[k_D]$ as a function of $F_{HF}$ at various temperatures (FIG. 15E) give, after extraction of slopes and ordinates at the origin, $X_D$ and $\ln[k_D^0]$ as a function of T (FIGS. 15F-G). $k_D^0$ is here the dissociation rate constant extrapolated to zero force: $k_D^0(T)=A^x\exp[-E_D/RT]$. By averaging the different of $X_D$ values, parameter that is theoretically independent of temperature, we find $X_D$=4.31 Å. By linear regression on the curve giving $\ln[k_D^0]$ as a function of T, a slope is extracted which is directly connected to the activation energy. We find $E_D$=58.8 kJ $mol^{-1}$.

In a second step, to estimate $\tau_D$, the characteristic dissociation time of the ternary complex and $\tau_A$, the characteristic association time of FRB with the very stable binary complex FKBP12-rapamycin, we used an experimental protocol based on the study of spontaneous fluctuations of extension at constant force (FIG. 9A). The temporal traces recorded at 25° C. and when $F_{CF}$=0.04 pN was applied (FIG. 17A) were converted into a histogram of $t_{CF-A}$, from which we could then extract $\tau_D$=30.4±2.7 s by monoexponential adjustment (FIG. 17B), and histogram of $t_{CF-D}$, which could then be extracted $\tau_A$=13.7±1.1 s by monoexponential adjustment (FIG. 17C). By averaging the results obtained with several DNA molecules and by inversion we obtain $k_D$=34.1 $s^{-1}$.

To determine the pair of constants $\{k_A, k_D\}$ spontaneous fluctuations of extension are recorded when, at 25° C., $F_{CF}$=0.04 pN is applied in the presence of increasing concentrations of FRB in solution, between 0 and 200 nM (FIG. 9B, FIG. 17D). From the histograms of $t_{CF-A}$ one can, as before and for each FRB concentration, calculate $\langle\tau_D\rangle$. The results obtained at different concentrations (FIG. 17E) are then averaged and the average inversed to obtain $k_D=32.7\times10^{-3}$ $s^{-1}$. Furthermore, from the temporal monitoring of fluctuations for various DNA molecules it is advantageously possible to determine, again for each FRB concentration, the fraction of time spent in associated form by the test molecules. Said fraction of time spent by the test molecules in associated form is determined according to $(\Sigma t_{CF-A})/t_{total}$, where $t_{total}$ is the total time during which the fluctuations are recorded and analyzed. The data is then adjusted using $(\Sigma t_{CF-A})/t_{total}=((1+K_0)+[FRB]/C_{eff})^{-1}$, which leads to the determination of $C_{eff}$ and $K_0$ (FIG. 17F). Here we find $C_{eff}$=12.3 nM and $K_0$=0.59. As we also have $K_0=K_D/C_{eff}$ with $K_D$ the equilibrium dissociation constant of the complex formed by FRB and FKBP12-rapamycin, it is $K_D$=7.26 nM. Finally, we derive the association constant with $k_A=k_D/K_D$; we find $k_A=4.50\ 10^{-6}$ $M^{-1}s^{-1}$.

Discussion

From a technical point of view, the protocol for measuring the characteristic dissociation time by cycling force is confirmed. It makes it possible to simply determine the dissociation rate constant. By performing these measurements at different high forces and/or at different temperatures, it is also possible to determine the activation energy of the dissociation reaction and the distance separating the transition state from the complex upon dissociation.

The study of spontaneous fluctuations of extension at constant force is highly advantageous as it makes it possible to obtain the characteristic dissociation time and the characteristic association time. By performing these measurements when the buffer contains different concentrations of one of the molecular partners, it is also advantageously possible to measure the equilibrium constant of the dissociation reaction as well as the association rate constant of reaction.

Example 11: Illustration of the Capability of the Device to Distinguish Specific Interactions from Non-Specific Interactions Materials and Methods As in Example 10, the double-stranded DNA molecule is that obtained according to the description given in Example 3, followed by Examples 1 and 2 (see also FIG. 6, FIG. 4 and FIG. 5, respectively for an illustration of these steps), using a DNA molecule having the sequences of SEQ ID NO: 30 and SEQ ID NO: 10, for DNA molecules (A) and (B) respectively. The FKBP12 and FRB proteins, which are grafted to the extremities of DNA molecules (1) and (2) in a specific manner, constitute the two test molecules here. Experiments are performed at 25° C. in the DB buffer.

Results

In addition to the conventionally observed A and D conformations, characterized by extensions $z_{LF}$, $z_{HF\text{-}A}$ and $z_{HF\text{-}D}$, the DNA molecule remains blocked here in a fourth conformation for a little less than 6000 s. This conformation, designated S for "support," is characterized by the extensions $z_{LF}$ and $z_{HF\text{-}S}$, the value of this latter parameter indicating an interaction of the extremity bearing one of the test molecules with one of the supports (see FIG. 16).

Discussion

Figure 16:
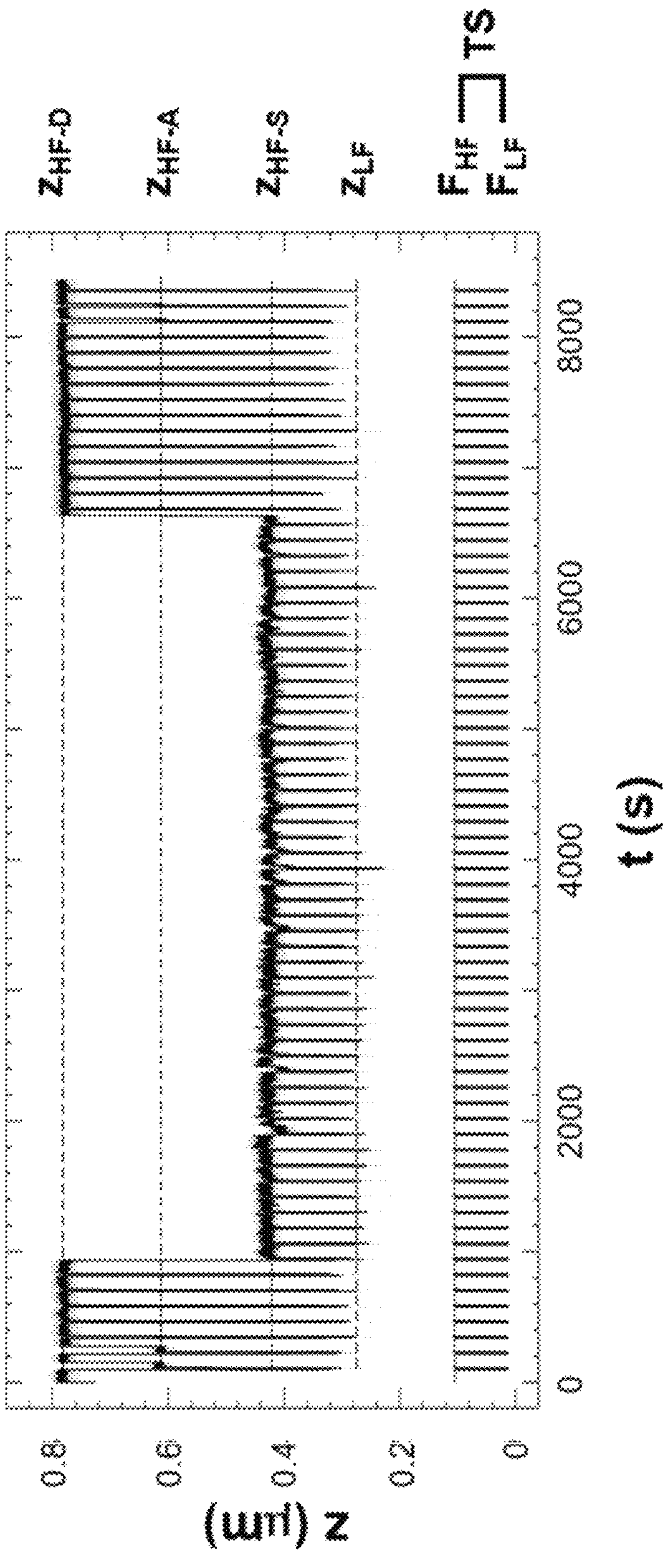
FIG. 16. Demonstration of the ability of the device to distinguish the specific interactions between one of the test molecules and one of the supports ($z_{HF-S}$, where "S" means support), in addition to the interactions between the test molecules ($z_{HF-D}$, $z_{HF-A}$), this during the study of the interactions between the FKBP12 and FRB proteins in the presence of rapamycin.

This example demonstrates the ability of the device to distinguish specific interactions from nonspecific interactions (e.g., between one of the test molecules and one of the supports may be observed, FIG. 16). Advantageously, the use of DNA molecules (1) and (2) of different lengths judiciously chosen with respect to that of the tether makes it possible to detect non-specific variations of the extension at high force (e.g. between one of the test molecules and one of the supports), and thus to avoid analyzing the corresponding events.

A strategy for attaching protein-type test molecules to the extremities and studying association/dissociation reactions between them, this in the presence of a small molecule-type test molecule in solution, has notably been implemented in these examples. Also, highly advantageously, the DNA molecule according to the invention, the device comprising said DNA molecule and its supports, as well as the method for characterizing one or more interactions can be used to detect and characterize molecular interactions in particular to identify, screen, and/or design new drugs, or to study the molecular interactions of current drugs.

Example 12: Use of Snap/Clip Type Protein Tags for the Attachment of Test Molecules to the DNA Molecule Materials and Methods The double-stranded DNA molecule is that obtained as described in Example 3, with the modifications and complements indicated in Examples 1 and 4 (see also FIG. 6, FIG. 4 and FIG. 7, respectively for an illustration of these steps). The two test molecules, which are specifically grafted to the extremities of DNA molecules (1) and (2), are either FRB and FKBP12, or the "PHloop" and gephyrin.

Results

The use of SNAP and CLIP tags to attach test molecules at the extremities of the DNA molecule was first used to study the interaction of FRB with FKBP12 mediated by rapamycin. As the force is cycled between high and low values, temporal traces are obtained which are similar to those obtained when the attachment strategy is based on the ligation of test molecules functionalized by oligonucleotides (compare FIG. 18A with FIG. 14A). Histograms of $t_{HF\text{-}A}$ can then be plotted (FIG. 18B). By repeating these experiments for multiple DNA molecules and with different high forces, the logarithmic variation of the dissociation rate constant as a function of $F_{HF}$ is ultimately obtained (FIG. 18C). It should be noted that the values of $\ln[k_D{}^0]$ and of $X_D$ that can then be extracted by linear adjustment, respectively −3.45±0.03 and 4.7±0.2 Å, are very close to those provided by the ligation attachment strategy at the same temperature, respectively −3.48±0.01 and 4.4±0.1 Å (FIG. 15E).

In a second phase, SNAP and CLIP tags were used to study interactions between the "PHloop" and gephyrin. Again, temporal traces were recorded allowing $t_{HF\text{-}A}$ to be determined (FIG. 18D).

Discussion

This example demonstrates the capacity of the device to evaluate interactions between different molecular partners attached to the extremities of double-stranded DNA molecules (1) and (2) by different strategies (here by the use of SNAP and CLIP-type tags).

REFERENCES

Ausubel et al., Current Protocols in Molecular Biology, Eds., John Wiley & Sons, Inc. New York, 1995.
Bedet et al., J. Biol. Chem., 2006; 281, 30046-56.
Bouchiat et al., Biophys. J. 1999; 76: 409-413.
Conroy, "Force Spectroscopy with Optical and Magnetic Tweezers," in the Handbook of Molecular Force Spectroscopy, pages 23-96 (ed. A. Noy, Springer, 2008).
Doi, Introduction to Polymer Physics, Clarendon Press, 1996.
Duboc et al., Methods Enzymol. 2017; 582: 275-296.
Gao et al., Science, 2012; 337(6100): 1340-1343.
Gautier et al., Chemistry & biology, 2008; 15: 128-136.
Grunewald et al., eNeuro, 2018, 5. doi: 10.1523/ENEURO.0042-17.2018.
Halvorsen et al., Nanotechnology. 2011; 22(49): 494005.
Hein et al., Pharm Res. 2008; 25(10): 2216-2230.
Keppler et al., Nat. Biotechnol., 2003; 21: 86-89.
Kilchherr et al., Science. 2016; 353(6304).
Kim et al., Nature. 2010; 466(7309): 992-5.
Lahann, Click Chemistry for Biotechnology and Materials Science, John Wiley E& Sons, Chichester, England, 2009.
Lionnet et al., Cold Spring Harbor Protoc. 2012: 133-138 (2012).
Pilling et Seakins, Reaction kinetics, Oxford University Press (1995).
Popa et al., J Biol Chem. 2011; 286 (36): 31072-31079.
Pingoud and Jeltsch, Nucleic Acids Res. 2001; 29 (18): 3705-3727.
Remington's Pharmaceutical Sciences, $17^{th}$ ed., Mack Publishing Co., Easton, Pa., 1985. "Restriction Endonucleases Technical Guide," New England Biolabs.
Rognoni et al., Proc Natl Acad Sci USA. 2012; 109(48): 19679-84.
Rothemund, Nature. 2006; 440(7082): 297-302.
Sambrook et al., Molecular cloning: A laboratory manual, $2^{nd}$ ed., Cold Spring Harbor Laboratory Press—Cold Spring Harbor, NY, USA, 1989.
Sarkar and Rybenkov, Frontiers Phys. 2016; 4: 48.
Wiita et al., Proc Natl Acad Sci USA. 2006; 103(19): 7222-7227.
Woodside et al., Proc Natl Acad Sci USA, 103(16): 6190-6195, 2006.
Yang et al., Nat Commun. 2016 Mar. 17; 7:11026. doi: 10.1038/ncomms11026.

SEQUENCE LISTING

<160> NUMBER OF SEQ ID NOS: 50

<210> SEQ ID NO 1
<211> LENGTH: 2285
<212> TYPE: DNA
<213> ORGANISM: Artificial
<220> FEATURE:
<223> OTHER INFORMATION: Amplification product for use as extremities
for the attachment of the molecule to the supports

<400> SEQUENCE: 1

```
gcgtattagc gacccatcgt ctttctgatt taataataga tgattcagtt aaatatgaag     60

gtaatttctt ttgtgcaagt ctgactaact tttttatacc aatgtttaac atactttcat    120

ttgtaataaa ctcaatgtca ttttcttcaa tgtaagatga aataagagta gcctttgcct    180

cgctatacat ttctaaatcg ccttgttttt ctatcgtatt gcgagaattt ttagcccaag    240

ccattaatgg atcatttttc catttttcaa taacattatt gttataccaa atgtcatatc    300

ctataatctg gtttttgttt ttttgaataa taaatgttac tgttcttgcg gtttggagga    360

attgattcaa attcaagcga aataattcag ggtcaaaata tgtatcaatg cagcatttga    420

gcaagtgcga taaatcttta agtcttcttt cccatggttt tttagtcata aaactctcca    480

ttttgatagg ttgcatgcta gatgctgata tattttagag gtgataaaat taactgctta    540

actgtcaatg taatacaagt tgtttgatct ttgcaatgat tcttatcaga aaccatatag    600

taaattagtt acacaggaaa tttttaatat tattattatc attcattatg tattaaaatt    660

agagttgtgg cttggctctg ctaacacgtt gctcatagga gatatggtag agccgcagac    720

acgtcgtatg caggaacgtg ctgcggctgg ctggtgaact tccgatagtg cgggtgttga    780

atgatttcca gttgctaccg attttacata ttttttgcat gagagaattt gtaccacctc    840

ccaccgacca tctatgactg tacgccactg tccctaggac tgctatgtgc cggagcggac    900

attacaaacg tccttctcgg tgcatgccac tgttgccaat gacctgccta ggaattggtt    960

agcaagttac taccggattt tgtaaaaaca gccctcctca tataaaaagt attcgttcac   1020

ttccgataag cgtcgtaatt ttctatcttt catcatattc tagatccctc tgaaaaaatc   1080

ttccgagttt gctaggcact gatacataac tcttttccaa taattgggga agtcattcaa   1140

atctataata ggtttcagat ttgcttcaat aaattctgac tgtagctgct gaaacgttgc   1200

ggttgaacta tatttcctta taacttttac gaaagagttt ctttgagtaa tcacttcact   1260

caagtgcttc cctgcctcca aacgatacct gttagcaata tttaatagct tgaaatgatg   1320

aagagctctg tgtttgtctt cctgcctcca gttcgccggg cattcaacat aaaaactgat   1380

agcacccgga gttccggaaa cgaaatttgc atatacccat tgctcacgaa aaaaaatgtc   1440

cttgtcgata tagggatgaa tcgcttggtg tacctcatct actgcgaaaa cttgaccttt   1500

ctctcccata ttgcagtcgc ggcacgatgg aactaaatta ataggcatca ccgaaaattc   1560

aggataatgt gcaataggaa gaaaatgatc tatatttttt gtctgtccta tatcaccaca   1620

aaatggacat ttttcacctg atgaaacaag catgtcatcg taatatgttc tagcgggttt   1680

gtttttatct cggagattat tttcataaag cttttctaat ttaacctttg tcaggttacc   1740

aactactaag gttgtaggct caagagggtg tgtcctgtcg taggtaaata actgacctgt   1800

cgagcttaat attctatatt gttgttcttt ctgcaaaaaa gtggggaagt gagtaatgaa   1860

attatttcta acatttatct gcatcatacc ttccgagcat ttattaagca tttcgctata   1920

agttctcgct ggaagaggta gttttttcat tgtactttac cttcatctct gttcattatc   1980
```

-continued atcgctttta aaacggttcg accttctaat cctatctgac cattataatt ttttagaatg 2040
gtttcataag aaagctctga atcaacggac tgcgataata agtggtggta tccagaattt 2100
gtcacttcaa gtaaaaacac ctcacgagtt aaaacaccta agttctcacc gaatgtctca 2160
atatccggac ggataatatt tattgcttct cttgaccgta ggactttcca catgcaggat 2220
tttggaacct cttgcagtac tactggggaa tgagttgcaa ttattgctac accattgcgt 2280
gcatc 2285

<210> SEQ ID NO 2
<211> LENGTH: 27
<212> TYPE: DNA
<213> ORGANISM: Artificial
<220> FEATURE:
<223> OTHER INFORMATION: Oligo - forward to amplify the extremity for attachment to a support

<400> SEQUENCE: 2
gcgtattagc gacccatcgt ctttctg 27

<210> SEQ ID NO 3
<211> LENGTH: 29
<212> TYPE: DNA
<213> ORGANISM: Artificial
<220> FEATURE:
<223> OTHER INFORMATION: Oligo - reverse to amplify the extremity for attachment to a support

<400> SEQUENCE: 3
gatgcacgca atggtgtagc aataattgc 29

<210> SEQ ID NO 4
<211> LENGTH: 10
<212> TYPE: DNA
<213> ORGANISM: Artificial
<220> FEATURE:
<223> OTHER INFORMATION: Oligo-TC1

<400> SEQUENCE: 4
tatatgaggc 10

<210> SEQ ID NO 5
<211> LENGTH: 10
<212> TYPE: DNA
<213> ORGANISM: Artificial
<220> FEATURE:
<223> OTHER INFORMATION: Oligo-TC2

<400> SEQUENCE: 5
ttgtaagagc 10

<210> SEQ ID NO 6
<211> LENGTH: 104
<212> TYPE: PRT
<213> ORGANISM: Artificial
<220> FEATURE:
<223> OTHER INFORMATION: FRB protein comprising a GPLGS cleavage residue in N-ter

<400> SEQUENCE: 6

Gly Pro Leu Gly Ser Phe Ile Leu Trp His Glu Met Trp His Glu Gly
1 5 10 15

Leu Glu Glu Ala Ser Arg Leu Tyr Phe Gly Glu Arg Asn Val Lys Gly
20 25 30

-continued

Met Phe Glu Val Leu Glu Pro Leu His Ala Met Met Glu Arg Gly Pro
35 40 45

Gln Thr Leu Lys Glu Thr Ser Phe Asn Gln Ala Tyr Gly Arg Asp Leu
50 55 60

Met Glu Ala Gln Glu Trp Cys Arg Lys Tyr Met Lys Ser Gly Asn Val
65 70 75 80

Lys Asp Leu Thr Gln Ala Trp Asp Leu Tyr Tyr His Val Phe Arg Arg
85 90 95

Ile Ser Lys Gln Leu Pro Gln Leu
100

<210> SEQ ID NO 7
<211> LENGTH: 113
<212> TYPE: PRT
<213> ORGANISM: Artificial
<220> FEATURE:
<223> OTHER INFORMATION: FKBP12 protein comprising a GPLGS cleavage residue in N-ter

<400> SEQUENCE: 7

Gly Pro Leu Gly Ser Phe Gly Val Gln Val Glu Thr Ile Ser Pro Gly
1 5 10 15

Asp Gly Arg Thr Phe Pro Lys Arg Gly Gln Thr Cys Val Val His Tyr
20 25 30

Thr Gly Met Leu Glu Asp Gly Lys Lys Phe Asp Ser Ser Arg Asp Arg
35 40 45

Asn Lys Pro Phe Lys Phe Met Leu Gly Lys Gln Glu Val Ile Arg Gly
50 55 60

Trp Glu Glu Gly Val Ala Gln Met Ser Val Gly Gln Arg Ala Lys Leu
65 70 75 80

Thr Ile Ser Pro Asp Tyr Ala Tyr Gly Ala Thr Gly His Pro Gly Ile
85 90 95

Ile Pro Pro His Ala Thr Leu Val Phe Asp Val Glu Leu Leu Lys Leu
100 105 110

Glu

<210> SEQ ID NO 8
<211> LENGTH: 5287
<212> TYPE: DNA
<213> ORGANISM: Artificial
<220> FEATURE:
<223> OTHER INFORMATION: Charomid 9-5 DSbfI plasmid

<400> SEQUENCE: 8
gaattcgagc tcggtacccg gggatcctct agagtcaaca gcagaaacat acaagctgtc 60
agctttgcac aagggcccaa caccctgctc atcaagaagc actgtggttg ctgtgttagt 120
aatgtgcaaa acaggaggca cattttcccc acctgtgtag gttccaaaat atctagtgtt 180
ttcattttta cttggatcag gaacccagca ctccactgga taagcattat ccttatccaa 240
aacagccttg tggtcagtgt tcatctgctg actgtcgacc tgcatgcagg catgcaagct 300
ttaatgcggt agtttatcac agttaaattg ctaacgcagt caggcaccgt gtatgaaatc 360
taacaatgcg ctcatcgtca tcctcggcac cgtcaccctg gatgctgtag gcataggctt 420
ggttatgccg gtactgccgg gcctcttgcg ggatatcgtc cattccgaca gcatcgccag 480
tcactatggc gtgctgctag cgctatatgc gttgatgcaa tttctatgcg cacccgttct 540
cggagcactg tccgaccgct ttggccgccg cccagtcctg ctcgcttcgc tacttggagc 600

-continued

```
cactatcgac tacgcgatca tggcgaccac acccgtcctg tggatctgcc tcgttggcct    660

gccgcagttc ttcaacctcc cggcgcagct tttcgttctc aatttcagca tccctttcgg    720

cataccattt tatgacggcg gcagagtcat aaagcacctc attacccttg ccaccgcctc    780

gcagaacggg cattccctgt tcctgccagt tctgaatggt acggatactc gcaccgaaaa    840

tgtcagccag ctgcttttg ttgacttcca ttgttcattc cacggacaaa aacagagaaa    900

ggaaacgaca gaggccaaaa agctcgcttt cagcacctgt cgtttccttt cttttcagag    960

ggtattttaa ataaaaacat taagttatga cgaagaagaa cggaaacgcc ttaaaccgga   1020

aaattttcat aaatagcgaa aacccgcgag gtcgccgccc cgtaacaagg cggatcgccg   1080

gaaaggaccc gcaaatgata ataattatca attgcatact atcgacggca ctgctgccag   1140

ataacaccac cggggaaaca ttccatcatg atggccgtgc ggacatagga agccagttca   1200

tccatcgctt tcttgtctgc tgccatttgc tttgtgacat ccagcgccgc acattcagca   1260

gcgtttttca gcgcgttttc gatcaacgtt tcaatgttgg tatcaacacc aggtttaact   1320

ttgaacttat cggcactgac ggttaccttg ttctgcgctg gctcatcacg ctggatacca   1380

aggctgatgt tgtagatatt ggtcaccggc tgaggtgttt cgattgccgc tgcgtggata   1440

gcaccatttg cgatagcggc gtccttgatg aatgacactc cattgcgaat aagttcgaag   1500

gagacggtgt cacgaatgcg ctggtccagc tcgtcgattg ccttttgtgc agcagaggta   1560

tcaatctcaa cgccaagcgt catcgaagcg caatattgct gctcaccaaa acgcgtattg   1620

accaggtgtt caacggcaaa tttctgccct tctgatgtca gaaaggtaaa gtgattttct   1680

ttctggtatt cagttgctgt gtgtctggtt tcagcaaaac caagctcgcg caattcggct   1740

gtgccagatt tagaaggcag atcaccagac agcaacgcgc cacggaaaaa cagcgcatac   1800

agaacatccg tcgccgcgcc ggacaacgtg ataattttat gacccatgat ttatttcctt   1860

ttagacgtga gcctgtcgca cagcaaagcc gccgaaagtt aacggtttgc ccaggctcac   1920

aactgaaaga ctttctacgg tgtgcgcgtg cgatgcgcgt agaagactga tttatcaacc   1980

tgtctttata tcaggattca ttacctgact atttgtgggt aaagttcgta gtgcgctgat   2040

cgtgcaaaat gattttagtt gggaacagtt cgcaactctg tcccataaaa atcagcatat   2100

tcccatctat cccatatcca gcgcattgac catcgggata ctgaagggag attccatcat   2160

ctcttagaaa gatcaccatc tcttttgttt caatttgcat atagctacct ggaggattta   2220

tgaatacaag gattttcatg gactattacc atgagattga ttttccatct ttattcgcga   2280

gagcagtgga aagcgatgac gatgtgggta ctacattgcg cattcaccta ctttgtgagc   2340

gcatggtcga agcatggata tgcgcatgct gtgactgcca agatcctcta cgccggacgc   2400

atcgtggccg gcatcaccgg cgccacaggt gcggttgctg gcgcctatat cgccgacatc   2460

accgatgggg aagatcgggc tcgccacttc gggctcatga gcgcttgttt cggcgtgggt   2520

atggtggcag gccccgtggc cgggggactg ttgggcgcca tctccttgca tgcaccattc   2580

cttgcggcgg cggtgctcaa cggcctcaac ctactactgg gctgcttcct aatgcaggag   2640

tcgcataagg gagagcgtcg accgatgccc ttgagagcct tcaacccagt cagctccttc   2700

cggtgggcgc ggggcatgac tatcgtcgcc gcacttatga ctgtcttctt tatcatgcaa   2760

ctcgtaggac aggtgccggc agcgctctgg gtcattttcg gcgaggaccg ctttcgctgg   2820

agcgcgacga tgatcggcct gtcgcttgcg gtattcggaa tcttgcacgc cctcgctcaa   2880

gccttcgtca ctggtcccgc caccaaacgt ttcggcgaga agcaggccat tatcgccggc   2940

atggcggccg acgcgctggg ctacgtcttg ctggcgttcg cgacgcgagg ctggatggcc   3000
```

ttccccatta tgattcttct cgcttccggc ggcatcggga tgcccgcgtt gcaggccatg 3060
ctgtccaggc aggtagatga cgaccatcag ggacagcttc aaggatcgct cgcggctctt 3120
accagcctaa cttcgatcat tggaccgctg atcgtcacgg cgatttatgc cgcctcggcg 3180
agcacatgga acgggttggc atggattgta ggcgccgccc tataccttgt ctgcctcccc 3240
gcgttgcgtc gcggtgcatg gagccgggcc acctcgacct gaatggaagc cggcggcacc 3300
tcgctaacgg attcaccact ccaagaattg gagccaatca attcttgcgg agaactgtga 3360
atgcgcaaac caacccttgg cagaacatat ccatcgcgtc cgccatctcc agcagccgca 3420
cgcggcgcat ctcgggccgc gttgctggcg tttttccata ggctccgccc ccctgacgag 3480
catcacaaaa atcgacgctc aagtcagagg tggcgaaacc cgacaggact ataaagatac 3540
caggcgtttc cccctggaag ctccctcgtg cgctctcctg ttccgaccct gccgcttacc 3600
ggatacctgt ccgcctttct cccttcggga agcgtggcgc tttctcatag ctcacgctgt 3660
aggtatctca gttcggtgta ggtcgttcgc tccaagctgg gctgtgtgca cgaacccccc 3720
gttcagcccg accgctgcgc cttatccggt aactatcgtc ttgagtccaa cccggtaaga 3780
cacgacttat cgccactggc agcagccact ggtaacagga ttagcagagc gaggtatgta 3840
ggcggtgcta cagagttctt gaagtggtgg cctaactacg gctacactag aaggacagta 3900
tttggtatct gcgctctgct gaagccagtt accttcggaa aaagagttgg tagctcttga 3960
tccggcaaac aaaccaccgc tggtagcggt ggtttttttg tttgcaagca gcagattacg 4020
cgcagaaaaa aaggatctca agaagatcct ttgatctttt ctacggggtc tgacgctcag 4080
tggaacgaaa actcacgtta agggattttg gtcatgagat tatcaaaaag gatcttcacc 4140
tagatccttt taaattaaaa atgaagtttt aaatcaatct aaagtatata tgagtaaact 4200
tggtctgaca gttaccaatg cttaatcagt gaggcaccta tctcagcgat ctgtctattt 4260
cgttcatccc atagttgcct gcaactcccc gtcgtgtaga taactacgat acgggagggc 4320
ttaccatctg gccccagtgc tgcaatgata ccgcgaagac ccacgctcac cggctccaga 4380
tttatcagca ataaaccagc cagccggaag ggccgagcgc agaagtggtc ctgcaacttt 4440
atccgcctcc atccagtcta ttaattgttg ccgggaagct agagtaagta gttcgccagt 4500
taatagtttg cgcaacgttg ttgccattgc tgcaggcatc gtggtgtcac gctcgtcgtt 4560
tggtatggct tcattcagct ccggttccca acgatcaagg cgagttacat gatcccccat 4620
gttgtgcaaa aaagcggtta gctccttcgg tcctccgatc gttgtcagaa gtaagttggc 4680
cgcagtgtta tcactcatgg ttatggcagc actgcataat tctcttactg tcatgccatc 4740
cgtaagatgc ttttctgtga ctggtgagta ctcaaccaag tcattctgag aatagtgtat 4800
gcggcgaccg agttgctctt gcccggcgtc aacacgggat aataccgcgc cacatagcag 4860
aactttaaaa gtgctcatca ttggaaaacg ttcttcgggg cgaaaactct caaggatctt 4920
accgctgttg agatccagtt cgatgtaacc cactcgtgca cccaactgat cttcagcatc 4980
ttttactttc accagcgttt ctgggtgagc aaaaacagga aggcaaaatg ccgcaaaaaa 5040
gggaataagg gcgacacgga aatgttgaat actcatactc ttcctttttc aatattattg 5100
aagcatttat cagggttatt gtctcatgag cggatacata tttgaatgta tttagaaaaa 5160
taaacaaata ggggttccgc gcacatttcc ccgaaaagtg ccacctgacg tctaagaaac 5220
cattattatc atgacattaa cctataaaaa taggcgtatc acgaggccct ttcgtcttca 5280
agaattc 5287

<210> SEQ ID NO 9
<211> LENGTH: 3040
<212> TYPE: DNA
<213> ORGANISM: Artificial
<220> FEATURE:
<223> OTHER INFORMATION: Synthesized

<400> SEQUENCE: 9

```
gagagacccg ggcacgactt atcgccactg gcagcagcca ctggtaacag gattagcaga     60
gcgaggtatg taggcggtgc tacagagttc ttgaagtggt ggcctaacta cggctacact    120
agaaggacag tatttggtat ctgcgctctg ctgaagccag ttaccttcgg aaaaagagtt    180
ggtagctctt gatccggcaa acaaaccacc gctggtagcg gtggtttttt tgtttgcaag    240
cagcagatta cgcgcagaaa aaaaggatct caagaagatc ctttgatctt ttctacgggg    300
tctgacgctc agtggaacga aaactcacgt taagggattt tggtcatgag attatcaaaa    360
aggatcttca cctagatcct tttaaattaa aaatgaagtt ttaaatcaat ctaaagtata    420
tatgagtaaa cttggtctga cagttaccaa tgcttaatca gtgaggcacc tatctcagcg    480
atctgtctat ttcgttcatc ccatagttgc ctgcaactcc ccgtcgtgta gataactacg    540
atacgggagg gcttaccatc tggccccagt gctgcaatga taccgcgaag acccacgctc    600
accggctcca gatttatcag caataaacca gccagccgga agggccgagc gcagaagtgg    660
tcctgcaact ttatccgcct ccatccagtc tattaattgt tgccgggaag ctagagtaag    720
tagttcgcca gttaatagtt tgcgcaacgt tgttgccatt gctgcaggca tcgtggtgtc    780
acgctcgtcg tttggtatgg cttcattcag ctccggttcc caacgatcaa ggcgagttac    840
atgatccccc atgttgtgca aaaaagcggt tagctccttc ggtcctccga tcgttgtcag    900
aagtaagttg gccgcagtgt tatcactcat ggttatggca gcactgcata attctcttac    960
tgtcatgcca tccgtaagat gcttttctgt gactggtgag tactcaacca agtcattctg   1020
agaatagtgt atgcggcgac cgagttgctc ttgcccggcg tcaacacggg ataataccgc   1080
gccacatagc agaactttaa aagtgctcat cattggaaaa cgttcttcgg ggcgaaaact   1140
ctcaaggatc ttaccgctgt tgagatccag ttcgatgtaa cccactcgtg cacccaactg   1200
atcttcagca tcttttactt tcaccagcgt ttctgggtga gcaaaaacag gaaggcaaaa   1260
tgccgcaaaa aagggaataa gggcgacacg gaaatgttga atactcatac tcttcctttt   1320
tcaatattat tgaagcattt atcagggtta ttgtctcatg agcggataca tatttgaatg   1380
tatttagaaa aataaacaaa taggggttcc gcgcacattt ccccgaaaag tgccacctga   1440
cgtctaagaa accattatta tcatgacatt aacctataaa aataggcgta tcacgaggcc   1500
ctttcgtctt caagaattcg aattcgagct cggtacccgg ggatcctcta gagtcaacag   1560
cagaaacata caagctgtca gctttgcaca agggcccaac accctgctca tcaagaagca   1620
ctgtggttgc tgtgttagta atgtgcaaaa caggaggcac attttcccca cctgtgtagg   1680
ttccaaaata tctagtgttt tcatttttac ttggatcagg aacccagcac tccactggat   1740
aagcattatc cttatccaaa acagccttgt ggtcagtgtt catctgctga ctgtcgacct   1800
gcatgcaggc atgcaagctt taatgcggta gtttatcaca gttaaattgc taacgcagtc   1860
aggcaccgtg tatgaaatct aacaatgcgc tcatcgtcat cctcggcacc gtcaccctgg   1920
atgctgtagg cataggcttg gttatgccgg tactgccggg cctcttgcgg gatatcgtcc   1980
attccgacag catcgccagt cactatggcg tgctgctagc gctatatgcg ttgatgcaat   2040
ttctatgcgc acccgttctc ggagcactgt ccgaccgctt tggccgccgc ccagtcctgc   2100
```

tcgcttcgct acttggagcc actatcgact acgcgatcat ggcgaccaca cccgtcctgt 2160
ggatctgcct cgttggcctg ccgcagttct tcaacctccc ggcgcagctt ttcgttctca 2220
atttcagcat ccctttcggc ataccatttt atgacggcgg cagagtcata aagcacctca 2280
ttacccttgc caccgcctcg cagaacgggc attccctgtt cctgccagtt ctgaatggta 2340
cggatactcg caccgaaaat gtcagccagc tgctttttgt tgacttccat tgttcattcc 2400
acggacaaaa acagagaaag gaaacgacag aggccaaaaa gctcgctttc agcacctgtc 2460
gtttcctttc ttttcagagg gtattttaaa taaaaacatt aagttatgac gaagaagaac 2520
ggaaacgcct taaaccggaa aattttcata aatagcgaaa acccgcgagg tcgccgcccc 2580
gtaacaaggc ggatcgccgg aaaggacccg caaatgataa taattatcaa ttgcatacta 2640
tcgacggcac tgctgccaga taacaccacc ggggaaacat tccatcatga tggccgtgcg 2700
gacataggaa gccagttcat ccatcgcttt cttgtctgct gccatttgct ttgtgacatc 2760
cagcgccgca cattcagcag cgtttttcag cgcgttttcg atcaacgttt caatgttggt 2820
atcaacacca ggtttaactt tgaacttatc ggcactgacg gttaccttgt tctgcgctgg 2880
ctcatcacgc tggataccaa ggctgatgtt gtagatattg gtcaccggct gaggtgtttc 2940
gattgccgct gcgtggatag caccatttgc gatagcggcg tccttgatga atgacactcc 3000
attgcgaata agttcgaagg agacggtgcc cgggtctctc 3040

<210> SEQ ID NO 10
<211> LENGTH: 689
<212> TYPE: DNA
<213> ORGANISM: Artificial
<220> FEATURE:
<223> OTHER INFORMATION: Synthesized

<400> SEQUENCE: 10
tccatgggca tactgatcgg tagggcgcgt tacctgtccg cctttctccc ttcgggaagc 60
gtggcgcttt ctcatagctc acgctgtagg tatctcagtt cggtgtaggt cgttcgctcc 120
aagctgggct gtgtgcacga accccccgtt cagcccgacc gctgcgcctt atccggtaac 180
tatcgtcttg agtccaaccc ggtaagacac gacttatcgc cactggcagc agccactggt 240
aacaggatta gcagagcgag gtatgtaggc ggtgctacag agttcttgaa gtggtggcct 300
aactacggct acactagaag gacagtattt ggtatctgcg ctctgctgaa gccagttacc 360
ttcggaaaaa gagttggtag ctcttgatcc ggcaaacaaa ccaccgctgg tagcggtggt 420
tttttgtttg caagcagca gattacgcgc agaaaaaaag gatctcaaga agatcctttg 480
atcttttcta cggggtctga cgctcagtgg aacgaaaact cacgttaagg gattttggtc 540
atgagattat caaaaaggat cttcacctag atccttttaa attaaaaatg aagttttaaa 600
tcaatctaaa gtatatatga gtaaacttgg tctgacagtt accaatgctt aatcagtgag 660
gcctgcatgg atggaggcgt cttggctca 689

<210> SEQ ID NO 11
<211> LENGTH: 62
<212> TYPE: DNA
<213> ORGANISM: Artificial
<220> FEATURE:
<223> OTHER INFORMATION: Oligo-TS1 Synthesized

<400> SEQUENCE: 11
gagagacccg ggcacgactt atcgccactg gcagcagcca ctggtaacag gattagcaga 60
gc 62

<210> SEQ ID NO 12
<211> LENGTH: 26
<212> TYPE: DNA
<213> ORGANISM: Artificial
<220> FEATURE:
<223> OTHER INFORMATION: Oligo-L1 Synthesized

<400> SEQUENCE: 12
tgagccaaga cgcctccatc catgca 26

<210> SEQ ID NO 13
<211> LENGTH: 62
<212> TYPE: DNA
<213> ORGANISM: Artificial
<220> FEATURE:
<223> OTHER INFORMATION: Oligo-TS2 Synthesized

<400> SEQUENCE: 13
gagagacccg ggcaccgtct ccttcgaact tattcgcaat ggagtgtcat tcatcaagga 60
cg 62

<210> SEQ ID NO 14
<211> LENGTH: 25
<212> TYPE: DNA
<213> ORGANISM: Artificial
<220> FEATURE:
<223> OTHER INFORMATION: Oligo-L2 Synthesized

<400> SEQUENCE: 14
tccatgggca tactgatcgg taggg 25

<210> SEQ ID NO 15
<211> LENGTH: 68
<212> TYPE: DNA
<213> ORGANISM: Artificial
<220> FEATURE:
<223> OTHER INFORMATION: Oligo-TS1 Synthesized

<400> SEQUENCE: 15
atatgaggct gaggaagcgg ttagctcctt cggtcctccg atcgttgtca gaagtaagtt 60
ggccgcag 68

<210> SEQ ID NO 16
<211> LENGTH: 25
<212> TYPE: DNA
<213> ORGANISM: Artificial
<220> FEATURE:
<223> OTHER INFORMATION: Oligo-L1 Synthesized

<400> SEQUENCE: 16
tccatgggca tactgatcgg taggg 25

<210> SEQ ID NO 17
<211> LENGTH: 59
<212> TYPE: DNA
<213> ORGANISM: Artificial
<220> FEATURE:
<223> OTHER INFORMATION: Oligo-TS2 Synthesized

<400> SEQUENCE: 17
tgtaagagct gaggcggtga ccaatatcta caacatcagc cttggtatcc agcgtgatg 59

<210> SEQ ID NO 18
<211> LENGTH: 26
<212> TYPE: DNA
<213> ORGANISM: Artificial
<220> FEATURE:
<223> OTHER INFORMATION: Oligo-L2 Synthesized

<400> SEQUENCE: 18
tgagccaaga cgcctccatc catgca 26

<210> SEQ ID NO 19
<211> LENGTH: 38
<212> TYPE: DNA
<213> ORGANISM: Artificial
<220> FEATURE:
<223> OTHER INFORMATION: Oligo - forward to amplify the tether

<400> SEQUENCE: 19
gagagaacgc gttacctgtc cgcctttctc ccttcggg 38

<210> SEQ ID NO 20
<211> LENGTH: 47
<212> TYPE: DNA
<213> ORGANISM: Artificial
<220> FEATURE:
<223> OTHER INFORMATION: Oligo - reverse to amplify the tether

<400> SEQUENCE: 20
gagagacctg caggcctcac tgattaagca ttggtaactg tcagacc 47

<210> SEQ ID NO 21
<211> LENGTH: 22
<212> TYPE: DNA
<213> ORGANISM: Artificial
<220> FEATURE:
<223> OTHER INFORMATION: Oligo-LC1 Synthesized

<400> SEQUENCE: 21
tggatggagg cgtcttggct ca 22

<210> SEQ ID NO 22
<211> LENGTH: 29
<212> TYPE: DNA
<213> ORGANISM: Artificial
<220> FEATURE:
<223> OTHER INFORMATION: Oligo-LC2 Synthesized

<400> SEQUENCE: 22
cgcgccctac cgatcagtat gcccatgga 29

<210> SEQ ID NO 23
<211> LENGTH: 29
<212> TYPE: DNA
<213> ORGANISM: Artificial
<220> FEATURE:
<223> OTHER INFORMATION: Oligo-LC1 Synthesized

<400> SEQUENCE: 23
cgcgccctac cgatcagtat gcccatgga 29

<210> SEQ ID NO 24
<211> LENGTH: 22
<212> TYPE: DNA
<213> ORGANISM: Artificial
<220> FEATURE:
<223> OTHER INFORMATION: Oligo-LC2 Synthesized

<400> SEQUENCE: 24
tggatggagg cgtcttggct ca 22

<210> SEQ ID NO 25
<211> LENGTH: 657
<212> TYPE: DNA
<213> ORGANISM: Artificial
<220> FEATURE:
<223> OTHER INFORMATION: Amplification product for use as a tether

<400> SEQUENCE: 25
gagagaacgc gttacctgtc cgcctttctc ccttcgggaa gcgtggcgct ttctcatagc 60
tcacgctgta ggtatctcag ttcggtgtag gtcgttcgct ccaagctggg ctgtgtgcac 120
gaaccccccg ttcagcccga ccgctgcgcc ttatccggta actatcgtct tgagtccaac 180
ccggtaagac acgacttatc gccactggca gcagccactg gtaacaggat tagcagagcg 240
aggtatgtag gcggtgctac agagttcttg aagtggtggc ctaactacgg ctacactaga 300
aggacagtat ttggtatctg cgctctgctg aagccagtta ccttcggaaa aagagttggt 360
agctcttgat ccggcaaaca aaccaccgct ggtagcggtg gtttttttgt ttgcaagcag 420
cagattacgc gcagaaaaaa aggatctcaa gaagatcctt tgatcttttc tacggggtct 480
gacgctcagt ggaacgaaaa ctcacgttaa gggattttgg tcatgagatt atcaaaaagg 540
atcttcacct agatcctttt aaattaaaaa tgaagtttta aatcaatcta aagtatatat 600
gagtaaactt ggtctgacag ttaccaatgc ttaatcagtg aggcctgcag gtctctc 657

<210> SEQ ID NO 26
<211> LENGTH: 2853
<212> TYPE: DNA
<213> ORGANISM: Artificial
<220> FEATURE:
<223> OTHER INFORMATION: Synthesized

<400> SEQUENCE: 26
gagagacccg ggcacgactt atcgccactg gcagcagcca ctggtaacag gattagcaga 60
gcgaggtatg taggcggtgc tacagagttc ttgaagtggt ggcctaacta cggctacact 120
agaaggacag tatttggtat ctgcgctctg ctgaagccag ttaccttcgg aaaaagagtt 180
ggtagctctt gatccggcaa acaaaccacc gctggtagcg gtggtttttt tgtttgcaag 240
cagcagatta cgcgcagaaa aaaaggatct caagaagatc ctttgatctt ttctacgggg 300
tctgacgctc agtggaacga aaactcacgt taagggattt tggtcatgag attatcaaaa 360
aggatcttca cctagatcct tttaaattaa aaatgaagtt ttaaatcaat ctaaagtata 420
tatgagtaaa cttggtctga cagttaccaa tgcttaatca gtgaggcacc tatctcagcg 480
atctgtctat ttcgttcatc ccatagttgc ctgcaactcc ccgtcgtgta gataactacg 540
atacgggagg gcttaccatc tggccccagt gctgcaatga taccgcgaag acccacgctc 600
accggctcca gatttatcag caataaacca gccagccgga agggccgagc gcagaagtgg 660
tcctgcaact ttatccgcct ccatccagtc tattaattgt tgccgggaag ctagagtaag 720
tagttcgcca gttaatagtt tgcgcaacgt tgttgccatt gctgcaggca tcgtggtgtc 780
acgctcgtcg tttggtatgg cttcattcag ctccggttcc caacgatcaa ggcgagttac 840
atgatccccc atgttgtgca aaaaagcggt tagctccttc ggtcctccga tcgttgtcag 900
aagtaagttg gccgcagtgt tatcactcat ggttatggca gcactgcata attctcttac 960
tgtcatgcca tccgtaagat gcttttctgt gactggtgag tactcaacca agtcattctg 1020

```
agaatagtgt atgcggcgac cgagttgctc ttgcccggcg tcaacacggg ataataccgc   1080
gccacatagc agaactttaa aagtgctcat cattggaaaa cgttcttcgg ggcgaaaact   1140
ctcaaggatc ttaccgctgt tgagatccag ttcgatgtaa cccactcgtg cacccaactg   1200
atcttcagca tcttttactt tcaccagcgt ttctgggtga gcaaaaacag gaaggcaaaa   1260
tgccgcaaaa aagggaataa gggcgacacg gaaatgttga atactcatac tcttcctttt   1320
tcaatattat tgaagcattt atcagggtta ttgtctcatg agcggataca tatttgaatg   1380
tatttagaaa aataaacaaa taggggttcc gcgcacattt ccccgaaaag tgccacctga   1440
cgtctaagaa accattatta tcatgacatt aacctataaa aataggcgta tcacgaggcc   1500
ctttcgtctt caagaattcg aattcgagct cttcatcatt tcaagctatt aaatattgct   1560
aacaggtatc gtttggaggc agggaagcac ttgagtgaag tgattactca aagaaactct   1620
ttcgtaaaag ttataaggaa atatagttca accgcaacgt ttcagcagct acagtcagaa   1680
tttattgaag caaatctgaa acctattata gatttgaatg acttccccaa ttattggaaa   1740
agagttatgt atcagtgcct agcaaactcg gaagattttt tcagagggat ctagaatatg   1800
atgaaagata gaaaattacg acgcttatcg gaagtgaacg aatacttttt atatgaggag   1860
ggctgttttt acaaaatccg gtagtaactt gctaaccaat tcctaggcag gtcattggca   1920
acagtggcat gcaccgagaa ggacgtttgt aatgtccgct ccggcacata gcagtcctag   1980
ggacagtggc gtacagtcat agatggtcgg tgggaggtgg tacaaattct ctcatgcaaa   2040
aaatatgtaa aatcggtagc aactggaaat cattcaacac ccgcactatc ggaagttcac   2100
cagccagccg cagcacgttc ctgcatacga cgtgtctgcg gctctaccat atctcctatg   2160
agcaacgtgt tagcagagcc aagccacaac tctaatttta atacataatg aatgataata   2220
ataatattaa aaatttcctg tgtaactaat ttactatatg gtttctgata agaatcattg   2280
caaagatcaa acaacttgta ttacattgac agttaagcag ttaattttat cacctctaaa   2340
atatatcagc atctagcatg caacctatca aaatggagag ttttatgact aaaaaaccat   2400
gggaaagaag acttaaagat ttatcgcact tgctcaaatg ctgcattgat acatattttg   2460
accctgaatt atttcgcttg aatttgaatc aattcctcca aaccgcaaga acagtaacat   2520
ttattattca aaaaaacaaa aaccagatta taggatatga catttggtat aacaataatg   2580
ttattgaaaa atggaaaaat gatccattaa tggcttgggc taaaaattct cgcaatacga   2640
tagaaaaaca aggcgattta gaaatgtata gcgaggcaaa ggctactctt atttcatctt   2700
acattgaaga aaatgacatt gagtttatta caaatgaaag tatgttaaac attggtataa   2760
aaaagttagt cagacttgca caaaagaaat taccttcata tttaactgaa tcatctatta   2820
ttaaatcaga aagacgatgg gtcgctaata cgc                               2853
```

```
<210> SEQ ID NO 27
<211> LENGTH: 2488
<212> TYPE: DNA
<213> ORGANISM: Artificial
<220> FEATURE:
<223> OTHER INFORMATION: Synthesized

<400> SEQUENCE: 27

gagagacccg ggcacgactt atcgccactg gcagcagcca ctggtaacag gattagcaga     60
gcgaggtatg taggcggtgc tacagagttc ttgaagtggt ggcctaacta cggctacact    120
agaaggacag tatttggtat ctgcgctctg ctgaagccag ttaccttcgg aaaaagagtt    180
```

-continued

```
ggtagctctt gatccggcaa acaaaccacc gctggtagcg gtggtttttt tgtttgcaag    240
cagcagatta cgcgcagaaa aaaaggatct caagaagatc ctttgatctt ttctacgggg    300
tctgacgctc agtggaacga aaactcacgt taagggattt tggtcatgag attatcaaaa    360
aggatcttca cctagatcct tttaaattaa aaatgaagtt ttaaatcaat ctaaagtata    420
tatgagtaaa cttggtctga cagttaccaa tgcttaatca gtgaggcacc tatctcagcg    480
atctgtctat ttcgttcatc catagttgc  ctgcaactcc ccgtcgtgta gataactacg    540
atacgggagg gcttaccatc tggccccagt gctgcaatga taccgcgaag acccacgctc    600
accggctcca gatttatcag caataaacca gccagccgga agggccgagc gcagaagtgg    660
tcctgcaact ttatccgcct ccatccagtc tattaattgt tgccgggaag ctagagtaag    720
tagttcgcca gttaatagtt tgcgcaacgt tgttgccatt gctgcaggca tcgtggtgtc    780
acgctcgtcg tttggtatgg cttcattcag ctccggttcc caacgatcaa ggcgagttac    840
atgatccccc atgttgtgca aaaaagcggt tagctccttc ggtcctccga tcgttgtcag    900
aagtaagttg gccgcagtgt tatcactcat ggttatggca gcactgcata attctcttac    960
tgtcatgcca tccgtaagat gcttttctgt gactggtgag tactcaacca agtcattctg   1020
agaatagtgt atgcggcgac cgagttgctc ttgcccggcg tcaacacggg ataataccgc   1080
gccacatagc agaactttaa aagtgctcat cattggaaaa cgttcttcgg ggcgaaaact   1140
ctcaaggatc ttaccgctgt tgagatccag ttcgatgtaa cccactcgtg cacccaactg   1200
atcttcagca tcttttactt tcaccagcgt ttctgggtga gcaaaaacag gaaggcaaaa   1260
tgccgcaaaa aagggaataa gggcgacacg gaaatgttga atactcatac tcttcctttt   1320
tcaatattat tgaagcattt atcagggtta ttgtctcatg agcggataca tatttgaatg   1380
tatttagaaa aataaacaaa taggggttcc gcgcacattt ccccgaaaag tgccacctga   1440
cgtctaagaa accattatta tcatgacatt aacctataaa aataggcgta tcacgaggcc   1500
ctttcgtctt caagaattcg aattcgagct ctgtgtttgt cttcctgcct ccagttcgcc   1560
gggcattcaa cataaaaact gatagcaccc ggagttccgg aaacgaaatt tgcatatacc   1620
cattgctcac gaaaaaaaat gtccttgtcg atatagggat gaatcgcttg gtgtacctca   1680
tctactgcga aaacttgacc tttctctccc atattgcagt cgcggcacga tggaactaaa   1740
ttaataggca tcaccgaaaa ttcaggataa tgtgcaatag gaagaaaatg atctatattt   1800
tttgtctgtc ctatatcacc acaaaatgga catttttcac ctgatgaaac aagcatgtca   1860
tcgtaatatg ttctagcggg tttgttttta tctcggagat tattttcata aagcttttct   1920
aatttaacct ttgtcaggtt accaactact aaggttgtag gctcaagagg gtgtgtcctg   1980
tcgtaggtaa ataactgacc tgtcgagctt aatattctat attgttgttc tttctgcaaa   2040
aaagtgggga agtgagtaat gaaattattt ctaacattta tctgcatcat accttccgag   2100
catttattaa gcatttcgct ataagttctc gctggaagag gtagtttttt cattgtactt   2160
taccttcatc tctgttcatt atcatcgctt ttaaaacggt tcgaccttct aatcctatct   2220
gaccattata attttttaga atggtttcat aagaaagctc tgaatcaacg gactgcgata   2280
ataagtggtg gtatccagaa tttgtcactt caagtaaaaa cacctcacga gttaaaacac   2340
ctaagttctc accgaatgtc tcaatatccg gacggataat atttattgct tctcttgacc   2400
gtaggacttt ccacatgcag gattttggaa cctcttgcag tactactggg gaatgagttg   2460
caattattgc tacaccattg cgtgcatc                                      2488
```

<210> SEQ ID NO 28
<211> LENGTH: 2552
<212> TYPE: DNA
<213> ORGANISM: Artificial
<220> FEATURE:
<223> OTHER INFORMATION: Synthesized

<400> SEQUENCE: 28
gagagacccg ggcaccgtct ccttcgaact tattcgcaat ggagtgtcat tcatcaagga 60
cgccgctatc gcaaatggtg ctatccacgc agcggcaatc gaaacacctc agccggtgac 120
caatatctac aacatcagcc ttggtatcca gcgtgatgag ccagcgcaga acaaggtaac 180
cgtcagtgcc gataagttca aagttaaacc tggtgttgat accaacattg aaacgttgat 240
cgaaaacgcg ctgaaaaacg ctgctgaatg tgcggcgctg gatgtcacaa agcaaatggc 300
agcagacaag aaagcgatgg atgaactggc ttcctatgtc cgcacggcca tcatgatgga 360
atgtttcccc ggtggtgtta tctggcagca gtgccgtcga tagtatgcaa ttgataatta 420
ttatcatttg cgggtccttt ccggcgatcc gccttgttac ggggcggcga cctcgcgggt 480
tttcgctatt tatgaaaatt ttccggttta aggcgtttcc gttcttcttc gtcataactt 540
aatgttttta tttaaaatac cctctgaaaa gaaaggaaac gacaggtgct gaaagcgagc 600
tttttggcct ctgtcgtttc ctttctctgt ttttgtccgt ggaatgaaca atggaagtca 660
acaaaaagca gctggctgac attttcggtg cgagtatccg taccattcag aactggcagg 720
aacagggaat gcccgttctg cgaggcggtg gcaagggtaa tgaggtgctt tatgactctg 780
ccgccgtcat aaaatggtat gccgaaaggg atgctgaaat tgagaacgaa aagctgcgcc 840
gggaggttga agaactgcgg caggccaacg aggcagatcc acaggacggg tgtggtcgcc 900
atgatcgcgt agtcgatagt ggctccaagt agcgaagcga gcaggactgg gcggcggcca 960
aagcggtcgg acagtgctcc gagaacgggt gcgcatagaa attgcatcaa cgcatatagc 1020
gctagcagca cgccatagtg actggcgatg ctgtcggaat ggacgatatc ccgcaagagg 1080
cccggcagta ccggcataac caagcctatg cctacagcat ccagggtgac ggtgccgagg 1140
atgacgatga gcgcattgtt agatttcata cacggtgcct gactgcgtta gcaatttaac 1200
tgtgataaac taccgcatta aagcttgcat gcctgcatgc aggtcgacag tcagcagatg 1260
aacactgacc acaaggctgt tttggataag gataatgctt atccagtgga gtgctgggtt 1320
cctgatccaa gtaaaaatga aaacactaga tattttggaa cctacacagg tggggaaaat 1380
gtgcctcctg ttttgcacat tactaacaca gcaaccacag tgcttcttga tgagcagggt 1440
gttgggccct tgtgcaaagc tgacagcttg tatgtttctg ctgttgactc tagaatatga 1500
tgaaagatag aaaattacga cgcttatcgg aagtgaacga atacttttta tatgaggagg 1560
gctgttttta caaaatccgg tagtaacttg ctaaccaatt cctaggcagg tcattggcaa 1620
cagtggcatg caccgagaag gacgtttgta atgtccgctc cggcacatag cagtcctagg 1680
gacagtggcg tacagtcata gatggtcggt gggaggtggt acaaattctc tcatgcaaaa 1740
aatatgtaaa atcggtagca actggaaatc attcaacacc cgcactatcg gaagttcacc 1800
agccagccgc agcacgttcc tgcatacgac gtgtctgcgg ctctaccata tctcctatga 1860
gcaacgtgtt agcagagcca agccacaact ctaattttaa tacataatga atgataataa 1920
taatattaaa aatttcctgt gtaactaatt tactatatgg tttctgataa gaatcattgc 1980
aaagatcaaa caacttgtat tacattgaca gttaagcagt taattttatc acctctaaaa 2040
tatatcagca tctagcatgc aacctatcaa aatggagagt tttatgacta aaaaaccatg 2100

```
ggaaagaaga cttaaagatt tatcgcactt gctcaaatgc tgcattgata catattttga   2160

ccctgaatta tttcgcttga atttgaatca attcctccaa accgcaagaa cagtaacatt   2220

tattattcaa aaaaacaaaa accagattat aggatatgac atttggtata acaataatgt   2280

tattgaaaaa tggaaaaatg atccattaat ggcttgggct aaaaattctc gcaatacgat   2340

agaaaaacaa ggcgatttag aaatgtatag cgaggcaaag gctactctta tttcatctta   2400

cattgaagaa aatgacattg agtttattac aaatgaaagt atgttaaaca ttggtataaa   2460

aaagttagtc agacttgcac aaaagaaatt accttcatat ttaactgaat catctattat   2520

taaatcagaa agacgatggg tcgctaatac gc                                 2552
```

<210> SEQ ID NO 29
<211> LENGTH: 2715
<212> TYPE: DNA
<213> ORGANISM: Artificial
<220> FEATURE:
<223> OTHER INFORMATION: Synthesized

<400> SEQUENCE: 29

```
gagagacccg ggcaccgtct ccttcgaact tattcgcaat ggagtgtcat tcatcaagga     60

cgccgctatc gcaaatggtg ctatccacgc agcggcaatc gaaacacctc agccggtgac    120

caatatctac aacatcagcc ttggtatcca gcgtgatgag ccagcgcaga acaaggtaac    180

cgtcagtgcc gataagttca aagttaaacc tggtgttgat accaacattg aaacgttgat    240

cgaaaacgcg ctgaaaaacg ctgctgaatg tgcggcgctg gatgtcacaa agcaaatggc    300

agcagacaag aaagcgatgg atgaactggc ttcctatgtc cgcacggcca tcatgatgga    360

atgtttcccc ggtggtgtta tctggcagca gtgccgtcga tagtatgcaa ttgataatta    420

ttatcatttg cgggtccttt ccggcgatcc gccttgttac ggggcggcga cctcgcgggt    480

tttcgctatt tatgaaaatt ttccggttta aggcgtttcc gttcttcttc gtcataactt    540

aatgttttta tttaaaatac cctctgaaaa gaaaggaaac gacaggtgct gaaagcgagc    600

tttttggcct ctgtcgtttc ctttctctgt tttgtccgt ggaatgaaca atggaagtca    660

acaaaaagca gctggctgac attttcggtg cgagtatccg taccattcag aactggcagg    720

aacagggaat gcccgttctg cgaggcggtg gcaagggtaa tgaggtgctt tatgactctg    780

ccgccgtcat aaaatggtat gccgaaaggg atgctgaaat tgagaacgaa aagctgcgcc    840

gggaggttga agaactgcgg caggccaacg aggcagatcc acaggacggg tgtggtcgcc    900

atgatcgcgt agtcgatagt ggctccaagt agcgaagcga gcaggactgg gcggcggcca    960

aagcggtcgg acagtgctcc gagaacgggt gcgcatagaa attgcatcaa cgcatatagc   1020

gctagcagca cgccatagtg actggcgatg ctgtcggaat ggacgatatc ccgcaagagg   1080

cccggcagta ccggcataac caagcctatg cctacagcat ccagggtgac ggtgccgagg   1140

atgacgatga gcgcattgtt agatttcata cacggtgcct gactgcgtta gcaatttaac   1200

tgtgataaac taccgcatta aagcttgcat gcctgcatgc aggtcgacag tcagcagatg   1260

aacactgacc acaaggctgt tttggataag gataatgctt atccagtgga gtgctgggtt   1320

cctgatccaa gtaaaaatga aaacactaga tattttggaa cctacacagg tggggaaaat   1380

gtgcctcctg ttttgcacat tactaacaca gcaaccacag tgcttcttga tgagcagggt   1440

gttgggccct tgtgcaaagc tgacagcttg tatgtttctg ctgttgactc tagatccctc   1500

tgaaaaaatc ttccgagttt gctaggcact gatacataac tcttttccaa taattgggga   1560

agtcattcaa atctataata ggtttcagat ttgcttcaat aaattctgac tgtagctgct   1620
```

gaaacgttgc ggttgaacta tatttcctta taacttttac gaaagagttt ctttgagtaa 1680
tcacttcact caagtgcttc cctgcctcca aacgatacct gttagcaata tttaatagct 1740
tgaaatgatg aagagctctg tgtttgtctt cctgcctcca gttcgccggg cattcaacat 1800
aaaaactgat agcacccgga gttccggaaa cgaaatttgc atatacccat tgctcacgaa 1860
aaaaaatgtc cttgtcgata tagggatgaa tcgcttggtg tacctcatct actgcgaaaa 1920
cttgaccttt ctctcccata ttgcagtcgc ggcacgatgg aactaaatta ataggcatca 1980
ccgaaaattc aggataatgt gcaataggaa gaaaatgatc tatatttttt gtctgtccta 2040
tatcaccaca aaatggacat ttttcacctg atgaaacaag catgtcatcg taatatgttc 2100
tagcgggttt gtttttatct cggagattat tttcataaag cttttctaat ttaacctttg 2160
tcaggttacc aactactaag gttgtaggct caagagggtg tgtcctgtcg taggtaaata 2220
actgacctgt cgagcttaat attctatatt gttgttcttt ctgcaaaaaa gtggggaagt 2280
gagtaatgaa attatttcta acatttatct gcatcatacc ttccgagcat ttattaagca 2340
tttcgctata agttctcgct ggaagaggta gtttttttcat tgtactttac cttcatctct 2400
gttcattatc atcgctttta aaacggttcg accttctaat cctatctgac cattataatt 2460
ttttagaatg gtttcataag aaagctctga atcaacggac tgcgataata agtggtggta 2520
tccagaattt gtcacttcaa gtaaaaacac ctcacgagtt aaaacaccta agttctcacc 2580
gaatgtctca atatccggac ggataatatt tattgcttct cttgaccgta ggactttcca 2640
catgcaggat tttggaacct cttgcagtac tactggggaa tgagttgcaa ttattgctac 2700
accattgcgt gcatc 2715

<210> SEQ ID NO 30
<211> LENGTH: 2092
<212> TYPE: DNA
<213> ORGANISM: Artificial
<220> FEATURE:
<223> OTHER INFORMATION: Synthesized

<400> SEQUENCE: 30
atatgaggct gaggaagcgg ttagctcctt cggtcctccg atcgttgtca gaagtaagtt 60
ggccgcagtg ttatcactca tggttatggc agcactgcat aattctctta ctgtcatgcc 120
atccgtaaga tgcttttctg tgactggtga gtactcaacc aagtcattct gagaatagtg 180
tatgcggcga ccgagttgct cttgcccggc gtcaacacgg gataataccg cgccacatag 240
cagaacttta aaagtgctca tcattggaaa acgttcttcg gggcgaaaac tctcaaggat 300
cttaccgctg ttgagatcca gttcgatgta acccactcgt gcacccaact gatcttcagc 360
atcttttact ttcaccagcg tttctgggtg agcaaaaaca ggaaggcaaa atgccgcaaa 420
aaagggaata agggcgacac ggaaatgttg aatactcata ctcttccttt ttcaatatta 480
ttgaagcatt tatcagggtt attgtctcat gagcggatac atatttgaat gtatttagaa 540
aaataaacaa ataggggttc cgcgcacatt tccccgaaaa gtgccacctg acgtctaaga 600
aaccattatt atcatgacat taacctataa aaataggcgt atcacgaggc cctttcgtct 660
tcaagaattc gaattcgagc tcggtacccg gggatcctct agagtcaaca gcagaaacat 720
acaagctgtc agctttgcac aagggcccaa caccctgctc atcaagaagc actgtggttg 780
ctgtgttagt aatgtgcaaa acaggaggca cattttcccc acctgtgtag gttccaaaat 840
atctagtgtt ttcattttta cttggatcag gaacccagca ctccactgga taagcattat 900
ccttatccaa aacagccttg tggtcagtgt tcatctgctg actgtcgacc tgcatgcagg 960
catgcaagct ttaatgcggt agtttatcac agttaaattg ctaacgcagt caggcaccgt 1020
gtatgaaatc taacaatgcg ctcatcgtca tcctcggcac cgtcaccctg gatgctgtag 1080
gcataggctt ggttatgccg gtactgccgg gcctcttgcg ggatatcgtc cattccgaca 1140
gcatcgccag tcactatggc gtgctgctag cgctatatgc gttgatgcaa tttctatgcg 1200
cacccgttct cggagcactg tccgaccgct ttggccgccg cccagtcctg ctcgcttcgc 1260
tacttggagc cactatcgac tacgcgatca tggcgaccac acccgtcctg tggatctgcc 1320
tcgttggcct gccgcagttc ttcaacctcc cggcgcagct tttcgttctc aatttcagca 1380
tccctttcgg cataccattt tatgacggcg gcagagtcat aaagcacctc attacccttg 1440
ccaccgcctc gcagaacggg cattccctgt tcctgccagt tctgaatggt acggatactc 1500
gcaccgaaaa tgtcagccag ctgctttttg ttgacttcca ttgttcattc cacggacaaa 1560
aacagagaaa ggaaacgaca gaggccaaaa agctcgcttt cagcacctgt cgtttccttt 1620
cttttcagag ggtattttaa ataaaaacat taagttatga cgaagaagaa cggaaacgcc 1680
ttaaaccgga aaattttcat aaatagcgaa aacccgcgag gtcgccgccc cgtaacaagg 1740
cggatcgccg gaaaggaccc gcaaatgata ataattatca attgcatact atcgacggca 1800
ctgctgccag ataacaccac cggggaaaca ttccatcatg atggccgtgc ggacatagga 1860
agccagttca tccatcgctt tcttgtctgc tgccatttgc tttgtgacat ccagcgccgc 1920
acattcagca gcgtttttca gcgcgttttc gatcaacgtt tcaatgttgg tatcaacacc 1980
aggtttaact ttgaacttat cggcactgac ggttaccttg ttctgcgctg gctcatcacg 2040
ctggatacca aggctgatgt tgtagatatt ggtcaccgcc tcagctctta ca 2092

<210> SEQ ID NO 31
<211> LENGTH: 2005
<212> TYPE: DNA
<213> ORGANISM: Artificial
<220> FEATURE:
<223> OTHER INFORMATION: Synthesized

<400> SEQUENCE: 31
tatatgaggc tgaggaagcg gttagctcct tcggtcctcc gatcgttgtc agaagtaagt 60
tggccgcagt gttatcactc atggttatgg cagcactgca taattctctt actgtcatgc 120
catccgtaag atgcttttct gtgactggtg agtactcaac caagtcattc tgagaatagt 180
gtatgcggcg accgagttgc tcttgcccgg cgtcaacacg ggataatacc gcgccacata 240
gcagaacttt aaaagtgctc atcattggaa aacgttcttc ggggcgaaaa ctctcaagga 300
tcttaccgct gttgagatcc agttcgatgt aacccactcg tgcacccaac tgatcttcag 360
catcttttac tttcaccagc gtttctgggt gagcaaaaac aggaaggcaa aatgccgcaa 420
aaaagggaat aagggcgaca cggaaatgtt gaatactcat actcttcctt tttcaatatt 480
attgaagcat ttatcagggt tattgtctca tgagcggata catatttgaa tgtatttaga 540
aaaataaaca aataggggtt ccgcgcacat ttccccgaaa agtgccacct gacgtctaag 600
aaaccattat tatcatgaca ttaacctata aaaataggcg tatcacgagg ccctttcgtc 660
ttcaagaatt cgaattcgag ctcttcatca tttcaagcta ttaaatattg ctaacaggta 720
tcgtttggag gcagggaagc acttgagtga agtgattact caaagaaact ctttcgtaaa 780
agttataagg aaatatagtt caaccgcaac gtttcagcag ctacagtcag aatttattga 840
agcaaatctg aaacctatta tagatttgaa tgacttcccc aattattgga aaagagttat 900
gtatcagtgc ctagcaaact cggaagattt tttcagaggg atctagaata tgatgaaaga 960
tagaaaatta cgacgcttat cggaagtgaa cgaatacttt ttatatgagg agggctgttt 1020
ttacaaaatc cggtagtaac ttgctaacca attcctaggc aggtcattgg caacagtggc 1080
atgcaccgag aaggacgttt gtaatgtccg ctccggcaca tagcagtcct agggacagtg 1140
gcgtacagtc atagatggtc ggtgggaggt ggtacaaatt ctctcatgca aaaaatatgt 1200
aaaatcggta gcaactggaa atcattcaac acccgcacta tcggaagttc accagccagc 1260
cgcagcacgt tcctgcatac gacgtgtctg cggctctacc atatctccta tgagcaacgt 1320
gttagcagag ccaagccaca actctaattt taatacataa tgaatgataa taataatatt 1380
aaaaatttcc tgtgtaacta atttactata tggtttctga taagaatcat tgcaaagatc 1440
aaacaacttg tattacattg acagttaagc agttaatttt atcacctcta aaatatatca 1500
gcatctagca tgcaacctat caaaatggag agttttatga ctaaaaaacc atgggaaaga 1560
agacttaaag atttatcgca cttgctcaaa tgctgcattg atacatattt tgaccctgaa 1620
ttatttcgct tgaatttgaa tcaattcctc caaaccgcaa gaacagtaac atttattatt 1680
caaaaaaaca aaaaccagat tataggatat gacatttggt ataacaataa tgttattgaa 1740
aaatggaaaa atgatccatt aatggcttgg gctaaaaatt ctcgcaatac gatagaaaaa 1800
caaggcgatt tagaaatgta tagcgaggca aaggctactc ttatttcatc ttacattgaa 1860
gaaaatgaca ttgagtttat tacaaatgaa agtatgttaa acattggtat aaaaaagtta 1920
gtcagacttg cacaaaagaa attaccttca tatttaactg aatcatctat tattaaatca 1980
gaaagacgat gggtcgctaa tacgc 2005

<210> SEQ ID NO 32
<211> LENGTH: 1640
<212> TYPE: DNA
<213> ORGANISM: Artificial
<220> FEATURE:
<223> OTHER INFORMATION: Synthesized

<400> SEQUENCE: 32
tatatgaggc tgaggaagcg gttagctcct tcggtcctcc gatcgttgtc agaagtaagt 60
tggccgcagt gttatcactc atggttatgg cagcactgca taattctctt actgtcatgc 120
catccgtaag atgcttttct gtgactggtg agtactcaac caagtcattc tgagaatagt 180
gtatgcggcg accgagttgc tcttgcccgg cgtcaacacg ggataatacc gcgccacata 240
gcagaacttt aaaagtgctc atcattggaa aacgttcttc ggggcgaaaa ctctcaagga 300
tcttaccgct gttgagatcc agttcgatgt aacccactcg tgcacccaac tgatcttcag 360
catcttttac tttcaccagc gtttctgggt gagcaaaaac aggaaggcaa aatgccgcaa 420
aaaagggaat aagggcgaca cggaaatgtt gaatactcat actcttcctt tttcaatatt 480
attgaagcat ttatcagggt tattgtctca tgagcggata catatttgaa tgtatttaga 540
aaaataaaca aataggggtt ccgcgcacat ttccccgaaa agtgccacct gacgtctaag 600
aaaccattat tatcatgaca ttaacctata aaaataggcg tatcacgagg ccctttcgtc 660
ttcaagaatt cgaattcgag ctctgtgttt gtcttcctgc ctccagttcg ccgggcattc 720
aacataaaaa ctgatagcac ccggagttcc ggaaacgaaa tttgcatata cccattgctc 780
acgaaaaaaa atgtccttgt cgatataggg atgaatcgct tggtgtacct catctactgc 840
gaaaacttga cctttctctc ccatattgca gtcgcggcac gatggaacta aattaatagg 900

```
catcaccgaa aattcaggat aatgtgcaat aggaagaaaa tgatctatat tttttgtctg     960

tcctatatca ccacaaaatg gacatttttc acctgatgaa acaagcatgt catcgtaata    1020

tgttctagcg ggtttgtttt tatctcggag attattttca taaagctttt ctaatttaac    1080

ctttgtcagg ttaccaacta ctaaggttgt aggctcaaga gggtgtgtcc tgtcgtaggt    1140

aaataactga cctgtcgagc ttaatattct atattgttgt tctttctgca aaaaagtggg    1200

gaagtgagta atgaaattat ttctaacatt tatctgcatc ataccttccg agcatttatt    1260

aagcatttcg ctataagttc tcgctggaag aggtagtttt ttcattgtac tttaccttca    1320

tctctgttca ttatcatcgc ttttaaaacg gttcgacctt ctaatcctat ctgaccatta    1380

taattttta gaatggtttc ataagaaagc tctgaatcaa cggactgcga taataagtgg     1440

tggtatccag aatttgtcac ttcaagtaaa aacacctcac gagttaaaac acctaagttc    1500

tcaccgaatg tctcaatatc cggacggata atatttattg cttctcttga ccgtaggact    1560

ttccacatgc aggattttgg aacctcttgc agtactactg ggaatgagt tgcaattatt     1620

gctacaccat tgcgtgcatc                                                1640
```

<210> SEQ ID NO 33
<211> LENGTH: 2453
<212> TYPE: DNA
<213> ORGANISM: Artificial
<220> FEATURE:
<223> OTHER INFORMATION: Synthesized

<400> SEQUENCE: 33

```
tgtaagagct gaggcggtga ccaatatcta caacatcagc cttggtatcc agcgtgatga      60

gccagcgcag aacaaggtaa ccgtcagtgc cgataagttc aaagttaaac ctggtgttga     120

taccaacatt gaaacgttga tcgaaaacgc gctgaaaaac gctgctgaat gtgcggcgct     180

ggatgtcaca aagcaaatgg cagcagacaa gaaagcgatg gatgaactgg cttcctatgt     240

ccgcacggcc atcatgatgg aatgtttccc cggtggtgtt atctggcagc agtgccgtcg     300

atagtatgca attgataatt attatcattt gcgggtcctt tccggcgatc cgccttgtta     360

cggggcggcg acctcgcggg ttttcgctat ttatgaaaat tttccggttt aaggcgtttc     420

cgttcttctt cgtcataact taatgttttt atttaaaata ccctctgaaa agaaaggaaa     480

cgacaggtgc tgaaagcgag ctttttggcc tctgtcgttt cctttctctg tttttgtccg     540

tggaatgaac aatggaagtc aacaaaaagc agctggctga cattttcggt gcgagtatcc     600

gtaccattca gaactggcag gaacagggaa tgcccgttct gcgaggcggt ggcaagggta     660

atgaggtgct ttatgactct gccgccgtca taaaatggta tgccgaaagg gatgctgaaa     720

ttgagaacga aaagctgcgc cgggaggttg aagaactgcg gcaggccaac gaggcagatc     780

cacaggacgg gtgtggtcgc catgatcgcg tagtcgatag tggctccaag tagcgaagcg     840

agcaggactg ggcggcggcc aaagcggtcg gacagtgctc cgagaacggg tgcgcataga     900

aattgcatca acgcatatag cgctagcagc acgccatagt gactggcgat gctgtcggaa     960

tggacgatat cccgcaagag gcccggcagt accggcataa ccaagcctat gcctacagca    1020

tccagggtga cggtgccgag gatgacgatg agcgcattgt tagatttcat acacggtgcc    1080

tgactgcgtt agcaatttaa ctgtgataaa ctaccgcatt aaagcttgca tgcctgcatg    1140

caggtcgaca gtcagcagat gaacactgac cacaaggctg ttttggataa ggataatgct    1200

tatccagtgg agtgctgggt tcctgatcca agtaaaaatg aaaacactag atattttgga    1260

acctacacag gtggggaaaa tgtgcctcct gttttgcaca ttactaacac agcaaccaca    1320
```

```
gtgcttcttg atgagcaggg tgttgggccc ttgtgcaaag ctgacagctt gtatgtttct   1380
gctgttgact ctagaatatg atgaaagata gaaaattacg acgcttatcg gaagtgaacg   1440
aatacttttt atatgaggag ggctgttttt acaaaatccg gtagtaactt gctaaccaat   1500
tcctaggcag gtcattggca acagtggcat gcaccgagaa ggacgtttgt aatgtccgct   1560
ccggcacata gcagtcctag ggacagtggc gtacagtcat agatggtcgg tgggaggtgg   1620
tacaaattct ctcatgcaaa aaatatgtaa aatcggtagc aactggaaat cattcaacac   1680
ccgcactatc ggaagttcac cagccagccg cagcacgttc ctgcatacga cgtgtctgcg   1740
gctctaccat atctcctatg agcaacgtgt tagcagagcc aagccacaac tctaatttta   1800
atacataatg aatgataata ataatattaa aaatttcctg tgtaactaat ttactatatg   1860
gtttctgata agaatcattg caaagatcaa acaacttgta ttacattgac agttaagcag   1920
ttaattttat cacctctaaa atatatcagc atctagcatg caacctatca aaatggagag   1980
ttttatgact aaaaaaccat gggaaagaag acttaaagat ttatcgcact tgctcaaatg   2040
ctgcattgat acatattttg accctgaatt atttcgcttg aatttgaatc aattcctcca   2100
aaccgcaaga acagtaacat ttattattca aaaaaacaaa aaccagatta taggatatga   2160
catttggtat aacaataatg ttattgaaaa atggaaaaat gatccattaa tggcttgggc   2220
taaaaattct cgcaatacga tagaaaaaca aggcgattta gaaatgtata gcgaggcaaa   2280
ggctactctt atttcatctt acattgaaga aaatgacatt gagtttatta caaatgaaag   2340
tatgttaaac attggtataa aaaagttagt cagacttgca caaaagaaat taccttcata   2400
tttaactgaa tcatctatta ttaaatcaga aagacgatgg gtcgctaata cgc          2453
```

<210> SEQ ID NO 34
<211> LENGTH: 2616
<212> TYPE: DNA
<213> ORGANISM: Artificial
<220> FEATURE:
<223> OTHER INFORMATION: Synthesized

<400> SEQUENCE: 34

```
tgtaagagct gaggcggtga ccaatatcta caacatcagc cttggtatcc agcgtgatga     60
gccagcgcag aacaaggtaa ccgtcagtgc cgataagttc aaagttaaac ctggtgttga    120
taccaacatt gaaacgttga tcgaaaacgc gctgaaaaac gctgctgaat gtgcggcgct    180
ggatgtcaca aagcaaatgg cagcagacaa gaaagcgatg gatgaactgg cttcctatgt    240
ccgcacggcc atcatgatgg aatgtttccc cggtggtgtt atctggcagc agtgccgtcg    300
atagtatgca attgataatt attatcattt gcgggtcctt tccggcgatc cgccttgtta    360
cggggcggcg acctcgcggg ttttcgctat ttatgaaaat ttccggttt aaggcgtttc     420
cgttcttctt cgtcataact taatgttttt atttaaaata ccctctgaaa agaaaggaaa    480
cgacaggtgc tgaaagcgag ctttttggcc tctgtcgttt cctttctctg tttttgtccg    540
tggaatgaac aatggaagtc aacaaaaagc agctggctga cattttcggt gcgagtatcc    600
gtaccattca gaactggcag gaacagggaa tgcccgttct gcgaggcggt ggcaagggta    660
atgaggtgct ttatgactct gccgccgtca taaaatggta tgccgaaagg gatgctgaaa    720
ttgagaacga aaagctgcgc cgggaggttg aagaactgcg gcaggccaac gaggcagatc    780
cacaggacgg gtgtggtcgc catgatcgcg tagtcgatag tggctccaag tagcgaagcg    840
agcaggactg ggcggcggcc aaagcggtcg gacagtgctc cgagaacggg tgcgcataga    900
```

```
aattgcatca acgcatatag cgctagcagc acgccatagt gactggcgat gctgtcggaa    960

tggacgatat cccgcaagag gcccggcagt accggcataa ccaagcctat gcctacagca   1020

tccagggtga cggtgccgag gatgacgatg agcgcattgt tagatttcat acacggtgcc   1080

tgactgcgtt agcaatttaa ctgtgataaa ctaccgcatt aaagcttgca tgcctgcatg   1140

caggtcgaca gtcagcagat gaacactgac cacaaggctg ttttggataa ggataatgct   1200

tatccagtgg agtgctgggt tcctgatcca agtaaaaatg aaaacactag atattttgga   1260

acctacacag gtggggaaaa tgtgcctcct gttttgcaca ttactaacac agcaaccaca   1320

gtgcttcttg atgagcaggg tgttgggccc ttgtgcaaag ctgacagctt gtatgtttct   1380

gctgttgact ctagatccct ctgaaaaaat cttccgagtt tgctaggcac tgatacataa   1440

ctcttttcca ataattgggg aagtcattca aatctataat aggtttcaga tttgcttcaa   1500

taaattctga ctgtagctgc tgaaacgttg cggttgaact atatttcctt ataactttta   1560

cgaaagagtt tctttgagta atcacttcac tcaagtgctt ccctgcctcc aaacgatacc   1620

tgttagcaat atttaatagc ttgaaatgat gaagagctct gtgtttgtct tcctgcctcc   1680

agttcgccgg gcattcaaca taaaaactga tagcacccgg agttccggaa acgaaatttg   1740

catataccca ttgctcacga aaaaaaatgt ccttgtcgat atagggatga atcgcttggt   1800

gtacctcatc tactgcgaaa acttgacctt tctctcccat attgcagtcg cggcacgatg   1860

gaactaaatt aataggcatc accgaaaatt caggataatg tgcaatagga agaaaatgat   1920

ctatattttt tgtctgtcct atatcaccac aaaatggaca tttttcacct gatgaaacaa   1980

gcatgtcatc gtaatatgtt ctagcgggtt tgtttttatc tcggagatta ttttcataaa   2040

gcttttctaa tttaaccttt gtcaggttac caactactaa ggttgtaggc tcaagagggt   2100

gtgtcctgtc gtaggtaaat aactgacctg tcgagcttaa tattctatat tgttgttctt   2160

tctgcaaaaa agtggggaag tgagtaatga aattatttct aacatttatc tgcatcatac   2220

cttccgagca tttattaagc atttcgctat aagttctcgc tggaagaggt agtttttttca   2280

ttgtacttta ccttcatctc tgttcattat catcgctttt aaaacggttc gaccttctaa   2340

tcctatctga ccattataat tttttagaat ggtttcataa gaaagctctg aatcaacgga   2400

ctgcgataat aagtggtggt atccagaatt tgtcacttca agtaaaaaca cctcacgagt   2460

taaaacacct aagttctcac cgaatgtctc aatatccgga cggataatat ttattgcttc   2520

tcttgaccgt aggactttcc acatgcagga ttttggaacc tcttgcagta ctactgggga   2580

atgagttgca attattgcta caccattgcg tgcatc                              2616
```

<210> SEQ ID NO 35
<211> LENGTH: 314
<212> TYPE: PRT
<213> ORGANISM: Artificial
<220> FEATURE:
<223> OTHER INFORMATION: Sequence 10xHis-SNAP-FRB

<400> SEQUENCE: 35

```
Met Gly His His His His His His His His His His Ser Ser Gly Met
1               5                   10                  15

Asp Lys Asp Cys Glu Met Lys Arg Thr Thr Leu Asp Ser Pro Leu Gly
            20                  25                  30

Lys Leu Glu Leu Ser Gly Cys Glu Gln Gly Leu His Glu Ile Lys Leu
        35                  40                  45

Leu Gly Lys Gly Thr Ser Ala Ala Asp Ala Val Glu Val Pro Ala Pro
    50                  55                  60
```

Ala Ala Val Leu Gly Gly Pro Glu Pro Leu Met Gln Ala Thr Ala Trp
65 70 75 80

Leu Asn Ala Tyr Phe His Gln Pro Glu Ala Ile Glu Glu Phe Pro Val
85 90 95

Pro Ala Leu His His Pro Val Phe Gln Gln Glu Ser Phe Thr Arg Gln
100 105 110

Val Leu Trp Lys Leu Leu Lys Val Val Lys Phe Gly Glu Val Ile Ser
115 120 125

Tyr Gln Gln Leu Ala Ala Leu Ala Gly Asn Pro Ala Ala Thr Ala Ala
130 135 140

Val Lys Thr Ala Leu Ser Gly Asn Pro Val Pro Ile Leu Ile Pro Cys
145 150 155 160

His Arg Val Val Ser Ser Ser Gly Ala Val Gly Gly Tyr Glu Gly Gly
165 170 175

Leu Ala Val Lys Glu Trp Leu Leu Ala His Glu Gly His Arg Leu Gly
180 185 190

Lys Pro Gly Leu Gly Ser Ser Gly Lys Leu Leu Glu Val Leu Phe Gln
195 200 205

Gly Pro Ser Ser Gly Glu Leu Ala Ile Leu Trp His Glu Met Trp His
210 215 220

Glu Gly Leu Glu Glu Ala Ser Arg Leu Tyr Phe Gly Glu Arg Asn Val
225 230 235 240

Lys Gly Met Phe Glu Val Leu Glu Pro Leu His Ala Met Met Glu Arg
245 250 255

Gly Pro Gln Thr Leu Lys Glu Thr Ser Phe Asn Gln Ala Tyr Gly Arg
260 265 270

Asp Leu Met Glu Ala Gln Glu Trp Cys Arg Lys Tyr Met Lys Ser Gly
275 280 285

Asn Val Lys Asp Leu Thr Gln Ala Trp Asp Leu Tyr Tyr His Val Phe
290 295 300

Arg Arg Ile Ser Lys Gln Leu Pro Gln Leu
305 310

<210> SEQ ID NO 36
<211> LENGTH: 323
<212> TYPE: PRT
<213> ORGANISM: Artificial
<220> FEATURE:
<223> OTHER INFORMATION: Sequence 10xHis-CLIP-FKBP12

<400> SEQUENCE: 36

Met Gly His His His His His His His His His His Ser Ser Gly Met
1 5 10 15

Asp Lys Asp Cys Glu Met Lys Arg Thr Thr Leu Asp Ser Pro Leu Gly
20 25 30

Lys Leu Glu Leu Ser Gly Cys Glu Gln Gly Leu His Arg Ile Ile Phe
35 40 45

Leu Gly Lys Gly Thr Ser Ala Ala Asp Ala Val Glu Val Pro Ala Pro
50 55 60

Ala Ala Val Leu Gly Gly Pro Glu Pro Leu Ile Gln Ala Thr Ala Trp
65 70 75 80

Leu Asn Ala Tyr Phe His Gln Pro Glu Ala Ile Glu Glu Phe Pro Val
85 90 95

Pro Ala Leu His His Pro Val Phe Gln Gln Glu Ser Phe Thr Arg Gln
100 105 110

```
Val Leu Trp Lys Leu Leu Lys Val Val Lys Phe Gly Glu Val Ile Ser
        115                 120                 125

Glu Ser His Leu Ala Ala Leu Val Gly Asn Pro Ala Ala Thr Ala Ala
    130                 135                 140

Val Asn Thr Ala Leu Asp Gly Asn Pro Val Pro Ile Leu Ile Pro Cys
145                 150                 155                 160

His Arg Val Val Gln Gly Asp Ser Asp Val Gly Pro Tyr Leu Gly Gly
                165                 170                 175

Leu Ala Val Lys Glu Trp Leu Leu Ala His Glu Gly His Arg Leu Gly
            180                 185                 190

Lys Pro Gly Leu Gly Ser Ser Gly Lys Leu Leu Glu Val Leu Phe Gln
        195                 200                 205

Gly Pro Ser Ser Gly Glu Leu Met Gly Val Gln Val Glu Thr Ile Ser
    210                 215                 220

Pro Gly Asp Gly Arg Thr Phe Pro Lys Arg Gly Gln Thr Cys Val Val
225                 230                 235                 240

His Tyr Thr Gly Met Leu Glu Asp Gly Lys Lys Phe Asp Ser Ser Arg
                245                 250                 255

Asp Arg Asn Lys Pro Phe Lys Phe Met Leu Gly Lys Gln Glu Val Ile
            260                 265                 270

Arg Gly Trp Glu Glu Gly Val Ala Gln Met Ser Val Gly Gln Arg Ala
        275                 280                 285

Lys Leu Thr Ile Ser Pro Asp Tyr Ala Tyr Gly Ala Thr Gly His Pro
    290                 295                 300

Gly Ile Ile Pro Pro His Ala Thr Leu Val Phe Asp Val Glu Leu Leu
305                 310                 315                 320

Lys Leu Glu


<210> SEQ ID NO 37
<211> LENGTH: 454
<212> TYPE: PRT
<213> ORGANISM: Artificial
<220> FEATURE:
<223> OTHER INFORMATION: Sequence 10xHis_CLIP_PHloop

<400> SEQUENCE: 37

Met Gly His His His His His His His His His His Ser Ser Gly Met
1               5                   10                  15

Asp Lys Asp Cys Glu Met Lys Arg Thr Thr Leu Asp Ser Pro Leu Gly
            20                  25                  30

Lys Leu Glu Leu Ser Gly Cys Glu Gln Gly Leu His Arg Ile Ile Phe
        35                  40                  45

Leu Gly Lys Gly Thr Ser Ala Ala Asp Ala Val Glu Val Pro Ala Pro
    50                  55                  60

Ala Ala Val Leu Gly Gly Pro Glu Pro Leu Ile Gln Ala Thr Ala Trp
65                  70                  75                  80

Leu Asn Ala Tyr Phe His Gln Pro Glu Ala Ile Glu Glu Phe Pro Val
                85                  90                  95

Pro Ala Leu His His Pro Val Phe Gln Gln Glu Ser Phe Thr Arg Gln
            100                 105                 110

Val Leu Trp Lys Leu Leu Lys Val Val Lys Phe Gly Glu Val Ile Ser
        115                 120                 125

Glu Ser His Leu Ala Ala Leu Val Gly Asn Pro Ala Ala Thr Ala Ala
    130                 135                 140
```

```
Val Asn Thr Ala Leu Asp Gly Asn Pro Val Pro Ile Leu Ile Pro Cys
145                 150                 155                 160

His Arg Val Val Gln Gly Asp Ser Asp Val Gly Pro Tyr Leu Gly Gly
                165                 170                 175

Leu Ala Val Lys Glu Trp Leu Leu Ala His Glu Gly His Arg Leu Gly
            180                 185                 190

Lys Pro Gly Leu Gly Ser Ser Gly Lys Leu Leu Glu Val Leu Phe Gln
        195                 200                 205

Gly Pro Ser Ser Gly Glu Leu Met Ala Asn Pro Asp Arg Glu Gly Trp
    210                 215                 220

Leu Leu Lys Leu Gly Gly Gly Arg Val Lys Thr Trp Lys Arg Arg Trp
225                 230                 235                 240

Phe Ile Leu Thr Asp Asn Ala Leu Tyr Tyr Phe Glu Tyr Thr Thr Asp
                245                 250                 255

Lys Glu Pro Arg Gly Ile Ile Pro Leu Glu Asn Leu Ser Ile Arg Glu
            260                 265                 270

Val Glu Asp Ser Lys Lys Pro Asn Val Phe Glu Leu Tyr Ile Pro Asp
        275                 280                 285

Asn Lys Asp Gln Val Ile Lys Ala Ala Lys Thr Glu Ala Lys Arg Val
    290                 295                 300

Glu Ala Glu Lys Ala Arg Ile Ala Lys Ala Glu Gln Ala Asp Gly Lys
305                 310                 315                 320

Gly Gly Asn Ala Ala Lys Lys Asn Thr Val Asn Gly Thr Gly Thr Pro
                325                 330                 335

Val His Ile Ser Thr Leu Gln Val Gly Glu Thr Arg Cys Lys Lys Val
            340                 345                 350

Cys Thr Ser Lys Ser Asp Leu Arg Ser Asn Asp Phe Ser Ile Val Gly
        355                 360                 365

Ser Leu Pro Arg Asp Phe Glu Leu Ser Asn Tyr Asp Cys Tyr Gly Lys
    370                 375                 380

Pro Ile Glu Val Asn Asn Gly Leu Gly Lys Pro Gln Ala Lys Asn Lys
385                 390                 395                 400

Lys Pro Pro Pro Ala Lys Pro Val Ile Pro Thr Ala Ala Lys Arg Ile
                405                 410                 415

Asp Leu Tyr Ala Arg Val Asp Gly Asn His Thr Val Tyr Arg Ile Ser
            420                 425                 430

Ala Pro Thr Pro Glu Glu Lys Glu Glu Trp Ile Lys Ala Ile Lys Ala
        435                 440                 445

Ala Ile Ser Arg Asp Gly
    450
```

<210> SEQ ID NO 38
<211> LENGTH: 968
<212> TYPE: PRT
<213> ORGANISM: Artificial
<220> FEATURE:
<223> OTHER INFORMATION: Sequence 6xHis_SNAP_GephyrinrC4

<400> SEQUENCE: 38

```
Met Arg Gly Ser His His His His His His Gly Ser Ala Cys Glu Leu
1               5                   10                  15

Ser Ser Gly Leu Glu Val Leu Phe Gln Gly Pro His Met Ala Ser Met
            20                  25                  30

Asp Lys Asp Cys Glu Met Lys Arg Thr Thr Leu Asp Ser Pro Leu Gly
        35                  40                  45
```

-continued

```
Lys Leu Glu Leu Ser Gly Cys Glu Gln Gly Leu His Glu Ile Lys Leu
    50                  55                  60

Leu Gly Lys Gly Thr Ser Ala Ala Asp Ala Val Glu Val Pro Ala Pro
65                  70                  75                  80

Ala Ala Val Leu Gly Gly Pro Glu Pro Leu Met Gln Ala Thr Ala Trp
                85                  90                  95

Leu Asn Ala Tyr Phe His Gln Pro Glu Ala Ile Glu Glu Phe Pro Val
            100                 105                 110

Pro Ala Leu His His Pro Val Phe Gln Gln Glu Ser Phe Thr Arg Gln
        115                 120                 125

Val Leu Trp Lys Leu Leu Lys Val Val Lys Phe Gly Glu Val Ile Ser
    130                 135                 140

Tyr Gln Gln Leu Ala Ala Leu Ala Gly Asn Pro Ala Ala Thr Ala Ala
145                 150                 155                 160

Val Lys Thr Ala Leu Ser Gly Asn Pro Val Pro Ile Leu Ile Pro Cys
                165                 170                 175

His Arg Val Val Ser Ser Ser Gly Ala Val Gly Gly Tyr Glu Gly Gly
            180                 185                 190

Leu Ala Val Lys Glu Trp Leu Leu Ala His Glu Gly His Arg Leu Gly
        195                 200                 205

Lys Pro Gly Leu Gly Ser Ser Gly Gly Thr Met Ala Thr Glu Gly Met
    210                 215                 220

Ile Leu Thr Asn His Asp His Gln Ile Arg Val Gly Val Leu Thr Val
225                 230                 235                 240

Ser Asp Ser Cys Phe Arg Asn Leu Ala Glu Asp Arg Ser Gly Ile Asn
                245                 250                 255

Leu Lys Asp Leu Val Gln Asp Pro Ser Leu Leu Gly Gly Thr Ile Ser
            260                 265                 270

Ala Tyr Lys Ile Val Pro Asp Glu Ile Glu Glu Ile Lys Glu Thr Leu
        275                 280                 285

Ile Asp Trp Cys Asp Glu Lys Glu Leu Asn Leu Ile Leu Thr Thr Gly
    290                 295                 300

Gly Thr Gly Phe Ala Pro Arg Asp Val Thr Pro Glu Ala Thr Lys Glu
305                 310                 315                 320

Val Ile Glu Arg Glu Ala Pro Gly Met Ala Leu Ala Met Leu Met Gly
                325                 330                 335

Ser Leu Asn Val Thr Pro Leu Gly Met Leu Ser Arg Pro Val Cys Gly
            340                 345                 350

Ile Arg Gly Lys Thr Leu Ile Ile Asn Leu Pro Gly Ser Lys Lys Gly
        355                 360                 365

Ser Gln Glu Cys Phe Gln Phe Ile Leu Pro Ala Leu Pro His Ala Ile
    370                 375                 380

Asp Leu Leu Arg Asp Ala Ile Val Lys Val Lys Glu Val His Asp Glu
385                 390                 395                 400

Leu Glu Asp Leu Pro Ser Pro Pro Pro Pro Leu Ser Pro Pro Pro Thr
                405                 410                 415

Thr Ser Pro His Lys Gln Thr Glu Asp Lys Gly Val Gln Cys Glu Glu
            420                 425                 430

Glu Glu Glu Glu Lys Lys Asp Ser Gly Val Ala Ser Thr Glu Asp Ser
        435                 440                 445

Ser Ser Ser His Ile Thr Ala Ala Ala Leu Ala Ala Lys Ile Pro Asp
    450                 455                 460

Ser Ile Ile Ser Arg Gly Val Gln Val Leu Pro Arg Asp Thr Ala Ser
```

```
465                 470                 475                 480

Leu Ser Thr Thr Pro Ser Glu Ser Pro Arg Ala Gln Ala Thr Ser Arg
                485                 490                 495

Leu Ser Thr Ala Ser Cys Pro Thr Pro Lys Ala Arg Leu Pro Ser Cys
            500                 505                 510

Ser Ser Thr Tyr Ser Val Ser Glu Val Gln Ser Arg Cys Ser Ser Lys
        515                 520                 525

Glu Asn Ile Leu Arg Ala Ser His Ser Ala Val Asp Ile Thr Lys Val
    530                 535                 540

Ala Arg Arg His Arg Met Ser Pro Phe Pro Leu Thr Ser Met Asp Lys
545                 550                 555                 560

Ala Phe Ile Thr Val Leu Glu Met Thr Pro Val Leu Gly Thr Glu Ile
                565                 570                 575

Ile Asn Tyr Arg Asp Gly Met Gly Arg Val Leu Ala Gln Asp Val Tyr
            580                 585                 590

Ala Lys Asp Asn Leu Pro Pro Phe Pro Ala Ser Val Lys Asp Gly Tyr
        595                 600                 605

Ala Val Arg Ala Ala Asp Gly Pro Gly Asp Arg Phe Ile Ile Gly Glu
    610                 615                 620

Ser Gln Ala Gly Glu Gln Pro Thr Gln Thr Val Met Pro Gly Gln Val
625                 630                 635                 640

Met Arg Val Thr Thr Gly Ala Pro Ile Pro Cys Gly Ala Asp Ala Val
                645                 650                 655

Val Gln Val Glu Asp Thr Glu Leu Ile Arg Glu Ser Asp Asp Gly Thr
            660                 665                 670

Glu Glu Leu Glu Val Arg Ile Leu Val Gln Ala Arg Pro Gly Gln Asp
        675                 680                 685

Ile Arg Pro Ile Gly His Asp Ile Lys Arg Gly Glu Cys Val Leu Ala
    690                 695                 700

Lys Gly Thr His Met Gly Pro Ser Glu Ile Gly Leu Leu Ala Thr Val
705                 710                 715                 720

Gly Val Thr Glu Val Glu Val Asn Lys Phe Pro Val Val Ala Val Met
                725                 730                 735

Ser Thr Gly Asn Glu Leu Leu Asn Pro Glu Asp Asp Leu Leu Pro Gly
            740                 745                 750

Lys Ile Arg Asp Ser Asn Arg Ser Thr Leu Leu Ala Thr Ile Gln Glu
        755                 760                 765

His Gly Tyr Pro Thr Ile Asn Leu Gly Ile Val Gly Asp Asn Pro Asp
    770                 775                 780

Asp Leu Leu Asn Ala Leu Asn Glu Gly Ile Ser Arg Ala Asp Val Ile
785                 790                 795                 800

Ile Thr Ser Gly Gly Val Ser Met Gly Glu Lys Asp Tyr Leu Lys Gln
                805                 810                 815

Val Leu Asp Ile Asp Leu His Ala Gln Ile His Phe Gly Arg Val Phe
            820                 825                 830

Met Lys Pro Gly Leu Pro Thr Thr Phe Ala Thr Leu Asp Ile Asp Gly
        835                 840                 845

Val Arg Lys Ile Ile Phe Ala Leu Pro Gly Asn Pro Val Ser Ala Val
    850                 855                 860

Val Thr Cys Asn Leu Phe Val Val Pro Ala Leu Arg Lys Met Gln Gly
865                 870                 875                 880

Ile Leu Asp Pro Arg Pro Thr Ile Ile Lys Ala Arg Leu Ser Cys Asp
                885                 890                 895
```

Val Lys Leu Asp Pro Arg Pro Glu Tyr His Arg Cys Ile Leu Thr Trp
900 905 910

His His Gln Glu Pro Leu Pro Trp Ala Gln Ser Thr Gly Asn Gln Met
915 920 925

Ser Ser Arg Leu Met Ser Met Arg Ser Ala Asn Gly Leu Leu Met Leu
930 935 940

Pro Pro Lys Thr Glu Gln Tyr Val Glu Leu His Lys Gly Glu Val Val
945 950 955 960

Asp Val Met Val Ile Gly Arg Leu
965

<210> SEQ ID NO 39
<211> LENGTH: 58
<212> TYPE: DNA
<213> ORGANISM: Artificial
<220> FEATURE:
<223> OTHER INFORMATION: Oligo-TS1 with an O2-benzylcytosine-dT at the 5' end

<400> SEQUENCE: 39
gtaagagctg aggcggtgac caatatctac aacatcagcc ttggtatcca gcgtgatg 58

<210> SEQ ID NO 40
<211> LENGTH: 67
<212> TYPE: DNA
<213> ORGANISM: Artificial
<220> FEATURE:
<223> OTHER INFORMATION: Oligo-TS2 with an O6-benzylguanine-dA at the 5' end

<400> SEQUENCE: 40
tctcaagctg aggaagcggt tagctccttc ggtcctccga tcgttgtcag aagtaagttg 60
gccgcag 67

<210> SEQ ID NO 41
<211> LENGTH: 42
<212> TYPE: DNA
<213> ORGANISM: Artificial
<220> FEATURE:
<223> OTHER INFORMATION: Oligonucleotide to amplify the lambda matrix by PCR

<400> SEQUENCE: 41
gagagaacgc gttccggatg cggagtctta tccgtggaaa tc 42

<210> SEQ ID NO 42
<211> LENGTH: 44
<212> TYPE: DNA
<213> ORGANISM: Artificial
<220> FEATURE:
<223> OTHER INFORMATION: Oligonucleotide to amplify the lambda matrix by PCR

<400> SEQUENCE: 42
gagagacctg caggaccaga gcggagataa tcgcggtgac tctg 44

<210> SEQ ID NO 43
<211> LENGTH: 6058
<212> TYPE: DNA
<213> ORGANISM: Artificial
<220> FEATURE:
<223> OTHER INFORMATION: Tether of about 6 kbp, obtained from DNA of the phage lambda matrix

<400> SEQUENCE: 43
tccatgggca tactgatcgg tagggcgcgt tccggatgcg gagtcttatc cgtggaaatc 60
aaacgcgcac tactggctgg ttaccaacct gtatcagaac atgcgggcca atgcgcttac 120
tgatgcggaa ttacgccgta aggccgcaga tgagcttgtc catatgactg cgagaattaa 180
ccgtggtgag gcgatccctg aaccagtaaa acaacttcct gtcatgggcg gtagacctct 240
aaatcgtgca caggctctgg cgaagatcgc agaaatcaaa gctaagttcg gactgaaagg 300
agcaagtgta tgacgggcaa agaggcaatt attcattacc tggggacgca taatagcttc 360
tgtgcgccgg acgttgccgc gctaacaggc gcaacagtaa ccagcataaa tcaggccgcg 420
gctaaaatgg cacgggcagg tcttctggtt atcgaaggta aggtctggcg aacggtgtat 480
taccggtttg ctaccaggga agaacgggaa ggaaagatga gcacgaacct ggtttttaag 540
gagtgtcgcc agagtgccgc gatgaaacgg gtattggcgg tatatggagt taaaagatga 600
ccatctacat tactgagcta ataacaggcc tgctggtaat cgcaggcctt tttatttggg 660
ggagagggaa gtcatgaaaa aactaacctt tgaaattcga tctccagcac atcagcaaaa 720
cgctattcac gcagtacagc aaatccttcc agacccaacc aaaccaatcg tagtaaccat 780
tcaggaacgc aaccgcagct tagaccaaaa caggaagcta tgggcctgct taggtgacgt 840
ctctcgtcag gttgaatggc atggtcgctg gctggatgca gaaagctgga agtgtgtgtt 900
taccgcagca ttaaagcagc aggatgttgt tcctaacctt gccgggaatg gctttgtggt 960
aataggccag tcaaccagca ggatgcgtgt aggcgaattt gcggagctat tagagcttat 1020
acaggcattc ggtacagagc gtggcgttaa gtggtcagac gaagcgagac tggctctgga 1080
gtggaaagcg agatggggag acagggctgc atgataaatg tcgttagttt ctccggtggc 1140
aggacgtcag catatttgct ctggctaatg gagcaaaagc gacgggcagg taaagacgtg 1200
cattacgttt tcatggatac aggttgtgaa catccaatga catatcggtt tgtcagggaa 1260
gttgtgaagt tctgggatat accgctcacc gtattgcagg ttgatatcaa cccggagctt 1320
ggacagccaa atggttatac ggtatgggaa ccaaaggata ttcagacgcg aatgcctgtt 1380
ctgaagccat ttatcgatat ggtaaagaaa tatggcactc catacgtcgg cggcgcgttc 1440
tgcactgaca gattaaaact cgttcccttc accaaatact gtgatgacca tttcgggcga 1500
gggaattaca ccacgtggat tggcatcaga gctgatgaac cgaagcggct aaagccaaag 1560
cctggaatca gatatcttgc tgaactgtca gactttgaga aggaagatat cctcgcatgg 1620
tggaagcaac aaccattcga tttgcaaata ccggaacatc tcggtaactg catattctgc 1680
attaaaaaat caacgcaaaa aatcggactt gcctgcaaag atgaggaggg attgcagcgt 1740
gtttttaatg aggtcatcac gggatcccat gtgcgtgacg gacatcggga aacgccaaag 1800
gagattatgt accgaggaag aatgtcgctg gacggtatcg cgaaaatgta ttcagaaaat 1860
gattatcaag ccctgtatca ggacatggta cgagctaaaa gattcgatac cggctcttgt 1920
tctgagtcat gcgaaatatt tggagggcag cttgatttcg acttcgggag ggaagctgca 1980
tgatgcgatg ttatcggtgc ggtgaatgca aagaagataa ccgcttccga ccaaatcaac 2040
cttactggaa tcgatggtgt ctccggtgtg aaagaacacc aacaggggtg ttaccactac 2100
cgcaggaaaa ggaggacgtg tggcgagaca gcgacgaagt atcaccgaca taatctgcga 2160
aaactgcaaa taccttccaa cgaaacgcac cagaaataaa cccaagccaa tcccaaaaga 2220
atctgacgta aaaaccttca actacacggc tcacctgtgg gatatccggt ggctaagacg 2280
tcgtgcgagg aaaacaaggt gattgaccaa aatcgaagtt acgaacaaga aagcgtcgag 2340

```
cgagctttaa cgtgcgctaa ctgcggtcag aagctgcatg tgctggaagt tcacgtgtgt   2400

gagcactgct gcgcagaact gatgagcgat ccgaatagct cgatgcacga ggaagaagat   2460

gatggctaaa ccagcgcgaa gacgatgtaa aaacgatgaa tgccgggaat ggtttcaccc   2520

tgcattcgct aatcagtggt ggtgctctcc agagtgtgga accaagatag cactcgaacg   2580

acgaagtaaa gaacgcgaaa aagcggaaaa agcagcagag aagaaacgac gacgagagga   2640

gcagaaacag aaagataaac ttaagattcg aaaactcgcc ttaaagcccc gcagttactg   2700

gattaaacaa gcccaacaag ccgtaaacgc cttcatcaga gaaagagacc gcgacttacc   2760

atgtatctcg tgcggaacgc tcacgtctgc tcagtgggat gccggacatt accggacaac   2820

tgctgcggca cctcaactcc gatttaatga acgcaatatt cacaagcaat gcgtggtgtg   2880

caaccagcac aaaagcggaa atctcgttcc gtatcgcgtc gaactgatta gccgcatcgg   2940

gcaggaagca gtagacgaaa tcgaatcaaa ccataaccgc catcgctgga ctatcgaaga   3000

gtgcaaggcg atcaaggcag agtaccaaca gaaactcaaa gacctgcgaa atagcagaag   3060

tgaggccgca tgacgttctc agtaaaaacc attccagaca tgctcgttga agcatacgga   3120

aatcagacag aagtagcacg cagactgaaa tgtagtcgcg gtacggtcag aaaatacgtt   3180

gatgataaag acgggaaaat gcacgccatc gtcaacgacg ttctcatggt tcatcgcgga   3240

tggagtgaaa gagatgcgct attacgaaaa aattgatggc agcaaatacc gaaatatttg   3300

ggtagttggc gatctgcacg gatgctacac gaacctgatg aacaaactgg atacgattgg   3360

attcgacaac aaaaaagacc tgcttatctc ggtgggcgat ttggttgatc gtggtgcaga   3420

gaacgttgaa tgcctggaat taatcacatt cccctggttc agagctgtac gtggaaacca   3480

tgagcaaatg atgattgatg gcttatcaga gcgtggaaac gttaatcact ggctgcttaa   3540

tggcggtggc tggttcttta atctcgatta cgacaaagaa attctggcta aagctcttgc   3600

ccataaagca gatgaacttc cgttaatcat cgaactggtg agcaaagata aaaaatatgt   3660

tatctgccac gccgattatc cctttgacga atacgagttt ggaaagccag ttgatcatca   3720

gcaggtaatc tggaaccgcg aacgaatcag caactcacaa aacgggatcg tgaaagaaat   3780

caaaggcgcg gacacgttca tctttggtca tacgccagca gtgaaaccac tcaagtttgc   3840

caaccaaatg tatatcgata ccggcgcagt gttctgcgga aacctaacat tgattcaggt   3900

acagggagaa ggcgcatgag actcgaaagc gtagctaaat ttcattcgcc aaaaagcccg   3960

atgatgagcg actcaccacg ggccacggct tctgactctc tttccggtac tgatgtgatg   4020

gctgctatgg ggatggcgca atcacaagcc ggattcggta tggctgcatt ctgcggtaag   4080

cacgaactca gccagaacga caaacaaaag gctatcaact atctgatgca atttgcacac   4140

aaggtatcgg ggaaataccg tggtgtggca aagcttgaag gaaatactaa ggcaaaggta   4200

ctgcaagtgc tcgcaacatt cgcttatgcg gattattgcc gtagtgccgc gacgccgggg   4260

gcaagatgca gagattgcca tggtacaggc cgtgcggttg atattgccaa aacagagctg   4320

tgggggagag ttgtcgagaa agagtgcgga agatgcaaag gcgtcggcta ttcaaggatg   4380

ccagcaagcg cagcatatcg cgctgtgacg atgctaatcc caaaccttac ccaacccacc   4440

tggtcacgca ctgttaagcc gctgtatgac gctctggtgg tgcaatgcca caaagaagag   4500

tcaatcgcag acaacatttt gaatgcggtc acacgttagc agcatgattg ccacggatgg   4560

caacatatta acggcatgat attgacttat tgaataaaat tgggtaaatt tgactcaacg   4620

atgggttaat tcgctcgttg tggtagtgag atgaaaagag gcggcgctta ctaccgattc   4680
```

```
cgcctagttg gtcacttcga cgtatcgtct ggaactccaa ccatcgcagg cagagaggtc   4740
tgcaaaatgc aatcccgaaa cagttcgcag gtaatagtta gagcctgcat aacggtttcg   4800
ggattttttta tatctgcaca acaggtaaga gcattgagtc gataatcgtg aagagtcggc   4860
gagcctggtt agccagtgct ctttccgttg tgctgaatta agcgaatacc ggaagcagaa   4920
ccggatcacc aaatgcgtac aggcgtcatc gccgcccagc aacagcacaa cccaaactga   4980
gccgtagcca ctgtctgtcc tgaattcatt agtaatagtt acgctgcggc cttttacaca   5040
tgaccttcgt gaaagcgggt ggcaggaggt cgcgctaaca acctcctgcc gttttgcccg   5100
tgcatatcgg tcacgaacaa atctgattac taaacacagt agcctggatt tgttctatca   5160
gtaatcgacc ttattcctaa ttaaatagag caaatcccct tattgggggt aagacatgaa   5220
gatgccagaa aaacatgacc tgttggccgc cattctcgcg gcaaaggaac aaggcatcgg   5280
ggcaatcctt gcgtttgcaa tggcgtacct tcgcggcaga tataatggcg gtgcgtttac   5340
aaaaacagta atcgacgcaa cgatgtgcgc cattatcgcc tggttcattc gtgaccttct   5400
cgacttcgcc ggactaagta gcaatctcgc ttatataacg agcgtgttta tcggctacat   5460
cggtactgac tcgattggtt cgcttatcaa acgcttcgct gctaaaaaag ccggagtaga   5520
agatggtaga aatcaataat caacgtaagg cgttcctcga tatgctggcg tggtcggagg   5580
gaactgataa cggacgtcag aaaaccagaa atcatggtta tgacgtcatt gtaggcggag   5640
agctatttac tgattactcc gatcaccctc gcaaacttgt cacgctaaac ccaaaactca   5700
aatcaacagg cgccggacgc taccagcttc tttcccgttg gtgggatgcc taccgcaagc   5760
agcttggcct gaaagacttc tctccgaaaa gtcaggacgc tgtggcattg cagcagatta   5820
aggagcgtgg cgctttacct atgattgatc gtggtgatat ccgtcaggca atcgaccgtt   5880
gcagcaatat ctgggcttca ctgccgggcg ctggttatgg tcagttcgag cataaggctg   5940
acagcctgat tgcaaaattc aaagaagcgg gcggaacggt cagagagatt gatgtatgag   6000
cagagtcacc gcgattatct ccgctctggt cctgcatgga tggaggcgtc ttggctca     6058
```

<210> SEQ ID NO 44
<211> LENGTH: 239
<212> TYPE: PRT
<213> ORGANISM: Artificial
<220> FEATURE:
<223> OTHER INFORMATION: PH-Loop

<400> SEQUENCE: 44

```
Met Ala Asn Pro Asp Arg Glu Gly Trp Leu Leu Lys Leu Gly Gly Gly
1               5                   10                  15

Arg Val Lys Thr Trp Lys Arg Arg Trp Phe Ile Leu Thr Asp Asn Ala
            20                  25                  30

Leu Tyr Tyr Phe Glu Tyr Thr Thr Asp Lys Glu Pro Arg Gly Ile Ile
        35                  40                  45

Pro Leu Glu Asn Leu Ser Ile Arg Glu Val Glu Asp Ser Lys Lys Pro
    50                  55                  60

Asn Val Phe Glu Leu Tyr Ile Pro Asp Asn Lys Asp Gln Val Ile Lys
65                  70                  75                  80

Ala Ala Lys Thr Glu Ala Lys Arg Val Glu Ala Glu Lys Ala Arg Ile
                85                  90                  95

Ala Lys Ala Glu Gln Ala Asp Gly Lys Gly Gly Asn Ala Ala Lys Lys
            100                 105                 110

Asn Thr Val Asn Gly Thr Gly Thr Pro Val His Ile Ser Thr Leu Gln
        115                 120                 125
```

```
Val Gly Glu Thr Arg Cys Lys Lys Val Cys Thr Ser Lys Ser Asp Leu
    130                 135                 140

Arg Ser Asn Asp Phe Ser Ile Val Gly Ser Leu Pro Arg Asp Phe Glu
145                 150                 155                 160

Leu Ser Asn Tyr Asp Cys Tyr Gly Lys Pro Ile Glu Val Asn Asn Gly
                165                 170                 175

Leu Gly Lys Pro Gln Ala Lys Asn Lys Lys Pro Pro Pro Ala Lys Pro
            180                 185                 190

Val Ile Pro Thr Ala Ala Lys Arg Ile Asp Leu Tyr Ala Arg Val Asp
        195                 200                 205

Gly Asn His Thr Val Tyr Arg Ile Ser Ala Pro Thr Pro Glu Glu Lys
    210                 215                 220

Glu Glu Trp Ile Lys Ala Ile Lys Ala Ala Ile Ser Arg Asp Gly
225                 230                 235


<210> SEQ ID NO 45
<211> LENGTH: 2091
<212> TYPE: DNA
<213> ORGANISM: Artificial
<220> FEATURE:
<223> OTHER INFORMATION: Synthesized

<400> SEQUENCE: 45

tctcaagctg aggaagcggt tagctccttc ggtcctccga tcgttgtcag aagtaagttg     60

gccgcagtgt tatcactcat ggttatggca gcactgcata attctcttac tgtcatgcca    120

tccgtaagat gcttttctgt gactggtgag tactcaacca agtcattctg agaatagtgt    180

atgcggcgac cgagttgctc ttgcccggcg tcaacacggg ataataccgc gccacatagc    240

agaactttaa aagtgctcat cattggaaaa cgttcttcgg ggcgaaaact ctcaaggatc    300

ttaccgctgt tgagatccag ttcgatgtaa cccactcgtg cacccaactg atcttcagca    360

tcttttactt tcaccagcgt ttctgggtga gcaaaaacag gaaggcaaaa tgccgcaaaa    420

aagggaataa gggcgacacg gaaatgttga atactcatac tcttcctttt tcaatattat    480

tgaagcattt atcagggtta ttgtctcatg agcggataca tatttgaatg tatttagaaa    540

aataaacaaa taggggttcc gcgcacattt ccccgaaaag tgccacctga cgtctaagaa    600

accattatta tcatgacatt aacctataaa aataggcgta tcacgaggcc ctttcgtctt    660

caagaattcg aattcgagct cggtacccgg ggatcctcta gagtcaacag cagaaacata    720

caagctgtca gctttgcaca agggcccaac accctgctca tcaagaagca ctgtggttgc    780

tgtgttagta atgtgcaaaa caggaggcac attttcccca cctgtgtagg ttccaaaata    840

tctagtgttt tcatttttac ttggatcagg aacccagcac tccactggat aagcattatc    900

cttatccaaa acagccttgt ggtcagtgtt catctgctga ctgtcgacct gcatgcaggc    960

atgcaagctt taatgcggta gtttatcaca gttaaattgc taacgcagtc aggcaccgtg   1020

tatgaaatct aacaatgcgc tcatcgtcat cctcggcacc gtcaccctgg atgctgtagg   1080

cataggcttg gttatgccgg tactgccggg cctcttgcgg gatatcgtcc attccgacag   1140

catcgccagt cactatggcg tgctgctagc gctatatgcg ttgatgcaat ttctatgcgc   1200

acccgttctc ggagcactgt ccgaccgctt tggccgccgc ccagtcctgc tcgcttcgct   1260

acttggagcc actatcgact acgcgatcat ggcgaccaca cccgtcctgt ggatctgcct   1320

cgttggcctg ccgcagttct tcaacctccc ggcgcagctt ttcgttctca atttcagcat   1380

ccctttcggc ataccatttt atgacggcgg cagagtcata aagcacctca ttacccttgc   1440
```

```
caccgcctcg cagaacgggc attccctgtt cctgccagtt ctgaatggta cggatactcg   1500
caccgaaaat gtcagccagc tgctttttgt tgacttccat tgttcattcc acggacaaaa   1560
acagagaaag gaaacgacag aggccaaaaa gctcgctttc agcacctgtc gtttcctttc   1620
ttttcagagg gtattttaaa taaaaacatt aagttatgac gaagaagaac ggaaacgcct   1680
taaaccggaa aattttcata aatagcgaaa acccgcgagg tcgccgcccc gtaacaaggc   1740
ggatcgccgg aaaggacccg caaatgataa taattatcaa ttgcatacta tcgacggcac   1800
tgctgccaga taacaccacc ggggaaacat tccatcatga tggccgtgcg gacataggaa   1860
gccagttcat ccatcgcttt cttgtctgct gccatttgct ttgtgacatc cagcgccgca   1920
cattcagcag cgtttttcag cgcgttttcg atcaacgttt caatgttggt atcaacacca   1980
ggtttaactt tgaacttatc ggcactgacg gttaccttgt tctgcgctgg ctcatcacgc   2040
tggataccaa ggctgatgtt gtagatattg gtcaccgcct cagctcttac a            2091
```

<210> SEQ ID NO 46
<211> LENGTH: 6011
<212> TYPE: DNA
<213> ORGANISM: Artificial
<220> FEATURE:
<223> OTHER INFORMATION: Digestion product which will be used as tether (6kbp)

<400> SEQUENCE: 46

```
cgcgttccgg atgcggagtc ttatccgtgg aaatcaaacg cgcactactg gctggttacc     60
aacctgtatc agaacatgcg ggccaatgcg cttactgatg cggaattacg ccgtaaggcc    120
gcagatgagc ttgtccatat gactgcgaga attaaccgtg gtgaggcgat ccctgaacca    180
gtaaaacaac ttcctgtcat gggcggtaga cctctaaatc gtgcacaggc tctggcgaag    240
atcgcagaaa tcaaagctaa gttcggactg aaaggagcaa gtgtatgacg ggcaaagagg    300
caattattca ttacctgggg acgcataata gcttctgtgc gccggacgtt gccgcgctaa    360
caggcgcaac agtaaccagc ataaatcagg ccgcggctaa aatggcacgg gcaggtcttc    420
tggttatcga aggtaaggtc tggcgaacgg tgtattaccg gtttgctacc agggaagaac    480
gggaaggaaa gatgagcacg aacctggttt ttaaggagtg tcgccagagt gccgcgatga    540
aacgggtatt ggcggtatat ggagttaaaa gatgaccatc tacattactg agctaataac    600
aggcctgctg gtaatcgcag gcctttttat ttgggggaga gggaagtcat gaaaaaacta    660
acctttgaaa ttcgatctcc agcacatcag caaaacgcta ttcacgcagt acagcaaatc    720
cttccagacc caaccaaacc aatcgtagta accattcagg aacgcaaccg cagcttagac    780
caaaacagga agctatgggc ctgcttaggt gacgtctctc gtcaggttga atggcatggt    840
cgctggctgg atgcagaaag ctggaagtgt gtgtttaccg cagcattaaa gcagcaggat    900
gttgttccta accttgccgg gaatggcttt gtggtaatag gccagtcaac cagcaggatg    960
cgtgtaggcg aatttgcgga gctattagag cttatacagg cattcggtac agagcgtggc   1020
gttaagtggt cagacgaagc gagactggct ctggagtgga aagcgagatg gggagacagg   1080
gctgcatgat aaatgtcgtt agtttctccg gtggcaggac gtcagcatat ttgctctggc   1140
taatggagca aaagcgacgg gcaggtaaag acgtgcatta cgttttcatg gatacaggtt   1200
gtgaacatcc aatgacatat cggtttgtca gggaagttgt gaagttctgg gatataccgc   1260
tcaccgtatt gcaggttgat atcaacccgg agcttggaca gccaaatggt tatacggtat   1320
gggaaccaaa ggatattcag acgcgaatgc ctgttctgaa gccatttatc gatatggtaa   1380
```

```
agaaatatgg cactccatac gtcggcggcg cgttctgcac tgacagatta aaactcgttc   1440
ccttcaccaa atactgtgat gaccatttcg ggcgagggaa ttacaccacg tggattggca   1500
tcagagctga tgaaccgaag cggctaaagc caaagcctgg aatcagatat cttgctgaac   1560
tgtcagactt tgagaaggaa gatatcctcg catggtggaa gcaacaacca ttcgatttgc   1620
aaataccgga acatctcggt aactgcatat tctgcattaa aaaatcaacg caaaaaatcg   1680
gacttgcctg caaagatgag gagggattgc agcgtgtttt taatgaggtc atcacgggat   1740
cccatgtgcg tgacggacat cgggaaacgc caaaggagat tatgtaccga ggaagaatgt   1800
cgctggacgg tatcgcgaaa atgtattcag aaaatgatta tcaagccctg tatcaggaca   1860
tggtacgagc taaaagattc gataccggct cttgttctga gtcatgcgaa atatttggag   1920
ggcagcttga tttcgacttc gggagggaag ctgcatgatg cgatgttatc ggtgcggtga   1980
atgcaaagaa gataaccgct tccgaccaaa tcaaccttac tggaatcgat ggtgtctccg   2040
gtgtgaaaga acaccaacag gggtgttacc actaccgcag gaaaaggagg acgtgtggcg   2100
agacagcgac gaagtatcac cgacataatc tgcgaaaact gcaaatacct tccaacgaaa   2160
cgcaccagaa ataaacccaa gccaatccca aaagaatctg acgtaaaaac cttcaactac   2220
acggctcacc tgtgggatat ccggtggcta agacgtcgtg cgaggaaaac aaggtgattg   2280
accaaaatcg aagttacgaa caagaaagcg tcgagcgagc tttaacgtgc gctaactgcg   2340
gtcagaagct gcatgtgctg gaagttcacg tgtgtgagca ctgctgcgca gaactgatga   2400
gcgatccgaa tagctcgatg cacgaggaag aagatgatgg ctaaaccagc gcgaagacga   2460
tgtaaaaacg atgaatgccg ggaatggttt caccctgcat tcgctaatca gtggtggtgc   2520
tctccagagt gtggaaccaa gatagcactc gaacgacgaa gtaaagaacg cgaaaaagcg   2580
gaaaaagcag cagagaagaa acgacgacga gaggagcaga aacagaaaga taaacttaag   2640
attcgaaaac tcgccttaaa gccccgcagt tactggatta aacaagccca acaagccgta   2700
aacgccttca tcagagaaag agaccgcgac ttaccatgta tctcgtgcgg aacgctcacg   2760
tctgctcagt gggatgccgg acattaccgg acaactgctg cggcacctca actccgattt   2820
aatgaacgca atattcacaa gcaatgcgtg gtgtgcaacc agcacaaaag cggaaatctc   2880
gttccgtatc gcgtcgaact gattagccgc atcgggcagg aagcagtaga cgaaatcgaa   2940
tcaaaccata accgccatcg ctggactatc gaagagtgca aggcgatcaa ggcagagtac   3000
caacagaaac tcaaagacct gcgaaatagc agaagtgagg ccgcatgacg ttctcagtaa   3060
aaaccattcc agacatgctc gttgaagcat acggaaatca gacagaagta gcacgcagac   3120
tgaaatgtag tcgcggtacg gtcagaaaat acgttgatga taaagacggg aaaatgcacg   3180
ccatcgtcaa cgacgttctc atggttcatc gcggatggag tgaaagagat gcgctattac   3240
gaaaaaattg atggcagcaa ataccgaaat atttgggtag ttggcgatct gcacggatgc   3300
tacacgaacc tgatgaacaa actggatacg attggattcg acaacaaaaa agacctgctt   3360
atctcggtgg gcgatttggt tgatcgtggt gcagagaacg ttgaatgcct ggaattaatc   3420
acattcccct ggttcagagc tgtacgtgga aaccatgagc aaatgatgat tgatggctta   3480
tcagagcgtg gaaacgttaa tcactggctg cttaatggcg gtggctggtt ctttaatctc   3540
gattacgaca aagaaattct ggctaaagct cttgcccata aagcagatga acttccgtta   3600
atcatcgaac tggtgagcaa agataaaaaa tatgttatct gccacgccga ttatcccttt   3660
gacgaatacg agtttggaaa gccagttgat catcagcagg taatctggaa ccgcgaacga   3720
```

-continued

```
atcagcaact cacaaaacgg gatcgtgaaa gaaatcaaag gcgcggacac gttcatcttt   3780
ggtcatacgc cagcagtgaa accactcaag tttgccaacc aaatgtatat cgataccggc   3840
gcagtgttct gcggaaacct aacattgatt caggtacagg gagaaggcgc atgagactcg   3900
aaagcgtagc taaatttcat tcgccaaaaa gcccgatgat gagcgactca ccacgggcca   3960
cggcttctga ctctctttcc ggtactgatg tgatggctgc tatggggatg gcgcaatcac   4020
aagccggatt cggtatggct gcattctgcg gtaagcacga actcagccag aacgacaaac   4080
aaaaggctat caactatctg atgcaatttg cacacaaggt atcggggaaa taccgtggtg   4140
tggcaaagct tgaaggaaat actaaggcaa aggtactgca agtgctcgca acattcgctt   4200
atgcggatta ttgccgtagt gccgcgacgc cgggggcaag atgcagagat tgccatggta   4260
caggccgtgc ggttgatatt gccaaaacag agctgtgggg gagagttgtc gagaaagagt   4320
gcggaagatg caaaggcgtc ggctattcaa ggatgccagc aagcgcagca tatcgcgctg   4380
tgacgatgct aatcccaaac cttacccaac ccacctggtc acgcactgtt aagccgctgt   4440
atgacgctct ggtggtgcaa tgccacaaag aagagtcaat cgcagacaac attttgaatg   4500
cggtcacacg ttagcagcat gattgccacg gatggcaaca tattaacggc atgatattga   4560
cttattgaat aaaattgggt aaatttgact caacgatggg ttaattcgct cgttgtggta   4620
gtgagatgaa aagaggcggc gcttactacc gattccgcct agttggtcac ttcgacgtat   4680
cgtctggaac tccaaccatc gcaggcagag aggtctgcaa aatgcaatcc cgaaacagtt   4740
cgcaggtaat agttagagcc tgcataacgg tttcgggatt ttttatatct gcacaacagg   4800
taagagcatt gagtcgataa tcgtgaagag tcggcgagcc tggttagcca gtgctctttc   4860
cgttgtgctg aattaagcga ataccggaag cagaaccgga tcaccaaatg cgtacaggcg   4920
tcatcgccgc ccagcaacag cacaacccaa actgagccgt agccactgtc tgtcctgaat   4980
tcattagtaa tagttacgct gcggcctttt acacatgacc ttcgtgaaag cgggtggcag   5040
gaggtcgcgc taacaacctc ctgccgtttt gcccgtgcat atcggtcacg aacaaatctg   5100
attactaaac acagtagcct ggatttgttc tatcagtaat cgaccttatt cctaattaaa   5160
tagagcaaat ccccttattg ggggtaagac atgaagatgc cagaaaaaca tgacctgttg   5220
gccgccattc tcgcggcaaa ggaacaaggc atcggggcaa tccttgcgtt tgcaatggcg   5280
taccttcgcg gcagatataa tggcggtgcg tttacaaaaa cagtaatcga cgcaacgatg   5340
tgcgccatta tcgcctggtt cattcgtgac cttctcgact tcgccggact aagtagcaat   5400
ctcgcttata taacgagcgt gtttatcggc tacatcggta ctgactcgat tggttcgctt   5460
atcaaacgct tcgctgctaa aaaagccgga gtagaagatg gtagaaatca ataatcaacg   5520
taaggcgttc ctcgatatgc tggcgtggtc ggagggaact gataacggac gtcagaaaac   5580
cagaaatcat ggttatgacg tcattgtagg cggagagcta tttactgatt actccgatca   5640
ccctcgcaaa cttgtcacgc taaacccaaa actcaaatca acaggcgccg gacgctacca   5700
gcttctttcc cgttggtggg atgcctaccg caagcagctt ggcctgaaag acttctctcc   5760
gaaaagtcag gacgctgtgg cattgcagca gattaaggag cgtggcgctt tacctatgat   5820
tgatcgtggt gatatccgtc aggcaatcga ccgttgcagc aatatctggg cttcactgcc   5880
gggcgctggt tatggtcagt tcgagcataa ggctgacagc ctgattgcaa aattcaaaga   5940
agcgggcgga acggtcagag agattgatgt atgagcagag tcaccgcgat tatctccgct   6000
ctggtcctgc a                                                         6011
```

<210> SEQ ID NO 47
<211> LENGTH: 2594
<212> TYPE: DNA
<213> ORGANISM: Artificial
<220> FEATURE:
<223> OTHER INFORMATION: Synthesized

<400> SEQUENCE: 47
gtaagagctg aggcggtgac caatatctac aacatcagcc tctcaagctg aggaagcggt 60
tagctccttc ggtcctccga tcgttgtgtc attcatcaag gacgccgcta tcgcaaatgg 120
tgctatccac gcagcggcaa tcgaaacacc tcagccggtg accaatatct acaacatcag 180
ccttggtatc cagcgtgatg agccagcgca gaacaaggta accgtcagtg ccgataagtt 240
caaagttaaa cctggtgttg ataccaacat tgaaacgttg atcgaaaacg cgctgaaaaa 300
cgctgctgaa tgtgcggcgc tggatgtcac aaagcaaatg gcagcagaca agaaagcgat 360
ggatgaactg gcttcctatg tccgcacggc catcatgatg gaatgtttcc ccggtggtgt 420
tatctggcag cagtgccgtc gatagtatgc aattgataat tattatcatt tgcgggtcct 480
ttccggcgat ccgccttgtt acggggcggc gacctcgcgg gttttcgcta tttatgaaaa 540
ttttccggtt taaggcgttt ccgttcttct tcgtcataac ttaatgtttt tatttaaaat 600
accctctgaa aagaaaggaa acgacaggtg ctgaaagcga gctttttggc ctctgtcgtt 660
tcctttctct gtttttgtcc gtggaatgaa caatggaagt caacaaaaag cagctggctg 720
acattttcgg tgcgagtatc cgtaccattc agaactggca ggaacaggga atgcccgttc 780
tgcgaggcgg tggcaagggt aatgaggtgc tttatgactc tgccgccgtc ataaaatggt 840
atgccgaaag ggatgctgaa attgagaacg aaaagctgcg ccgggaggtt gaagaactgc 900
ggcaggccaa cgaggcagat ccacaggacg ggtgtggtcg ccatgatcgc gtagtcgata 960
gtggctccaa gtagcgaagc gagcaggact gggcggcggc caaagcggtc ggacagtgct 1020
ccgagaacgg gtgcgcatag aaattgcatc aacgcatata gcgctagcag cacgccatag 1080
tgactggcga tgctgtcgga atggacgata tcccgcaaga ggcccggcag taccggcata 1140
accaagccta tgcctacagc atccagggtg acggtgccga ggatgacgat gagcgcattg 1200
ttagatttca tacacggtgc ctgactgcgt tagcaattta actgtgataa actaccgcat 1260
taaagcttgc atgcctgcat gcaggtcgac agtcagcaga tgaacactga ccacaaggct 1320
gttttggata aggataatgc ttatccagtg gagtgctggg ttcctgatcc aagtaaaaat 1380
gaaaacacta gatattttgg aacctacaca ggtggggaaa atgtgcctcc tgttttgcac 1440
attactaaca cagcaaccac agtgcttctt gatgagcagg gtgttgggcc cttgtgcaaa 1500
gctgacagct tgtatgtttc tgctgttgac tctagaatat gatgaaagat agaaaattac 1560
gacgcttatc ggaagtgaac gaatactttt tatatgagga gggctgtttt tacaaaatcc 1620
ggtagtaact tgctaaccaa ttcctaggca ggtcattggc aacagtggca tgcaccgaga 1680
aggacgtttg taatgtccgc tccggcacat agcagtccta gggacagtgg cgtacagtca 1740
tagatggtcg gtgggaggtg gtacaaattc tctcatgcaa aaaatatgta aaatcggtag 1800
caactggaaa tcattcaaca cccgcactat cggaagttca ccagccagcc gcagcacgtt 1860
cctgcatacg acgtgtctgc ggctctacca tatctcctat gagcaacgtg ttagcagagc 1920
caagccacaa ctctaatttt aatacataat gaatgataat aataatatta aaaatttcct 1980
gtgtaactaa tttactatat ggtttctgat aagaatcatt gcaaagatca aacaacttgt 2040
attacattga cagttaagca gttaatttta tcacctctaa aatatatcag catctagcat 2100
gcaacctatc aaaatggaga gttttatgac taaaaaacca tgggaaagaa gacttaaaga 2160
tttatcgcac ttgctcaaat gctgcattga tacatatttt gaccctgaat tatttcgctt 2220
gaatttgaat caattcctcc aaaccgcaag aacagtaaca tttattattc aaaaaaacaa 2280
aaaccagatt ataggatatg acatttggta taacaataat gttattgaaa aatggaaaaa 2340
tgatccatta atggcttggg ctaaaaattc tcgcaatacg atagaaaaac aaggcgattt 2400
agaaatgtat agcgaggcaa aggctactct tatttcatct tacattgaag aaaatgacat 2460
tgagtttatt acaaatgaaa gtatgttaaa cattggtata aaaaagttag tcagacttgc 2520
acaaaagaaa ttaccttcat atttaactga atcatctatt attaaatcag aaagacgatg 2580
ggtcgctaat acgc 2594

<210> SEQ ID NO 48
<211> LENGTH: 2717
<212> TYPE: DNA
<213> ORGANISM: Artificial
<220> FEATURE:
<223> OTHER INFORMATION: Synthesized

<400> SEQUENCE: 48
tctcaagctg aggaagcggt tagctccttc ggtcctccga tcgttgtgtc attcatcaag 60
gacgccgcta tcgcaaatgg tgctatccac gcagcggcaa tcgaaacacc tcagccggtg 120
accaatatct acaacatcag ccttggtatc cagcgtgatg agccagcgca gaacaaggta 180
accgtcagtg ccgataagtt caaagttaaa cctggtgttg ataccaacat tgaaacgttg 240
atcgaaaacg cgctgaaaaa cgctgctgaa tgtgcggcgc tggatgtcac aaagcaaatg 300
gcagcagaca agaaagcgat ggatgaactg gcttcctatg tccgcacggc catcatgatg 360
gaatgtttcc ccggtggtgt tatctggcag cagtgccgtc gatagtatgc aattgataat 420
tattatcatt tgcgggtcct ttccggcgat ccgccttgtt acggggcggc gacctcgcgg 480
gttttcgcta tttatgaaaa ttttccggtt taaggcgttt ccgttcttct tcgtcataac 540
ttaatgtttt tatttaaaat accctctgaa aagaaaggaa acgacaggtg ctgaaagcga 600
gctttttggc ctctgtcgtt tcctttctct gtttttgtcc gtggaatgaa caatggaagt 660
caacaaaaag cagctggctg acattttcgg tgcgagtatc cgtaccattc agaactggca 720
ggaacaggga atgcccgttc tgcgaggcgg tggcaagggt aatgaggtgc tttatgactc 780
tgccgccgtc ataaaatggt atgccgaaag ggatgctgaa attgagaacg aaaagctgcg 840
ccgggaggtt gaagaactgc ggcaggccaa cgaggcagat ccacaggacg ggtgtggtcg 900
ccatgatcgc gtagtcgata gtggctccaa gtagcgaagc gagcaggact gggcggcggc 960
caaagcggtc ggacagtgct ccgagaacgg gtgcgcatag aaattgcatc aacgcatata 1020
gcgctagcag cacgccatag tgactggcga tgctgtcgga atggacgata tcccgcaaga 1080
ggcccggcag taccggcata accaagccta tgcctacagc atccagggtg acggtgccga 1140
ggatgacgat gagcgcattg ttagatttca tacacggtgc ctgactgcgt tagcaattta 1200
actgtgataa actaccgcat taaagcttgc atgcctgcat gcaggtcgac agtcagcaga 1260
tgaacactga ccacaaggct gttttggata aggataatgc ttatccagtg gagtgctggg 1320
ttcctgatcc aagtaaaaat gaaaacacta gatattttgg aacctacaca ggtggggaaa 1380
atgtgcctcc tgttttgcac attactaaca cagcaaccac agtgcttctt gatgagcagg 1440
gtgttgggcc cttgtgcaaa gctgacagct tgtatgtttc tgctgttgac tctagatccc 1500
tctgaaaaaa tcttccgagt ttgctaggca ctgatacata actcttttcc aataattggg 1560
gaagtcattc aaatctataa taggtttcag atttgcttca ataaattctg actgtagctg 1620
ctgaaacgtt gcggttgaac tatatttcct tataactttt acgaaagagt ttctttgagt 1680
aatcacttca ctcaagtgct tccctgcctc caaacgatac ctgttagcaa tatttaatag 1740
cttgaaatga tgaagagctc tgtgtttgtc ttcctgcctc cagttcgccg ggcattcaac 1800
ataaaaactg atagcacccg gagttccgga aacgaaattt gcatataccc attgctcacg 1860
aaaaaaaatg tccttgtcga tatagggatg aatcgcttgg tgtacctcat ctactgcgaa 1920
aacttgacct ttctctccca tattgcagtc gcggcacgat ggaactaaat taataggcat 1980
caccgaaaat tcaggataat gtgcaatagg aagaaaatga tctatatttt ttgtctgtcc 2040
tatatcacca caaaatggac atttttcacc tgatgaaaca agcatgtcat cgtaatatgt 2100
tctagcgggt ttgtttttat ctcggagatt attttcataa agcttttcta atttaacctt 2160
tgtcaggtta ccaactacta aggttgtagg ctcaagaggg tgtgtcctgt cgtaggtaaa 2220
taactgacct gtcgagctta atattctata ttgttgttct ttctgcaaaa aagtggggaa 2280
gtgagtaatg aaattatttc taacatttat ctgcatcata ccttccgagc atttattaag 2340
catttcgcta taagttctcg ctggaagagg tagtttttc attgtacttt accttcatct 2400
ctgttcatta tcatcgcttt taaaacggtt cgaccttcta atcctatctg accattataa 2460 tttttagaa tggtttcata agaaagctct gaatcaacgg actgcgataa taagtggtgg 2520
tatccagaat ttgtcacttc aagtaaaaac acctcacgag ttaaaacacc taagttctca 2580
ccgaatgtct caatatccgg acggataata tttattgctt ctcttgaccg taggactttc 2640
cacatgcagg attttggaac ctcttgcagt actactgggg aatgagttgc aattattgct 2700
acaccattgc gtgcatc 2717

<210> SEQ ID NO 49
<211> LENGTH: 2412
<212> TYPE: DNA
<213> ORGANISM: Artificial
<220> FEATURE:
<223> OTHER INFORMATION: Synthesized

<400> SEQUENCE: 49
ttggtatcca gcgtgatgag ccagcgcaga acaaggtaac cgtcagtgcc gataagttca 60
aagttaaacc tggtgttgat accaacattg aaacgttgat cgaaaacgcg ctgaaaaacg 120
ctgctgaatg tgcggcgctg gatgtcacaa agcaaatggc agcagacaag aaagcgatgg 180
atgaactggc ttcctatgtc cgcacggcca tcatgatgga atgtttcccc ggtggtgtta 240
tctggcagca gtgccgtcga tagtatgcaa ttgataatta ttatcatttg cgggtccttt 300
ccggcgatcc gccttgttac ggggcggcga cctcgcgggt tttcgctatt tatgaaaatt 360
ttccggttta aggcgtttcc gttcttcttc gtcataactt aatgttttta tttaaaatac 420
cctctgaaaa gaaaggaaac gacaggtgct gaaagcgagc tttttggcct ctgtcgtttc 480
ctttctctgt ttttgtccgt ggaatgaaca atggaagtca acaaaaagca gctggctgac 540
attttcggtg cgagtatccg taccattcag aactggcagg aacagggaat gcccgttctg 600
cgaggcggtg gcaagggtaa tgaggtgctt tatgactctg ccgccgtcat aaaatggtat 660
gccgaaaggg atgctgaaat tgagaacgaa aagctgcgcc gggaggttga agaactgcgg 720
caggccaacg aggcagatcc acaggacggg tgtggtcgcc atgatcgcgt agtcgatagt 780
ggctccaagt agcgaagcga gcaggactgg gcggcggcca aagcggtcgg acagtgctcc 840

```
gagaacgggt gcgcatagaa attgcatcaa cgcatatagc gctagcagca cgccatagtg    900

actggcgatg ctgtcggaat ggacgatatc ccgcaagagg cccggcagta ccggcataac    960

caagcctatg cctacagcat ccagggtgac ggtgccgagg atgacgatga gcgcattgtt   1020

agatttcata cacggtgcct gactgcgtta gcaatttaac tgtgataaac taccgcatta   1080

aagcttgcat gcctgcatgc aggtcgacag tcagcagatg aacactgacc acaaggctgt   1140

tttggataag gataatgctt atccagtgga gtgctgggtt cctgatccaa gtaaaaatga   1200

aaacactaga tattttggaa cctacacagg tggggaaaat gtgcctcctg ttttgcacat   1260

tactaacaca gcaaccacag tgcttcttga tgagcagggt gttgggccct tgtgcaaagc   1320

tgacagcttg tatgtttctg ctgttgactc tagaatatga tgaaagatag aaaattacga   1380

cgcttatcgg aagtgaacga atacttttta tatgaggagg gctgttttta caaaatccgg   1440

tagtaacttg ctaaccaatt cctaggcagg tcattggcaa cagtggcatg caccgagaag   1500

gacgtttgta atgtccgctc cggcacatag cagtcctagg gacagtggcg tacagtcata   1560

gatggtcggt gggaggtggt acaaattctc tcatgcaaaa aatatgtaaa atcggtagca   1620

actggaaatc attcaacacc cgcactatcg gaagttcacc agccagccgc agcacgttcc   1680

tgcatacgac gtgtctgcgg ctctaccata tctcctatga gcaacgtgtt agcagagcca   1740

agccacaact ctaattttaa tacataatga atgataataa taatattaaa aatttcctgt   1800

gtaactaatt tactatatgg tttctgataa gaatcattgc aaagatcaaa caacttgtat   1860

tacattgaca gttaagcagt taattttatc acctctaaaa tatatcagca tctagcatgc   1920

aacctatcaa aatggagagt tttatgacta aaaaaccatg ggaaagaaga cttaaagatt   1980

tatcgcactt gctcaaatgc tgcattgata catattttga ccctgaatta tttcgcttga   2040

atttgaatca attcctccaa accgcaagaa cagtaacatt tattattcaa aaaaacaaaa   2100

accagattat aggatatgac atttggtata acaataatgt tattgaaaaa tggaaaaatg   2160

atccattaat ggcttgggct aaaaattctc gcaatacgat agaaaaacaa ggcgatttag   2220

aaatgtatag cgaggcaaag gctactctta tttcatctta cattgaagaa aatgacattg   2280

agtttattac aaatgaaagt atgttaaaca ttggtataaa aaagttagtc agacttgcac   2340

aaaagaaatt accttcatat ttaactgaat catctattat taaatcagaa agacgatggg   2400

tcgctaatac gc                                                       2412
```

<210> SEQ ID NO 50
<211> LENGTH: 2615
<212> TYPE: DNA
<213> ORGANISM: Artificial
<220> FEATURE:
<223> OTHER INFORMATION: Synthesized

<400> SEQUENCE: 50

```
gtaagagctg aggcggtgac caatatctac aacatcagcc ttggtatcca gcgtgatgag     60

ccagcgcaga acaaggtaac cgtcagtgcc gataagttca aagttaaacc tggtgttgat    120

accaacattg aaacgttgat cgaaaacgcg ctgaaaaacg ctgctgaatg tgcggcgctg    180

gatgtcacaa agcaaatggc agcagacaag aaagcgatgg atgaactggc ttcctatgtc    240

cgcacggcca tcatgatgga atgtttcccc ggtggtgtta tctggcagca gtgccgtcga    300

tagtatgcaa ttgataatta ttatcatttg cgggtccttt ccggcgatcc gccttgttac    360

ggggcggcga cctcgcgggt tttcgctatt tatgaaaatt ttccggttta aggcgtttcc    420

gttcttcttc gtcataactt aatgttttta tttaaaatac cctctgaaaa gaaaggaaac    480
```

```
gacaggtgct gaaagcgagc tttttggcct ctgtcgtttc ctttctctgt ttttgtccgt    540
ggaatgaaca atggaagtca acaaaaagca gctggctgac attttcggtg cgagtatccg    600
taccattcag aactggcagg aacagggaat gcccgttctg cgaggcggtg gcaagggtaa    660
tgaggtgctt tatgactctg ccgccgtcat aaaatggtat gccgaaaggg atgctgaaat    720
tgagaacgaa aagctgcgcc gggaggttga agaactgcgg caggccaacg aggcagatcc    780
acaggacggg tgtggtcgcc atgatcgcgt agtcgatagt ggctccaagt agcgaagcga    840
gcaggactgg gcggcggcca aagcggtcgg acagtgctcc gagaacgggt gcgcatagaa    900
attgcatcaa cgcatatagc gctagcagca cgccatagtg actggcgatg ctgtcggaat    960
ggacgatatc ccgcaagagg cccggcagta ccggcataac caagcctatg cctacagcat   1020
ccagggtgac ggtgccgagg atgacgatga gcgcattgtt agatttcata cacggtgcct   1080
gactgcgtta gcaatttaac tgtgataaac taccgcatta aagcttgcat gcctgcatgc   1140
aggtcgacag tcagcagatg aacactgacc acaaggctgt tttggataag gataatgctt   1200
atccagtgga gtgctgggtt cctgatccaa gtaaaaatga aaacactaga tattttggaa   1260
cctacacagg tggggaaaat gtgcctcctg ttttgcacat tactaacaca gcaaccacag   1320
tgcttcttga tgagcagggt gttgggccct tgtgcaaagc tgacagcttg tatgtttctg   1380
ctgttgactc tagatccctc tgaaaaaatc ttccgagttt gctaggcact gatacataac   1440
tcttttccaa taattgggga agtcattcaa atctataata ggtttcagat ttgcttcaat   1500
aaattctgac tgtagctgct gaaacgttgc ggttgaacta tatttcctta taacttttac   1560
gaaagagttt ctttgagtaa tcacttcact caagtgcttc cctgcctcca aacgatacct   1620
gttagcaata tttaatagct tgaaatgatg aagagctctg tgtttgtctt cctgcctcca   1680
gttcgccggg cattcaacat aaaaactgat agcacccgga gttccggaaa cgaaatttgc   1740
atatacccat tgctcacgaa aaaaaatgtc cttgtcgata tagggatgaa tcgcttggtg   1800
tacctcatct actgcgaaaa cttgaccttt ctctcccata ttgcagtcgc ggcacgatgg   1860
aactaaatta ataggcatca ccgaaaattc aggataatgt gcaataggaa gaaaatgatc   1920
tatatttttt gtctgtccta tatcaccaca aaatggacat tttcacctg atgaaacaag    1980
catgtcatcg taatatgttc tagcgggttt gtttttatct cggagattat tttcataaag   2040
cttttctaat ttaacctttg tcaggttacc aactactaag gttgtaggct caagagggtg   2100
tgtcctgtcg taggtaaata actgacctgt cgagcttaat attctatatt gttgttcttt   2160
ctgcaaaaaa gtggggaagt gagtaatgaa attatttcta acatttatct gcatcatacc   2220
ttccgagcat ttattaagca tttcgctata agttctcgct ggaagaggta gttttttcat   2280
tgtactttac cttcatctct gttcattatc atcgctttta aaacggttcg accttctaat   2340
cctatctgac cattataatt ttttagaatg gtttcataag aaagctctga atcaacggac   2400
tgcgataata agtggtggta tccagaattt gtcacttcaa gtaaaaacac ctcacgagtt   2460
aaaacaccta agttctcacc gaatgtctca atatccggac ggataatatt tattgcttct   2520
cttgaccgta ggactttcca catgcaggat tttggaacct cttgcagtac tactggggaa   2580
tgagttgcaa ttattgctac accattgcgt gcatc                              2615
```

The invention claimed is:

1. A double-stranded DNA molecule comprising a first double-stranded DNA molecule (1) connected to a second double-stranded DNA molecule (2) by a tether comprising double-stranded DNA, wherein the tether is attached by (i) at least one covalent bond to a first nucleotide in the first double-stranded DNA molecule (1), and by (ii) at least one covalent bond to a second nucleotide in the second double-stranded DNA molecule (2), wherein the at least one covalent bond of (i) and the at least one covalent bond of (ii) are not phosphodiester bonds, phosphorothioate bonds, phosphoramidate bonds or phosphorodiamidate bonds, the first nucleotide in the first double-stranded DNA molecule (1) is neither the 5'-terminal nor the 3'-terminal nucleotide of either strand of the first double-stranded DNA molecule (1), and the second nucleotide in the second double-stranded DNA molecule (1) is neither the 5'-terminal nor the 3'-terminal nucleotide of either strand of the second double-stranded DNA molecule (2);

and wherein the first double-stranded DNA molecule (1) and the second double-stranded DNA molecule (2) are in linear form;

the first double-stranded DNA molecule (1) and/or the second double-stranded DNA molecule (2) has a length of 300 to 5000 base pairs; and the tether has a length of 300 to 50,000 base pairs.

2. The double-stranded DNA molecule according to claim 1, wherein the tether consists of a double-stranded DNA molecule.

3. The double-stranded DNA molecule according to claim 1, wherein the tether is attached to the first double-stranded DNA molecule (1) by first covalent bond(s) between at least one nucleotide of a first double-stranded DNA extremity of the tether and at least one nucleotide of an intermediate region of the first double-stranded DNA molecule (1), and to the second double-stranded DNA molecule (2) by second covalent bond(s) between at least one nucleotide of a second double-stranded DNA extremity of the tether and at least one nucleotide of an intermediate region of the second double-stranded DNA molecule (2).

4. The double-stranded DNA molecule according to claim 1, wherein a first test molecule is linked to a nucleotide of a first double-stranded DNA extremity of the first double-stranded DNA molecule (1) and a second test molecule is linked to a nucleotide of a first double-stranded DNA extremity of the second double-stranded DNA molecule (2), wherein the first extremity of the first double-stranded DNA molecule (1) and/or the first extremity of the second double-stranded DNA molecule (2) has a length of 10 to 150 base pair.

5. The double-stranded DNA molecule according to claim 4, wherein the second double-stranded DNA extremity of the first double-stranded DNA molecule (1) is linked to a first support and the second double-stranded DNA extremity of the second double-stranded DNA molecule (2) is linked to a second support, wherein said supports are surface or solid substrates, at least one of them being a moveable support.

6. The double-stranded DNA molecule according to claim 4, wherein the first and/or second test molecule is selected from the group consisting of amino acids, peptides, polypeptides, and proteins.

7. A device comprising the double-stranded DNA molecule according to claim 1, wherein the first and second double-stranded DNA molecules (1) and (2) are specifically attached to supports which are surface or solid substrates, and wherein at least one of the supports is a moveable support.

8. A double-stranded DNA molecule comprising a first double-stranded DNA molecule (A) and a second double-stranded DNA molecule (B), wherein the first double-stranded DNA molecule (A) comprises a cleavage site which is present only in the first double-stranded DNA molecule (A), the first double-stranded DNA molecule (A) is connected to the second double-stranded DNA molecule (B) by two covalent bonds which are not phosphodiester bonds, phosphorothioate bonds, phosphoramidate bonds or phosphorodiamidate bonds, and the two covalent bonds are located on either side of the cleavage site.

9. A process for manufacturing a double-stranded DNA molecule according to claim 1, comprising a step of:

a) cleaving a precursor molecule of the first and second double-stranded DNA molecules (1) and (2) at a cleavage site that is present only in the precursor molecule, thereby generating a double-stranded DNA molecule comprising a first double-stranded DNA molecule (1) and a second double-stranded DNA molecule (2).

10. The double-stranded DNA molecule according to claim 5, wherein at least one of the two supports is a movable support.

11. The double-stranded DNA molecule according to claim 1, wherein the first double-stranded DNA molecule (1) and/or the second double-stranded DNA molecule (2) has a length of 650 to 1500 base pairs.

12. The double-stranded DNA molecule according to claim 4, wherein the first extremity of the first double-stranded DNA molecule (1) and/or the first extremity of the second double-stranded DNA molecule (2) has a length of 30 to 50 base pairs.

13. The double-stranded DNA molecule according to claim 4, wherein the first and/or second test molecule is selected from the group consisting of nucleosides, nucleotides, polynucleotides, and oligonucleotides.

* * * * *